United States Patent
Loose et al.

(10) Patent No.: US 11,162,071 B2
(45) Date of Patent: Nov. 2, 2021

(54) COMPOSITIONS AND METHODS FOR GENERATING HAIR CELLS BY UPREGULATING JAG-1

(71) Applicant: Frequency Therapeutics, Inc., Lexington, MA (US)

(72) Inventors: Christopher Loose, Winchester, MA (US); Will McLean, North Haven, CT (US); Megan Harrison, Middletown, CT (US)

(73) Assignee: Frequency Therapeutics, Inc., Lexington, MA (US)

(*) Notice: Subject to any disclaimer, the term of this patent is extended or adjusted under 35 U.S.C. 154(b) by 0 days.

(21) Appl. No.: 16/544,792

(22) Filed: Aug. 19, 2019

(65) Prior Publication Data

US 2020/0080054 A1   Mar. 12, 2020

Related U.S. Application Data

(60) Provisional application No. 62/719,218, filed on Aug. 17, 2018.

(51) Int. Cl.

| | | |
|---|---|---|
| *A61K 31/47* | (2006.01) | |
| *C12N 5/071* | (2010.01) | |
| *A61K 31/4375* | (2006.01) | |
| *A61K 31/472* | (2006.01) | |
| *A61K 31/506* | (2006.01) | |
| *A61K 38/10* | (2006.01) | |

(52) U.S. Cl.
CPC ........ *C12N 5/0627* (2013.01); *A61K 31/4375* (2013.01); *A61K 31/47* (2013.01); *A61K 31/472* (2013.01); *A61K 31/506* (2013.01); *A61K 38/10* (2013.01); *C12N 2501/999* (2013.01)

(58) Field of Classification Search
CPC ............ C12N 5/0627; C12N 2501/999; C12N 5/0623; C12N 2501/73; C12N 2533/54; C12N 2501/11; C12N 2501/115; C12N 2501/105; C12N 5/062; A61K 31/4375; A61K 31/47; A61K 31/472; A61K 31/506; A61K 38/10; A61K 38/177; A61K 31/551; A61K 31/5377; A61K 31/44; A61K 31/167; A61K 31/519; A61K 31/4745; A61K 31/515; A61K 45/06; A61K 9/0046; A61P 27/16
See application file for complete search history.

(56) References Cited

U.S. PATENT DOCUMENTS

| | | |
|---|---|---|
| 5,059,591 A | 10/1991 | Janoff et al. |
| 5,421,818 A | 6/1995 | Arenberg |
| 5,474,529 A | 12/1995 | Arenberg |
| 5,476,446 A | 12/1995 | Arenberg |
| 5,731,144 A | 3/1998 | Toothman et al. |
| 5,731,424 A | 3/1998 | Toothman et al. |
| 5,837,681 A | 11/1998 | Magal |
| 6,045,528 A | 4/2000 | Arenberg et al. |
| 6,124,449 A | 6/2000 | Gold et al. |
| 6,090,383 A | 7/2000 | Dasch et al. |
| 6,177,434 B1 | 1/2001 | Kopke et al. |
| 6,194,466 B1 | 2/2001 | Cottingham et al. |
| 6,419,928 B1 | 7/2002 | Dasch et al. |
| 6,476,031 B1 | 11/2002 | Chakravarty et al. |
| 6,509,318 B1 | 1/2003 | Bhatnagar et al. |
| 6,593,290 B1 | 7/2003 | Gao |
| 6,943,191 B1 | 9/2005 | Narayanan et al. |
| 7,030,125 B2 | 4/2006 | Munchhof et al. |
| 7,087,626 B2 | 8/2006 | Beight et al. |
| 7,151,169 B2 | 12/2006 | Thompson et al. |
| 7,223,766 B2 | 5/2007 | Dugar et al. |
| 7,387,614 B2 | 6/2008 | Staecker |
| 7,498,031 B2 | 3/2009 | Fujioka et al. |
| 7,514,445 B2 | 4/2009 | Freyne et al. |
| 7,723,486 B2 | 5/2010 | Ledbetter et al. |
| 8,071,591 B2 | 12/2011 | Nomura et al. |
| 8,207,216 B2 | 6/2012 | Kozikowski et al. |
| 8,298,825 B1 | 10/2012 | Hochedlinger et al. |
| 8,377,886 B2 | 2/2013 | Susztak et al. |
| 8,575,122 B1 | 11/2013 | Lichter et al. |
| 8,686,042 B2 | 4/2014 | Gil et al. |
| 8,709,385 B2 | 4/2014 | Tamarkin et al. |
| 8,771,754 B2 | 7/2014 | Hallahan |
| 8,784,870 B2 | 7/2014 | Lichter et al. |
| 8,852,626 B2 | 10/2014 | Lichter et al. |
| 9,333,171 B2 | 5/2016 | Lichter et al. |
| 9,347,042 B2 | 5/2016 | Shimmura et al. |
| 10,041,046 B2 | 8/2018 | Karp et al. |
| 10,041,047 B2 | 8/2018 | Karp et al. |

(Continued)

FOREIGN PATENT DOCUMENTS

| | | |
|---|---|---|
| CA | 2268331 | 5/1998 |
| CN | 1319968 | 6/2007 |

(Continued)

OTHER PUBLICATIONS

Bowie et al (Science, 1990, 247:1306-1310) (Year: 1990).*
Burgess et al (J. Cell Biol. 111:2129-2138, 1990) (Year: 1990).*
Lazar et al (Mol. Cell. Biol., 8:1247-1252, 1988) (Year: 1988).*
Ahn et al. (2014). "GSK3?, but not GSK3?, inhibits the neuronal differentiation of neural progenitor cells as a downstream target of mammalian target of rapamycin complex1." Stem cells and development. 23(10): 1121-33.

(Continued)

*Primary Examiner* — Sudhakar Katakam
(74) *Attorney, Agent, or Firm* — Cooley LLP; Cynthia A. Kozakiewicz; Andrew Henderson

(57) ABSTRACT

Provided are compositions and methods comprising Jag-1 agonists for increasing proliferation of cochlear supporting cells or vestibular supporting cells, and related methods of treating hearing or balance disorders.

14 Claims, 33 Drawing Sheets

Specification includes a Sequence Listing.

(56) References Cited

U.S. PATENT DOCUMENTS

| | | |
|---|---|---|
| 10,568,883 B2 | 2/2020 | Karp et al. |
| 10,954,490 B2 | 3/2021 | Karp et al. |
| 2003/0028905 A1 | 2/2003 | Knaus et al. |
| 2004/0006030 A1 | 1/2004 | Monia et al. |
| 2004/0015781 A1 | 1/2004 | Brown et al. |
| 2004/0038856 A1 | 2/2004 | Chakravarty et al. |
| 2004/0138188 A1 | 7/2004 | Higgins et al. |
| 2004/0147574 A1 | 7/2004 | Munchhof |
| 2004/0204431 A1 | 10/2004 | Scarborough et al. |
| 2005/0032835 A1 | 2/2005 | Pandey et al. |
| 2005/0227936 A1 | 10/2005 | McSwiggen et al. |
| 2005/0245508 A1 | 11/2005 | Weller et al. |
| 2005/0245520 A1 | 11/2005 | Dodic et al. |
| 2005/0287127 A1 | 12/2005 | Li et al. |
| 2005/0287128 A1 | 12/2005 | Guerciolini et al. |
| 2006/0003929 A1 | 1/2006 | Bier et al. |
| 2006/0229266 A1 | 10/2006 | Kumar et al. |
| 2007/0066632 A1 | 3/2007 | Hart et al. |
| 2007/0088080 A1 | 4/2007 | Gordillo et al. |
| 2007/0155722 A1 | 7/2007 | Li et al. |
| 2007/0167918 A1 | 7/2007 | Reed et al. |
| 2008/0015161 A1 | 1/2008 | Vornlocher et al. |
| 2008/0108656 A1 | 5/2008 | Pandey et al. |
| 2008/0275030 A1 | 11/2008 | Gizurarson et al. |
| 2009/0036382 A1 | 2/2009 | Bressan et al. |
| 2009/0270497 A1 | 10/2009 | Buggy |
| 2009/0325938 A1 | 12/2009 | Lichter et al. |
| 2010/0267141 A1 | 10/2010 | Shi |
| 2010/0292205 A1 | 11/2010 | Lefker et al. |
| 2011/0135756 A1 | 6/2011 | Owens et al. |
| 2011/0166060 A1 | 7/2011 | Simons et al. |
| 2011/0305674 A1 | 12/2011 | Edge et al. |
| 2012/0059021 A1 | 3/2012 | Biechele |
| 2012/0196312 A1 | 8/2012 | Sato et al. |
| 2012/0277199 A1 | 11/2012 | Ye et al. |
| 2013/0079329 A1 | 3/2013 | Hood |
| 2013/0189327 A1 | 7/2013 | Ortega et al. |
| 2013/0324594 A1 | 12/2013 | Guthrie |
| 2014/0004556 A1 | 1/2014 | Heller et al. |
| 2014/0023615 A1 | 1/2014 | Hsu |
| 2014/0243227 A1 | 8/2014 | Clevers et al. |
| 2014/0248696 A1 | 9/2014 | Zhang et al. |
| 2015/0025096 A1 | 1/2015 | Thies et al. |
| 2015/0240212 A1 | 8/2015 | Peterson et al. |
| 2015/0250747 A1 | 9/2015 | Bumpus et al. |
| 2015/0320877 A1 | 11/2015 | Messersmith et al. |
| 2015/0329821 A1 | 11/2015 | Ang et al. |
| 2016/0032240 A1 | 2/2016 | Heller et al. |
| 2016/0194604 A1 | 7/2016 | Karp et al. |
| 2017/0000728 A1 | 1/2017 | Lichter et al. |
| 2017/0071937 A1 | 3/2017 | Karp et al. |
| 2017/0226477 A1 | 8/2017 | Karp et al. |
| 2017/0252449 A1 | 9/2017 | Loose et al. |
| 2017/0349884 A1 | 12/2017 | Karp et al. |
| 2018/0214458 A1 | 8/2018 | Loose et al. |
| 2019/0017015 A1 | 1/2019 | Karp et al. |
| 2019/0060371 A1 | 2/2019 | McLean |
| 2019/0093079 A1 | 3/2019 | Loose et al. |
| 2019/0350845 A1 | 11/2019 | Lichter et al. |
| 2020/0078350 A1 | 3/2020 | Loose et al. |
| 2020/0080055 A1 | 3/2020 | Loose et al. |
| 2020/0323853 A1 | 10/2020 | Karp et al. |

FOREIGN PATENT DOCUMENTS

| | | |
|---|---|---|
| CN | 101341138 | 11/2012 |
| CN | 103361300 | 10/2013 |
| CN | 105853421 | 8/2016 |
| CN | 107073042 | 8/2017 |
| EP | 0945464 | 9/1999 |
| EP | 1739087 | 1/2007 |
| EP | 1961748 | 8/2008 |
| EP | 2636731 | 9/2013 |
| EP | 2765188 | 8/2014 |
| EP | 2963108 | 1/2016 |
| JP | 2012148995 | 8/2012 |
| WO | WO-1996/027610 | 9/1996 |
| WO | WO-1996/040094 | 12/1996 |
| WO | WO-1998/019700 | 5/1998 |
| WO | WO-1999/058128 | 11/1999 |
| WO | WO-2000/012497 | 3/2000 |
| WO | WO-2000/031135 | 6/2000 |
| WO | WO-2000/059939 | 10/2000 |
| WO | WO-2001/085685 | 11/2001 |
| WO | WO-2002/094833 | 11/2002 |
| WO | WO-2003/037891 | 5/2003 |
| WO | WO-2003/097639 | 11/2003 |
| WO | WO-2004/013135 | 2/2004 |
| WO | WO-2004/021989 | 3/2004 |
| WO | WO-2004/026307 | 4/2004 |
| WO | WO-2004/026865 | 4/2004 |
| WO | WO-2004/026871 | 4/2004 |
| WO | WO-2004/067530 | 8/2004 |
| WO | WO-2005/009939 | 2/2005 |
| WO | WO-2005/039570 | 5/2005 |
| WO | WO-2006/018633 | 2/2006 |
| WO | WO-2006/018967 | 2/2006 |
| WO | WO-2006/100490 | 9/2006 |
| WO | WO-2007/018818 | 2/2007 |
| WO | WO-2007/048857 | 5/2007 |
| WO | WO-2007/102770 | 9/2007 |
| WO | WO-2008/010852 | 1/2008 |
| WO | WO-2008/076556 | 6/2008 |
| WO | WO-2008/077138 | 6/2008 |
| WO | WO-2009/017453 | 2/2009 |
| WO | WO-2009/017455 | 2/2009 |
| WO | WO-2009/032667 | 3/2009 |
| WO | WO-2009/132050 | 10/2009 |
| WO | WO-2010/060088 | 5/2010 |
| WO | WO-2010/068955 | 6/2010 |
| WO | WO-2010/075551 | 7/2010 |
| WO | WO-2010/104205 | 9/2010 |
| WO | WO-2011/019957 | 2/2011 |
| WO | WO-2011/050476 | 5/2011 |
| WO | WO-2011/079841 | 7/2011 |
| WO | WO-2011/089416 | 7/2011 |
| WO | WO-2011/116930 | 9/2011 |
| WO | WO-2011/143511 | 11/2011 |
| WO | WO-2012/018933 | 2/2012 |
| WO | WO-2012/024404 | 2/2012 |
| WO | WO-2012/103012 | 8/2012 |
| WO | WO-2013/051722 | 4/2013 |
| WO | WO 2013/124413 | 8/2013 |
| WO | WO-2014/003098 | 1/2014 |
| WO | WO-2014/013255 | 1/2014 |
| WO | WO-2014/039908 | 3/2014 |
| WO | WO-2014/050779 | 4/2014 |
| WO | WO-2014/059383 | 4/2014 |
| WO | WO-2014/083132 | 6/2014 |
| WO | WO-2014/159356 | 10/2014 |
| WO | WO-2015/038704 A1 | 3/2015 |
| WO | WO-2015/168149 | 11/2015 |
| WO | WO-2015/175783 | 11/2015 |
| WO | WO-2016/029021 | 2/2016 |
| WO | WO-2016/037016 | 3/2016 |
| WO | WO-2017/120543 | 7/2017 |
| WO | WO-2017/132530 | 8/2017 |
| WO | WO-2017/151907 | 9/2017 |
| WO | WO-2018/125746 | 7/2018 |
| WO | WO-2020/037323 | 2/2020 |
| WO | WO-2020/037325 | 2/2020 |
| WO | WO-2020/037326 | 2/2020 |

OTHER PUBLICATIONS

Alford et al. (2014). "American College of Medical Genetics and Genomics Guideline for the Clinical Evaluation and Etiologic Diagnosis of Hearing Loss." Genetics in Medicine: Official Journal of the American College of Medical Genetics. vol. 16, pp. 347-355.

Almeida et al. (2014). "In Situ Gelling Systems: A Strategy to Improve the Bioavailability of Ophthalmic Pharmaceutical Formulations." Drug Discov. Today, 19(4): 400-12.

(56) References Cited

OTHER PUBLICATIONS

Arnold et al. (2011). "Zinc for Attention-Deficit/Hyperactivity Disorder: Placebo-Controlled Double-Blind Pilot Trial Alone and Combined with Amphetamine." Journal of Child and Adolescent Psychopharmacology, vol. 21(1): 1-19.
Associacao Brasileira de Otorrinolaringologia e Cirurgia Cervicofacial et al. (2012). "Sensorineural Hearing Loss: Radiologic Diagnosis." Revista da Associacao Medica Brasileira, vol. 58, pp. 519-529.
Barker et al. (2007). "Identification of stem cells in small intestines and colon by marker gene Lgr5." Nature Publishing Group. vol. 449, No. 25 1003-7.
Barker et al. (2010). "Lgr5-'-ve stem cells drive self-renewal in the stomach and build long-lived gastric units in vitro." Cell Stem Cell. vol. 6, 25-36.
Bermingham et al. (1999). "Math 1: An Essential Gene for the Generation of Inner Ear Hair Cells." Science, 284: 1837-1841.
Bohl et al. (2012). "Development of a Specially Tailored Local Drug Delivery System for the Prevention of Fibrosis After Insertion of Cochlear Implants Into the Inner Ear." Journal of Materials ScienceMaterials in Medicine, vol. 23:2151-2162.
Borenstein, J.T. (2011). "Intracochlear Drug Delivery Systems." Expert Opinion on Drug Delivery, vol. 8, No. 9, pp. 1161-1174.
Bramhall et al. (2014). "Lgr5-Positive Supporting Cells Generate New Hair Cells in the Postnatal Cochlea." Stem Cell Reports. 2(3): 311-322.
Brigande et al. (2009). "Quo vadis, hair cell regeneration?" Nat. Neurosci., 12(6): 679-685.
Bryan. (2011). "Presenting the 2011 DRF Grantees. Hearing Health: A Publication of Deafness Research Foundation." p. 42-50, Retrieved from the Internet: URL:http://hearinghealthfoundation.org/lib/sitefiles/pdf/HH_Fall2011_Grantees_REV.11.11.11.pdf.
Buczacki et al. (2013). "Intestinal label-retaining cells are secretory precursors expressing Lgr5," Nature, 495: 65-72.
Butler et al. (2010). "Rational Design and Simple Chemistry Yield a Superior, Neuroprotective HDAC Inhibitor, Tubastatin A," J. Am. Chem. Soc., vol. 132: 10842-10846.
Byfield et al. (2004). "Lateral Signaling Enhances TGF-J3 Response Complexity." Trends Cell Biol., 14(3): 107-111.
Byfield et al. (2004). "SB-505124 Is a Selective Inhibitor of Transforming Growth Factor-J3 Type I Receptors ALK4, ALK5, and ALK7." Molecular Pharmacology. vol. 65, No. 3, pp. 744-752.
Callahan et al. (2002). "Identification of Novel Inhibitors of the Transforming Growth Factor Betal (TGF-betal) Type 1 Receptor (ALK5)." J. Med. Chem., vol. 45., No. 5, pp. 999-1001.
Causey et al. (1984). "The Maryland CNC Test: normative studies." Audiology 23(6): 552-568.
Chai et al. (2011). "Dynamic Expression of Lgr5, a Wnt Target Gene, in the Developing and Mature Mouse Cochlea." J. Assoc. Res. Otolaryngology. 12(4): 455-469.
Chai et al. (2012). "Wnt signaling induces proliferation of sensory precursors in the postnatal mouse cochlea." Proc. Nat'l. Acad. Sci. USA. 109(21): 8167-8172.
Chen et al. (2005). ""Inner Ear Drug Delivery Via a Reciprocating Perfusion System in the Guinea Pig,"" Journal of Controlled Release : Official Journal of the Controlled Release Society, 110: 1-9.
Chen et al. (2007) "Preliminary Study on Brain-Targeted Drug Delivery Via Inner Ear," Actapharmaceutica Sinica, 42(10):1102-1106.
Chen et al. (2009). "Aminoglycoside-induced histone deacetylation and hair cell death in the mouse cochlea," J. Neurochem., 108(5): 1226-1236.
Cox et al. (2014). "Spontaneous Hair Cell Regeneration in the Neonatal Mouse Cochlea in Vivo." Development. vol. 141, No. 4, pp. 816-829.
Crosnier et al. (2006). "Organizing cell renewal in the intestine: stem cells, signals and combinatorial control." Nature Reviews Genetics, 7: 349-359.
Dai et al. (2002). "Human Serum and Glucocorticoid-Inducible Kinase-Like Kinase (SGKL) Phosphorylates Glycogen Syntheses Kinase 3 Beta (GSK-3beta) at Serine-9 Through Direct Interation." Biolchem. Biophys. Res. Commun., vol. 293, No. 4, pp. 1191-1196.
Database accession No. NLM25167568. Yeap Li-Ling et al. (2014). "Valproate-induced reversible sensorineural hearing loss: a case report with serial audiometry and pharmacokinetic modelling during a valproate rechallenge." Epileptic Disorders : International Epilepsy Journal With Videotape Sep. 2014, vol. 16, No. 3, Sep. 2014 (Sep. 2014), pp. 375-379, ISSN: 1294-9361.
Database accession No. PREV199191056930. Armon C. et al. (1990). "Sensorineural Hearing Loss a Reversible Effect of Valproic Acid." vol. 40, No. 12 pp. 1896-1898, ISSN: 0028-3878.
Database accession No. PREV201600270745. Benajiba Lina et al. (2015). "Identification of a First in Class GSK3-Alpha Selective Inhibitor as a New Differentiation Therapy for AML." Blood,vol. 126, No. 23. ISSN: 0006-4971 (print).
Davies et al. (2001). "The Interaction Between J3-Catenin, GSK3J3 and APC After Motogen Induced Cell-Cell Dissociation, and Their Involvement in Signal Transduction Pathways in Prostate Cancer." International Journal of Oncology. vol. 18, No. 4, pp. 843-847.
Davis et al. (2008). "Mesodermal Fate Decisions of a Stem Cell: the Wnt Switch," Cell Mol Life Sci., 65(17):2658-74. (abstract only).
De Los Angeles et al. (2013). "A chemical logic for reprogramming to pluripotency," Cell Research, vol. 23, No. 12, pp. 1337-1338.
Doble et al. (2007). "Functional redundancy of GSK-3alpha and GSK-3beta in Wnt/beta-catenin signaling shown by using an allelic series of embryonic stem cell lines." Developmental Cell, vol. 12, No. 6, p. 957-971.
Drottar et al. (2006). "The Histone Deacetylase Inhibitor Sodium Butyrate Protects Against Cisplatin-Induced Hearing Loss in Guinea Pigs," Laryngoscope, 116(2): 292-296.
Dumont et al. (2003). "Targeting the TGFJ3 Signaling Network in Hun1an Neoplasia." Cancer Cell. vol. 3, No. 6, pp. 531-536.
Engleder et al. (2014). "Preclinical Evaluation of Thermo reversible Triamcinolone Acetonide Hydrogels for Drug Delivery to the Inner Ear." International Journal of Pharmaceutics. vol. 471, No. 1-2, pp. 297-302.
Espinoza et al. (2003). "Phosphorylation by Glycogen Synthase Kinase-3J3 Down-Regulates Notch Activity, a Link for Notch and Wnt Pathways." Journal of Biological Chemistry. vol. 278, No. 34, pp. 32227-32235.
Farin et al. (2012). "Redundant sources of Wnt regulate intestinal stem cells and promote formation ofPaneth cells," Gastroenterology, 143: 1518-1529.
Foltz et al. (2002). "Glycogen Synthase Kinase-3J3 Modulates Notch Signaling and Stability." Current Biology, vol. 12, No. 12, pp. 1006-1011.
Fu et al. (2008). "SM16, an Orally Active Tfg-f3 Type I Receptor Inhibitor Prevents Myofibroblast Induction and Vascular Fibrosis in the Rat Carotid Injury Model." Arteriosclerosis, Thrombosis and Vascular Biology, vol. 28, No. 4, pp. 665-671.
Fujioka et al. (2011). "Development of Auditory-Specific Brain Rhythm in Infants," European Journal of Neuroscience, 33:521-529.
Fujioka et al. (2015). "Manipulating cell fate in the cochlea: a feasible therapy for hearing loss." Trends Neurosci. 38, 139-44.
Fuller et al. (2012). "Intestinal crypts reproducibly expand in culture", J. Surg. Res., 178(1): 48-54.
Gale et al. (2010). "Cochlear Supporting Cells," Chapter 11 in Oxford Handbook of Auditory Science: The Ear, 31 pages.
Garcia-Berrocal Jr. et al. (2006). "Alternatives to Systemic Steroid Therapy for Refractory Immune-Mediated Inner Ear Disease: A Physiopathologic Approach." Eur. Arch. Otorhinolarynqol. vol. 263, No. 11, pp. 977-982.
Gellibert et al. (2004). "Identification of 1, 5-Naphthyridine Derivatives as a Novel Series of Potent and Selective TGF-Beta Type 1 Receptor Inhibitors." J. Med. Chem. vol. 47, No. 18, pp. 4494-4506.
Gupta et al. (2006). "Fast-Gelling Injectable Blend ofHyaluronan and Methylcellulose for Intrathecal, Localized Delivery to the Injured Spinal Cord." Biomaterials, 27: 2370-2379.
Haegebarth et al. (2009). "Wnt Signaling, Lgr5, and Stem Cells in the Intestine and Skin." The American Jounral of Pathology. vol. 174, No. 3, pp. 715-721.

(56) References Cited

OTHER PUBLICATIONS

Haggarty et al. (2003). "Domain-Selective Small-Molecule Inhibitor ofHistone Deacetylase 6 (HDAC6)-Mediated Tubulin Deacetylation", Proc. Nat '1. Acad Sci. USA, 100(8): 4389-4394.
Halder et al. (2005). "A Specific Inhibitor of TGF-f3 Receptor Kinase, SB-431542, as a Potent Antitumor Agent for Human Cancers." Neoplasia. vol. 7, No. 5, pp. 509-521.
Harding et al. (2005). "The effect of an age-related hearing loss gene (Ahl) on noise induced hearing loss and cochlear damage from low-frequency noise." Hearing Research, 204: 90-100.
Herraiz et al. (2010). "Intratympanic Drug Delivery for the Treatment ofInner Ear Diseases," Acta Otorrinolaringologica Espanola, 61(3): 225-232.
Hirsh et al. (1952). "Development of Materials for Speech Audiometry." Journal of Speech, Language, and Hearing Research, 17(3), 321-337.
Hong et al. (1998). "Human Dynamin-Like Protein Interacts with the Glycogen Synthase Kinase 3f3." Biochem. Biophys. Res. Commun. vol. 249, No. 3, pp. 697-703.
Hoskison et al. (2013). "Drug Delivery to the Ear," Therapeutic Delivery, 4(1): 115-124.
Hou et al. (2013). "Pluripotent Stem Cells Induced from Mouse Somatic Cells by Small-Molecule Compounds." Science. 341(6146): 651-654.
Huang et al. (2009). "Systematic and Integrative Analysis of Large Gene Lists Using DAVID Bioinformatics Resources," Nature Protocols, 4(1):44-57.
Huang et al. (2009). "RAD18 Transmits DNA Damage Signaling to Elicit Homologous Recombination Repair." Nat. Cell. Biol., vol. 11, No. 5, pp. 592-603.
Huang et al. (2009). "Directed, Efficient, and Versatile Modifications of the *Drosophila* Genome by Genomic Engineering." PNAS. vol. 106, No. 20, pp. 8284-9290.
International Search Report for Int'l Application No. PCT/US2014/023197, titled:"Compositions and Methods for Epithelial Stem Cell Expansion and Culture"; dated May 28, 2014.
International Preliminary Report on Patentability for Int'l Application No. PCT/US2014/023197, titled: "Compositions and Methods for Epithelial Stem Cell Expansion and Culture"; dated Sep. 15, 2015.
International Preliminary Report on Patentability for Int'l Application No. PCT/US2015/048442, titled: "Compositions, Systems, and Methods for Generating Inner Ear Hair Cells for Treatment of Hearing Loss"; dated Mar. 7, 2017.
Isaacson et al. (2003). "Differential Diagnosis and Treatment of Hearing Loss." American Family Physician. vol. 18, pp. 1125-1132.
Itoh et al. (2016). "False HDAC inhibition by aurone compound." Chemical and Pharmaceutical Bulletin, vol. 64, pp. 1124-1128.
Izumikawa et al. (2005). "Auditory Hair Cell Replacement and Hearing Improvement by Atohl Gene Therapy in Deaf Mammals." Nat Med., 11(3): 271-276.
Jadali et al. (2016). "Activation of PI3K signaling prevents aminoglycoside-induced hair cell death in the murine cochlea", Biology Open,vol. 5, No. 6, 03, p. 698-708, XP055630999.
Jeon et al. (2011). "Notch Signaling Alters Sensory or Neuronal Cell Fate Specification OfInner Ear Stem Cells." Journal Neurosci. vol. 31, No. 23, pp. 8351-8358.
Jung et al. (2011). "Isolation and in vitro expansion of human colonic stem cells," Nat. Med., 17, 1225-1227.
Kanzaki et al. (2012). "Novel in Vivo Imaging Analysis of an Inner Ear Drug Delivery System in Mice: Comparison of Inner Ear Drug Concentrations Over TimeAfter Transtympanic and Systemic Injections." PloS One, vol. 7:e48480.
Kawamoto, T. (2003). "Use of a New Adhesive Film for the Preparation of Multi-Purpose Fresh-Frozen Sections from Hard Tissues, Whole-Animals, Insects and Plants." Arch. Histol. Cytol. vol. 66, No. 2, pp. 123-143.

Kazanjian et al. (2010). "Atonal homolog 1 is required for growth and differentiation effects of notch/gamma-secretase inhibitors on normal and cancerous intestinal epithelial cells," Gastroenterology, 139: 918-928.
Kim et al. (2015). "Development of a Drug Delivery System for the Inner Ear Using Poly(amino acid)-Based Nanoparticles," Drug Delivery, 22(3): 367-374.
Kimmel. (1987). "Identification and Characterization of Specific Clones: Strategy for Confirming the Validity of Presumptive Clones", Methods Enzymol. vol. 152, p. 507-511.
Koch et al. (2013). "Stem cells living with a Notch." The Company of Biologists Ltd. Development, vol. 140, pp. 689-704.
Kujavva et al. (1997). "Conditioning-Related Protection from Acoustic Injury: Effects of Chronic Deefferentation and Sham Surgery," J. Neurophysiol., vol. 78, pp. 3095-3106.
Kuo et al. (2015). "In Vivo Cochlear Hair Cell Generation and Survival by Coactivation of beta-Catenin and Atohl." Journal of Neuroscience, vol. 35, No. 30, p. 10786-10798.
Lajud et al. (2013). "A Regulated Delivery System for Inner Ear Drug Application," Journal of Controlled Release: Official Journal of the Controlled Release Society, 166:268-276.
Lanford et al. (1999). "Notch Signaling Pathway Mediates Hair Cell Development in Mammalian Cochlea." Nature Genetics. vol. 21, pp. 289-292.
Lasak et al. (2014). "Hearing Loss: Diagnosis and Management." Primary Care, vol. 41, pp. 19-31.
Lehiste et al. (1959). "Linguistic considerations in the study of speech intelligibility." Journal of the Acoustical Society of America 31(3): 280-286.
Lehner et al. (1997). "A Totally Implantable Drug Delivery System for Local Therapy of the Middle and Inner Ear." Ear, Nose, & Throat Journal, 76(8):567-570.
Li et al. (1998). "Interaction of Glycogen Synthase Kinase 3(3 with the DF3/MUC1 Carcinoma-Associated Antigen and f3-Catenin." Molecular and Cellular Biology, vol. 18, No. 12, pp. 7216-7224.
Li et al. (2003). "Pluripotent stem cells from the adult mouse inner ear", Nature Medicine. vol. 9, No. 10, p. 1293-1299.
Li et al. (2003). "Retinoic Acid Stimulates Chondrocyte Differentiation and Enhances Bone Morphogenetic Protein Effects through Induction of Smadl and Smad5." Endocrinology. vol. 144, No. 6, pp. 2514-2523.
Li et al. (2010). "Generation of iPSCs from mouse fibroblasts with a single gene, Oct4, and small molecules." Cell Research. 21(1): 196-204.
Li et al. (2013). "A Novel Aerosol-Mediated Drug Delivery System for Inner Ear Therapy: Intratympanic Aerosol Methylprednisolone Can Attenuate Acoustic Trauma," IEEE Transactions on Bio-Medical Engineering, 60(9): 2450-2460.
Li et al. (2017). "Advances in nano-based inner ear delivery systems for the treatment of sensorineural hearing loss." Adv. Drug Deliv. Rev. 108, 2-12.
Liberman et al. (2017). "Cochlear synaptopathy in acquired sensorineural hearing loss: Manifestations and mechanisms." Hearing research. 349:138-47.
Lin et al. (2011). "Inhibition of Notch Activity Promotes Nonmitotic Regeneration of Hair Cells in the Adult Mouse Utricles," The Journal of Neurosciencce, vol. 31, No. 43, pp. 15329-15339.
Liu et al. (2012). "In vivo Notch reactivation in differentiating cochlear hair cells induces Sox2 and Proxl expression but does not disrupt hair cell maturation." Dev Dyn., vol. 241, pp. 684-696.
Liu et al (2015). "Identification of Stage-Specific Markers During Differentiation of Hair Cells From Mouse Inner Ear Stem Cells or Progenitor Cells in Vitro." Int. J. Biochem. Cell. Biol., vol. 60, pp. 99-111.
Lu et al. (2008). "The Influence of Glycogen Synthase Kinase 3 in Limiting Cell Addition in the Mammalian Ear," pp. 1059-1075, published online in Wiley InterScience (www.interscience.wiley. com).
Lukacs et al. (2010). "Isolation, cultivation and characterization of adult murine prostate stem cells," Nat. Protoc., 5(4):702-713.
Lumpkin et al. (2003). "Mathl-Driven GFP Expression in the Developing Nervous System of Transgenic Mice," Gene Expr Patters, 3(4): 389-395.

(56) References Cited

OTHER PUBLICATIONS

Maison et al. (2003). "Olivocochlear Innervation in the Mouse: munocytochemical Maps, Crossed Versus Uncrossed Contributions, and Transmitter Colocalization." J. Comp. Neural., vol. 455, No. 3, pp. 406-416.

Mak et al. (2003). "The Tuberin-Hamartin Complex Negatively Regulates ,8-Catenin Signaling Activity." The Journal of Biological Chemistry. vol. 278, No. 8, 5947-5951.

Martinez-Monedero et al. (2008). "Differentiation of Inner Ear Stem Cells to Functional Sensory Neurons." Developmental Neurobiology. vol. 68, No. 5, pp. 669-684.

McCall et al. (2010). "Drug Delivery for Treatment of Inner Ear Disease: Current State of Knavvledge." Ear and Hearing, vol. 31, No. 2, pp. 156-165.

McLean et al. (2017). "Clonal Expansion of Lgr5-Positive Cells from Mammalian Cochlea and High-Purity Generation of Sensory Hair Cells." Cell Reports,vol. 18, No. 8, p. 1917-1929.

Mendel et al. (2014). "Normative data for the Maryland CNC Test. Journal of the American Academy of Audiology." 25, 775-781.

Meng et al. (2009). "Gamma-Secretase Inhibitors Abrogate Oxaliplatin-Induced Activation of the Notch-1 Signaling Pathway in Colon Cancer Cells Resulting in Enhanced Chemosensitivity." Cancer Research. vol. 69, pp. 573-582.

Mikulec et al. (2008). "Permeability of the Round Window Membrane is Influenced by the Composition of Applied Drug Solutions and by Common Surgical Procedures." Otol. Neurotol. vol. 29, No. 7, pp. 1020-1026.

Mills, D.M. (2006). "Determining the Cause of Hearing Loss: Differential Diagnosis Using a Comparison of Audiometric and Otoacoustic Emission Responses," Ear and Hearing, 27(5):508-525.

Mimasu et al. (2008). "Crystal structure of histone demelhylase LSD1 and tranylcypromine at 2.25 A," Biochemical and Biophysical Research ommunications, vol. 366, pp. 15-22.

Mimura et al. (2006). "Topical Ocular Drug Delivery to Inner Ear Disease and Sinusitis," Southern Medical Journal, 99(11): 1287-1289.

Mittal et al. (2017). "Recent advancements in the regeneration of auditory hair cells and hearing restoration." Frontiers in molecular neuroscience. 10:236.

Mizutari et al. (2013). "Notch Inhibition Induces Cochlear Hair Cell Regeneration and Recovery of Hearing after Acoustic Trauma." Neuron, vol. 77, No. 1, pp. 58-69.

Mizutari et al. (2014). "Spontaneous Recovery of Cochlear Fibrocytes After Severe Degeneration Caused by Acute Energy Failure." Frontiers in Phamcacology, vol. 5, No. 198, pp. 1-3.

Mundada et al. (2009). "In Situ Gelling Polymers in Ocular Drug Delivery Systems: A Review," Critical Reviews in Therapeutic Drug Carrier Systems, 26(1):85-118. (Impact Factor—3.99).

Nakagawa et al. (2011). "Local Drug Delivery to the Inner Ear Using Biodegradable Materials," Therapeutic Delivery, 2(6):807-814.

Nakamura et al. (1998). "Axin, an Inhibitor of the Wnt Signalling Pathway, Interacts ,vith f3-Catenin, GSK-3(3 and APC and Reduces the f3-Catenin Level." Genes Cells, vol. 3, No. 6, pp. 395-403.

Nekrassov et al. (2006). "Additive effects of antiepileptic drugs and pentylenetetrazole on hearing." Neuroscience Letters. 406(3): 276-80.

Olsauskas-Kuprys et al. (2013). "Gamma Secretase Inhibitors of Notch Signaling." OncoTargets and Therapy, vol. 6, pp. 943-955.

Oshima et al. (2007). "Phylogenetic Relationships Among Mycoplasmas Based on the Whole Genomic Information," J. Mol. Evol., 65(3):249-258.

Paasche et al. (2003). "Technical Report: Modification of a Cochlear Implant Electrode for Drug Delivery to the Inner Ear," Otology & Neurotology, 24:222-227.

Pararas et al. (2011). "Kinetics of Reciprocating Drug Delivery to the Inner Ear." Journal of Controlled Release: Official Journal of the Controlled Release Society, 152:270-277.

Pararas et al. (2012). "Microsystems Technologies for Drug Delivery to the Inner Ear," Advanced Drug Delivery Reviews, 64:1650-1660.

Park et al. (2009). "Selective GSK-3? inhibitors attenuate the cisplatin-induced cytotoxicity of auditory cells." Hearing research. 257(1-2): 53-62.

Paulson et al. (2008). "A Novel Controlled Local Drug Delivery System for Inner Ear Disease," Otology/Basic and Clinical Research; The Laryngoscope, vol. 118:706-711.

Peer et al. (2007). "Nanocarriers as an Emerging Platform for Cancer Therapy," Nature Nanotechnology, 2:751-760.

Peterson et al. (1962). "Revised CNC lists for auditory tests." Journal of Speech and Hearing Disorders 27:62-70.

Peterson et al. (2008). "Oral Administration of GW788388, an Inhibitor ofTGF-f3 Type I and II Receptor Kinases, Decreases Renal Fibrosis." Kidney International, vol. 73, pp. 705-715.

Plontke et al. (2002). "Pharrnacokinetic Considerations in Intratympanic Drug Delivery to the Inner Ear," Acta Oto-Rhino-Laryngologica Belgica, 56(4): 369-370.

Plontke et al. (2002). Transtympanic Endoscopy for Drug Delivery to the Inner Ear Using a New Microendoscope/ Advances in Oto-Rhino-Laryngology, 59: 149-155.

Plontke et al. (2004). "ID-and 3D-Computer Simulation for Experimental Planning and Interpretation of Pharmacokinetic Studies in the Inner Ear After Local Drug Delivery." Altex, vol. 21, Suppl 3, pp. 77-85.

Plontke et al. (2006). "Simulation of Application Strategies for Local Drug Delivery to the Inner Ear." ORL Journal for Oto-Rhino-Laryngology and Its Related Specialties. vol. 68, No. 6, pp. 386-392.

Plontke et al. (2006). "Technical Note on Microcatheter Implantation for Local Inner Ear Drug Delivery: Surgical Technique and Safety Aspects," Otology & Neurotology, 27(7):912-917.

Plontke et al. (2007). "Cochlear Pharmacokinetics With Local Inner Ear Drug Delivery Using a Three-Dimensional Finite-Element Computer Model." Audiology & Neuro-Otology, vol. 12, pp. 37-48.

Plontke et al. (2008). "Dexamethasone Concentration Gradients Along Scala Tympani After Application to the Round Window Membrane," Otology & Neurotology, 29(3):401-406.

Plontke et al. (2009). "Randomized Double Blind, Placebo Controlled Trial on the Safety and Efficacy of Continuous Intratympanic Dexamethasone Delivered Via a Round Window Catheter for Severe to Profound Sudden Idiopathic Sensorineural Hearing Loss After Failure of Systemic Therapy." The Laryngoscope, 119:359-369 (2009).

Plontke, S.K. (2011). "Evaluation of the Round Window Niche Before Local Drug Delivery to the Inner Ear Using a New Mini-Otoscope," Otology & Neurotology, 32(1):183-185.

Pritz et al. (2013). "Nanomedicine Strategies for Drug Delivery to the Ear." Nanomedicine, 8(7): 1155-1172.

Provenzano et al. (2007). "A role for epigenetics in hearing: Establishment and maintenance of auditory specific gene expression patterns," Hearing Res., 233(1-2): 1-13.

Purow, B. (2012). "Notch Inhibition as a Promising New Approach to Cancer Therapy," Advances in Experimental Medicine and Biology, 727:305-319.

Ramakers et al. (2015). "The effect of cochlear implantation on tinnitus in patients with bilateral hearing loss: A systematic review." Laryngoscope 125, 2584-92.

Raman et al. (2011). "Effectiveness of Cochlear Implants in Adults with Sensorineural Hearing Loss." Agency for Healthcare Research and Quality (US).

Raphael, Y. (1992). "Evidence for Supporting Cell Mitosis in Response to Acoustic Trauma in the Avian Inner Ear." Journal of Neurocytology, 21:663-671.

Richardson et al. (2008). "Novel Drug Delivery Systems for Inner Ear Protection and Regeneration After Hearing Loss," Expert Opinion on Drug Delivery, 5(10): 1059-1076.

Rivera et al. (2012). "Drug Delivery to the Inner Ear: Strategies and their Therapeutic Implications for Sensorineural Hearing Loss," Current Drug Delivery, 9(3): 231-242.

(56) References Cited

OTHER PUBLICATIONS

Roccio et al. (2015). "Cell cycle reactivation of cochlear progenitor cells in neonatal FUCCI mice by a GSK3 small molecule inhibitor." Scientific reports. 5: 17886.
Roche et al. (2015). "On the Horizon: Cochlear implant technology." Otolaryngol. Clin. North Am. 48, 1097-116.
Roy et al. (2010). "Cell-Specific Targeting in the Mouse Inner Ear Using Nanoparticles Conjugated with a Neurotrophin-Derived Peptide Ligand: Potential Tool for Drug Delivery," International Journal of Pharmaceutics, 390: 214-224.
Roy et al. (2012). "Strategies for Drug Delivery to the Human Inner Ear by Multifunctional Nanoparticles," Nanomedicine, 7(1):55-63.
Ryals et al. (2013). "Return of Function After Hair Cell Regeneration," Hearing Research, 297: 113-120.
Sage et al. (2005). "Proliferation of Functional Hair Cells in Vivo in the Absence of the Retinoblastoma Protein." Science. vol. 307, pp. 1114-1118.
Sage et al. (2006). "Essential role of retinoblastoma protein in mammalian hair cell development and hearing." Proc. Natl. Acad. Sci. USA. vol. 103, pp. 7345-7350.
Sakamoto et al. (2010). "Inner Ear Drug Delivery System from the Clinical Point of View." Acta Oto-Laryngologica, 130:sup563: 101-104.
Salt et al. (2005). "Local Inner Ear Drug Delivery and Phannacokinetics." Drug. Discov. Today, vol. 10, No. 19, pp. 1299-1306.
Salt et al. (2008). "Dependence of Hearing Changes on the Dose ofintratympanically Applied Gentamicin: A Meta-Analysis Using Mathematical Simulations of Clinical Drug Delivery Protocols." The Laryngoscope, 118(10): 1793-1800.
Salt et al. (2008). "Dexamethasone Concentration Gradients Along Scala Tympani After Application to the Round Windmv Membrane," Otology & Neurotology, 29(3):401-406.
Salt et al. (2009). "Principles of Local Drug Delivery to the Inner Ear." Audiol. Neurotol. vol. 14, No. 6, pp. 350-360.
Salt, A. (2010). "Guest Editorial: Drug Delivery for Treatment ofInner Ear Disease: Current State of Knowledge." Ear and Hearing, vol. 31, p. 155.
Salt et al. (2011). "Distribution of Dexamethasone and Preservation of Inner Ear Function Following Intratympanic Delivery of a Gel-Based Formulation." Audiology & Neuro-otology, vol. 16, pp. 323-335.
Salvi et al. (2008). "Hair Cell Regeneration, Repair, and Protection." Springer Handbook of Auditory Research. vols. 1-33, 323.
Sataloff, et al. (2001). "Differential Diagnosis of Occupational Hearing Loss." Occupational Health & Safety, 70(9): 126-129.
Sato et al. (2011). "Long-term expansion of epithelial organoids from human colon, adenoma, adenocarcinoma, and Barrett's epithelium," Gastroenterology, 141: 1762-1772.
Sato et al. (2011). "Paneth cells constitute the niche for Lgr5 stem cells in intestinal crypts," Nature, 469: 415-418.
Sawyer et al. (2003). "Synthesis and Activity of New Aryl-and Heteroaryl-Substituted Pyrazole Inhibitors of the Transforming Gro'1h Factor-Beta Type 1 Receptor Kinase Domain." J. Med. Chem., vol. 46, No. 19, pp. 3953-3956.
Sawyer et al. (2004). "Synthesis and Activity of New Aryl- and Heteroaryl-Substituted 5, 6-Dihiydro-4HPyrrolo[l,2-b]Pyrazole Inhibitors of the Transforming Growth Factor—Beta Type I Receptor Kinase Domain," Bioorg. Med. Chem. Lett., vol. 14, No. 13, pp. 3581-3584.
Schwarz-Romond et al. (2002). "The Ankyrin Repeat Protein Diversin Recruits Casein Kinase le to the f3-Catenin Degradation Complex and Acts in Both Canonical Wnt and Wnt/JNK Signaling." Genes, Dev., vol. 16, No. 16, pp. 2073-2084.
Scoville et al. (2008). "Current view: intestinal stem cells and signaling," Gastroenterology, 134(3): 849-864.
Seidman, M.D. (1998). "Glutamate Antagonists, Steroids, and Antioxidants as Therapeutic Options for Hearing Loss and Tinnitus and the Use of an Inner Ear Drug Delivery System." The International Tinnitus Journal, vol. 4, pp. 148-154.
Sekine et al. (2006). "Hath1 Up-Regulates Gastric Mucin Gene Expression in Gastric Cells." Biochem. Biophys. Res. Commun., 344(4): 1166-71.
Shariatmadari et al. (2005). "Increased Wnt Levels in the Neural Tube Impair the Function of Adherens Junctions During Neurulation," Mol Cell Neurosci.,30(3): 437-51. Epub (abstract only).
Shi et al. (2010). "Beta-Catenin Up-Regulates Atoh1 Expression in Neural Progenitor Cells by Interaction with an Atoh1 3' Enhancer." The Journal of Biological Chemistry, vol. 285, pp. 392-400.
Shi et al. (2012). "Wnt-Responsive Lgr5-Expressing Stem Cells Are Hair Cell Progenitors in the Cochlea." J Neuroscience, 32 (28): 9639-9648.
Shi et al. (2013). "Generation of Hair Cells in Neonatal Mice by f3-Catenin Overexpression in Lgr5-Positive Cochlear Progenitors." Proc Natl Acad Sci USA, vol. 110, No. 34, pp. 13851-13856.
Shih et al. (2007). "Notch Signaling, Gamma-Secretase Inhibitors, and Cancer Therapy." Cancer Research, vol. 67, pp. 1879-1882.
Shoichet et al. (2007). "Intrathecal Drug Delivery Strategy is Safe and Efficacious for Localized Delivery to the Spinal Cord," Progress in Brain Research, 161:385-392.
Snippert et al. (2010). "Intestinal crypt homeostasis results from neutral competition between symmetrically dividing Lgr5 stem cells," Cell, 143: 134-144.
Staecker et al. (2004). "Drug Delivery to the Inner Ear Using Gene Therapy," Otolaryngologic Clinics of North America, vol. 37, pp. 1091-1108.
Staecker et al. (2013). "Developments in Delivery of Medications for Inner Ear Disease," Expert Opinion on Drug Delivery, 10(5): 639-650.
Surovtseva et al. (2012). "Prestin Binding Peptides as Ligands for Targeted Polymersome Mediated Drug Delivery to Outer Hair Cells in the Inner Ear," International Journal of Pharmaceutics, 424: 121-127.
Swan et al. (2008). "Inner Ear Drug Delivery for Auditory Applications." Adv. Drug. Deliv. Rev., vol. 60, No. 15, pp. 1583-1599.
Tillman et al. (1966). "An expanded test for speech discrimination utilizing CNC monosyllabic words: Northwestern University Auditory Test No. 6." Northwestern Univ Evanston 11 Auditory Research Lab.
Tojo et al. (2005). "The ALK-5 Inhibitor A-83-01 Inhibits Smad Signaling and Epithelial-to-Mesenchymal Transition by Transforming Grovvth Factor-f3." Cancer Sci., vol. 96, No. 11, pp. 791-800.
Valdimarsdottir et al. (2005). "Functions of the TGFf3 Superfamily in Human Embryonic StempCells." APMIS. vol. 113, pp. 773-389.
Van Der Flier et al. (2009). "Stem cells, self-renewal, and differentiation in the intestinal epithelium," Annual Review of Physiology, 71: 241-260.
Van Dussen et al. (2012). "Notch signaling modulates proliferation and differentiation of intestinal crypt base columnar stem cells." The Company of Biologists Ltd., Development 139, pp. 488-497.
Van Es et al. (2005). "Notch/gamma-secretase inhibition turns proliferative cells in intestinal crypts and adenomas into goblet cells," Nature, 435: 959-963.
Van Es et al. (2010). "Intestinal stem cells lacking the Math1 tumour suppressor are refractory to Notch inhibitors." Nat. Commun., 1(18): 1-5.
Van Tomme et al. (2008). "In Situ Gelling Hydrogels for Phannaceutical and Biomedical Applications." Int. J. Pharm., 355(1-2): 1-18.
Von Kries et al. (2000). "Hot Spots in Beta-Catenin for Interactions with LEF-1, Conductin and APC." Nat. Struct. Biol., vol. 7, No. 9, pp. 800-807.
Voytik-Harbin et al. (1998). "Small Intestinal Submucosa: A Tissue-Derived Extracellular Matrix That Promotes Tissue-Specific Growth and Differentiation of Cells in Vitro." Tissue Engineering, 4(2): 157-174.
Wahl et al. (1987). "Molecular Hybridization of Nucleic Acids", Methods in Enzymology. vol. 152, p. 399-407.
Wang et al. (2002). "Dynamics of Noise-Induced Cellular Injury and Repair in the Mouse Cochlea," J. of the Assoc. of Research in Otolaryngology, 3:248-268.

(56) References Cited

OTHER PUBLICATIONS

Wang et al. (2004). "Suppression of Androgen Receptor-Mediated Transactivation and Cell Growth by the Glycogen Synthase Kinase 3f3 in Prostate Cells." Journal of Biological Chemistry, vol. 279, No. 31, pp. 32444-32452.
Warchol et al. (1996). "Regenerative Proliferation in Organ Cultures of the Avian Cochlea: Identification of the Initial Progenitors and Determination of the Latency of the Proliferative Response." The Journal of Neuroscience: the Official Journal of the Society for Neuroscience. vol. 16, pp. 5466-5477.
White et al. (2006). "Mammalian Cochlear Supporting Cells Can Divide and Trans-Differentiate Into Hair Cells." Nature, vol. 441, No. 7096, pp. 984-987.
Wilson et al. (2003). "A word-recognition task in multi-talker babble using a descending presentation mode from 24 dB to O dB signal to babble." Journal of Rehabilitation Research and Development, 40(4), 321-328.
Wise et al. (2012). "Drug Delivery to the Inner Ear." Journal of Neural Engineering, 9(6):065002, 10 pages.
Wong et al. (2015). "Mechanisms of sensorineural cell damage, death and survival in the cochlea." Frontiers in Aging Neuroscience. vol. 7, Article 58, pp. 1-15.
Written Opinion of the International Searching Authority for Int'l Application No. PCT/US2014/023197, titled: "Compositions and Methods for Epithelial Stem Cell Expansion and Culture"; dated May 28, 2014.
Wu et al. (2004). Modulation of Notch Signaling by Mastermind-Like (MAML) Transcriptional Co-Activators and Their Involvement in Tumorigenesis/ Seminars in Cancer Biology, 14: 348-356.
Yang et al. (2012). "Functional Features of Trans-Differentiated Hair Cells Mediated by Atohl Reveals a Primordial Mechanism." J. ofNeuroscience, 32(11):3712-3725.
Yang et al. (2013). "Ectopic Hair Cell-Like Cell Induction by Math! Mainly Involves Direct Transdifferentiation in Neonatal Mammalian Cochlea," Neuroscience Letters, 549:7-11.
Yao et al. (2010). "Prostate-regenerating capacity of cultured human adult prostate epithelial cells," Cells Tissues Organs, 191: 203-212.
Yilmaz et al. (2012). "mTORCI in the Paneth cell niche couples intestinal stem-cell function to calorie intake," Nature, 486: 490-495.
Yin et al. (2013). "Niche-Independent High-Purity Cultures ofLgr5+ Intestinal Stem Cells and Their Progeny." Nat. Methods, vol. 11, No. 1, pp. 106-112.
Ying et al. (2008). "The ground state of embryonic stem cell self-renewal," Nature, 453: 519-523.
Yingling et al. (2004). "Development of TGF-B Signalling Inhibitors for Cancer Therapy." Nature Reviews Drug Discovery. vol. 3, No. 12, pp. 1011-1022.
Yu et al. (2010). "In vivo proliferation of postmitotic cochlear supporting cells by acute ablation of the retinoblastoma protein in neonatal mice." J Neurosci, vol. 30, pp. 5927-5936.
Yuge et al. (2004). "Transplanted Human Amniotic Epithelial Cells Express Connexin 26 and Na-Kadenosine Triphophatase in the Inner Ear." Transplantation. vol. 77, No. 9, pp. 1452-1454.
Yui et al. (2012). "Functional engraftment of colon epithelium expanded in vitro from a single adult Lgr5+ stem cell," Nature Medicine, 18(4): 618-623.
Zahnert, T. (2011). "The Differential Diagnosis of Hearing Loss." Deutsches Arzteblatt International. vol. 108, pp. 433-443, quiz 44.
Zhang et al. (2003). "Inhibitory Phosphorylation of Glycogen Synthase Kinase-3 (GSK-3) in Response to Lithium," J. Bio. Chem., 278(3): 33067-33077.
Zhao et al. (2015). "A XEN-like State Bridges Somatic Cells to Pluripotency during Chemical Reprogramming." Cell. 163(7): 1678-1691.
Zheng et al. (2000). "Overexpresson of Mathl Induces Robust Production of Extra Hair Cells in Postnatal Rat Inner Ears," Nature Neuroscience, 3(6): 580-586.
Murillo-Cuesta et al. (2015). "Transforming growth factor ?1 inhibition protects from noise-induced hearing loss." Frontiers in Aging Neuroscience. vol. 7, Article 32, pp. 1-13.
Nagashima et al. (2010). "Discovery of Novel Forkhead Box 01 Inhibitors for Treating Type 2 Diabetes: Improvement of Fasting Glycemia in Diabetic db/db Mice." Molecular Pharmacology.The Amer. Soc. Pharm. & Exp. Ther., vol. 78(5), pp. 961-970.
Suenaga et al. (2013). "Bmp4 expressed in preadipocytes is required for the onset of adipocyte differentiation." Cytokine 64.1 138-145.
Tate. (1994). "Anatomy and physiology of the ear." Principles of Hearing Aid Audiology. Chapter 2, pp. 20-40.
Zheng et al. (1997). "Induction of cell proliferation by fibroblast and insulin-like growth factors in pure rat inner ear epithelial cell cultures." Journal of Neuroscience. 17(1): 216-26.
Zheng. (2009). "Polymers in Pharmaceuticals," China Medical Science and Technology Press, p. 219.

\* cited by examiner

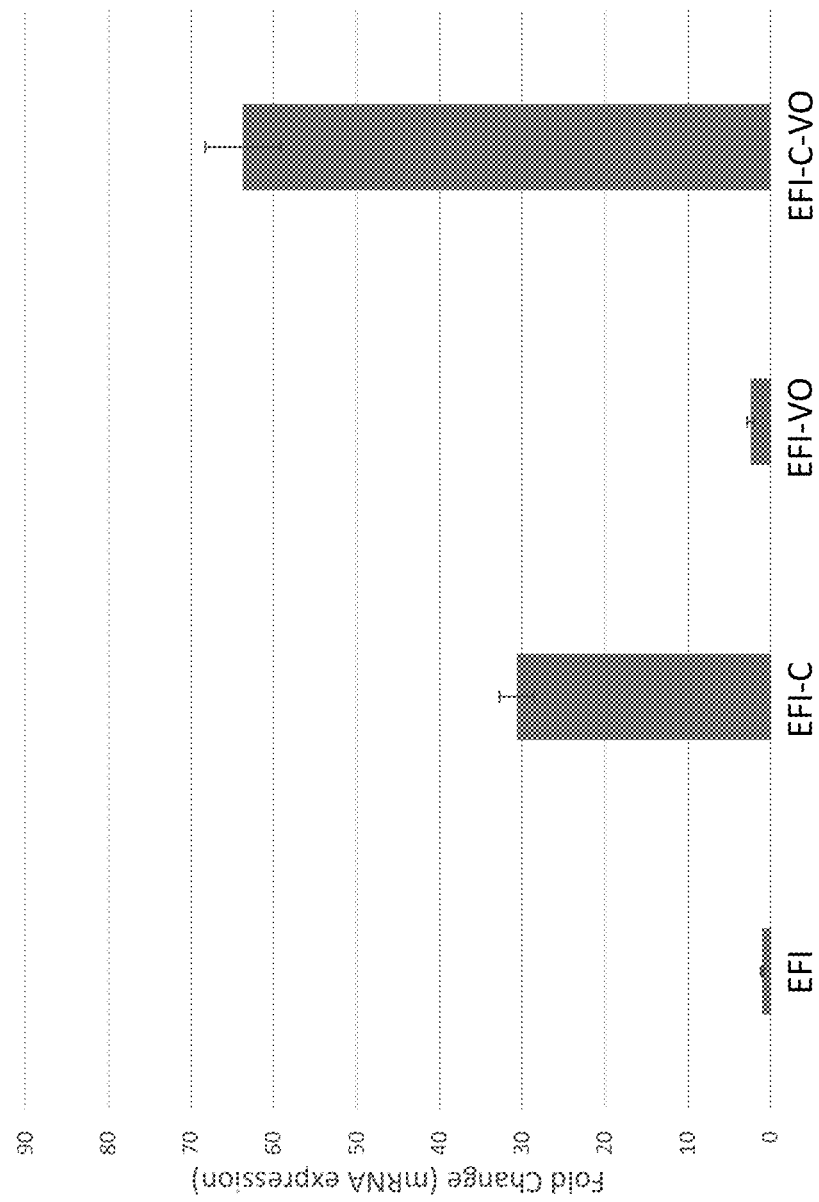

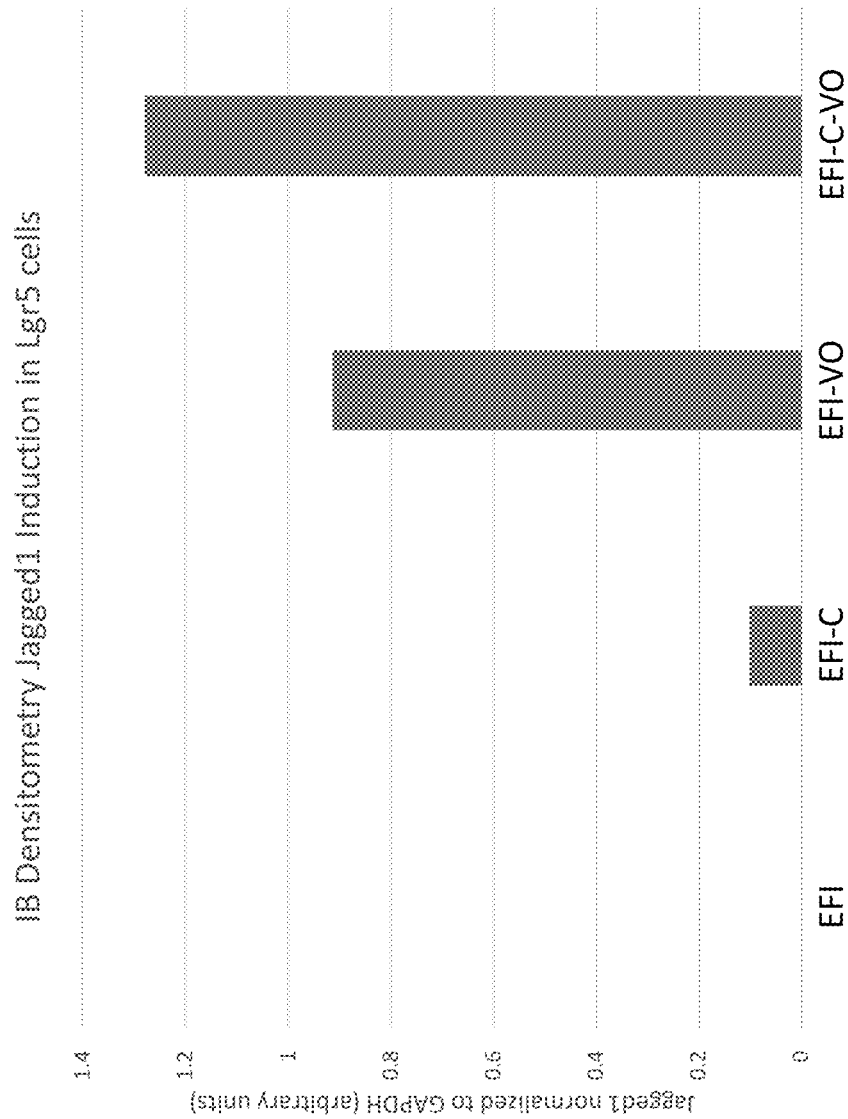

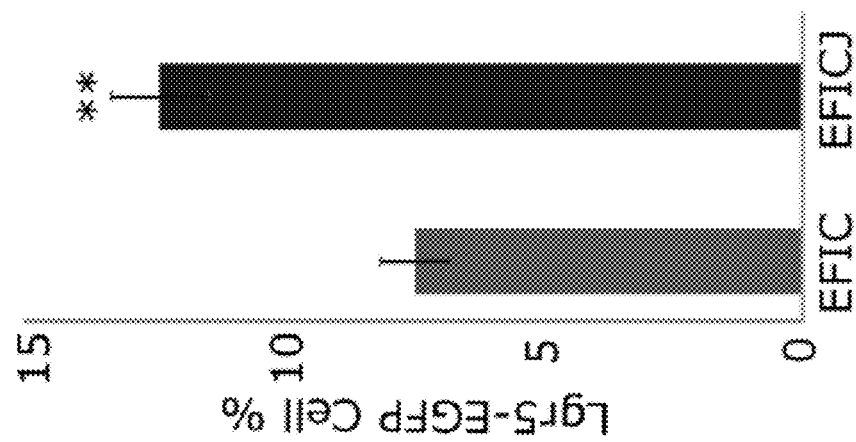

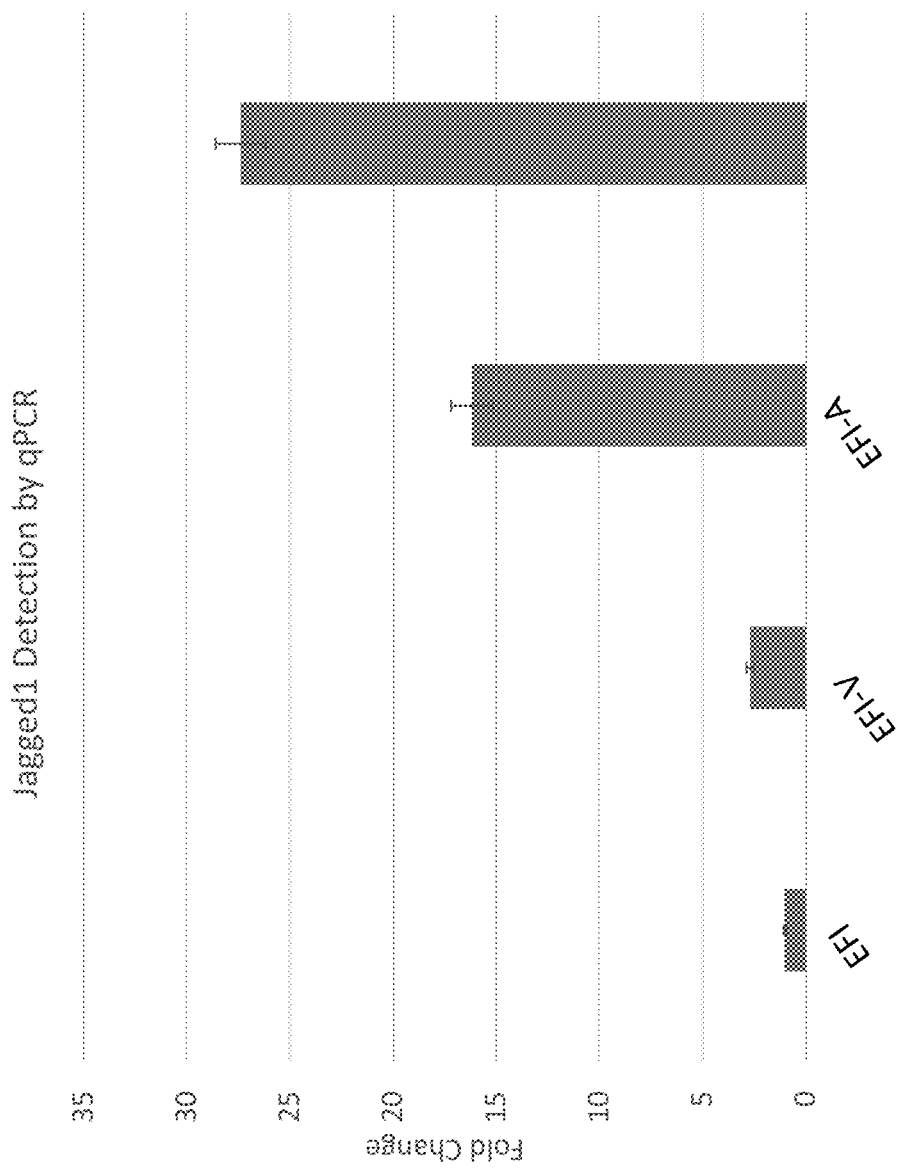

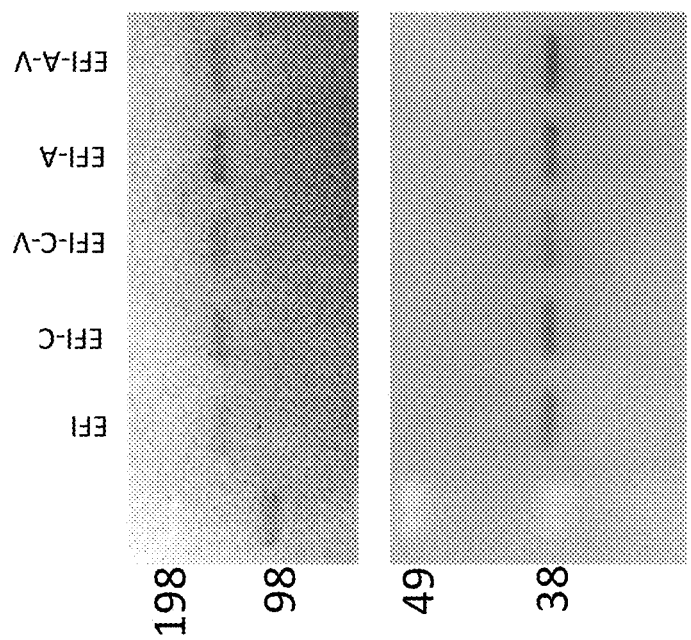

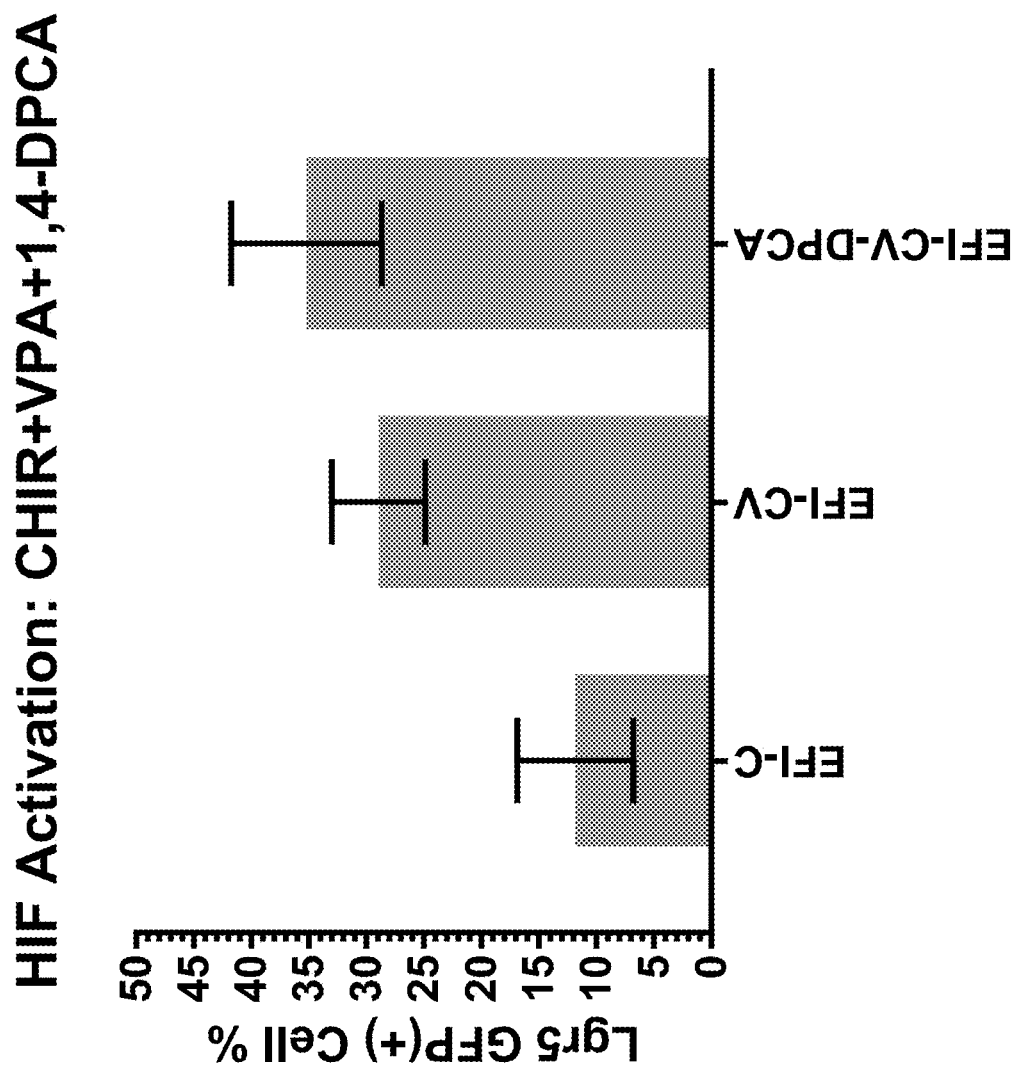

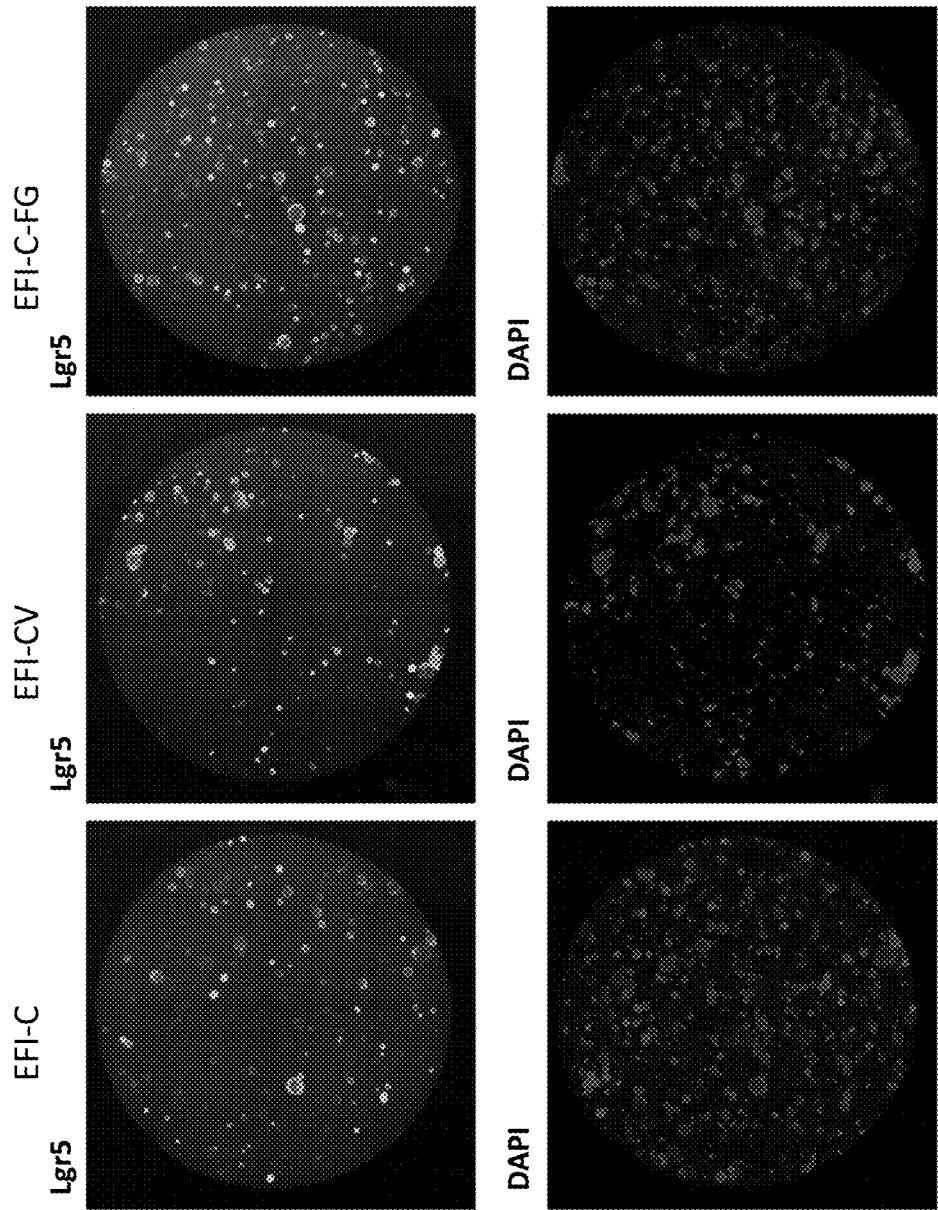

SEQUENCE LISTING

<160> NUMBER OF SEQ ID NOS: 1

<210> SEQ ID NO 1
<211> LENGTH: 17
<212> TYPE: PRT
<213> ORGANISM: Homo sapiens

<400> SEQUENCE: 1

Cys Asp Asp Tyr Tyr Tyr Gly Phe Gly Cys Asn Lys Phe Cys Arg Pro
1               5                   10                  15

Arg

COMPOSITIONS AND METHODS FOR GENERATING HAIR CELLS BY UPREGULATING JAG-1

RELATED APPLICATIONS

This application claims priority to U.S. Patent Application No. 62/719,218, filed Aug. 17, 2018, the contents of which are herein incorporated by reference in their entirety.

INCORPORATION BY REFERENCE OF SEQUENCE LISTING

The contents of the text file named "FREQ-025_01US SeqList_ST25.txt" which was created on Aug. 17, 2019, and is 1 KB in size, are hereby incorporated by reference in their entirety.

FIELD OF THE INVENTION

The present disclosure relates to compositions and methods comprising Jag-1 agonists and Jag-1 synergists for increasing proliferation of cochlear supporting cells or vestibular supporting cells, production of an expanded population of cochlear or vestibular cells, in particular Lgr5+ cells, and related methods of treating an hearing or balance disorder. In addition, the invention relates to the extent to which such patients can improve in hearing function.

BACKGROUND OF THE INVENTION

Sensorineural hearing loss (SNHL) accounts for about 90% of all hearing loss (Li et al., Adv. Drug Deliv. Rev. 108, 2-12, 2017), with leading causes of SNHL being advanced age, ototoxic medications, and noise exposure (Liberman & Kujawa, Hear. Res. 349, 138-147, 2017). SNHL typically arises from damage and loss of sensory transducer cells (the hair cells) within the sensory epithelium of the cochlea in the inner ear. Hair cells are susceptible to damage and, although other species such as birds, fish, and amphibians can regenerate hair cells throughout life, mammals lack this regenerative ability (Fujioka et al., Trends Neurosci. 38, 139-44, 2015).

There is currently no therapeutic option to restore function in the damaged mammalian inner ear, and the inability of the human cochlea to replace loss or damaged hair cells means that the majority of patients with SNHL are managed with hearing aids or cochlear implants (see, for example, Ramakers et al., Laryngoscope 125, 2584-92, 2015; Raman et al., Effectiveness of Cochlear Implants in Adults with Sensorineural Hearing Loss. Agency for Healthcare Research and Quality (US), 2011; and Roche & Hansen, Otolaryngol. Clin. North Am. 48, 1097-116, 2015). However, fewer than 25% of candidates use hearing devices because of discomfort, stigma, and dissatisfaction with sound quality (Lerner, 2019; Pratt, 2018; Sawyer et. al., 2019; Willink et. al., 2019). Despite improvements in implant technology, some users still experience poor or declining speech recognition, poor sound quality, and complications in up to 15%-20% (Health Quality Ontario, 2018).

SNHL typically leads to increased hearing level thresholds in a patient when measured by audiometry. However, there are also patients that have normal hearing thresholds when assessed by audiometry but experience poor speech recognition in noisy environments. This condition is known as hidden hearing loss, and although debilitating for these patients, may not warrant intervention with a hearing aid and certainly not a cochlea implant (which is used for patients with more severe hearing loss).

Thus, a regenerative treatment approach that improves hearing function, for example by lowering hearing level thresholds, and/or by improving speech recognition, offers a major breakthrough for patients with sensorineural hearing loss or hidden hearing loss. Such a regenerative approach to treatment is in marked contrast to existing approaches that use hearing devices which essentially manage the condition as opposed to treating the condition by restoring cochlear function.

Several approaches are being investigated to regenerate damaged or absent hair cells in mammalian inner ear sensory epithelia (reviewed in Mittal et al. Front Mol Neurosci. (2017); 10: 236). These include cell-based approaches (which aim to deliver exogenous cells to the inner ear to restore the sensory epithelia) and gene-based approaches (which aim to deliver exogenous genes to the sensory epithelia and reprogram endogenous cells to generate hair cells). For example, adenovirus-mediated delivery of genes has shown some promise in animal models, with exogenous Atoh1 able to stimulate cells within the sensory epithelia to differentiate into hair cells. One drawback with these approaches is the requirement to deliver cells or vectors into the inner of the patient, which can be challenging in the complex system of the inner ear. Molecular approaches, in which the endogenous signaling pathways of inner ear cells are modulated by exogenous agents are therefore attractive, as the delivery of such agents is likely to be more straightforward than cell-based or gene-based approaches.

Using molecular agents to initiate transdifferentiation, in which existing supporting cells of the cochlear are stimulated to differentiate into replacement hair cells, is one area of interest. Another area of interest is the activation of proliferative response in the supporting cells, in order to provide a new population of cells that could differentiate into hair cells, thereby replacing lost or damaged hair cells.

The combination of a Wnt pathway agonist (a GSK inhibitor) in combination with an histone deacetylase complex (HDAC) inhibitor has shown promising results in stimulating the expansion of supporting cells in vitro and an in vivo animal model, as well as providing an improvement in hearing function in animal model (see (McLean et al. Cell Rep. 2017 Feb. 21; 18(8): 1917-1929; WO 2017/151907).

There remains a need for the development of effective hair cell regeneration strategies in the inner ear, both in vitro and in vivo which may include boosting the proliferation of supporting cells of sensory epithelium of the inner ear beyond that which has been achieved previously.

SUMMARY OF THE INVENTION

In various aspects the disclosure provides a method for increasing proliferation of a cochlear supporting cell or a vestibular supporting cell, comprising contacting the supporting cell with a Jagged-1 (Jag-1) agonist, wherein the Jag-1 agonist is not a WNT agonist or a GSK3 inhibitor thereby increasing cochlear supporting cell or vestibular supporting cell proliferation compared to a vehicle control.

In some embodiments of the methods of the disclosure, the method further comprises contacting the Lgr5+ cochlear cell with a Jag-1 synergist or Deltex-1 synergist, wherein the Lgr5+ cochlear cell is contacted with the Jag-1 agonist Jag-1 synergist and/or the Deltex-1 synergist in any order or simultaneously.

In some embodiments of the methods of the disclosure, the Jag-1 synergist or Deltex-1 synergist is not an HDAC inhibitor. In some embodiments of the methods of the disclosure, the Jag-1 synergist or Deltex-1 synergist is not Valproic Acid (VPA).

In some embodiments of the methods of the disclosure, the Jag-1 agonist increases the expression or activity of Deltex-1 or Hif-1; the Jag-1 agonist increases non-canonical Notch signaling genes other than Deltex-1 or Hif-1 without increasing expression of Deltex-1 or Hif-1; the Jag-1 agonist in combination with the Jag-1 synergist increases the expression or activity of Deltex-1 or Hif-1; or the Jag-1 agonist in combination with the Jag-1 synergist increases non-canonical Notch signaling genes without increasing expression of Deltex-1 or Hif-1.

The disclosure provided a method for increasing proliferation of a cochlear supporting cell or a vestibular supporting cell, comprising contacting the supporting cell with a Deltex-1 agonist, wherein the Deltex-1 agonist is not a WNT agonist or a GSK3 inhibitor thereby increasing cochlear supporting cell or vestibular supporting cell proliferation compared to a vehicle control. In some embodiments the method further comprises contacting the Lgr5+ cochlear cell with a Jag-1 synergist or a Deltex-1 synergist, wherein the Lgr5+ cochlear cell is contacted with the Jag-1 agonist Jag-1 synergist and/or the Deltex-1 synergist in any order or simultaneously.

In some embodiments of the methods of the disclosure, the Jag-1 synergist or Deltex-1 synergist that is not an HDAC inhibitor.

In some embodiments of the methods of the disclosure, the Jag-1 synergist or Deltex-1 synergist that is not VPA dependent. In some embodiments of the methods of the disclosure, the Deltex-1 agonist increases non-canonical Notch signaling independent of Jag-1; or the Deltex-1 agonist increases non-canonical Notch signaling at least partially by increasing HIF-1.

In some embodiments of the methods of the disclosure, the Deltex-1 synergist in combination with the Wnt agonist or GSK3 inhibitor increases non-canonical Notch signaling independent of Jag-1; or the Deltex-1 synergist in combination with the Wnt agonist or GSK3 inhibitor increases non-canonical Notch signaling by increasing Hif-1.

The disclosure provides a method for increasing proliferation of a cochlear supporting cell or a vestibular supporting cell, comprising contacting the supporting cell with a non-canonical Notch signaling agonist, thereby increasing cochlear supporting cell or vestibular supporting cell proliferation compared to a vehicle control.

In some embodiments of the methods of the disclosure, the non-canonical Notch signaling agonist is not a Wnt agonist or GSK3-inhibitor. In some embodiments of the methods of the disclosure further comprises contacting the Lgr5+ cochlear cell with a Jag-1 synergist or Deltex-1 agonist wherein the Lgr5+ cochlear cell is contacted with the non-canonical Notch signaling agonist, Jag-1 synergist and/or the Deltex-1 synergist in any order or simultaneously.

In some embodiments of the methods of the disclosure, non-canonical Notch signaling agonist is characterized by one or more of the following: increasing the expression and/or activity of Jag-1 and/or Deltex-1 in a Lgr5+ cochlear cell by at least about 10, 20, 30, 40, 50, 60, 70, 80, 90, 100, 150, or 200, % more than a vehicle control; increasing Lgr5+ cochlear cell proliferation by at least about 10, 20, 30, 40, 50, 60, 70, 80, 90, 100, 150, or 200% more than a vehicle control, the non-canonical Notch signaling agonist in combination with a Wnt agonist increases the expression and/or activity of Jag-1 and/or Deltex-1 in a Lgr5+ cochlear cell by at least about 10, 20, 30, 40, 50, 60, 70, 80, 90, 100, 150, or 200% more than the Wnt agonist alone; the non-canonical Notch signaling agonist in combination with a Wnt agonist increases Lgr5+ cochlear cell proliferation by at least about 10, 20, 30, 40, 50, 60, 70, 80, 90, 100, 150, or 200% more than the Wnt agonist alone.

The disclosure provides a method for producing an expanded population of cochlear or vestibular cells, comprising contacting a population of cochlear supporting cells or vestibular supporting cells with a Jagged-1 (Jag-1) agonist, wherein the Jag-1 agonist is not a WNT agonist or a GSK3 inhibitor, thereby producing an expanded population of cochlear or vestibular cells compared to a vehicle control.

The disclosure provides a method for producing an expanded population of cochlear or vestibular cells, comprising contacting a population of cochlear supporting cells or vestibular supporting cells with a Deltex-1 agonist, wherein the Jag-1 agonist is not a WNT agonist or a GSK3, thereby producing an expanded population of cochlear or vestibular cells compared to a vehicle control.

The disclosure provides a method for producing an expanded population of cochlear or vestibular cells, comprising contacting a population of cochlear supporting cells or vestibular supporting cells with a non-canonical Notch signaling agonist, thereby producing an expanded population of cochlear or vestibular cells compared to a vehicle control.

In some embodiments of the methods of the disclosure, the cochlear supporting cell(s) or vestibular supporting cell(s) express(es) leucine-rich repeat-containing G-protein coupled receptor 5 (Lgr5).

In some embodiments of the methods of the disclosure, the cochlear supporting cell(s) or vestibular supporting cell(s) are/is a mature cell(s). In some embodiments of the methods of the disclosure, the expanded population of cochlear or vestibular cells expresses leucine-rich repeat-containing G-protein coupled receptor 5 (Lgr5). In some embodiments of the methods of the disclosure, the cochlear supporting cell(s) or vestibular supporting cell(s) are/is a cochlear supporting cell(s).

In some embodiments of the methods of the disclosure, the expanded population of cochlear or vestibular cells are cochlear cells.

The disclosure provides a method of treating a subject who has, or is at risk of, developing an inner ear hearing or balance disorder, comprising administering to the subject: a Jagged-1 (Jag-1) agonist, wherein the Jag-1 agonist is not a Wnt agonist or a GSK3 inhibitor; a Deltex-1 agonist, wherein the Deltex-1 agonist is not a Wnt agonist or a GSK3 inhibitor; or a non-canonical Notch signaling agonist.

In some embodiments of the methods of the disclosure, the subject has an inner ear hearing or balance disorder. In some embodiments of the methods of the disclosure, the disorder is an inner ear hearing disorder. In some embodiments of the methods of the disclosure, the disorder is a balance disorder In some embodiments of the methods of the disclosure, the inner ear hearing or balance disorder is sensorineural hearing loss.

In some embodiments of the methods of the disclosure, the treatment results in improved auditory function when assessed by behavioral audiometry or auditory brainstem response (ABR) testing.

In some embodiments of the methods of the disclosure further comprises administering the subject a Jag-1 synergist or Deltex-1 synergist wherein the administration of the Jag-1 agonist, Deltex-1 agonist or the non-canonical Notch signaling agonist, and the Jag-1 synergist and/or the Deltex-1 synergist occurs in any order or simultaneously.

In some embodiments of the methods of the disclosure, the Jag-1 synergist or Deltex-1 synergist is not an HDAC inhibitor.

In some embodiments of the methods of the disclosure, the Jag-1 synergist or Deltex-1 synergist is not Valproic Acid (VPA). In some embodiments of the methods of the disclosure, the Jag-1 agonist and/or Deltex-1 agonist is a soluble Jag-1 protein, a phosphatidylinositide 3-kinase (PI3K) agonist or a HIF1-α activator.

In some embodiments of the methods of the disclosure, the PI3K agonist is a Forkhead box-O transcription factor (FOXO) inhibitor. In some embodiments of the methods of the disclosure, the FOXO inhibiter is AS1842856.

In some embodiments of the methods of the disclosure, a HIF1-α activator is 4,4α-dihydro-4-oxo-1,10-phenanthroline-3-carboxylic acid (1,4-DPCA), N-[(1-chloro-4-hydroxy-3-isoquinolinyl)carbonyl]-glycine (FG-2216) or N-[(1,3-dicyclohexylhexahydro-2,4,6-trioxo-5-pyrimidinyl)carbonyl]-glycine (daprodusat).

In some embodiments of the methods of the disclosure, the Jag-1 synergist and/or Deltex-1 synergist is a PI3K synergist.

In some embodiments of the methods of the disclosure, the PI3K synergist is a phosphatase and tensin homolog (PTEN) inhibitor.

In some embodiments of the methods of the disclosure, the PTEN inhibitor is SF1670, VO-Ohpic, bpV(phen), or bpV(pic).

In some embodiments of the methods of the disclosure, the Jag-1 synergist is a soluble Jag-1 peptide. In some embodiments of the methods of the disclosure, the soluble Jag-1 peptide comprises the amino acid sequence of CDDYYYGFGCNKFCRPR (SEQ ID NO:1), or a variant thereof that is at least 90% identical to SEQ ID NO:1.

In some embodiments of the methods of the disclosure, the Wnt agonist or GSK3 inhibitor is CHIR99021, AZD1080, LY2090314, a substituted 3-Imidazo[1,2-a]pyridin-3-yl-4-(1,2,3,4-tetrahydro-[1,4]diazepino-[6,7,1-hi]indol-7-yl)pyrrole-2,5-dione, or GSK3 inhibitor XXII.

In some embodiments of the methods of the disclosure, the HIF1-α activator is 1,4-DPCA. In some embodiments of the methods of the disclosure, the HIF1-α activator is FG-2216. In some embodiments of the methods of the disclosure, the HIF1-α activator daprodusat.

In some embodiments of the methods of the disclosure, the PTEN inhibitor is SF1670. In some embodiments of the methods of the disclosure, the PTEN inhibitor is VO-Ohpic. In some embodiments of the methods of the disclosure, the PTEN inhibitor is bpV(phen). In some embodiments of the methods of the disclosure, the PTEN inhibitor is bpV(pic).

In some embodiments of the methods of the disclosure, the AS1842856 is at a concentration of about between 0.1 nM to 100 µM.

In some embodiments of the methods of the disclosure, the 1,4-DPCA is at a concentration of about between 1 nM to 100 mM.

In some embodiments of the methods of the disclosure, the FG-2216 is at a concentration of about between 1 nM to 1000 mM.

In some embodiments of the methods of the disclosure, the daprodusat is at a concentration of about between 1 nM to 1000 mM.

In some embodiments of the methods of the disclosure, the SF1670 is at a concentration of about between 1 nM to 100 mM.

In some embodiments of the methods of the disclosure, the VO-Ohpic is at a concentration of about between 1 nM to 100 mM.

In some embodiments of the methods of the disclosure, the bpV(phen) is at a concentration of about between 1 nM to 100 mM.

In some embodiments of the methods of the disclosure, the bpV(pic) is at a concentration of about between 1 nM to 100 mM.

In some embodiments of the methods of the disclosure, the soluble Jag-1 peptide is at a concentration of about between 1 µM to 10 µM.

In some embodiments of the methods of the disclosure, the GSK3 inhibitor is AZD1080.

In some embodiments of the methods of the disclosure, the GSK3 inhibitor is LY2090314.

In some embodiments of the methods of the disclosure, the GSK3 inhibitor is a substituted 3-Imidazo[1,2-a]pyridin-3-yl-4-(1,2,3,4-tetrahydro-[1,4]diazepino-[6,7,1-hi]indol-7-yl)pyrrole-2,5-dione.

In some embodiments of the methods of the disclosure, the GSK3 inhibitor is GSK3 inhibitor XXII.

In some embodiments of the methods of the disclosure, the GSK3 inhibitor is CHIR99021.

In some embodiments of the methods of the disclosure, AZD1080 is at a concentration of about between 0.5 µM to 5 µM.

In some embodiments of the methods of the disclosure, LY2090314 is at a concentration of about between 4 nM to 40 nM.

In some embodiments of the methods of the disclosure, a substituted 3-Imidazo[1,2-a]pyridin-3-yl-4-(1,2,3,4-tetrahydro-[1,4]diazepino-[6,7,1-hi]indol-7-yl)pyrrole-2,5-dione is at a concentration of about between 5 nM to 500 nM.

In some embodiments of the methods of the disclosure, GSK3 inhibitor XXII at a concentration of about between 0.1 µM to 1 µM.

In some embodiments of the methods of the disclosure, CHIR99021 is at a concentration of about between 1 µM to 10 µM.

In some embodiments of the methods of the disclosure, the Jag-1 agonist is administered locally and/or systemically. In some embodiments of the methods of the disclosure, the Jag-1 agonist is administered locally In some embodiments of the methods of the disclosure, the Jag-1 agonist is administered systemically. In some embodiments of the methods of the disclosure, the Jag-1 agonist is administered locally and systemically. In some embodiments of the methods of the disclosure, the Deltex-1 agonist is administered locally and/or systemically. In some embodiments of the methods of the disclosure, the Deltex-1 agonist is administered locally. In some embodiments of the methods of the disclosure, the Deltex-1 agonist is administered systemically.

In some embodiments of the methods of the disclosure, the non-canonical Notch signaling agonist is administered locally and systemically. In some embodiments of the methods of the disclosure, the non-canonical Notch signaling agonist is administered locally and/or systemically. In some embodiments of the methods of the disclosure, the non-canonical Notch signaling agonist is administered locally. In some embodiments of the methods of the disclosure, the non-canonical Notch signaling agonist is administered systemically. In some embodiments of the methods of the disclosure, the non-canonical Notch signaling agonist is administered locally and systemically.

In some embodiments of the methods of the disclosure, the Wnt agonist or GSK3 inhibitor is administered locally and/or systemically. In some embodiments of the methods of the disclosure, the Wnt agonist or GSK3 inhibitor is administered locally. In some embodiments of the methods of the disclosure, the Wnt agonist or GSK3 inhibitor is administered systemically. In some embodiments of the methods of the disclosure, the Wnt agonist or GSK3 inhibitor is administered locally and systemically.

In some embodiments of the methods of the disclosure, the local administration is to the tympanic membrane, the middle ear or the inner ear. In some embodiments of the methods of the disclosure, the local administration is to the middle ear. In some embodiments of the methods of the disclosure, the systemic administration is oral or parenteral. In some embodiments of the methods of the disclosure, the systemic administration is oral.

The disclosure provides a pharmaceutical composition comprising a Jag-1 agonist and/or Deltex-1 agonist and a pharmaceutically acceptable carrier.

In some embodiments of the compositions of the disclosure, the Jag-1 agonist and/or Deltex-1 agonist is a soluble Jag-1 protein, a phosphatidylinositide 3-kinase (PI3K) agonist or a HIF1-α activator.

In some embodiments of the compositions of the disclosure, the PI3K agonist is a Forkhead box-O transcription factor (FOXO) inhibitor.

In some embodiments of the compositions of the disclosure, the FOXO inhibiter is AS1842856.

In some embodiments of the compositions of the disclosure, the HIF1-α activator is 4,4α-dihydro-4-oxo-1,10-phenanthroline-3-carboxylic acid (1,4, DPCA), N-[(1-chloro-4-hydroxy-3-isoquinolinyl)carbonyl]-glycine (FG-2216) or N-[(1,3-dicyclohexylhexahydro-2,4,6-trioxo-5-pyrimidinyl)carbonyl]-glycine (daprodusat).

The disclosure provides a pharmaceutical composition comprising a Jag-1 synergist and/or Deltex-1 synergist is a PI3K synergist.

In some embodiments of the compositions of the disclosure, the Jag-1 synergist and/or Deltex-1 synergist is a PI3K synergist.

In some embodiments of the compositions of the disclosure, the PI3K synergist is a phosphatase and tensin homolog (PTEN) inhibitor.

In some embodiments of the compositions of the disclosure, the PTEN inhibitor is SF1670, VO-Ohpic, bpV(phen), or bpV(pic).

In some embodiments of the compositions of the disclosure, the Jag-1 synergist is a soluble Jag-1 peptide.

In some embodiments of the compositions of the disclosure, the soluble Jag-1 peptide comprises the amino acid sequence of CDDYYYGFGCNKFCRPR (SEQ ID NO: 1), or a variant thereof that is at least 90% identical to SEQ ID NO:1.

In some embodiments of the compositions of the disclosure, the HIF1-α activator is 1,4-DPCA.

In some embodiments of the compositions of the disclosure, the HIF1-α activator is FG-2216.

In some embodiments of the compositions of the disclosure, the HIF1-α activator daprodusat.

In some embodiments of the compositions of the disclosure, the PTEN inhibitor is SF1670.

In some embodiments of the compositions of the disclosure, the PTEN inhibitor is VO-Ohpic.

In some embodiments of the compositions of the disclosure, the PTEN inhibitor is bpV(phen).

In some embodiments of the compositions of the disclosure, the PTEN inhibitor is bpV(pic).

In some embodiments of the compositions of the disclosure, the AS1842856 is at a concentration of about between 10 μM to 1,000,000 mM.

In some embodiments of the compositions of the disclosure, the 1,4, DPCA is at a concentration of about between 10 μM to 1,000,000 mM.

In some embodiments of the compositions of the disclosure, the FG-2216 is at a concentration of about between 10 μM to 1,000,000 mM.

In some embodiments of the compositions of the disclosure, the daprodusat is at a concentration of about between 10 μM to 1,000,000 mM.

In some embodiments of the compositions of the disclosure, the SF1670 is at a concentration of about between 10 μM to 1,000,000 mM.

In some embodiments of the compositions of the disclosure, the VO-Ohpic is at a concentration of about between 10 μM to 1,000,000 mM.

In some embodiments of the compositions of the disclosure, the bpV(phen) is at a concentration of about between 10 μM to 1,000,000 mM.

In some embodiments of the compositions of the disclosure, the bpV(pic) is at a concentration of about between 10 μM to 1,000,000 mM.

In some embodiments of the compositions of the disclosure, the soluble Jag-1 peptide is at a concentration of about between 1 μM to 10 μM.

In some embodiments of the compositions of the disclosure, the pharmaceutical composition is in a biocompatible matrix. In some embodiments of the compositions of the disclosure, the biocompatible matrix comprises hyaluronic acid, hyaluronates, lecithin gels, pluronics, poly(ethyleneglycol), poloxamers, chitosans, xyloglucans, collagens, fibrins, polyesters, poly(lactides), poly(glycolide), poly(lactic-co-glycolic acid (PLGA), sucrose acetate isobutyrate, glycerol monooleate, poly anhydrides, poly caprolactone sucrose, glycerol monooleate, silk materials, or a combination thereof. In some embodiments of the compositions of the disclosure, the pharmaceutical composition is formulated for administration.

In some embodiments of the compositions of the disclosure are for use in treating or preventing an inner ear hearing or balance disorder.

In some embodiments the pharmaceutical composition for use, the inner ear hearing or balance disorder is sensorineural hearing loss.

In some embodiments the pharmaceutical composition for use in the manufacture of a medicament for the treatment or prevention of an inner ear hearing or balance disorder.

In some embodiments the pharmaceutical composition for use, the inner ear hearing or balance disorder is sensorineural hearing loss.

The disclosure provides a container comprising a Jag-1 agonist, a Deltex-1 agonist or a non-canonical notch signaling agonist and instructions, where those instructions describe Jag-1 agonist, a Deltex-1 agonist or a non-canonical notch signaling agonist use for treating or preventing an inner ear hearing or balance disorder in a subject In some embodiments, the inner ear hearing or balance disorder is sensorineural hearing loss.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present invention, suitable methods and materials are described below. In the case of conflict, the present specification, including definitions, will control. In addition, the materials, methods and examples are illustrative only and are not intended to be limiting.

Other features and advantages of the invention will be apparent from the following detailed description and claims.

BRIEF DESCRIPTION OF THE DRAWINGS

FIG. 3 is a graph that demonstrates that CHIR upregulates Jag-1, while VO does not. Jag-1 upregulation is enhanced by addition of the PTEN inhibitor/PI3K synergist VO-Ohpic at 3 µM to CHIR in a background of growth factors including: 50 ng/mL EGF (E), 50 ng/mL bFGF (F), and 50 ng/mL IGF1 (I).

FIG. 4 is a graph that displays the effects of VO-OHpic (3 µM) and CHIR (4 µM) alone and in combination on Jag-1 expression in Lgr5+ cells, as measured by Western blot band intensity. Calculated Jag-1 normalized to GAPDH using GelQuant software and bands quantified. Net volumes of Jag-1 bands were divided by net volume values of matched GAPDH bands. These values were normalized to vehicle in a background of growth factors including: 50 ng/mL EGF (E), 50 ng/mL bFGF (F), and 50 ng/mL IGF1 (I).

FIG. 6A is a graph that shows that adding 0.25 µM Jag-1 peptide (J) to 4 µM CHIR is able to recapitulate enhancement of Lgr5+ cell proliferation when combined with CHIR (EFICJ) in a background of growth factors including: 50 ng/mL EGF (E), 50 ng/mL bFGF (F), and 50 ng/mL IGF1 (I).

FIG. 9 is a graph that demonstrates that 425 nM AS21842856 (EFI-A) upregulates Jag-1 expression, which is enhanced by the addition of VPA (EFI-A-V), as detected by qPCR in a background of growth factors including: 50 ng/mL EGF (E), 50 ng/mL bFGF (F), and 50 ng/mL IGF1 (I).

FIG. 10A is a series of images that demonstrates the effects of 4 µM CHIR (EFI-C) or 425 nM AS21842856 (EFI-A) alone or with 1 mM VPA (EFI-C-V) (EFI-A-V) on Jag-1 expression in cultured Lgr5+ cells, as measured by Western blot band intensity. Cultures contained a background of growth factors including: 50 ng/mL EGF (E), 50 ng/mL bFGF (F), and 50 ng/mL IGF1 (I).

FIG. 12B is a graph depicting that the demonstrating that the HIF1-α activator/prolyl 4-hydroxylation inhibitor, 1,4-DPCA (370 nM DPCA), shows a trend for enrichment of Lgr5 GFP+ progenitor cell proliferation over CHIR (4 μM)+VPA (1 mM) when combined with CHIR (4 μM)+VPA (1 mM) in a background of growth factors including: 50 ng/mL EGF (E), 50 ng/mL bFGF (F), and 50 ng/mL IGF1 (I).

FIG. 14C is a series of images depicting the culture of Lgr5 GFP+ cells treated with CHIR (4 CHIR (4 μM)+VPA (1 mM), or CHIR (4 μM)+FG-2216 (30 μM; FG) in a background of growth factors including: 50 ng/mL EGF (E), 50 ng/mL bFGF (F), and 50 ng/mL IGF1 (I).

DETAILED DESCRIPTION

Figure 1A:
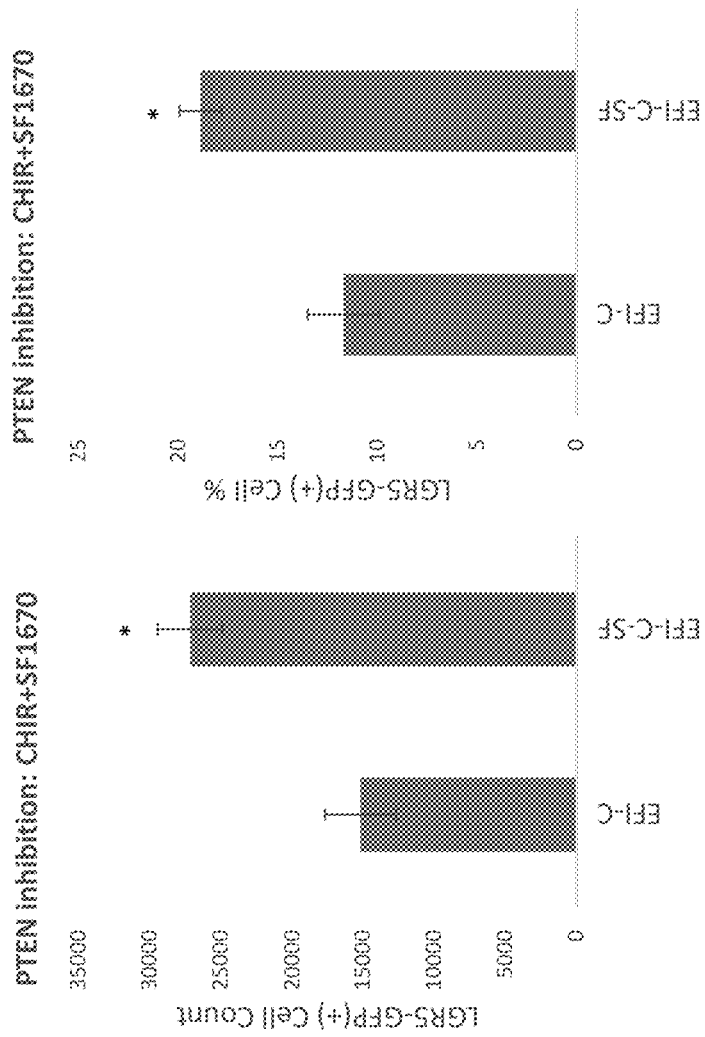
FIG. 1A is a series of graphs that demonstrates that CHIR (C) elicits the expansion (LGR5-GFP(+) cell count) and enrichment (percent LGR5-GFP(+) cell) of cochlear Lgr5 progenitor cells in culture, which is enhanced by addition of the PTEN inhibitor/PI3K agonist SF1670 (0.1 µM) in a background of growth factors including: 50 ng/mL EGF (E), 50 ng/mL bFGF (F), and 50 ng/mL IGF1 (I).

The invention is based upon the discovery that increasing non-canonical notch signaling by increasing, for example Jag-1, Deltex-1 expression results in the proliferation of cochlear supporting cells or vestibular supporting cells while maintaining, in the daughter cells, the capacity to differentiate into cochlear hair cells or vestibular hair cells.

The methods described herein increase the proliferation of cochlear supporting cells or vestibular supporting cells. Typically, the cochlear supporting cell or vestibular supporting cell in which proliferation is stimulated expresses Lgr5 (Leucine-rich repeat-containing G-protein coupled receptor 5). However the methods described herein may also stimulate proliferation of supporting cells with little or no Lgr5 expression.

The methods described herein produce an expanded population of cochlea or vestibular cells. In some embodiments, the expanded cells are enriched for Lgr5 expression (i.e. a greater percentage of the expanded cell population express Lgr5 compared to the starting cell population).

Lgr5 is a member of GPCR class A receptor proteins that is expressed across a diverse range of tissues such as in the muscle, placenta, spinal cord and brain, and particularly as a biomarker of adult stem cells in certain tissues. Lgr5+ stem cells are the precursors for sensory hair cells that are present in cochlea and vestibular organs of the inner ear. Increasing the population of Lgr5+ cochlear or vestibular cells is therefore beneficial because it increases the population of precursor cells which may differentiate into sensory hair cells.

The present invention provides compositions and methods for inducing the self-renewal of a cochlear supporting cells and vestibular supporting cells by increasing Jag-1 expression, Deltex-1 expression or non-canonical Notch signaling.

Thus, in various aspects the invention provides compositions and methods for increasing proliferation of a cochlear supporting cell or vestibular supporting cell; producing an expanded population of cochlear or vestibular cells and treating an inner ear hearing or balance disorder in a subject by contacting a cochlear supporting cell or vestibular supporting cell, or administering to a subject, a Jag-1 agonist, a Deltex-1 agonist or a non-canonical Notch signaling agonist.

In another aspect of the invention, the cochlear supporting cell or vestibular supporting cell is further contacted with, or a subject is further administered with, an additional agent. The addition of another agent to the Jag-1 agonist, a Deltex-1 agonist or a non-canonical Notch signaling agonist is advantageous because proliferation of the supporting cell population is increased compared a Jag-1 agonist, a Deltex-1 agonist or a non-canonical Notch signaling agonist alone or in combination.

In some embodiments, the expanded population of cells that is produced following treatment with and a Jag-1 agonist, a Deltex-1 agonist or a non-canonical Notch signaling agonist and an additional agent is larger than the expanded population of cells that is produced compared to the combination of a Jag-1 agonist, a Deltex-1 agonist or a non-canonical Notch signaling agonist.

The Lgr5+ cell population is more enriched when an additional agent is used compared to the Jag-1 agonist, a Deltex-1 agonist or a non-canonical Notch signaling agonist.

In some embodiments, the additional agent is a Jag-1 synergist or a Deltex-1 synergist.

Alternatively an additional agent may be an epigenetic agent. Epigenetic agents included epigenetic modifiers, mediators and modulators. Epigenetic modifiers are genes whose products modify the epigenome directly through DNA methylation, the post-translational modification of chromatin or the alteration of the structure of chromatin. The epigenetic mediators, are often the target of epigenetic modification, although they are rarely mutated themselves. The epigenetic mediators largely overlap with the genes involved in stem cell reprogramming and their role in cancer followed directly from the discovery of their reprogramming role. Epigenetic mediators are those genes whose products are the targets of the epigenetic modifiers. Epigenetic modulators are the as genes lying upstream of the modifiers and mediators in signalling and metabolic pathways.

Hair Cell Regeneration Agents

As used herein the term hair cell regeneration agent refers to Jag-1 agonist, a Deltex-1 agonist or a non-canonical Notch signaling agonist and any addition agents described herein that promotes regeneration of hair cells.

A hair cell regeneration agent stimulates proliferation of cochlear supporting cells in which proliferation is stimulated expresses Lgr5 (Leucine-rich repeat-containing G-protein coupled receptor 5). However, the hair cell regeneration agent may also stimulate proliferation of supporting cells with little or no Lgr5 expression. In some embodiments, the hair cell regeneration agent produces an expanded population of cochlea cells. In some embodiments, the expanded cells are enriched for Lgr5 expression (i.e. a greater percentage of the expanded cell population express Lgr5 compared to the starting cell population).

In some embodiments a hair cell regeneration agent may promote regeneration of hair cells by stimulating transdifferentiation of supporting cells within the sensory epithelium of cochlea into replacement hair cells. Alternatively, or additionally, a hair cell regeneration agent may activate a proliferative response in the sensory epithelium of the cochlea, thereby providing a new population of cells that can subsequently differentiate into supporting cells.

A single agent may be used as a hair cell regeneration agent or a combination of agents may provide the hair cell regenerative function. Thus, in some embodiments, the hair cell regeneration agent is a single agent. In other embodiments the hair cell regeneration agent is a combination of agents. In certain such embodiments, the combination of agents may be formulated together in a single composition. In other embodiments, the combination of agents may formulated individually and provided to a patient separately.

Hair regeneration agents include Jag-1 agonist, a Deltex-1 agonist or a non-canonical Notch signaling agonist. Other additional agents include fir example, Wnt agonists or HDAC inhibitors JAG-1 AGONISTS Jagged-1 (Jag-1) is a ligand of the Notch receptors that triggers the Notch signaling pathway, a highly conserved pathway which regulates cell fate decisions in a variety of tissue types. The Jag-1-Notch interaction triggers the Notch signaling pathway by releasing the intracellular unit of the Notch receptor from the membrane, causing a cascade of proteolytic cleavage that activates the transcription of downstream target genes.

A Jag-1 agonist is a compound that causes an increase in the expression, levels, and/or activity of a Jag-1 gene, protein, and/or pathway. In some embodiments, the Jag-1 agonist binds to and activates Jag-1 and/or increases the activity of the Jag-1 Intracellular Domain (JICD). Alternatively, the Jag-1 agonist may bind to and modulate the activity of one or more Jag-1 pathway components such as by inhibiting the activity of negative regulator of the pathway, or by activating upstream or downstream regulator of the pathway.

In some embodiments, a Jag-1 agonist acts as a non-canonical Notch signaling agonist. In some embodiments, the Jag-1 agonist does not substantially activate canonical Notch signaling genes. In some embodiments, the Jag-1 agonist does not substantially activate canonical Notch signaling genes in an amount sufficient to activate Wnt signaling. In some embodiments, the Jag-1 agonist acts directly on Jag-1 and does not substantially upregulate HES or HEY genes or promote their activity. In some embodiments, a Jag-1 agonist is not a Wnt agonist. In some embodiments, the Jag-1 agonist is not a GSK3-inhibitor. In some embodiments, the Jag-1 agonist increases non-canonical Notch signaling. In some embodiments, the Jag-1 agonist increases non-canonical Notch signaling by increasing the expression or activity of Deltex-1 or Hif-1.

In some embodiments, a Jag-1 agonist binds directly to Jag-1. In other embodiments, the Jag-1 agonist modulates one or more Jag-1 pathway downstream components, such as Deltex-1 or Hif-1. In other embodiments, the Jag-1 agonist modulates one or more Jag-1 pathway downstream components excluding Hes of Hey. In some embodiments, the Jag-1 agonist preferentially activates non-canonical notch pathway genes relative to canonical notch pathway genes. In some embodiments, the Jag-1 agonist preferentially upregulates Deltex-1 or Hif-1 more that the Jag-1 agonist upregulates Hes or Hey. In some embodiments, the Jag-1 agonist increases the expression of Deltex-1 and/or Hif-1 5%, 10%, 25%, 50%, 75%, 100%, or more than it increases the expression or activity of Hes and Hey.

In some embodiments, the Jag-1 agonist increases the expression of Deltex-1 5%, 10%, 25%, 50%, 75%, 100%, or more than it increases the expression or activity of Hes.

In some embodiments, the Jag-1 agonist increases the expression of Deltex-1 5%, 10%, 25%, 50%, 75%, 100%, or more than it increases the expression or activity of Hey.

In some embodiments, the Jag-1 agonist increases the expression of Hif-1 5%, 10%, 25%, 50%, 75%, 100%, or more than it increases the expression or activity of Hes.

In some embodiments, the Jag-1 agonist increases the expression of Hif-1 5%, 10%, 25%, 50%, 75%, 100%, or more than it increases the expression or activity of He7.

In some embodiments the Jag-1 agonist is a protein or peptide, a PI3K agonist or a FOXO inhibitor.

Exemplary agents having activity as a Jag-1 agonist are provide in Table 1 below, including ant pharmaceutically acceptable salts thereof.

TABLE 1

Jag-1 Agonists

| Class/Target | Agent | CAS Number |
|---|---|---|
| Protein/Peptide | Jag-1 | Protein |
|  | Jag-1 (soluble peptide) CDDYYYGFGCNKFCRPR (SEQ ID NO: 1) | Protein |
| PI3K agonist/FOXO inhibitor | AS1842856 | 836620-48-5 |
| HIF1-α activator | 1,4-DPCA | 331830-20-7 |
|  | FG-2216 | 223387-75-5 |
|  | Daprodustat | 960539-70-2 |

In particular embodiments, the Jag-1 agonist is a soluble Jag-1 peptide (residues 188-204) that optionally comprises, consists, or consists essentially of CDDYYYGFGCNKFCRPR (SEQ ID NO:1). Also included are Jag-1 peptide variants and fragments thereof that are at least 90%, 95%, 96%, 97%, 98%, or 99% identical to SEQ ID NO:1. The Jag-1 peptide variants and fragments thereof mediate Notch signaling.

Thus, a "Jag-1 agonist" refers to an agent causes an increase in the expression, levels, and/or activity of Jag-1, for example, in a Lgr5+ cochlear cell. Certain Jag-1 agonists increase the expression and/or levels of Jag-1 in a Lgr5+ cochlear cell by about or at least about 10, 20, 30, 40, 50, 60, 70, 80, 90, or, 100% relative to a control, for example relative to a baseline level of activity.

Certain Jag-1 agonists increase the expression and/or levels of Jag-1 in a Lgr5+ cochlear cell by about or at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more relative to a control for example relative to a baseline level of activity.

In some embodiments, the Jag-1 agonist in combination with a Jag-1 synergist and/or a Deltex-1 synergist increases Jag-1 expression, levels and/or activity in a Lgr5+ cochlear cell by at least about 10, 20, 30, 40, 50, 60, 70, 80, 90, or 100% relative to the Jag-1 agonist alone.

In other embodiments, the Jag-1 agonist in combination with a Jag-1 synergist and/or a Deltex-1 synergist increases Jag-1 expression, levels and/or activity in a Lgr5+ cochlear cell by about or at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more relative to the Jag-1 agonist alone.

Alternatively, the Jag-1 agonist increases the Lgr5+ cochlear cell proliferation by at least about 10, 20, 30, 40, 50, 60, 70, 80, 90, or 100% relative to a control for example relative to a baseline level of activity.

In other embodiments, the Jag-1 agonist increases the Lgr5+ cochlear cell proliferation by about or at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold relative to a control for example relative to a baseline level of activity.

Lgr5+ cochlear cell proliferation can be measured for example in a Stem Cell Proliferation Assay.

A non-canonical Notch signaling agonist is characterized by one or more of the following: 1) increasing the expression and/or activity of Jag-1 and/or Deltex-1 in a Lgr5+ cochlear cell by at least about 10, 20, 30, 40, 50, 60, 70, 80, 90, 100, 150, 200, 250, 300, 350, 400, 450, or 500% more than a vehicle control; or 2) increasing the expression and/or activity of Jag-1 and/or Deltex-1 relative to Hair and Enhancer of Split (Hes) or Hairy/enhancer-of-split related with YRPW (Hey) in a Lgr5+ cochlear cell by 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold.

In some embodiments, the Jag-1 agonist is HIF1-α activator. HIF1-α activarors include for example an agent that inhibits prolyl 4-hydroxylation (P4H), for instance, in a cochlear cell. Inhibition of α-prolyl 4-hydroxylase, an oxygen-sensing enzyme targets the pro-angiogenic factor HIF-la for destruction upon hydroxylation of a specific proline residue.

Alternatively, a HIF1-α activator refers to an agent that inhibits hypoxia-inducible factor (HIF) prolyl hydroxylase (PHD) enzymes (HIF-PH inhibitors), for instance, in a cochlear cell. Inhibiting of hypoxia-inducible factor (HIF) prolyl hydroxylase that increases HIF stability and action.

Exemplary HIF1-α activators include 4,4α-dihydro-4-oxo-1,10-phenanthroline-3-carboxylic acid (1,4-DPCA), N-[(1-chloro-4-hydroxy-3-isoquinolinyl)carbonyl]-glycine (FG-2216) and N-[(1,3-dicyclohexylhexahydro-2,4,6-trioxo-5-pyrimidinyl)carbonyl]-glycine (daprodusat)

In some embodiments, the Jag-1 agonist is a phosphatidylinositide 3-kinase (PI3K, PI3-kinase; also phosphoinositide 3-kinase) agonist. Thus, in certain embodiments, a "PI3K agonist" refers to an agent that causes an increase in the expression, levels, and/or activity of at least one PI3K gene, protein, and/or pathway (such as Fibroblast Growth Factor (FGF) upregulation or AKT phosphorylation), for instance, in a cochlear cell. In some instances, a PI3K agonist is a "direct PI3K agonist", which directly binds to at least one PI3K protein, and optionally increases or otherwise activates binding of the PI3K protein by or to other molecules in the PI3K pathway. In some embodiments, a PI3K agonist is an "downstream PI3K target", which binds to and/or modulates a gene or protein that is downstream of PI3K, including a gene or protein that is directly or immediately downstream of PI3K such as AKT or FOXO. Examples of "downstream PI3K agonists" include FOXO inhibitors, as described herein. In some embodiments, the Jag-1 agonist preferentially upregulates Deltex-1 or Hif-1 more that the PI3K agonist upregulates Hes or Hey. In some embodiments, the PI3K agonist increases the expression of Deltex-1 and/or Hif-1 10%, 25%, 50%, 75%, or than it increases the expression or activity of Hes and Hey.

PI3-kinases are a family of related intracellular signal transducer enzymes capable of phosphorylating the 3 position hydroxyl group of the inositol ring of phosphatidylinositol. PI3-kinases have a diverse group of cellular functions, including cell growth, proliferation, differentiation, motility, survival, and intracellular trafficking. Many of these functions relate to the ability of class I PI3-kinases to activate protein kinase B (PKB, or Akt) in the PI3K/AKT/mTOR pathway. PI3K activity also interacts positively with the Jag-1 pathway.

Exemplary classes of PI3-kinases include Class I, II, III, and IV PI3Ks. Class I PI3Ks kinases produce phosphatidylinositol 3-phosphate (PI(3)P), phosphatidylinositol (3,4)-bisphosphate (PI(3,4)P2), and phosphatidylinositol (3,4,5)-trisphosphate (PI(3,4,5)P3), and are activated by G protein-coupled receptors and tyrosine kinase receptors. Examples of Class I PI3Ks include catalytic kinases such as PIK3CA, PIK3CB, PIK3CG, and PIK3CD, and regulatory kinases such as PIK3R1, PIK3R2, PIK3R3, PIK3R4, PIK3R5, and PIK3R6.

Class II and III PI3K differ from Class I in both structure and function. Class II PI3Ks differ in the C-terminal C2 domain, which lacks critical Asp residues to coordinate binding of Ca2+, suggesting that class II PI3Ks bind lipids in a Ca2+-independent manner. Class II includes at least three catalytic isoforms (C2α, C2β, and C2γ) no regulatory isoforms. Class II PI3Ks catalyze the production of PI(3)P from PI and PI(3,4)P2 from PI. Class III are more similar to Class I in structure (i.e., they exist as heterodimers of a catalytic (Vps34) and a regulatory (Vps15/p150) subunits) but produce only PI(3)P from PI. Examples of Class II PI3Ks include PIK3C2A, PIK3C2B, and PIK3C2G, and examples of Class III PI3Ks include PIK3C3.

In some embodiments, the PI3K agonist increases the expression, levels, and/or activity of at least one PI3K gene or protein (such as Fibroblast Growth Factor (FGF) upregulation or AKT phosphorylation) in a cochlear cell or cochlear cell population by about or at least about 10, 20, 30, 40, 50, 60, 70, 80, 90, or 100% or more (or at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more) relative to a control for example relative to a baseline level of activity.

In some embodiments, the PI3K agonist increases the ability of a PI3K (for example, a Class I PI3K) to activate AKT (ie, to increase AKT protein expression) in the PI3K/AKT pathway in a cochlear cell by about or at least about 10, 20, 30, 40, 50, 60, 70, 80, 90, 100, 200, 300, 400, or 500% or more (or at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more) relative to a control for example relative to a baseline level of activity.

General examples of PI3K agonists include Forkhead box-O transcription factor (FOXO) inhibitors.

In certain embodiments, the Jag-1/PI3K agonist is a FOXO inhibitor. Forkhead box-O transcription factor (FOXO) refers to a family of transcription factors that regulate the expression of genes involved in cell growth, proliferation, differentiation, and other processes. A feature of the FOX proteins is the forkhead box, a sequence of 80 to 100 amino acids forming a motif that binds to DNA. This forkhead motif is also known as the winged helix due to the butterfly-like appearance of the loops in the protein structure of the domain. Forkhead proteins are a subgroup of the helix-turn-helix class of proteins.

Exemplary FOXO transcription factors include FOXO1, FOXO3 (or FOXO3a), FOXO4, and FOXO6. Thus, a "FOXO inhibitor" refers to an agent that causes a decrease in the expression, levels, and/or activity of at least one FOXO gene, transcription factor protein, and/or pathway, for instance, in a cochlear cell. A "FOXO antagonist" refers to an agent that binds to at least one FOXO protein, and which optionally decreases, reduces, or otherwise eliminates binding of the FOXO protein by or to other molecules. A particular example of a FOXO inhibitor includes AS1842856.

In certain embodiments, a FOXO inhibitor decreases expression or activity of a FOXO transcription factor in a cochlear cell by about or at least about 10, 20, 30, 40, 50, 60, 70, 80, 90, 100% relative to a control for example relative to a baseline level of activity.

Examples of these and related FOXO inhibitors include inhibitory nucleic acids (e.g., antisense, siRNA) agents which are directed against and decrease the expression of a FOXO gene/protein.

In some instances, a FOXO inhibitor decreases binding of a FOXO transcription factor to DNA in a cochlear cell by about or at least about 10, 20, 30, 40, 50, 60, 70, 80, 90, 100, 200, 300, 400, or 500% or more (or at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more relative to a control for example relative to a baseline level of activity.

In some embodiments, a FOXO inhibitor decreases nuclear localization of a FOXO transcription factor in a cochlear cell by about or at least about 10, 20, 30, 40, 50, 60, 70, 80, 90, or 100% relative to a control for example relative to a baseline level of activity.

In some embodiments, a FOXO inhibitor increases phosphorylation and optionally ubiquitination/degradation of a FOXO transcription factor in a cochlear cell by about or at least about 10, 20, 30, 40, 50, 60, 70, 80, 90, or 100% relative to a control for example relative to a baseline level of activity.

In some embodiments, a FOXO inhibitor increases acetylation of a FOXO transcription factor in a cochlear cell by about or at least about 10, 20, 30, 40, 50, 60, 70, 80, 90, or 100% or more (or at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more) relative to a control for example relative to a baseline level of activity.

Deltex-1 Agonists

Deltex-1E3 ubiquitin ligase 1 (Deltex-1) is a ligand of the Notch receptors that triggers the non-canonical Notch signaling pathway, a highly conserved pathway which regulates cell fate decisions in a variety of tissue types. Deltex-1 is modulated downstream of Jag-1.

A Deltex-1 agonist is compound that causes an increase in the expression, levels, and/or activity of a Deltex-1 gene and/or protein expression or activity. For example, the Deltex-1 agonist increases the expression or activity of a Deltex-1 gene and/or protein expression or activity about or at least about 10, 20, 30, 40, 50, 60, 70, 80, 90, 100% (or at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more) relative to a control for example relative to a baseline level of activity.

In some embodiments, the Deltex-1 agonist directly binds to and activates Deltex-1. Alternatively, the Deltex-1 agonist binds to and modulates the activity of one or more Jag-1 pathway components such as by inhibiting the activity of negative regulator of the pathway, or by activating upstream or downstream regulator of the pathway.

In some embodiments Deltex-1 agonist acts directly on Deltex-1 (i.e. binds to Deltex-1). In other embodiments, the Deltex-1 agonist modulates one or more Deltex-1 pathway downstream components such as Hif-1. In some embodiments, the Deltex-1 agonist increases non-canonical Notch signaling independent of Jag-1. By independent of Jag-1 is meant that the agonist does not activate Jag-1 such that a component of the canonical Notch pathway activated such as for example Wnt, Hes or Hey. In some embodiments, the Deltex-1 agonist increases non-canonical Notch signaling by increasing Hif-1. A Deltex-1 agonist is compound that causes an increase in the expression, levels, and/or activity of a Hif-1 gene and/or protein expression or activity. For example, the Deltex-1 agonist increases the expression or activity of a Hif-1 gene and/or protein expression or activity about or at least about 10, 20, 30, 40, 50, 60, 70, 80, 90, or 100% (or at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more) relative to a control for example relative to a baseline level of activity.

In some embodiments, the Deltex-1 agonist preferentially upregulates Deltex-1 or Hif-1 more that the Deltex-1 agonist upregulates Hes or Hey. In some embodiments, the Deltex-1 agonist increases the expression of Deltex-1 and/or Hif-1 10%, 25%, 50%, 75%, or 100%, than it increases the expression or activity of Hes and Hey.

Jag-1 Synergists, Deltex-1 Synergists and PI3K Synergists

The Jag-1 agonists or Deltex-1 agonist can be used in combination with one or more additional agents such as Jag-1 synergists, Deltex-1 synergists or PI3K synergists as defined herein In certain embodiments, a Jag-1 synergist acts as a non-canonical Notch signaling synergist. Within a Stem Cell Proliferation Assay, the Jag-1 agonist used in combination with the Jag-1 synergist increases non-canonical Notch signaling at least partially by increasing the expression or activity of Deltex-1 or Hif-1 by about by about 10, 20, 30, 40, 50, 60, 70, 80, 90, or 100% more than the Jag-1 agonist alone. Alternatively, the Jag-1 agonist in combination with the Jag-1 synergist increases non-canonical Notch signaling independent of Deltex-1 or Hif-1 by about by about 10, 20, 30, 40, 50, 60, 70, 80, 90, or 100%.

In some embodiments, the Jag-1 synergist preferentially upregulates Jag-1, Deltex-1 or Hif-1 more that the Jag-1 synergist upregulates Hes or Hey. In some embodiments, the Jag-1 synergist increases the expression of Jag-1, Deltex-1 and/or Hif-1 10%, 25%, 50%, 75%, or 100%, than it increases the expression or activity of Hes and Hey The Deltex-1 synergist in combination with a Wnt agonist or GSK3 inhibitor increases non-canonical Notch signaling independent of Jag-1 by about 10, 20, 30, 40, 50, 60, 70, 80, 90, or 100% relative to a control for example relative to a baseline level of activity.

Alternatively, the Deltex-1 synergist in combination with Wnt agonist or GSK3 inhibitor increases non-canonical Notch signaling by increasing Hif-1 about 10, 20, 30, 40, 50, 60, 70, 80, 90, or 100% relative to a control for example relative to a baseline level of activity.

In some embodiments, the Deltex-1 synergist preferentially upregulates Jag-1, Deltex-1 or Hif-1 more that the Deltex-1 synergist upregulates Hes or Hey. In some embodiments, the Deltex-1 synergist increases the expression of Jag-1, Deltex-1 and/or Hif-1 10%, 25%, 50%, 75%, or 100 than it increases the expression or activity of Hes and Hey.

In some embodiments, a Jag-1 synergist or Deltex-1 synergist is a PI3K synergist.

In some embodiments, a PI3K synergist is an "upstream PI3K target", which binds to and/or modulates a gene or protein that is upstream of PI3K, for example, by reducing the expression, levels, and/or activity of a gene or protein that negatively regulates PI3K, or by increasing the expression, levels, and/or activity of a gene or protein that positively regulates PI3K, such as FGF upregulation or AKT phosphorylation.

In some embodiments, the Jag-1/PI3K synergist is a PTEN inhibitor. PTEN is a phosphatidylinositol-3,4,5-trisphosphate 3-phosphatase. It contains a tensin-like domain and a catalytic domain, and preferentially dephosphorylates phosphoinositide substrates. It negatively regulates intracellular levels of phosphatidylinositol-3,4,5-trisphosphate in cells. PTEN specifically catalyzes the dephosphorylation of the 3' phosphate of the inositol ring in PIP3, resulting in the biphosphate product PIP2 (PtdIns(4,5)P2). This dephosphorylation results in inhibition of the AKT signaling pathway. PTEN therefore negatively regulates or inhibits the PI3K/Akt and optionally PKB signaling pathway.

Thus, a "PTEN inhibitor" refers to an agent that causes a decrease in the expression, levels, and/or activity of a PTEN gene and or protein expression or activity, for instance, in a cochlear cell. A "PTEN antagonist" refers to an agent that binds to at least one PTEN protein, and which optionally decreases, reduces, or otherwise eliminates binding of the PTEN protein by or to other molecules. Exemplary PTEN inhibitors include bisperoxovanadium compounds. Specific examples of PTEN inhibitors include SF1670, VO-Ohpic, bpV(phen), and bpV(pic).

In certain embodiments, a PTEN inhibitor decreases expression of PTEN in a cochlear cell by about or at least about 10, 20, 30, 40, 50, 60, 70, 80, 90, or 100 500% or more (or at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, -fold or more) relative to a control for example relative to a baseline level of activity.

Examples of these and related PTEN inhibitors include inhibitory nucleic acids (e.g., antisense, siRNA) agents which are directed against and decrease the expression of a PTEN gene/protein. Certain PTEN inhibitors reduce the ability of PTEN to catalyze the dephosphorylation of the 3' phosphate of the inositol ring in PIP3 in a cochlear cell by about or at least about 10, 20, 30, 40, 50, 60, 70, 80, 90, or 100% (or at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, -fold or more) relative to a control for example relative to a baseline level of activity.

Some PTEN inhibitors directly bind to the active site of PTEN. Some PTEN inhibitors increase cochlear cellular PIP3 levels and/or phosphorylation of Akt by about or at least about 10, 20, 30, 40, 50, 60, 70, 80, 90, 100% or at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, -fold or more) relative to a control for example relative to a baseline level of activity.

TABLE 2

Jag-1 Synergists, Deltex-1 Synergists or PI3K Synergists

| Class/Target | Agent | CAS Number |
|---|---|---|
| Protein/Peptide | Jag-1 | Protein |
| | Jag-1 (soluble peptide) CDDYYYGFGCNKFCRPR (SEQ ID NO: 1) | Protein |
| PI3K asynergist/ PTEN Inhibitor | SF1670 | 345630-40-2 |
| | VO-Ohpic | 476310-60-8 |
| | bpV(phen) | 171202-16-7 |
| | bpV(pic) | 148556-27-8 |

Wnt Agonists

A Wnt agonist refers to an agent that increases the expression, levels, and/or activity of a Wnt gene, protein, or signaling pathway (e.g. TCF/LEF, Frizzled receptor family, Wif1, Lef1, Axin2, β-catenin) in a cell, for example, a cochlear cell. A Wnt agonist includes a GSK3 inhibitor, such as a GSK3-α or a GSK3-β inhibitor. In preferred embodiments, the GSK3 inhibitor is a GSK3-β inhibitor.

The TCF/LEF family is a group of transcription factors that bind to DNA through a high mobility group domain, and which are involved in the Wnt signaling pathway where they recruit the coactivator β-catenin to enhancer elements of targeted genes. Frizzled is a family of G protein-coupled receptor proteins that serves as receptors in the Wnt signaling pathway. Frizzled receptors inhibit intracellular β-catenin degradation and activate TCF/LEF-mediated transcription.

In some embodiments, the Wnt agonist increases Wnt signaling in a cochlear or vestibular cell by about or at least about 10, 20, 30, 40, 50, 60, 70, 80, 90, 100, 200, 300, 400, or 500% or more (or at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more) or more relative to a control, for example relative to a baseline level of activity.

In some embodiments, the Wnt agonist increases TCF/LEF-mediated transcription in a cochlear or vestibular cell, for example, by about or at least about 10, 20, 30, 40, 50, 60, 70, 80, 90, 100, 200, 300, 400, or 500% or more (or at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more) or more relative to a control, for example relative to a baseline level of activity.

In some embodiments, the Wnt agonist binds and activates a Frizzled receptor family member, for example, by about or at least about 10, 20, 30, 40, 50, 60, 70, 80, 90, 100, 200, 300, 400, or 500% or more (or at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more) or more relative to a control, for example relative to a baseline level of activity.

In some embodiments, the Wnt agonist inhibits GSK3 for example, by about or at least about 10, 20, 30, 40, 50, 60, 70, 80, 90, or 100% (or at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more or more relative to a control, for example relative to a baseline level of activity.

In some embodiments, the Wnt agonist preferentially upregulates Jag-1, Deltex-1 or Hif-1 more that the Wnt agonist upregulates Hes or Hey. In some embodiments, the Wnt agonist increases the expression of Jag-1, Deltex-1 and/or Hif-1 10%, 25%, 50%, 75%, 100%, 125%, 150%, 175%, 200%, 250% or more than it increases the expression or activity of Hes and Hey.

Exemplary agents having activity as a Wnt agonist are provided in Table 3 and 4 below, including pharmaceutically-acceptable salts thereof.

TABLE 3

Exemplary Wnt Agonists

| Agent | CAS | GSK-3 alpha | GSK-3 alpha | Lgr5+ Assay | Perilymph Conc. | Formul. Conc. Intraymp |
|---|---|---|---|---|---|---|
| CHIR99021 | 252917-06-9 | 4.4 nM | 6.6 nM | 2-6 uM | 2-6 uM | 2-6 mM |
| AZD 1080 | 612487-72-6 | 6.9 nM | 31 nM | 1-5 uM | 1-5 uM | 1-5 mM |
| GSK XXII | 1195901-31-5 | 2.3 nM | 2.0 nM | 0.2-1 uM | 0.2-1 uM | 0.2-1 mM |
| LY2090314 | 603288-22-8 | 2.1 nM | 0.9 nM | 5-20 nM | 5-20 nM | 5-20 uM |

TABLE 4

Wnt Agonists

| Class | Agent | CAS |
|---|---|---|
| WNT | | |
| ARFGAP1 | QS 11 | 944328-88-5 |
| ARFGAP1 | WASP-1, ZINC00087877 | 352328-82-6 |
| Axin | Cpd1 | 1357473-75-6 |
| Axin | Cpd2 | 1228659-47-9 |
| Axin | HLY78 | 854847-61-3 |
| Axin | SKL2001 | 909089-13-0 |
| beta-catenin | DCA | 56-47-3 |
| Disrupts the Axin Complex | Compound 2 | 1360540-82-4 |
| Disrupts the Axin Complex | Compound 71 | 1622429-71-3 |
| Disrupts the Axin Complex | ISX 9 | 832115-62-5 |
| DKK1 inhibitor | WAY-262611 | 1123231-07-1 |
| MEK | Radicicol | 12772-57-5 |
| MEK | Selumetinib (AZD6244) | 606143-52-6 |
| PP2A | IQ 1 | 331001-62-8 |
| sFRP-1 inhibitor | (Dimethylamino)propyl)-2-ethyl-5-(phenylsulfonyl)benzenesulfonamide | 915754-88-0 |
| sFRP-1 inhibitor | Cyclosporine A (CsA) | 59865-13-3 |
| sFRP-1 inhibitor | Cyclosporine analogs | |
| sFRP-1 inhibitor | PSC833 (Valspodar) | 121584-18-7 |

TABLE 4-continued

Wnt Agonists

| Class | Agent | CAS |
| --- | --- | --- |
| sFRP-1 inhibitor | WAY 316606 | 915759-45-4 |
| Target Undetermined | Diketones | WO 2016029021 A1; WO 2012024404 A1 |
| Target Undetermined | Diketones | 1622429-56-4 |
| Target Undetermined | Diketones | 1360540-88-0 |
| Target Undetermined | Diketones | 1360540-89-1 |
| Target Undetermined | Diketones | 1622429-79-1 |
| Target Undetermined | Diketones | 1622429-75-7 |
| Target Undetermined | Diketones | 1622429-74-6 |
| Target Undetermined | Diketones | 1622430-76-5 |
| Target Undetermined | Diketones | 1622430-31-2 |
| Target Undetermined | Diketones | 1622430-52-7 |
| Target Undetermined | Diketones | 1622429-67-7 |
| Target Undetermined | Diketones | 1622429-65-5 |
| Target Undetermined | Diketones | 1622429-69-9 |
| van-Gogh-like receptor proteins (Vangl) | Compound 109 | 1314885-81-8 |
| Wnt Ligand | Wnt-1 | Protein |
| Wnt Ligand | Wnt-10a | Protein |
| Wnt Ligand | Wnt-10b/12 | Protein |
| Wnt Ligand | Wnt-11 | Protein |
| Wnt Ligand | Wnt-16 | Protein |
| Wnt Ligand | Wnt-2/Irp (Int-I-related protein) | Protein |
| Wnt Ligand | Wnt-2b/13 | Protein |
| Wnt Ligand | Wnt-3/Int-4 | Protein |
| Wnt Ligand | Wnt-3a | Protein |
| Wnt Ligand | Wnt-4 | Protein |
| Wnt Ligand | Wnt-5a | Protein |
| Wnt Ligand | Wnt-5b | Protein |
| Wnt Ligand | Wnt-6 | Protein |
| Wnt Ligand | Wnt-7a | Protein |
| Wnt Ligand | Wnt-7b | Protein |
| Wnt Ligand | Wnt-8a/8d | Protein |
| Wnt Ligand | Wnt-8b | Protein |
| Wnt Ligand | Wnt-9a/14 | Protein |
| Wnt Ligand | Wnt-9b/14b/15 | Protein |
| Wnt Related Protein | Norrin | Protein |
| Wnt Related Protein | R-Spondin 1/2/3/4 | Protein |
| Wnt-3a/Dkk-1 | BML-284 | 853220-52-7 |
| Wnt-3a/Dkk-1 | Compound 1 | 1084833-94-2 |
| Wnt-3a/Dkk-1 | Compound 25 | 1084834-05-8 |
| GSK3 alpha | | |
| CREB knockdown | 666-15 | 1433286-70-4 |
| Isonicotinamides | Compound 29 | 1772823-37-6 |
| Isonicotinamides | Compound 33 | 1772823-64-9 |
| Isonicotinamides | Compound 39 | 1772824-10-8 |
| Maleimide | I5 | 264217-24-5 |
| Maleimide | Tivantinib | 905854-02-6 |
| Organometallic | Compound (R)-DW12 | 1047684-07-0 |
| Organometallic | Compound 3 | 1498285-39-4 1498285-48-5 |
| Organometallic | Compound lambda-OS1 | 1291104-51-2 1292843-11-8 |
| Oxadiazoles | Compound 14d | 1374671-64-3 |
| Oxadiazoles | Compound 15b | 1374671-66-5 |
| Oxadiazoles | Compound 27 | 1820758-44-8 |
| Oxindole | AZD1080 | 612487-72-6 |
| Pyrazole | AT 7519 | 844442-38-2 |
| Pyrazole | Compound 4a | 1627557-91-8 |
| Pyrazole | Compound 4t | 1627558-10-4 |
| Pyrazole | Compound 4z | 1627558-16-0 |
| Pyrazole | GSK-3b XXII | 1195901-31-5 |
| Pyrazolopyridazines | Compound 18 | 405223-20-3 |
| Pyrazolopyridazines | Compound 19 | 405223-71-4 |
| Pyrazolopyridines | Compound 14 | 583038-63-5 |
| Pyrazolopyridines | Compound 23 | 583038-76-0 |
| Pyrazolopyridines | Pyrazolopyridine 34 | 583039-27-4 |
| Pyrazolo-tetrahydroquinolinone | BRD1172 | 1597438-86-2 |
| Pyrazolo-tetrahydroquinolinone | BRD1652 | 1597438-93-1 |
| Pyrazolo-tetrahydroquinolinone | BRD4003 chiral | 1597439-60-5 |
| Pyrazolo-tetrahydroquinolinone | BRD4003 chiral | 1597439-59-2 |

TABLE 4-continued

Wnt Agonists

| Class | Agent | CAS |
|---|---|---|
| Pyrazolo-tetrahydroquinolinone | Compound 11 | 1597439-12-7 |
| Pyrazolo-tetrahydroquinolinone | Compound 16 | 1597440-17-9 |
| Pyrazolo-tetrahydroquinolinone | Compound 8 | 1597439-01-4 |
| Pyrazolo-tetrahydroquinolinone | Compound 9 | 1597439-02-5 |
| Triazolpyrimidine | Compound 90 | 91322-11-1 |
| Triazolpyrimidine | Compound 92 | 1043429-30-6 |
| Urea | AR-A014418 | 487021-52-3 |
| GSK3-beta | | |
| Acid | Bikinin | 188011-69-0 |
| Acid | Valproic Acid, Sodium Salt | 99-66-1 |
| Aloisines | Aloisine A | 496864-16-5 |
| Aloisines | Aloisine B | 496864-14-3 |
| Aloisines | TWS119 | 1507095-58-0 |
| Aminopyrimidine | CHIR98014 (CT98014) | 252935-94-7 |
| Aminopyrimidine | CHIR98023 (CT98023) | 252904-84-0 |
| Aminopyrimidine | CHIR98024 (CT98024) | 556813-39-9 |
| Aminopyrimidine | CHIR99021 (CT99021) | 252917-06-9 |
| Aminopyrimidine | CT20026 | 403808-63-9 |
| Aminopyrimidinyl | CGP60474 | 164658-13-3 |
| Aminopyrimidinyl | GSK-3β Inhibitor XVIII | 1139875-74-3 |
| Azaindolylmaleimide | Compound 29 | 436866-61-4 |
| Azaindolylmaleimide | Compound 46 | 682807-74-5 |
| Bisindolylmaleimide | Bisindolylmaleimide X HCl | 131848-97-0 |
| Bisindolylmaleimide | Compound 5a | 436866-54-5 |
| Bisindolylmaleimide | Enzastaurin (LY317615) | 170364-57-5 |
| Bisindolylmaleimide | GF109203x | 176504-36-2 |
| Bisindolylmaleimide | Ro318220 | 125314-64-9 |
| Dihydropyridine | ML320 | 1597438-84-0 |
| Flavone | Flavopiridol | 146426-40-6 |
| Furanosesquiterpenes | Palinurin | 254901-27-4 |
| Furanosesquiterpenes | Tricantin | 853885-55-9 |
| Furopyrimidine | Compound 100 | 744255-19-4 |
| Halomethylketones | Compound 17 | 62673-69-2 |
| Halomethylketones | GSK-3β Inhibitor VI | 62673-69-2 |
| Halomethylketones | GSK-3β Inhibitor VII | 99-73-0 |
| Hymenidin | Hymenidin | 107019-95-4 |
| Indirubins | 5-Iodo-indirubin-3'-monoxime | 331467-03-9 |
| Indirubins | 6-Bromoindirubin-3-acetoxime | 667463-85-6 |
| Indirubins | GSK-3 Inhibitor IX | 667463-62-9 |
| Indirubins | GSK-3 Inhibitor X | 740841-15-0 |
| Indirubins | Indirubin | 479-41-4 |
| Indirubins | Indirubin-3'-monoxime | 160807-49-8 |
| Indirubins | Indirubin-5-sulfonic acid sodium salt | 331467-05-1 |
| Inorganic atom | Beryllium | |
| Inorganic atom | Lithium Chloride | |
| Inorganic atom | Tungstate | |
| Inorganic atom | Zinc | |
| Isoindolone | Staurosporine | 62996-74-1 |
| Isonicotinamides | Compound 29 | 1772823-37-6 |
| Isonicotinamides | Compound 33 | 1772823-64-9 |
| Isonicotinamides | Compound 39 | 1772824-10-8 |
| Maleimide | 3F8 | 159109-11-2 |
| Maleimide | 603281-31-8 | 603281-31-8 |
| Maleimide | BIP-135 | 941575-71-9 |
| Maleimide | Compound 34 | 396091-16-0 |
| Maleimide | CP21R7 | 125314-13-8 |
| Maleimide | GSK-3 inhibitor 1 | 603272-51-1 |
| Maleimide | GSK-3β Inhibitor XI | 626604-39-5 |
| Maleimide | I5 | 264217-24-5 |
| Maleimide | IM-12 | 1129669-05-1 |
| Maleimide | Isogranulatimide | 244148-46-7 |
| Maleimide | KT 5720 | 108068-98-0 |
| Maleimide | LY2090314 | 603288-22-8 |
| Maleimide | SB-216763 | 280744-09-4 |
| Maleimide | SB-415286 (SB-41528) | 264218-23-7 |
| Maleimide | TCS 21311 | 1260181-14-3 |
| Maleimide | Tivantinib | 905854-02-6 |
| Manzamines | Manzamine A | 104196-68-1 |
| Miscellaneous | AZD2858 (AR28) | 486424-20-8 |
| Miscellaneous | CID 755673 | 521937-07-5 |
| Miscellaneous | Dibromocantharelline | 101481-34-9 |

TABLE 4-continued

Wnt Agonists

| Class | Agent | CAS |
|---|---|---|
| Miscellaneous | TCS 2002 | 1005201-24-0 |
| Organometallic | (RRu)-HB1229 | |
| Organometallic | (RRu)-NP549 | |
| Organometallic | Compound (R)-DW12 | 1047684-07-0 |
| Organometallic | Compound 3 | 1498285-39-4, 1498285-48-5 |
| Organometallic | Compound lambda-OS1 | 1291104-51-2, 1292843-11-8 |
| Organometallic | DW12 | 861251-33-4 |
| Organometallic | HB12 | 800384-87-6 |
| Organometallic | NP309 | 937810-13-4 |
| Oxadiazol | Compound 14d | 1374671-64-3 |
| Oxadiazol | Compound 15b | 1374671-66-5 |
| Oxadiazol | Compound 20x | 1005201-80-8 |
| Oxadiazol | GSK-3 Inhibitor II | 478482-75-6 |
| Oxadiazol | GSK3 Inhibitor, 2 | 1377154-01-2 |
| Oxadiazol | TC-G 24 | 1257256-44-2 |
| Oxindole | AZD1080 | 612487-72-6 |
| Oxindole | SU9516 | 77090-84-1 |
| Patent | CN 101341138 B | |
| Patent | CN 1319968 C | |
| Patent | CP-70949 | |
| Patent | CT118637 | |
| Patent | EP 1739087 A1 | |
| Patent | EP 1961748 A2 | |
| Patent | EP 2765188 A1 | |
| Patent | GI179186X | |
| Patent | GW784752X | |
| Patent | GW784775X | |
| Patent | US 20070088080 A1 | |
| Patent | US 20100292205 A1 | |
| Patent | U.S. Pat. No. 7,514,445 B2 | |
| Patent | U.S. Pat. No. 8,071,591 B2 | |
| Patent | U.S. Pat. No. 8,207,216 B2 | |
| Patent | U.S. Pat. No. 8,686,042 B2 | |
| Patent | U.S. Pat. No. 8,771,754 B2 | |
| Patent | WO 2001085685 A1 | |
| Patent | WO 2003037891 A1 | |
| Patent | WO 2006018633 A1 | |
| Patent | WO 2007102770 A1 | |
| Patent | WO 2008077138 A1 | |
| Patent | WO 2009017453 A1 | |
| Patent | WO 2010075551 A1 | |
| Patent | WO 2010104205 A1 | |
| Patent | WO 2011089416 A1 | |
| Patent | WO 2013124413 A1 | |
| Patent | WO 2014003098 A1 | |
| Patent | WO 2014013255 A1 | |
| Patent | WO 2014050779 A1 | |
| Patent | WO 2014059383 A1 | |
| Patent | WO 2014083132 A1 | |
| Patent | WO2006100490A1/EP 1863904 A1 | |
| Patent | WO2009017455 A1 | |
| Paullone | Cmpd 17b | 408532-42-3 |
| Paullone | Kenpaullone | 142273-20-9 |
| Paullones | Alsterpaullone | 237430-03-4 |
| Paullones | Alsterpaullone CN Ethyl | 852529-97-0 |
| Paullones | Azakenpaullone | 676596-65-9 |
| Paullones | Cazpaullone | 914088-64-5 |
| Peptide | FRATtide | |
| Peptide | L803 | |
| Peptides | L803-mts | |
| Publication | 705701 | |

TABLE 4-continued

Wnt Agonists

| Class | Agent | CAS |
|---|---|---|
| Publication | 708244 | |
| Publication | 709125 | |
| Publication | AR79 | |
| Publication | AZ13282107 | No Structure |
| Publication | AZ13282107 | |
| Publication | CEP-16805 | No Structure |
| Publication | CG-301338 | No Structure |
| Publication | CT73911 | |
| Publication | LY2064827 | |
| Publication | NP-103 | No Structure |
| Publication | SAR 502250 | No Structure |
| Publication | SAR 502250 (Sanofi) | 1073653-58-3 |
| Publication | XD-4241 | No Structure |
| Pyrazole | AT 7519 | 844442-38-2 |
| Pyrazole | Compound 4a | 1627557-91-8 |
| Pyrazole | Compound 4t | 1627558-10-4 |
| Pyrazole | Compound 4z | 1627558-16-0 |
| Pyrazole | GSK-3 Inhibitor XXII | 1195901-31-5 |
| Pyrazolone | GSK-3beta Inhibitor XXVI | 871843-09-3 |
| Pyrazolopyridazines | Compound 18 | 405223-20-3 |
| Pyrazolopyridazines | Compound 19 | 405223-71-4 |
| Pyrazolopyridine | Pyrazolopyridine 18 | 405221-39-8 |
| Pyrazolopyridine | Pyrazolopyridine 34 | 583039-27-4 |
| Pyrazolopyridine | Pyrazolopyridine 9 | 923029-74-7 |
| Pyrazolopyridines | Compound 14 | 583038-63-5 |
| Pyrazolopyridines | Compound 14 | 583038-63-5 |
| Pyrazolopyridines | Compound 23 | 583038-76-0 |
| Pyrazoloquinoxaline | NSC 693868 (Compound 1) | 40254-90-8 |
| Pyrazoloquinoxaline | NSC 693868 (Compound 1) | 40254-90-8 |
| Pyridinone | Compound 150 | 1282042-18-5 |
| Pyrrolopyridinyl | Compound 12 | 2025388-10-5 |
| Pyrrolopyridinyl | Compound 27 | 2025388-25-2 |
| Pyrroloazepine | Hymenialdisine | 82005-12-7 |
| Quinazolin | GSK-3 Inhibitor XIII | 404828-08-6 |
| Quinolinecarb | VP0.7 | 331963-23-6 |
| Quinolinecarboxamide | | 1132813-46-7 |
| Quinolinecarboxamide | | 1132812-98-6 |
| Quinolinecarboxamide | | 950727-66-9 |
| Thiadiazolidindiones | GSK-3β Inhibitor I | 327036-89-5 |
| Thiadiazolidindiones | NP031112 (Tideglusib) | 865854-05-3 |
| Thiadiazolidindiones | NP031115 | 1400575-57-6 |
| Triazolpyrimidine | Compound 90 | 91322-11-1 |
| Triazolpyrimidine | Compound 92 | 1043429-30-6 |
| Urea | GSK-3β Inh. VIII AR-A014418 | 487021-52-3 |
| Urea | A-1070722 | 1384424-80-9 |

In some embodiments, an agent of having activity as a Wnt agonist is a GSK3 inhibitor. Preferably, the GSK3 inhibitor is AZD1080, GSK3 inhibitor XXII, CHIR99021 or LY2090314. In a preferred embodiment, the Wnt agonist is CHIR99021. In other preferred embodiments, Wnt agonist and/or GSK3 inhibitor is a substituted 3-Imidazo[1,2-a]pyridin-3-yl-4-(1,2,3,4-tetrahydro-[1,4]diazepino-[6,7,1-hi]indol-7-yl)pyrrole-2,5-dione. (Formula A.)

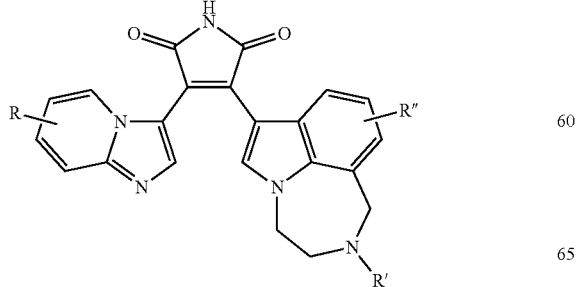

Formula A

-continued

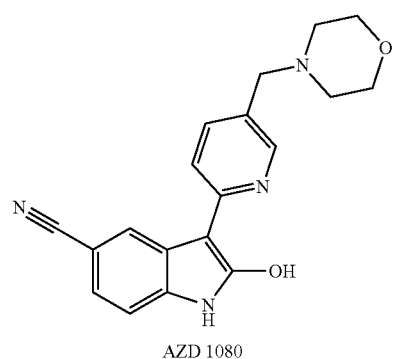

AZD 1080

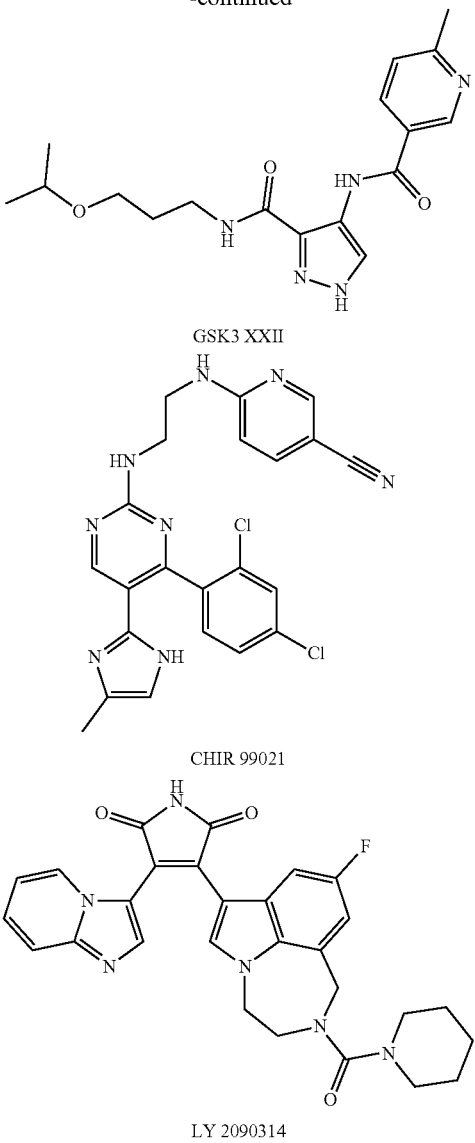

GSK3 XXII

CHIR 99021

LY 2090314

The Wnt agonist can be any selected from WO 2018/125746, which is hereby incorporated by reference. In some embodiments, the Wnt agonist can be the compound as defined in claim 1 of WO 2018/125746. In some embodiments, the Wnt agonist can be the compound as defined in claim 12 of WO 2018/125746."

Exemplary, substituted 3-Imidazo[1,2-a]pyridin-3-yl-4-(1,2,3,4-tetrahydro-[1,4]diazepino-[6,7,1-hi]indol-7-yl)pyrrole-2,5-dione include: 3-(imidazo[1,2-a]pyridin-3-yl)-4-(2-(piperidine-1-carbonyl)-9-(trifluoromethyl)-1,2,3,4-tetrahydro-[1,4]diazepino[6,7,1-hi]indol-7-yl)-1H-pyrrole-2,5-dione; 7-(4-(imidazo[1,2-a]pyridin-3-yl)-2,5-dioxo-2,5-dihydro-1H-pyrrol-3-yl)-2-(piperidine-1-carbonyl)-1,2,3,4-tetrahydro-[1,4]diazepino[6,7,1-hi]indole-9-carbonitrile; 3-(9-ethynyl-2-(piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione; 3-(9-amino-2-(piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione; 1-(9-fluoro-7-(4-(imidazo[1,2-a]pyridin-3-yl)-2,5-dioxo-2,5-dihydro-1H-pyrrol-3-yl)-1,2,3,4-tetrahydro-[1,4]diazepino[6,7,1-hi]indole-2-carbonyl)piperidine-4-carbaldehyde; 3-(9-fluoro-2-(4-(hydroxymethyl)piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione; 3-(2-(4,4-difluoropiperidine-1-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione; 3-(2-(8-oxa-3-azabicyclo[3.2.1]octane-3-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione; 3-(benzo[d]isoxazol-3-yl)-4-(9-fluoro-2-(piperidine-1-carbonyl)-1,2,3,4-tetrahydro-[1,4]diazepino[6,7,1-hi]indol-7-yl)-1H-pyrrole-2,5-dione; N-(7-(4-(imidazo[1,2-a]pyridin-3-yl)-2,5-dioxo-2,5-dihydro-1H-pyrrol-3-yl)-2-(piperidine-1-carbonyl)-1,2,3,4-tetrahydro-[1,4]diazepino[6,7,1-hi]indol-9-yl)acetamide; 3-(9-(difluoromethyl)-2-(piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione; 3-(2-(3,3-difluoropiperidine-1-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione; 3-(2-((1R,4R)-2,5-diazabicyclo[2.2.1]heptane-2-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione; 2-(8-oxa-3-azabicyclo[3.2.1]octane-3-carbonyl)-7-(4-(imidazo[1,2-a]pyridin-3-yl)-2,5-dioxo-2,5-dihydro-1H-pyrrol-3-yl)-1,2,3,4-tetrahydro-[1,4]diazepino[6,7,1-hi]indole-9-carbonitrile; difluoropiperidine-1-carbonyl)-7-(4-(imidazo[1,2-a]pyridin-3-yl)-2,5-dioxo-2,5-dihydro-1H-pyrrol-3-yl)-1,2,3,4-tetrahydro-[1,4]diazepino[6,7,1-hi]indole-9-carbonitrile; difluoropiperidine-1-carbonyl)-7-(4-(imidazo[1,2-a]pyridin-3-yl)-2,5-dioxo-2,5-dihydro-1H-pyrrol-3-yl)-1,2,3,4-tetrahydro-[1,4]diazepino[6,7,1-hi]indole-9-carbonitrile; 3-(2-(4,4-difluoropiperidine-1-carbonyl)-9-(trifluoromethyl)-1,2,3,4-tetrahydro-[1,4]diazepino[6,7,1-hi]indol-7-yl)-4-(imidazo[1,2-a]pyridin-3-yl)-1H-pyrrole-2,5-dione; 3-(2-(8-oxa-3-azabicyclo[3.2.1]octane-3-carbonyl)-9-(trifluoromethyl)-1,2,3,4-tetrahydro-[1,4]diazepino[6,7,1-hi]indol-7-yl)-4-(imidazo[1,2-a]pyridin-3-yl)-1H-pyrrole-2,5-dione; 34244-(aminomethyl)piperidine-1-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione; 3-(2-(4-(hydroxymethyl)piperidine-1-carbonyl)-9-(trifluoromethyl)-1,2,3,4-tetrahydro-[1,4]diazepino[6,7,1-hi]indol-7-yl)-4-(imidazo[1,2-a]pyridin-3-yl)-1H-pyrrole-2,5-dione; 2-(4-(hydroxymethyl)piperidine-1-carbonyl)-7-(4-(imidazo[1,2-a]pyridin-3-yl)-2,5-dioxo-2,5-dihydro-1H-pyrrol-3-yl)-1,2,3,4-tetrahydro-[1,4]diazepino[6,7,1-hi]indole-9-carbonitrile; 3-(9-fluoro-2-(3,3,4,4,5,5-hexafluoropiperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione; 3-(9-fluoro-2-(3,3,5,5-tetrafluoropiperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione; 3-(9-fluoro-2-(2,2,6,6-tetrafluoromorpholine-4-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione; 3-(2-(4,4-difluoro-3-hydroxypiperidine-1-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione; 3-(2-(4-(difluoro(hydroxy)methyl)piperidine-1-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione; 3-(2-(6,6-difluoro-1,4-oxazepane-4-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione; 3-([1,2,4]

triazolo[4,3-a]pyridin-3-yl)-4-(9-fluoro-2-(piperidine-1-carbonyl)-1,2,3,4-tetrahydro-[1,4]diazepino[6,7,1-hi]indol-7-yl)-1H-pyrrole-2,5-dione; 3-(9-fluoro-2-(piperidine-1-carbonyl-d10)-1,2,3,4-tetrahydro-[1,4]diazepino[6,7,1-hi]indol-7-yl)-4-(imidazo[1,2-a]pyridin-3-yl)-1H-pyrrole-2,5-dione; 3-(9-fluoro-2-(piperidine-1-carbonyl)-1,2,3,4-tetrahydro-[1,4]diazepino[6,7,1-hi]indol-7-yl-3,3,4,4-d4)-4-(imidazo[1,2-a]pyridin-3-yl)-1H-pyrrole-2,5-dione; 3-(9-fluoro-2-(4-(2,2,2-trifluoro-1-hydroxyethyl)piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione; 3-(9-fluoro-2-(4-((methylamino)methyl)piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione; 3-(2-(4-((dimethylamino)methyl)piperidine-1-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione; 3-(2-(4-aminopiperidine-1-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione; 3-(9-fluoro-2-(4-(methylamino)piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione; 3-(2-(4-(dimethylamino)piperidine-1-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione; 9-fluoro-7-(4-(imidazo[1,2-a]pyridin-3-yl)-2,5-dioxo-2,5-dihydro-1H-pyrrol-3-yl)-N-(piperidin-4-ylmethyl)-3,4-dihydro-[1,4]diazepino[6,7,1-hi]indole-2(1H)-carboxamide; 9-fluoro-7-(4-(imidazo[1,2-a]pyridin-3-yl)-2,5-dioxo-2,5-dihydro-1H-pyrrol-3-yl)-N-methyl-N-(piperidin-4-ylmethyl)-3,4-dihydro-[1,4]diazepino[6,7,1-hi]indole-2(1H)-carboxamide; 9-fluoro-7-(4-(imidazo[1,2-a]pyridin-3-yl)-2,5-dioxo-2,5-dihydro-1H-pyrrol-3-yl)-N-methyl-N-((1-methylpiperidin-4-yl)methyl)-3,4-dihydro-[1,4]diazepino[6,7,1-hi]indole-2(1H)-carboxamide; 3-(9-fluoro-2-((1R,4R)-5-methyl-2,5-diazabicyclo[2.2.1]heptane-2-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione; 3-(9-fluoro-2-(2-methyl-2,8-diazaspiro[4.5]decane-8-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione; 3-(9-fluoro-2-(8-methyl-2,8-diazaspiro[4.5]decane-2-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione; 3-(imidazo[1,2-a]pyridin-3-yl)-4-(2-(2,2,6,6-tetrafluoromorpholine-4-carbonyl)-9-(trifluoromethyl)-1,2,3,4-tetrahydro-[1,4]diazepino[6,7,1-hi]indol-7-yl)-1H-pyrrole-2,5-dione; 3-(2-(6,6-difluoro-1,4-oxazepane-4-carbonyl)-9-(trifluoromethyl)-1,2,3,4-tetrahydro-[1,4]diazepino[6,7,1-hi]indol-7-yl)-4-(imidazo[1,2-a]pyridin-3-yl)-1H-pyrrole-2,5-dione; 2-(4-(dimethylamino)piperidine-1-carbonyl)-7-(4-(imidazo[1,2-a]pyridin-3-yl)-2,5-dioxo-2,5-dihydro-1H-pyrrol-3-yl)-1,2,3,4-tetrahydro-[1,4]diazepino[6,7,1-hi]indole-9-carbonitrile; 9-cyano-7-(4-(imidazo[1,2-a]pyridin-3-yl)-2,5-dioxo-2,5-dihydro-1H-pyrrol-3-yl)-N-methyl-N-((1-methylpiperidin-4-yl)methyl)-3,4-dihydro-[1,4]diazepino[6,7,1-hi]indole-2(1H)-carboxamide; 7-(4-(imidazo[1,2-a]pyridin-3-yl)-2,5-dioxo-2,5-dihydro-1H-pyrrol-3-yl)-2-(8-methyl-2,8-diazaspiro[4.5]decane-2-carbonyl)-1,2,3,4-tetrahydro-[1,4]diazepino[6,7,1-hi]indole-9-carbonitrile; 3-(8,9-difluoro-2-(piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione; or 3-(9-fluoro-2-(piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione (LY20900314).

Preferably, the substituted 3-Imidazo[1,2-a]pyridin-3-yl-4-(1,2,3,4-tetrahydro-[1,4]diazepino-[6,7,1-hi]indol-7-yl)pyrrole-2,5-dione is: 3-(imidazo[1,2-a]pyridin-3-yl)-4-(2-(piperidine-1-carbonyl)-9-(trifluoromethyl)-1,2,3,4-tetrahydro-[1,4]diazepino[6,7,1-hi]indol-7-yl)-1H-pyrrole-2,5-dione; 7-(4-(imidazo[1,2-a]pyridin-3-yl)-2,5-dioxo-2,5-dihydro-1H-pyrrol-3-yl)-2-(piperidine-1-carbonyl)-1,2,3,4-tetrahydro-[1,4]diazepino[6,7,1-hi]indole-9-carbonitrile; 3-(9-ethynyl-2-(piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione; 3-(9-fluoro-2-(4-(hydroxymethyl)piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione; 3-(2-(4,4-difluoropiperidine-1-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione; 3-(2-(8-oxa-3-azabicyclo[3.2.1]octane-3-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione; 3-(9-(difluoromethyl)-2-(piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione; 3-(2-(3,3-difluoropiperidine-1-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione; 2-(4,4-difluoropiperidine-1-carbonyl)-7-(4-(imidazo[1,2-a]pyridin-3-yl)-2,5-dioxo-2,5-dihydro-1H-pyrrol-3-yl)-1,2,3,4-tetrahydro-[1,4]diazepino[6,7,1-hi]indole-9-carbonitrile; 3-(2-(8-oxa-3-azabicyclo[3.2.1]octane-3-carbonyl)-9-(trifluoromethyl)-1,2,3,4-tetrahydro-[1,4]diazepino[6,7,1-hi]indol-7-yl)-4-(imidazo[1,2-a]pyridin-3-yl)-1H-pyrrole-2,5-dione; 3-(2-(4-(hydroxymethyl)piperidine-1-carbonyl)-9-(trifluoromethyl)-1,2,3,4-tetrahydro-[1,4]diazepino[6,7,1-hi]indol-7-yl)-4-(imidazo[1,2-a]pyridin-3-yl)-1H-pyrrole-2,5-dione; 3-(9-fluoro-2-(3,3,4,4,5,5-hexafluoropiperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione; 3-(9-fluoro-2-(3,3,5,5-tetrafluoropiperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione; 3-(9-fluoro-2-(2,2,6,6-tetrafluoromorpholine-4-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione; 3-(2-(4,4-difluoro-3-hydroxypiperidine-1-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione; 3-(2-(4-(difluoro(hydroxy)methyl)piperidine-1-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione; 3-(2-(6,6-difluoro-1,4-oxazepane-4-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione; 3-(9-fluoro-2-(piperidine-1-carbonyl-d10)-1,2,3,4-tetrahydro-[1,4]diazepino[6,7,1-hi]indol-7-yl)-4-(imidazo[1,2-a]pyridin-3-yl)-1H-pyrrole-2,5-dione; 3-(9-fluoro-2-(piperidine-1-carbonyl)-1,2,3,4-tetrahydro-[1,4]diazepino[6,7,1-hi]indol-7-yl-3,3,4,4-d4)-4-(imidazo[1,2-a]pyridin-3-yl)-1H-pyrrole-2,5-dione; 3-(9-fluoro-2-(4-(2,2,2-trifluoro-1-hydroxyethyl)piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione; 3-(2-(4-((dimethylamino)methyl)piperidine-1-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione; 3-(2-(4-(dimethylamino)piperidine-1-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione; 9-fluoro-7-(4-

(imidazo[1,2-a]pyridin-3-yl)-2,5-dioxo-2,5-dihydro-1H-pyrrol-3-yl)-N-methyl-N-((l-methylpiperidin-4-yl)methyl)-3,4-dihydro-[1,4]diazepino[6,7,1-hi]indole-2(1H)-carboxamide; 3-(imidazo[1,2-a]pyridin-3-yl)-4-(2-(2,2,6,6-tetrafluoromorpholine-4-carbonyl)-9-(trifluoromethyl)-1,2,3,4-tetrahydro-[1,4]diazepino[6,7,1-hi]indol-7-yl)-1H-pyrrole-2,5-dione; 3-(2-(6,6-difluoro-1,4-oxazepane-4-carbonyl)-9-(trifluoromethyl)-1,2,3,4-tetrahydro-[1,4]diazepino[6,7,1-hi]indol-7-yl)-4-(imidazo[1,2-a]pyridin-3-yl)-1H-pyrrole-2,5-dione; 3-(8,9-difluoro-2-(piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione; or 3-(9-fluoro-2-(piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione. (LY2090314).

Most preferably, the substituted 3-Imidazo[1,2-a]pyridin-3-yl-4-(1,2,3,4-tetrahydro-[1,4]diazepino-[6,7,1-hi]indol-7-yl)pyrrole-2,5-dione is 3-(9-fluoro-2-(piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione. (LY2090314).

The structures of the substituted 3-Imidazo[1,2-a]pyridin-3-yl-4-(1,2,3,4-tetrahydro-[1,4]diazepino-[6,7,1-hi]indol-7-yl)pyrrole-2,5-dione are shown below in Table 5.

TABLE 5

| | | |
|---|---|---|
| Compound I-1 | 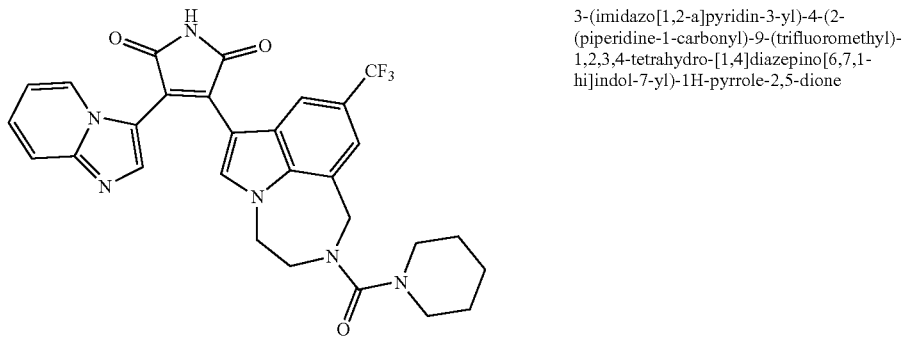 | 3-(imidazo[1,2-a]pyridin-3-yl)-4-(2-(piperidine-1-carbonyl)-9-(trifluoromethyl)-1,2,3,4-tetrahydro-[1,4]diazepino[6,7,1-hi]indol-7-yl)-1H-pyrrole-2,5-dione |
| Compound I-2 | 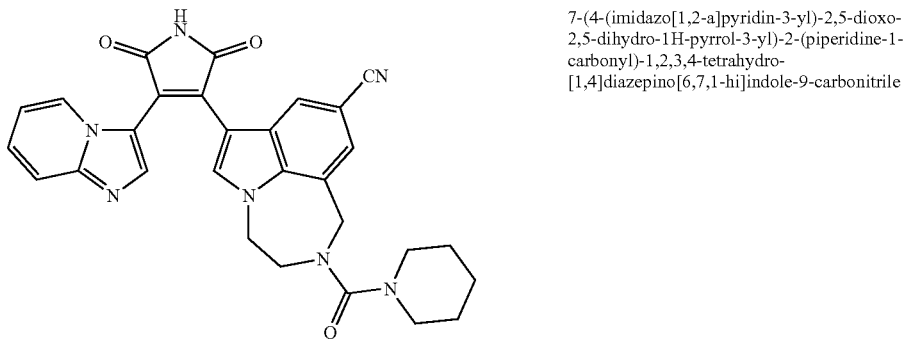 | 7-(4-(imidazo[1,2-a]pyridin-3-yl)-2,5-dioxo-2,5-dihydro-1H-pyrrol-3-yl)-2-(piperidine-1-carbonyl)-1,2,3,4-tetrahydro-[1,4]diazepino[6,7,1-hi]indole-9-carbonitrile |
| Compound I-3 | 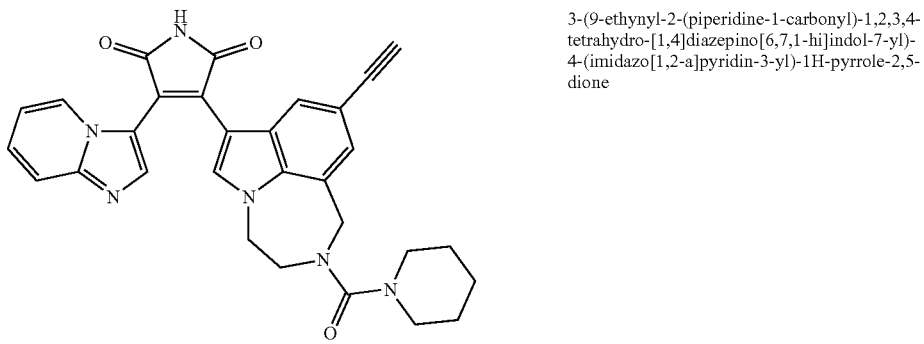 | 3-(9-ethynyl-2-(piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione |

TABLE 5-continued

| | | |
|---|---|---|
| Compound I-4 | 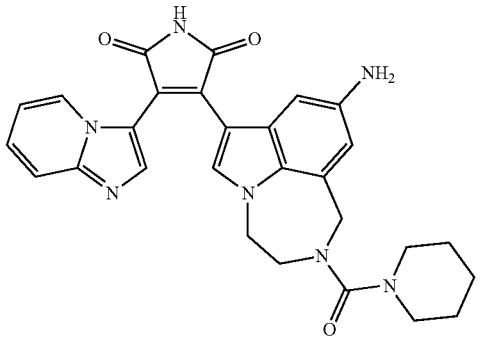 [SMILES: Nc1cc2c3c(c1)c(C1=C(c4cnc5ccccn45)C(=O)NC1=O)cn3CCN(C(=O)N1CCCCC1)C2] | 3-(9-amino-2-(piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione |
| Compound I-5 | 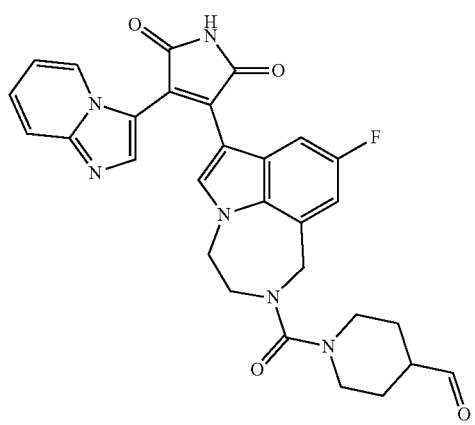 [SMILES: O=CC1CCN(C(=O)N2CCn3cc(C4=C(c5cnc6ccccn56)C(=O)NC4=O)c4cc(F)cc(c43)C2)CC1] | 1-(9-fluoro-7-(4-(imidazo[1,2-a]pyridin-3-yl)-2,5-dioxo-2,5-dihydro-1H-pyrrol-3-yl)-1,2,3,4-tetrahydro-[1,4]diazepino[6,7,1-hi]indole-2-carbonyl)piperidine-4-carbaldehyde |
| Compound I-6 | 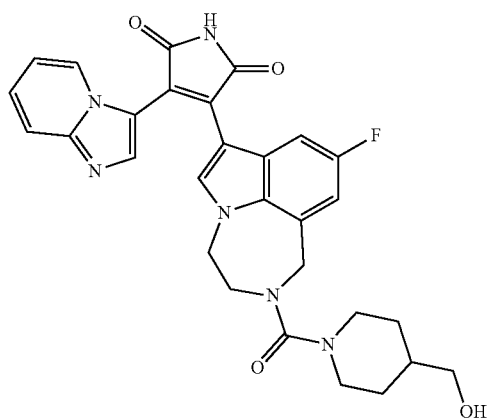 [SMILES: O=C1NC(=O)C(c2cnc3ccccn23)=C1c1cn2c3c(cc(F)cc13)CN(C(=O)N1CCC(CO)CC1)CC2] | 3-(9-fluoro-2-(4-(hydroxymethyl)piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione |
| Compound I-7 | 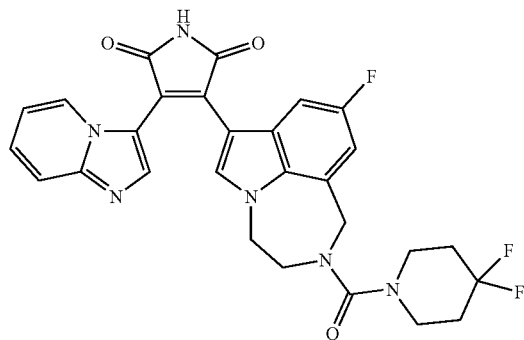 [SMILES: O=C1NC(=O)C(c2cnc3ccccn23)=C1c1cn2c3c(cc(F)cc13)CN(C(=O)N1CCC(F)(F)CC1)CC2] | 3-(2-(4,4-difluoropiperidine-1-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione |

TABLE 5-continued

| | | |
|---|---|---|
| Compound I-8 | 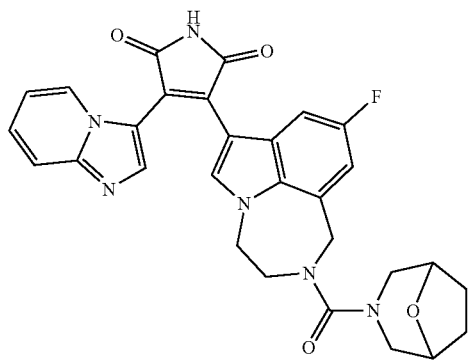 [SMILES: O=C1NC(=O)C(c2cnc3ccccn23)=C1c1cn2c3c(cc(F)cc13)CN(C(=O)N1CC3CCC(C1)O3)CC2] | 3-(2-(8-oxa-3-azabicyclo[3.2.1]octane-3-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione |
| Compound I-9 | 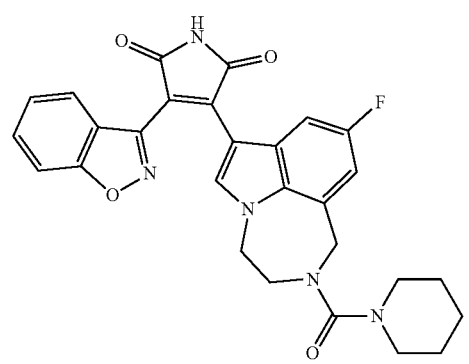 [SMILES: O=C1NC(=O)C(c2cn3c4c(cc(F)cc24)CN(C(=O)N2CCCCC2)CC3)=C1c1noc2ccccc12] | 3-(benzo[d]isoxazol-3-yl)-4-(9-fluoro-2-(piperidine-1-carbonyl)-1,2,3,4-tetrahydro-[1,4]diazepino[6,7,1-hi]indol-7-yl)-1H-pyrrole-2,5-dione |
| Compound I-10 | 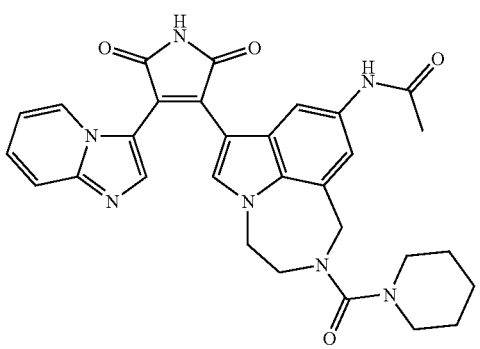 [SMILES: CC(=O)Nc1cc2c3c(c1)c(C1=C(c4cnc5ccccn45)C(=O)NC1=O)cn3CCN(C(=O)N1CCCCC1)C2] | N-(7-(4-(imidazo[1,2-a]pyridin-3-yl)-2,5-dioxo-2,5-dihydro-1H-pyrrol-3-yl)-2-(piperidine-1-carbonyl)-1,2,3,4-tetrahydro-[1,4]diazepino[6,7,1-hi]indol-9-yl)acetamide |
| Compound I-11 | 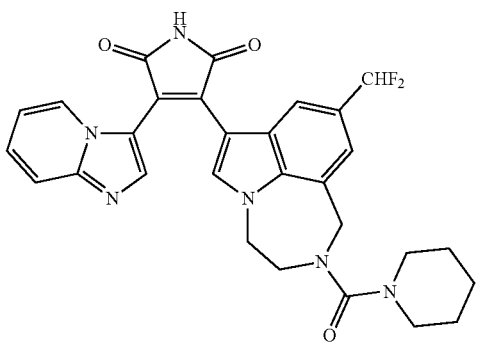 [SMILES: O=C1NC(=O)C(c2cnc3ccccn23)=C1c1cn2c3c(cc(C(F)F)cc13)CN(C(=O)N1CCCCC1)CC2] | 3-(9-(difluoromethyl)-2-(piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione |

TABLE 5-continued

| Compound I-12 | 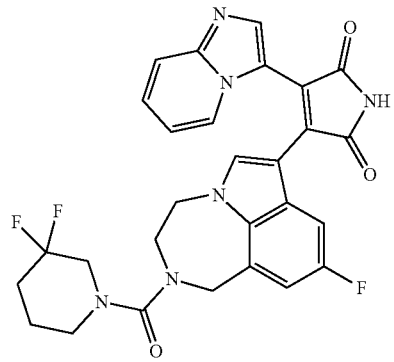 [SMILES: O=C1NC(=O)C(c2cnc3ccccn23)=C1c1cn2c3c(cc(F)cc13)CN(C(=O)N1CCCC(F)(F)C1)CC2] | 3-(2-(3,3-difluoropiperidine-1-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione |
| --- | --- | --- |
| Compound I-13 | 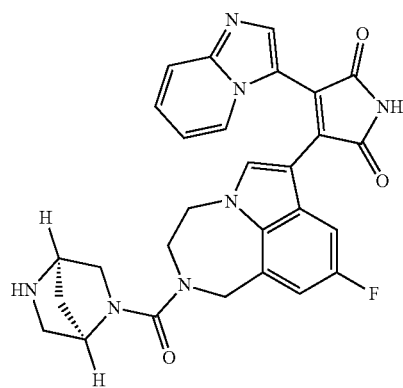 [SMILES: O=C1NC(=O)C(c2cnc3ccccn23)=C1c1cn2c3c(cc(F)cc13)CN(C(=O)N1C[C@H]3C[C@@H]1CN3)CC2] | 3-(2-(((1R,4R)-2,5-diazabicyclo[2.2.1]heptane-2-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione |
| Compound I-14 | 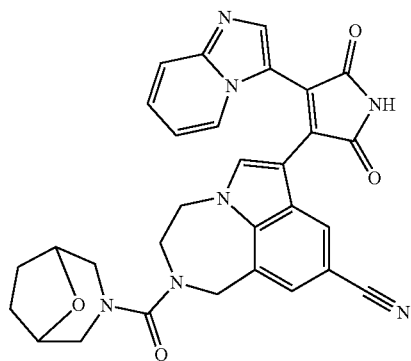 [SMILES: N#Cc1cc2c3c(c1)c(C1=C(c4cnc5ccccn45)C(=O)NC1=O)cn3CCN(C(=O)N1CC3CCC(C1)O3)C2] | 2-(8-oxa-3-azabicyclo[3.2.1]octane-3-carbonyl)-7-(4-(imidazo[1,2-a]pyridin-3-yl)-2,5-dioxo-2,5-dihydro-1H-pyrrol-3-yl)-1,2,3,4-tetrahydro-[1,4]diazepino[6,7,1-hi]indole-9-carbonitrile |
| Compound I-15 | 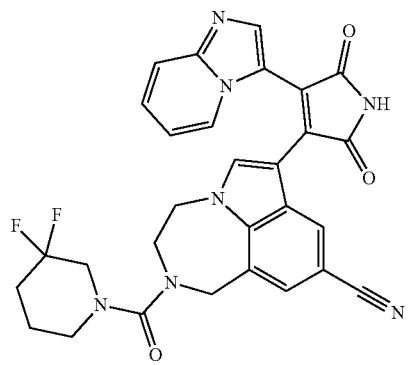 [SMILES: N#Cc1cc2c3c(c1)c(C1=C(c4cnc5ccccn45)C(=O)NC1=O)cn3CCN(C(=O)N1CCCC(F)(F)C1)C2] | 2-(3,3-difluoropiperidine-1-carbonyl)-7-(4-(imidazo[1,2-a]pyridin-3-yl)-2,5-dioxo-2,5-dihydro-1H-pyrrol-3-yl)-1,2,3,4-tetrahydro-[1,4]diazepino[6,7,1-hi]indole-9-carbonitrile |

TABLE 5-continued

Compound I-16 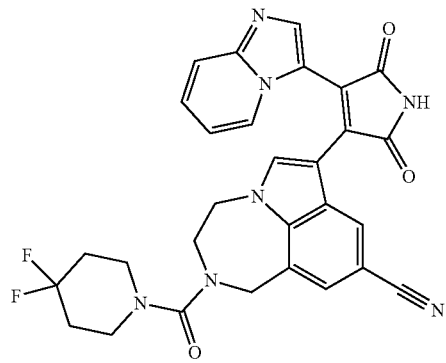 [SMILES: N#Cc1cc2c3c(c1)c(C1=C(c4cnc5ccccn45)C(=O)NC1=O)cn3CCN(C(=O)N1CCC(F)(F)CC1)C2] 2-(4,4-difluoropiperidine-1-carbonyl)-7-(4-(imidazo[1,2-a]pyridine-3-yl)-2,5-dioxo-2,5-dihydro-1H-pyrrol-3-yl)-1,2,3,4-tetrahydro-[1,4]diazepino[6,7,1-hi]indole-9-carbonitrile Compound I-17 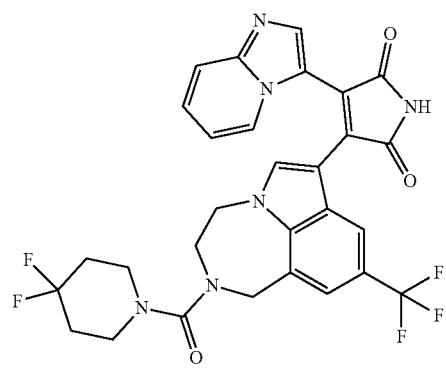 [SMILES: O=C1NC(=O)C(c2cnc3ccccn23)=C1c1cn2c3c(cc(C(F)(F)F)cc13)CN(C(=O)N1CCC(F)(F)CC1)CC2] 3-(2-(4,4-difluoropiperidine-1-carbonyl)-9-(trifluoromethyl)-1,2,3,4-tetrahydro-[1,4]diazepino[6,7,1-hi]indol-7-yl)-4-(imidazo[1,2-a]pyridin-3-yl)-1H-pyrrole-2,5-dione Compound I-18 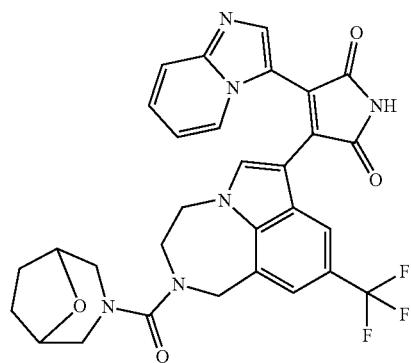 [SMILES: O=C1NC(=O)C(c2cnc3ccccn23)=C1c1cn2c3c(cc(C(F)(F)F)cc13)CN(C(=O)N1CC3CCC(C1)O3)CC2] 3-(2-(8-oxa-3-azabicyclo[3.2.1]octane-3-carbonyl)-9-(trifluoromethyl)-1,2,3,4-tetrahydro-[1,4]diazepino[6,7,1-hi]indol-7-yl)-4-(imidazo[1,2-a]pyridin-3-yl)-1H-pyrrole-2,5-dione Compound I-19 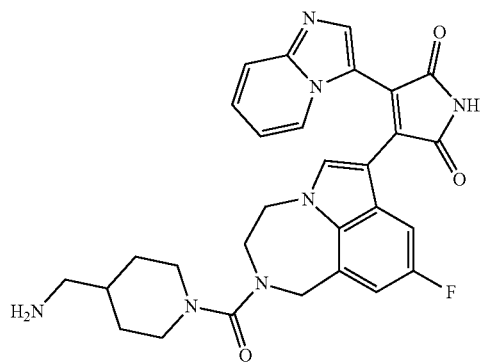 [SMILES: NCC1CCN(C(=O)N2CCn3cc(C4=C(c5cnc6ccccn56)C(=O)NC4=O)c4cc(F)cc(c43)C2)CC1] 3-(2-(4-(aminomethyl)piperidine-1-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione TABLE 5-continued

| Compound I-20 | 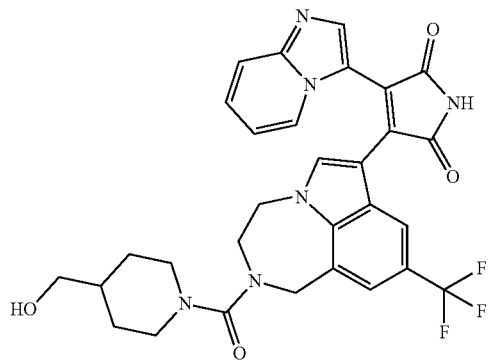 [SMILES: O=C1NC(=O)C(c2cnc3ccccn23)=C1c1cn2c3c(cc(C(F)(F)F)cc13)CN(C(=O)N1CCC(CO)CC1)CC2] | 3-(2-(4-(hydroxymethyl)piperidine-1-carbonyl)-9-(trifluoromethyl)-1,2,3,4-tetrahydro-[1,4]diazepino[6,7,1-hi]indol-7-yl)-4-(imidazo[1,2-a]pyridin-3-yl)-1H-pyrrole-2,5-dione |
| --- | --- | --- |
| Compound I-21 | 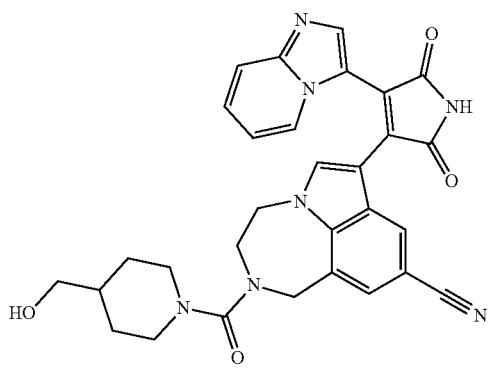 [SMILES: N#Cc1cc2c3c(c1)c(C1=C(c4cnc5ccccn45)C(=O)NC1=O)cn3CCN(C(=O)N1CCC(CO)CC1)C2] | 2-(4-(hydroxymethyl)piperidine-1-carbonyl)-7-(4-(imidazo[1,2-a]pyridin-3-yl)-2,5-dioxo-2,5-dihydro-1H-pyrrol-3-yl)-1,2,3,4-tetrahydro-[1,4]diazepino[6,7,1-hi]indole-9-carbonitrile |
| Compound I-22 | 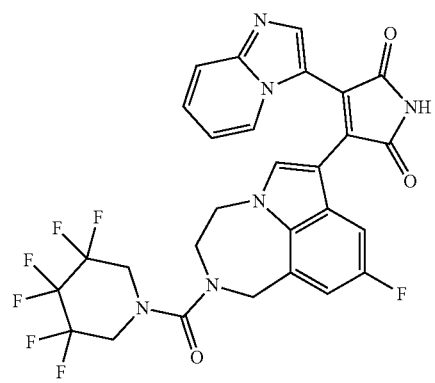 [SMILES: O=C1NC(=O)C(c2cnc3ccccn23)=C1c1cn2c3c(cc(F)cc13)CN(C(=O)N1CC(F)(F)C(F)(F)C(F)(F)C1)CC2] | 3-(9-fluoro-2-(3,3,4,4,5,5-hexafluoropiperidine-1-carbonyl)1,2,3,4-tetrahydro-[1,4]diazepino[6,7,1-hi]indol-7-yl)-4-(imidazo[1,2-a]pyridin-3-yl)-1H-pyrrole-2,5-dione |
| Compound I-23 | 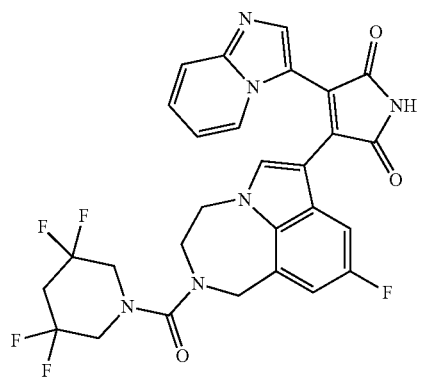 [SMILES: O=C1NC(=O)C(c2cnc3ccccn23)=C1c1cn2c3c(cc(F)cc13)CN(C(=O)N1CC(F)(F)CC(F)(F)C1)CC2] | 3-(9-fluoro-2-(3,3,5,5,-tetrafluoropiperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione |

TABLE 5-continued

| | | |
|---|---|---|
| Compound I-24 | 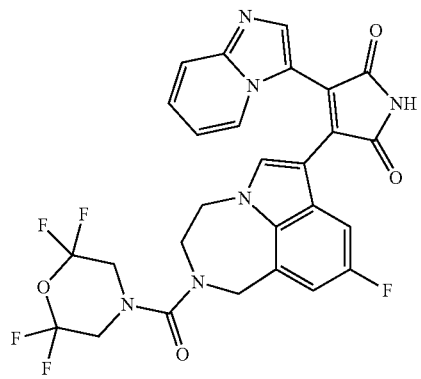 [SMILES: O=C1NC(=O)C(c2cnc3ccccn23)=C1c1cn2c3c(cc(F)cc13)CN(C(=O)N1CC(F)(F)OC(F)(F)C1)CC2] | 3-(9-fluoro-2-(2,2,6,6-tetrafluoromorpholine-4-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione |
| Compound I-25 | 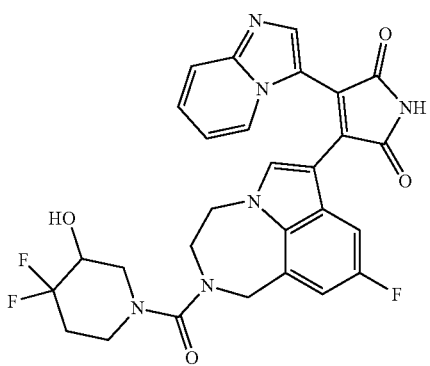 [SMILES: O=C1NC(=O)C(c2cnc3ccccn23)=C1c1cn2c3c(cc(F)cc13)CN(C(=O)N1CCC(F)(F)C(O)C1)CC2] | 3-(2-(4,4-difluoro-3-hydroxypiperidine-1-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione |
| Compound I-26 | 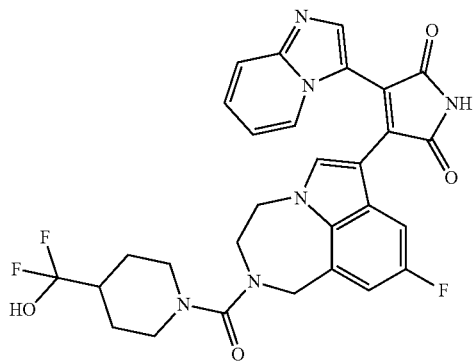 [SMILES: O=C1NC(=O)C(c2cnc3ccccn23)=C1c1cn2c3c(cc(F)cc13)CN(C(=O)N1CCC(C(O)(F)F)CC1)CC2] | 3-(2-(4-(difluoro(hydroxy)methyl)piperidine-1-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione |
| Compound I-27 | 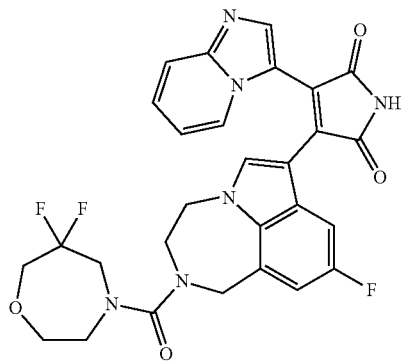 [SMILES: O=C1NC(=O)C(c2cnc3ccccn23)=C1c1cn2c3c(cc(F)cc13)CN(C(=O)N1CCOCC(F)(F)C1)CC2] | 3-(2-(6,6-difluoro-1,4-oxazepane-4-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione |

TABLE 5-continued

Compound I-28 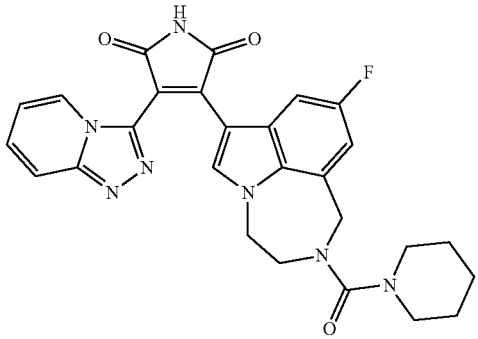 [SMILES: O=C1NC(=O)C(c2nnc3ccccn23)=C1c1cn2c3c(cc(F)cc13)CN(C(=O)N1CCCCC1)CC2] 3-([1,2,4]triazolo[4,3-a]pyridin-3-yl)-4-(9-fluoro-2-(piperidine-1-carbonyl)-1,2,3,4-tetrahydro-[1,4]diazepino[6,7,1-hi]indol-7-yl)-1H-pyrrole-2,5-dione Compound I-29 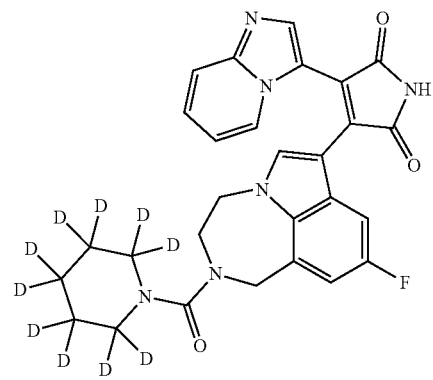 [SMILES: [2H]C1([2H])N(C(=O)N2CCn3cc(C4=C(c5cnc6ccccn56)C(=O)NC4=O)c4cc(F)cc(c43)C2)C([2H])([2H])C([2H])([2H])C([2H])([2H])C1([2H])[2H]] 3-(9-fluoro-2-(piperidine-1-carbonyl-d10)-1,2,3,4-tetrahydro-[1,4]diazepino[6,7,1-hi]indol-7-yl)-4-(imidazo[1,2-a]pyridin-3-yl)-1H-pyrrole-2,5-dione Compound I-30 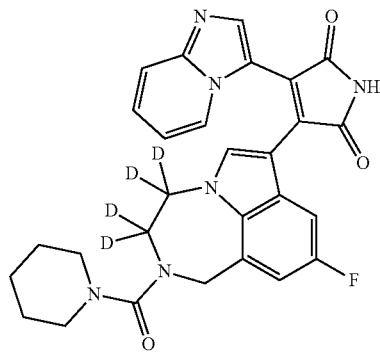 [SMILES: [2H]C1([2H])N(C(=O)N2CCCCC2)Cc2cc(F)cc3c(C4=C(c5cnc6ccccn56)C(=O)NC4=O)cn(c23)C1([2H])[2H]] 3-(9-fluoro-2-(piperidine-1-carbonyl)-1,2,3,4-tetrahydro-[1,4]diazepino[6,7,1-hi]indol-7-yl-3,3,4,4-d4)-4-(imidazo[1,2-a]pyridin-3-yl)-1H-pyrrole-2,5-dione Compound I-31 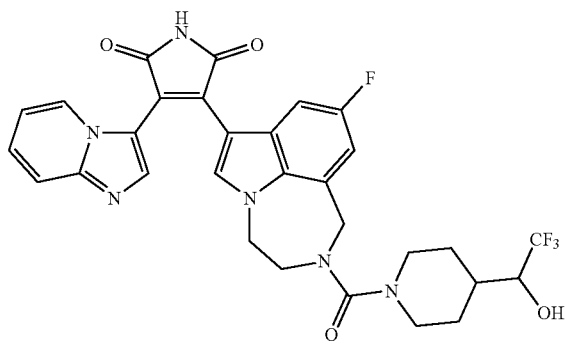 [SMILES: O=C1NC(=O)C(c2cnc3ccccn23)=C1c1cn2c3c(cc(F)cc13)CN(C(=O)N1CCC(C(O)C(F)(F)F)CC1)CC2] 3-(9-fluoro-2-(4-(2,2,2-trifluoro-1-hydroxyethyl)piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione TABLE 5-continued Compound I-32 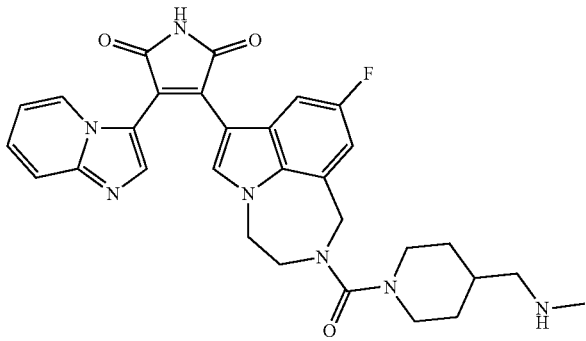 [SMILES: CNCC1CCN(C(=O)N2CCn3cc(C4=C(c5cnc6ccccn56)C(=O)NC4=O)c4cc(F)cc(c43)C2)CC1] 3-(9-fluoro-2-(4-((methylamino)methyl)piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione Compound I-33 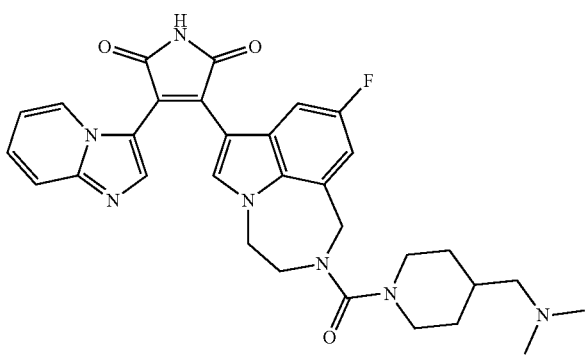 [SMILES: CN(C)CC1CCN(C(=O)N2CCn3cc(C4=C(c5cnc6ccccn56)C(=O)NC4=O)c4cc(F)cc(c43)C2)CC1] 3-(2-(4-((dimethylamino)methyl)piperidine-1-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione Compound I-34 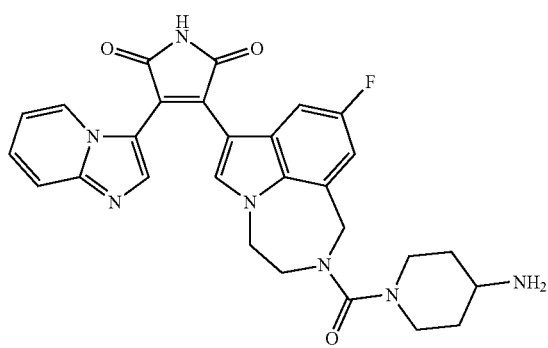 [SMILES: NC1CCN(C(=O)N2CCn3cc(C4=C(c5cnc6ccccn56)C(=O)NC4=O)c4cc(F)cc(c43)C2)CC1] 3-(2-(4-aminopiperidine-1-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione Compound I-35 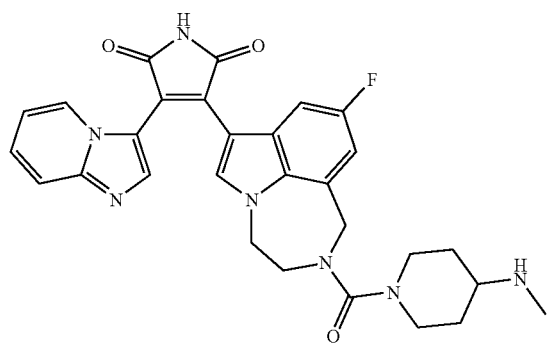 [SMILES: CNC1CCN(C(=O)N2CCn3cc(C4=C(c5cnc6ccccn56)C(=O)NC4=O)c4cc(F)cc(c43)C2)CC1] 3-(9-fluoro-2-(4-(methylamino)piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione TABLE 5-continued Compound I-36 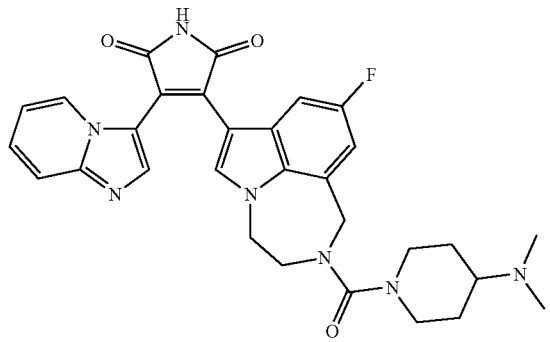 [SMILES: CN(C)C1CCN(C(=O)N2CCn3cc(C4=C(c5cnc6ccccn56)C(=O)NC4=O)c4cc(F)cc(c43)C2)CC1] 3-(2-(4-(dimethylamino)piperidine-1-carbonyl)-9-fluoro-1,2,3,4-tetrahydro-[1,4]diazepino[6,7,1-hi]indol-7-yl)-4-(imidazo[1,2-a]pyridin-3-yl)-1H-pyrrole-2,5-dione Compound I-37 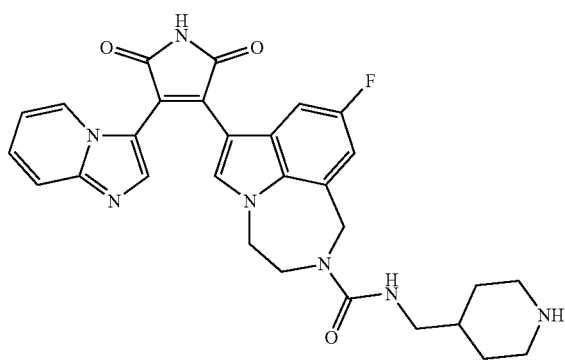 [SMILES: O=C1NC(=O)C(c2cnc3ccccn23)=C1c1cn2c3c(cc(F)cc13)CN(C(=O)NCC1CCNCC1)CC2] 9-fluoro-7-(4-(imidazo[1,2-a]pyridin-3-yl)-2,5-dioxo-2,5-dihydro-1H-pyrrol-3-yl)-N-(piperidin-4-ylmethyl)-3,4-dihydro-[1,4]diazepino[6,7,1-hi]indole-2(1H)-carboxamide Compound I-38 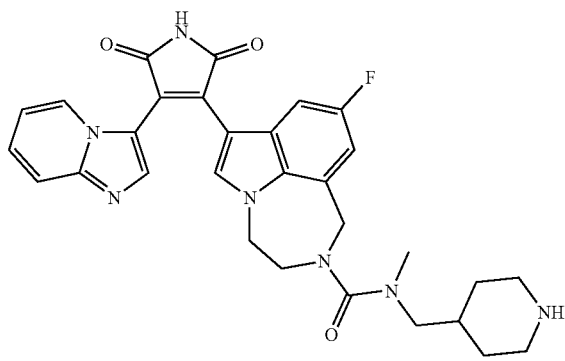 [SMILES: CN(CC1CCNCC1)C(=O)N1CCn2cc(C3=C(c4cnc5ccccn45)C(=O)NC3=O)c3cc(F)cc(c32)C1] 9-fluoro-7-(4-(imidazo[1,2-a]pyridin-3-yl)-2,5-dioxo-2,5-dihydro-1H-pyrrol-3-yl)-N-methyl-N-(piperidin-4-ylmethyl)-3,4-dihydro-[1,4]diazepino[6,7,1-hi]indole-2(1H)-carboxamide Compound I-39 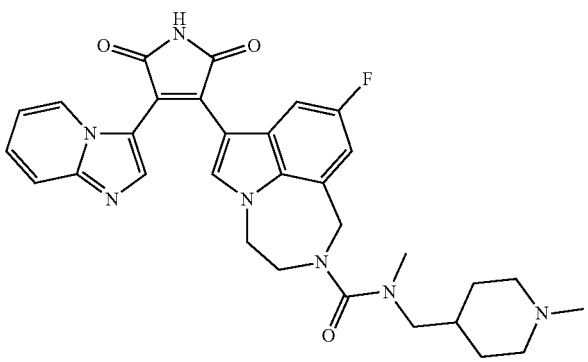 [SMILES: CN1CCC(CN(C)C(=O)N2CCn3cc(C4=C(c5cnc6ccccn56)C(=O)NC4=O)c4cc(F)cc(c43)C2)CC1] 9-fluoro-7-(4-(imidazo[1,2-a]pyridin-3-yl)-2,5-dioxo-2,5-dihydro-1H-pyrrol-3-yl)-N-methyl-N-((1-methylpiperidin-4-yl)methyl)-3,4-dihydro-[1,4]diazepino[6,7,1-hi]indole-2(1H)-carboxamide TABLE 5-continued Compound I-40 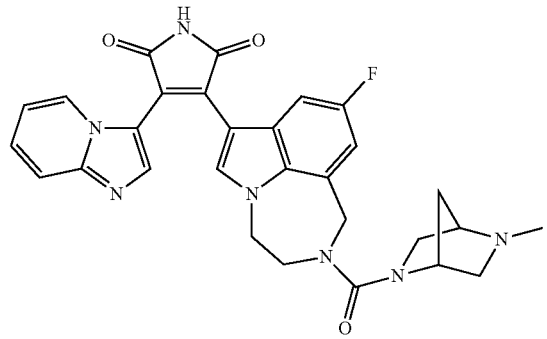 [SMILES: CN1CC2CC1CN2C(=O)N1CCn2cc(C3=C(c4cnc5ccccn45)C(=O)NC3=O)c3cc(F)cc(c32)C1] 3-(9-fluoro-2-((1R,4R)-5-methyl-2,5-diazabicyclo[2.2.1]heptane-2-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione Compound I-41 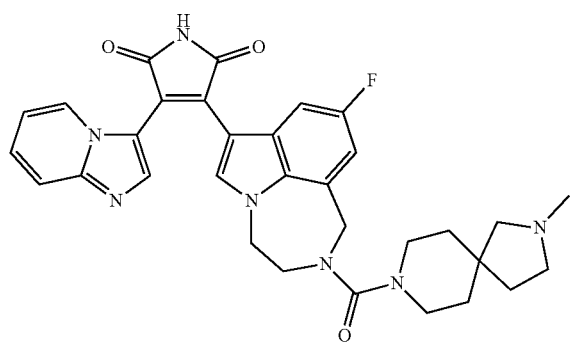 [SMILES: CN1CCC2(CCN(C(=O)N3CCn4cc(C5=C(c6cnc7ccccn67)C(=O)NC5=O)c5cc(F)cc(c54)C3)CC2)C1] 3-(9-fluoro-2-(2-methyl-2,8-diazaspiro[4.5]decane-8-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione Compound I-42 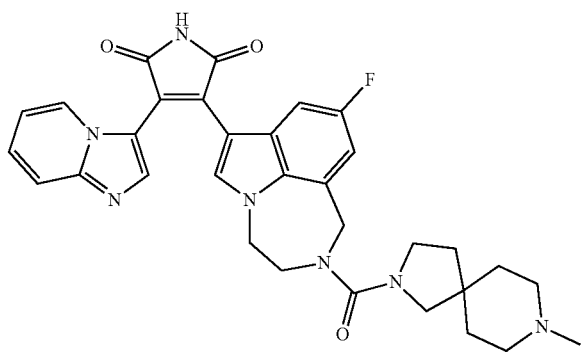 [SMILES: CN1CCC2(CC1)CCN(C(=O)N1CCn3cc(C4=C(c5cnc6ccccn56)C(=O)NC4=O)c4cc(F)cc(c43)C1)C2] 3-(9-fluoro-2-(8-methyl-2,8-diazaspiro[4.5]decane-2-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione Compound I-43 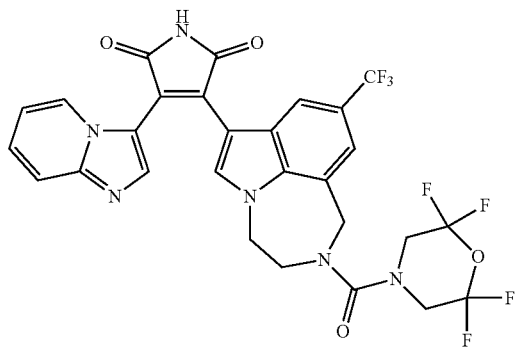 [SMILES: O=C1NC(=O)C(c2cnc3ccccn23)=C1c1cn2c3c(cc(C(F)(F)F)cc13)CN(C(=O)N1CC(F)(F)OC(F)(F)C1)CC2] 3-(imidazo[1,2-a]pyridin-3-yl)-4-(2-(2,2,6,6-tetrafluoromorpholine-4-carbonyl)-9-(trifluoromethyl)-1,2,3,4-tetrahydro-[1,4]diazepino[6,7,1-hi]indol-7-yl)-1H-pyrrole-2,5-dione TABLE 5-continued

| Compound I-44 | 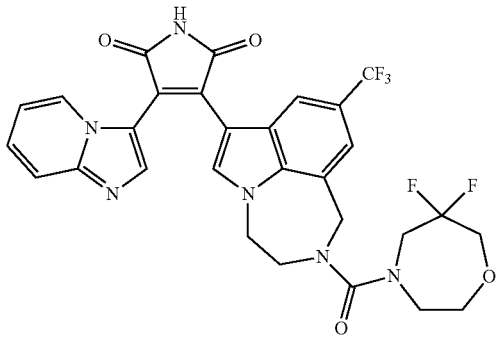 [SMILES: O=C1NC(=O)C(c2cnc3ccccn23)=C1c1cn2c3c(cc(C(F)(F)F)cc13)CN(C(=O)N1CCOCC(F)(F)C1)CC2] | 3-(2-(6,6-difluoro-1,4-oxazepane-4-carbonyl)-9-(trifluoromethyl)-1,2,3,4-tetrahydro-[1,4]diazepino[6,7,1-hi]indol-7-yl)-4-(imidazo[1,2-a]pyridin-3-yl)-1H-pyrrole-2,5-dione |
| --- | --- | --- |
| Compound I-45 | 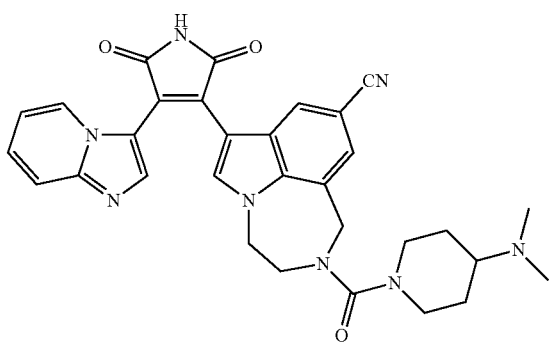 [SMILES: CN(C)C1CCN(C(=O)N2CCn3cc(C4=C(c5cnc6ccccn56)C(=O)NC4=O)c4cc(C#N)cc(c43)C2)CC1] | 2-(4-(dimethylamino)piperidine-1-carbonyl)-7-(4-(imidazo[1,2-a]pyridin-3-yl)-2,5-dioxo-2,5-dihydro-1H-pyrrol-3-yl)-1,2,3,4-tetrahydro-[1,4]diazepino[6,7,1-hi]indole-9-carbonitrile |
| Compound I-46 | 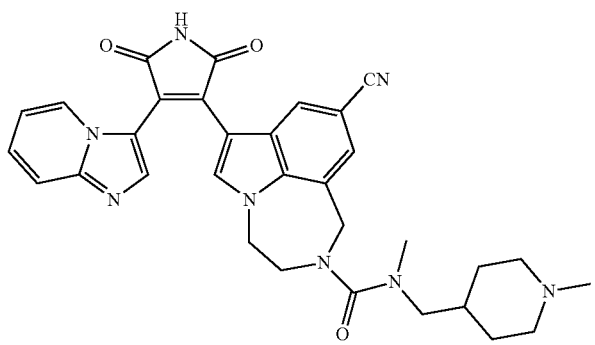 [SMILES: CN1CCC(CN(C)C(=O)N2CCn3cc(C4=C(c5cnc6ccccn56)C(=O)NC4=O)c4cc(C#N)cc(c43)C2)CC1] | 9-cyano-7-(4-(imidazo[1,2-a]pyridin-3-yl)-2,5-dioxo-2,5-dihydro-1H-pyrrol-3-yl)-N-methyl-N-((1-methylpiperidin-4-yl)methyl)-3,4-dihydro-[1,4]diazepino[6,7,1-hi]indole-2(1H)-carboxamide |
| Compound I-47 | 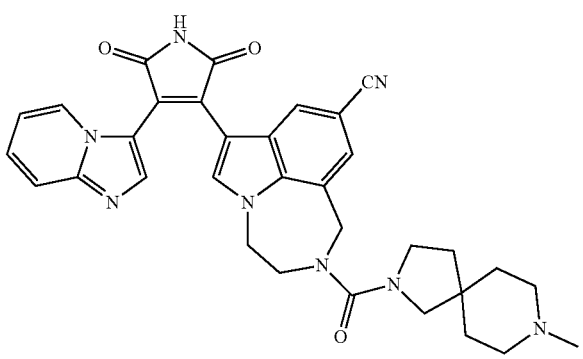 [SMILES: CN1CCC2(CC1)CCN(C(=O)N1CCn3cc(C4=C(c5cnc6ccccn56)C(=O)NC4=O)c4cc(C#N)cc(c43)C1)C2] | 7-(4-(imidazo[1,2-a]pyridin-3-yl)-2,5-dioxo-2,5-dihydro-1H-pyrrol-3-yl)-2-(8-methyl-2,8-diazaspiro[4.5]decane-2-carbonyl)-1,2,3,4-tetrahydro-[1,4]diazepino[6,7,1-hi]indole-9-carbonitrile |

TABLE 5-continued

Compound I-48

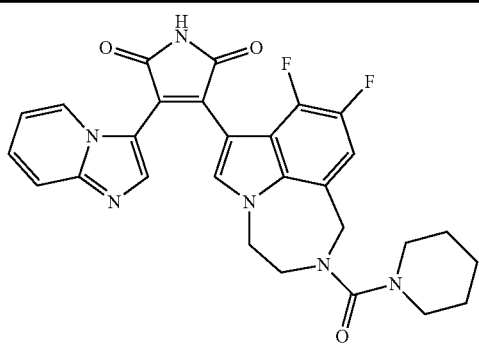

3-(8,9-difluoro-2-(piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione In other embodiments, a Wnt agonist and/or a GSK3 inhibitor as described in WO 2018/125746, US 20180214458 and U.S. Ser. No. 62/608,663 the contents of which are each incorporated by reference in their entireties.

HDAC Inhibitors

Histone deacetylases (HDAC) are a class of enzymes that remove acetyl groups (O=C—CH3) from an ε-N-acetyl lysine amino acid on a histone, allowing the histones to wrap the DNA more tightly. This is important because DNA is wrapped around histones, and DNA expression is regulated by acetylation and de-acetylation.

HDACs are classified in four classes depending on sequence homology to the yeast original enzymes and domain organization. The HDAC classes include HDACI, HDAC IIA, HDAC IIB, HDAC III and HDAC IV.

Histone deacetylase (HDAC) inhibitors (HDACi, HDIs) are chemical compounds that inhibit histone deacetylases.

Thus, "HDAC inhibitor" refers to an agent capable of the decreasing the expression or enzymatic activity of HDAC.

For example HDAC inhibitor results in a decrease in histone deacetylation of a target gene in a cell.

In certain embodiments, the HDAC inhibitor decreases the expression or enzymatic activity of HDAC by at least 5, 10, 20, 30, 40, 50, 60, 70, 80, 90, or 100% relative to a control, for example relative to a baseline level of activity.

In certain embodiments, the HDAC inhibitor decreases histone deacetylation of a target gene by at least 5, 10, 20, 30, 40, 50, 60, 70, 80, 90, or 100% relative to a control, for example relative to a baseline level of activity.

In some embodiments, the HDAC inhibitor increases expression or activity of a target gene by at least 5, 10, 20, 30, 40, 50, 60, 70, 80, 90, or 100% relative to a control, for example relative to a baseline level of activity.

In some embodiments, the HDAC inhibitor decreases expression or enzymatic activity of HDAC by at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more relative to a control, for example relative to a baseline level of activity.

In some embodiments, the HDAC inhibitor decreases histone deacetylation of a target gene by at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more relative to a control, for example relative to a baseline level of activity.

In some embodiments, the HDAC inhibitor increases expression or activity of a target gene by at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more relative to a control, for example relative to a baseline level of activity. In various embodiments, the methods and compositions of the invention include use an HDAC inhibitor. Exemplary HDAC inhibitors are provide in Table 6 and 7 below

TABLE 6

Exemplary HDAC Inhibitor

| Agent | CAS | Chemo-type | Mechanism HDAC Inhib | Class selectivity | HDAC Potenc | Lgr5+ Assay | Perilymph Conc | Formulation Conc |
|---|---|---|---|---|---|---|---|---|
| Sodium Valproate | 1069-66-5 | Acid | 1, 2, 3, 8 | Class I | 39-161 uM | 100 uM-4 mM | 100 uM-4mM | 100 mM-4000 mM |
| 2-hexyl-4-pentynoic acid | 96017-59-3 | Acid | 1, 2, 3, 8 | Class I | 13 uM | 100 uM-4 mM | 100 uM-4mM | 100 mM-4000 mM |
| Na phenylbutyrate | 1716-12-7 | Acid | 1, 2, 3, 8 | Class I > Class IIb | 9-16 uM | 100 uM-4 mM | 100 uM-4 mM | 100 mM-4000 mM |

TABLE 7

Additional Exemplary HDAC Inhibitors

| Class | Agent | CAS |
|---|---|---|
| Aliphatic Acid | Butyrate | 107-92-6 |
| Aliphatic Acid | Phenyl butyrate | 1821-12-1 |
| Aliphatic Acid | Valproic Acid | 99-66-1 |
| Aliphatic Acid Ester | AN-9 | 122110-53-6 |
| Amine | 932718-22-4 | 932718-22-4 |
| Benzamide | 4SC-202 | 1186222-89-8 |
| Benzamide | BML-210 | 537034-17-6 |
| Benzamide | Chidamide | 743438-44-0 |
| Benzamide | Entinostat (MS-275) | 209783-80-2 |
| Benzamide | HDAC Inhibitor IV | 537034-15-4 |
| Benzamide | Mocetinostat (MGCD0103) | 726169-73-9 |
| Benzamide | NKL 22 | 537034-15-4 |
| Benzamide | RGFP109 | 1215493-56-3 |
| Benzamide | RGFP136 | 1215493-97-2 |

TABLE 7-continued

Additional Exemplary HDAC Inhibitors

| Class | Agent | CAS |
|---|---|---|
| Benzamide | RGFP966 | 1357389-11-7 |
| Benzamide | Tacedinaline | 112522-64-2 |
| Benzamide | TC-H 106, HDAC Inhibitor VII | 937039-45-7 |
| Cyclic peptide | Apicidin | 183506-66-3 |
| Cyclic peptide | Dihydrochlamydocin | 52574-64-8 |
| Cyclic peptide | HC Toxin | 83209-65-8 |
| Cyclic peptide | Romidepsin | 128517-07-7 |
| Cyclic Peptide | Thailandepsin A | 1269219-30-8 |
| Cyclic peptide | Trapoxin A | 133155-89-2 |
| Epoxide | (−)-Depudecin | 139508-73-9 |
| Epoxide | Parthenolide | 20554-84-1 |
| Hydroxamate | (S)-HDAC-42 | 935881-37-1 |
| Hydroxamate | 4-(dimethylamino)-N-[6-(hydroxyamino)-6-oxohexyl]-benzamide | 193551-00-7 |
| Hydroxamate | 4-iodo-SAHA | 1219807-87-0 |
| Hydroxamate | 4SC-201 (Resminostat) | 864814-88-0 |
| Hydroxamate | ACY1215 | 1316214-52-4 |
| Hydroxamate | APHA Compound 8 | 676599-90-9 |
| Hydroxamate | BRD9757 | 1423058-85-8 |
| Hydroxamate | Bufexamac | 2438-72-4 |
| Hydroxamate | Butyrylhydroxamic acid | 4312-91-8 |
| Hydroxamate | CAY10603 | 1045792-66-2 |
| Hydroxamate | CBHA | 174664-65-4 |
| Hydroxamate | CG200745 | 936221-33-9 |
| Hydroxamate | CHR-3996 | 1256448-47-1 |
| Hydroxamate | CUDC-101 | 1012054-59-9 |
| Hydroxamate | Droxinostat | 99873-43-5 |
| Hydroxamate | HDAC Inhibitor II | 174664-65-4 |
| Hydroxamate | HDAC Inhibitor VI | 926908-04-5 |
| Hydroxamate | HDAC Inhibitor XXIV | 854779-95-6 |
| Hydroxamate | HDAC6 Inhibitor III | 1450618-49-1 |
| Hydroxamate | HDAC-IN-1 | 1239610-44-6 |
| Hydroxamate | HNHA | 926908-04-5 |
| Hydroxamate | HPOB | 1429651-50-2 |
| Hydroxamate | ITF2357 | 497833-27-9 |
| Hydroxamate | ITF2357 (Givinostat) | 497833-27-9 |
| Hydroxamate | LAQ-824 | 591207-53-3 |
| Hydroxamate | LBH-589 (panobinostat) | 404950-80-7 |
| Hydroxamate | LMK235 | 1418033-25-6 |
| Hydroxamate | M344 | 251456-60-7 |
| Hydroxamate | MC 1568 | 852475-26-4 |
| Hydroxamate | Nexturastat A | 1403783-31-2 |
| Hydroxamate | NSC 57457 | 6953-61-3 |
| Hydroxamate | Oxamflatin | 151720-43-3 |
| Hydroxamate | PCI-24781 (Abexinostat) | 783355-60-2 |
| Hydroxamate | PCI-34051 | 950762-95-5 |
| Hydroxamate | PDX-101 (belinostat) | 866323-14-0 |
| Hydroxamate | Pyroxamide | 382180-17-8 |
| Hydroxamate | SAHA (Zolinza, vorinostat) | 149647-78-9 |
| Hydroxamate | SB939 (Pracinostat) | 929016-96-6 |
| Hydroxamate | SBHA | 38937-66-5 |
| Hydroxamate | Scriptaid | 287383-59-9 |
| Hydroxamate | Tefinostat (CHR-2845) | 914382-60-8 |
| Hydroxamate | Trichostatin A (TSA) | 58880-19-6 |
| Hydroxamate | Tubacin | 537049-40-4 |
| Hydroxamate | Tubastatin A | 1252003-15-8 |
| Hydroxamate | VAHA | 106132-78-9 |
| Ketone | Compound 43 | 891259-76-0 |
| Ketone - a-ketoamides | 436150-82-2 | 436150-82-2 |
| Ketone - CF3 | Compound 27 | 946499-86-1 |
| Ketone - CF3 | Compound 6e | 946500-31-8 |
| Ketone - CF3 | Compound 6H | 946500-39-6 |
| Non classical | Tasquinimod | 254964-60-8 |
| Non classical | TMP269 | 1314890-29-3 |
| Polyketide | Ratjadone A | 163564-92-9 |
| Silylalcohol | 1587636-32-5 | 1587636-32-5 |
| Sulphonamide | 1587636-33-6 | 1587636-33-6 |
| Sulphonamide | 329967-25-1 | 329967-25-1 |
| Sulphonyl Urea | 960130-17-0 | 960130-17-0 |
| Thioester | HDAC Inhibitor XXII | 848354-66-5 |
| Thioester | KD 5170 | 940943-37-3 |
| Thioester | PTACH | 848354-66-5 |
| Thioester | TCS HDAC6 20b | 956154-63-5 |
| Thioketone | SIRT1/2 Inhibitor VII | 143034-06-4 |
| Thiol | 1368806-68-1 | 1368806-68-1 |
| Thiol | 1428536-05-3 | 1428536-05-3 |
| Thiol | 827036-76-0 | 827036-76-0 |
| Thiol | 828920-13-4 | 828920-13-4 |
| Thiol | 908860-21-9 | 908860-21-9 |
| Tropones | 1411673-95-4 | 1411673-95-4 |
| Tropones | 46189-88-2 | 46189-88-2 |

In some embodiments the HDAC inhibitor is a class I HDAC inhibitor. In these embodiments, the class I HDAC inhibitor may be a short chain carboxylic acid. In a preferred embodiment, the HDAC inhibitor is valproic acid (VPA), 2-hexyl-4-pentynoic acid, or Na phenylbutyrate. More preferably, the HDAC inhibitor is valproic acid (VPA).

As used herein the terms "valproic acid", "VPA" and "sodium valproate" are used interchnagably to refer to the same compound.

Methods of Use

In certain embodiments, the present disclosure relates to inducing, promoting, or enhancing the growth, proliferation or regeneration of inner ear tissue, particularly inner ear supporting cells and hair cells. Some embodiments relate to methods for controlled proliferation of stem cells comprising an initial phase of inducing stemness while inhibiting differentiation and a subsequent phase of differentiation of the stem cells into tissue cells.

When cochlear supporting cell or vestibular supporting cell populations are treated with a hair cell regeneration agent in accordance to the methods of the invention, whether the population is in vivo or in vitro, the treated supporting cells exhibit stem-like behavior in that the treated supporting cells have the capacity to proliferate and differentiate and, more specifically, differentiate into cochlear hair cells or vestibular hair cells. In some instances, an agent induces and maintains the supporting cells to produce daughter stem cells that can divide for many generations and maintain the ability to have a high proportion of the resulting cells differentiate into hair cells. In certain embodiments, the proliferating stem cells express stem cell marker(s) selected from one or more of Lgr5, Sox2, Opem1, Phex, lin28, Lgr6, cyclin D1, Msx1, Myb, Kit, Gdnf3, Zic3, Dppa3, Dppa4, Dppa5, Nanog, Esrrb, Rex1, Dnmt3a, Dnmt3b, Dnmt31, Utf1, Tcl1, Oct4, Klf4, Pax6, Six2, Zic1, Zic2, Otx2, Bmi1, CDX2, STAT3, Smad1, Smad2, smad2/3, smad4, smad5, and smad7. Preferably, the proliferating stem cells express stem cell marker(s) selected from one or more of Lgr5, the In some embodiments, the methods may be used to maintain, or even transiently increase stemness (i.e., self-renewal) of a pre-existing supporting cell population prior to significant hair cell formation. In some embodiments, the pre-existing supporting cell population comprises inner pillar cells, outer pillar cells, inner phalangeal cells, Deiter cells, Hensen cells, Boettcher cells, and/or Claudius cells. Morphological analyses with immunostaining (including cell counts) and lineage tracing across a Representative Microscopy Samples may be used to confirm expansion of one or more of these cell-types. In some embodiments, the pre-existing supporting cells comprise Lgr5+ cells. Morphological analyses with immunostaining (including cell counts) and qPCR and RNA hybridization may be used to confirm Lgr5 upregulation amongst the cell population.

Advantageously, methods described herein can achieve these goals without the use of genetic manipulation. Germ-line manipulation used in many academic studies is not a therapeutically desirable approach to treating hearing loss. In general, the therapy preferably involves the administration of a small molecule, peptide, antibody, or other non-nucleic acid molecule or nucleic acid delivery vector unaccompanied by gene therapy. In certain embodiments, the therapy involves the administration of a small organic molecule. In some instances, hearing protection or restoration is achieved through the use of a (non-genetic) therapeutic that is injected in the middle ear and diffuses into the cochlea.

The cochlea relies heavily on all present cell types, and the organization of these cells is important to their function. As supporting cells play an important role in neurotransmitter cycling and cochlear mechanics. Thus, maintaining a rosette patterning within the organ of Corti may be important for function. Cochlear mechanics of the basilar membrane activate hair cell transduction. Due to the high sensitivity of cochlear mechanics, it is also desirable to avoid masses of cells. In all, maintaining proper distribution and relation of hair cells and supporting cells along the basilar membrane, even after proliferation, is likely a desired feature for hearing as supporting cell function and proper mechanics is necessary for normal hearing.

In some embodiments, the cell density of hair cells in a cochlear cell population is expanded in a manner that maintains, or even establishes, the rosette pattern characteristic of cochlear epithelia.

In certain embodiments, the cell density of hair cells is increased in a population of cochlear cells comprising both hair cells and supporting cells. The cochlear cell population may be an in vivo population (i.e., comprised by the cochlear epithelium of a subject) or the cochlear cell population may be an in vitro (ex vivo) population. If the population is an in vitro population, the increase in cell density may be determined by reference to a Representative Microscopy Sample of the population taken prior and subsequent to any treatment. If the population is an in vivo population, the increase in cell density may be determined indirectly by determining an effect upon the hearing of the subject with an increase in hair cell density correlating to an improvement in hearing.

In some embodiments, supporting cells placed in a Stem Cell Proliferation Assay in the absence of neuronal cells form ribbon synapses.

In a native cochlea, patterning of hair cells and supporting cells occurs in a manner parallel to the basilar membrane. In some embodiments, the proliferation of supporting cells in a cochlear cell population is expanded in a manner that the basilar membrane characteristic of cochlear epithelia.

In some embodiments, the number of supporting cells in an initial cochlear cell population is selectively expanded by treating the initial cochlear cell population with a composition of the present disclosure to form an intermediate cochlear cell population, wherein the ratio of supporting cells to hair cells in the intermediate cochlear cell population exceeds the ratio of supporting cells to hair cells in the initial cochlear cell population. The expanded cochlear cell population may be, for example, an in vivo population, an in vitro population or even an in vitro explant. In some embodiments, the ratio of supporting cells to hair cells in the intermediate cochlear cell population exceeds the ratio of supporting cells to hair cells in the initial cochlear cell population. For example, in some embodiments, the ratio of supporting cells to hair cells in the intermediate cochlear cell population exceeds the ratio of supporting cells to hair cells in the initial cochlear cell population by a factor of 1.1, 1.5, 2, 3, 4, 5 or more. In some instances, the capacity of a composition to expand a cochlear cell population is be determined by means of a Stem Cell Proliferation Assay.

In some embodiments, the number of stem cells in a cochlear cell population is expanded to form an intermediate cochlear cell population by treating a cochlear cell population with a composition of the present disclosure wherein the cell density of stem cells in the intermediate cochlear cell population exceeds the cell density of stem cells in the initial cochlear cell population. The treated cochlear cell population may be, for example, an in vivo population, an in vitro population or even an in vitro explant. In one such embodiment, the cell density of stem cells in the treated cochlear cell population exceeds the cell density of stem cells in the initial cochlear cell population by a factor of at least 1.1, 1.25, 1.5, 2, 3, 4, 5 or more. In vitro cochlear cell populations may expand significantly more than in vivo populations; for example, in certain embodiments the cell density of stem cells in an expanded in vitro population of stem cells may be at least 4, 5, 6, 7, 8, 9, 10, 15, 20, 25, 30, 35, 40, 45, 50, 75, 100, 200, 300, 400, 500, 600, 700, 800, 900, 1000, 2000 or even 3000 times greater than the cell density of the stem cells in the initial cochlear cell population. In some instances, the capacity of a composition to expand a cochlear cell population is determined by means of a Stem Cell Proliferation Assay.

In some embodiments, a cochlear supporting cell population or a vestibular supporting cell population is treated with a hair cell regeneration agent of the present disclosure to increase the Lgr5 activity of the population. For example, in some instances a Jag-1 agonist, a Deltex-1 agonist or a non-canonical Notch signaling agonist.

has the capacity to increase and maintain the Lgr5 activity of an in vitro population of cochlear supporting cells or vestibular supporting cells by factor of at least 1.2, 1.5, 2, 3, 4, 5, or more. In some embodiments, the Jag-1 agonist, the Deltex-1 agonist or the non-canonical Notch signaling agonist.

has the capacity to increase the Lgr5 activity of an in vitro population of cochlear supporting cells or vestibular supporting cells by factor of 2, 3, 5 10, 100, 500, 1000, 2000 or even 3000. Increases in Lgr5 activity may also be observed for in vivo populations but the observed increase may be less than in vitro populations. In some instances, of the Jag-1 agonist, the Deltex-1 agonist and/or the non-canonical Notch signaling agonist and a Wnt agonist inhibitor has the capacity to increase the Lgr5 activity of an in vivo population of cochlear supporting cells or vestibular supporting cells by about or at least about 5%, 10%, 20%, 30% or more. In some instances, the capacity of the Jag-1 agonist, the Deltex-1 agonist or the non-canonical Notch signaling agonist for such an increase in Lgr5 activity is demonstrated, for example, in an In Vitro Lgr5+ Activity Assay, and in an in vivo population is demonstrated, for example, in an In Vivo Lgr5+ Activity Assay, as measured by isolating the organ and performing morphological analyses using immunostaining, endogenous fluorescent protein expression of Lgr5, and qPCR for Lgr5.

In some embodiments, the Jag-1 agonist, the Deltex-1 agonist and/or the non-canonical Notch signaling agonist in combination with a has the capacity to increase the Lgr5 Activity of an in vitro population of cochlear supporting cells or vestibular supporting cells by a factor of 10, 20, 30, 40, 50, 75, 100 or 200% compared to a Wnt agonist alone as measured for example in an In Vitro Lgr5+ Activity Assay.

In some embodiments, the Jag-1 agonist, the Deltex-1 agonist or the non-canonical Notch signaling agonist has the capacity to increase the Lgr5 proliferation of an in vitro population of cochlear supporting cells or vestibular supporting cells by factor of 10, 20, 30, 40, 50, 75, or 100% compared to a Wnt agonist alone as measured for example in a in a in a Stem Cell Proliferation Assay.

In some embodiments, the Jag-1 agonist, the Deltex-1 agonist and/or the non-canonical Notch signaling agonist has the capacity to increase the Lgr5 proliferation of an in vitro population of cochlear supporting cells or vestibular supporting cells by factor of 10, 20, 30, 40, 50, 75, or 100% compared to a Wnt agonist in combination with VPA as measured for example in a in a in a Stem Cell Proliferation Assay.

In addition to increasing the Lgr5 activity of the population, the number of Lgr5+ supporting cells in a cochlear or vestibular cell population may be increased by treating a cochlear or vestibular cell population containing Lgr5+ supporting cells (whether in vivo or in vitro) with a hair cell rejeneration agent of the present disclosure. In general, the cell density of the stem/progenitor supporting cells may expand relative to the initial cell population via one or more of several mechanisms. For example, in some embodiments, newly generated Lgr5+ supporting cells may be generated that have increased stem cell propensity (i.e., greater capacity to differentiate into hair cell). By way of further example, in some embodiments no daughter Lgr5+ cells are generated by cell division, but pre-existing Lgr5+ supporting cells are induced to differentiate into hair cells. By way of further example, in some embodiments no daughter cells are generated by cell division, but Lgr5-supporting cells are activated to a greater level of Lgr5 activity and the activated supporting cells are then able to differentiate into hair cells. Regardless of the mechanism, in some embodiment a hair cell regeneration agent of the present disclosure has the capacity to increase the cell density of Lgr5+ supporting cells in an in vitro isolated cell population of cochlear supporting cells or vestibular supporting cells by factor of at least 5, 10, 50, 100, 500, 1000, or 2000. Increases in the cell density of Lgr5+ supporting cells may also be observed for in vivo populations but the observed increase may be somewhat more modest. For example, in some embodiments the composition has the capacity to increase the cell density of Lgr5+ supporting cells in an in vivo population of cochlear supporting cells or vestibular supporting cells by about or at least about 5%, 10%, 20%, 30% or more. The capacity of the composition (for such an increase in Lgr5+ supporting cells in an in vitro population may be demonstrated, for example, in a Stem Cell Proliferation Assay or in an appropriate in vivo assay. In some embodiments, a composition of the present disclosure has the capacity to increase the number of Lgr5+ cells in the cochlea by inducing expression of Lgr5 in cells with absent or low detection levels of the protein, while maintaining Native Morphology. In some embodiments, a composition has the capacity to increase the number of Lgr5$^+$ cells in the cochlea or vestibular organ by inducing expression of Lgr5 in cells with absent or low detection levels of the protein, while maintaining Native Morphology and without producing Cell Aggregates.

Included in the invention are methods of increasing proliferation of a Lgr5+ cochlear supporting cell by contacting a cochlear supporting cell with a Jag-1 agonist, a Deltex-1 agonist and/or a non-canonical Notch signaling agonist. In some embodiments the cell is further contacted with a Jag-1 synergist or a Deltex synergist and/or a Wnt agonist. Optionally, the cell is further contacted with an epigenetic agent such as an HDAC inhibitor. Preferably, the HDAC inhibitor is VPA.

Included in the invention are methods of increasing proliferation of a vestibular supporting cell by contacting a vestibular supporting cell with a Jag-1 agonist, a Deltex-1 agonist and/or a non-canonical Notch signaling agonist. In some embodiments the cell is further contacted with a Jag-1 synergist or a Deltex synergist and/or a Wnt agonist. Optionally, the cell is further contacted with an epigenetic agent such as an HDAC inhibitor. Preferably, the HDAC inhibitor is VPA.

In the various methods Lgr5+ cochlear cell or vestibular cell proliferation is increased compared to a vehicle control.

In some embodiments, the Jag-1 agonist, the Deltex-1 agonist or the non-canonical Notch signaling agonist increases Lgr5+ cochlear supporting cell or vestibular supporting cell proliferation by at least 10, 20, 30, 40, 50, 60, 70, 80, 90, 100, 150, 200, 250, 300, 350, 400, 450, or 500% or more (or at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more), relative to a vehicle control.

In some embodiments, the Jag-1 agonist, the Deltex-1 agonist or the non-canonical Notch signaling agonist in combination with an additional agent as described herein increases Lgr5+ cochlear supporting cell or vestibular supporting cell proliferation by at least 10, 20, 30, 40, 50, 60, 70, 80, 90, 100, 150, 200, 250, 300, 350, 400, 450, or 500% more (or at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more) relative to a Wnt agonist alone in a Stem Cell Proliferation Assay.

In some embodiments, the Jag-1 agonist, the Deltex-1 agonist or the non-canonical Notch signaling agonist in combination with an additional agent as described herein increases Lgr5+ cochlear supporting cell or vestibular supporting cell proliferation by at least 10, 20, 30, 40, 50, 60, 70, 80, 90, 100, 150, 200, 250, 300, 350, 400, 450, or 500% more (or at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more) relative to Wnt agonist in combination with VPA in a Stem Cell Proliferation Assay.

Also included are methods for expanding a population of cochlear cells in a cochlear tissue comprising a parent population of cells by contacting the cochlear tissue with a Jag-1 agonist, a Deltex-1 agonist and or a non-canonical Notch signaling agonist to form an expanded population of cells in the cochlear tissue. In some embodiments the cell is further contacted with a Jag-1 synergist or a Deltex synergist and/or a Wnt agonist. Optionally, the cell is further contacted with an epigenetic agent such as an HDAC inhibitor such as a class I HDAC inhibitor In some embodiment, the class I HDAC inhibitor is a short chain carboxylic acid such as for example, valproic acid (VPA).

The invention also includes methods of producing an expanded population of Lgr5+ cochlear cells by contacting the cell population with a Jag-1 agonist, a Deltex-1 agonist and or a non-canonical Notch signaling agonist to form an expanded population of cells in the cochlear tissue. In some embodiments the cell is further contacted with a Jag-1 synergist or a Deltex synergist and/or a Wnt agonist. a Jag-1 agonist, a Deltex-1 agonist and or a non-canonical Notch signaling agonist The expanded population is capable of differentiating into hair cells as measured in a stem cell differentiation assay.

The Jag-1 agonist, the Deltex-1 agonist and/or the non-canonical Notch signaling agonist (optionally in combination with an additional) is capable of (i) forming a proliferation assay final cell population from a proliferation assay initial cell population over a proliferation assay time period in a stem cell proliferation assay, and/or (ii) forming a differentiation assay final cell population from a differentiation assay initial cell population over a differentiation assay time period in a stem cell differentiation assay wherein: (a) the proliferation assay initial cell population has (i) a proliferation assay initial number of total cells, (ii) a proliferation assay initial number of Lgr5+ cells, (iii) a proliferation assay initial number of hair cells, (iv) a proliferation assay initial Lgr5+ cell fraction that equals the ratio of the proliferation assay initial number of Lgr5+ cells to the proliferation assay initial number of total cells, and (v) a proliferation assay initial hair cell fraction that equals the ratio of the proliferation assay initial number of hair cells to the proliferation assay initial number of total cells; (b) the proliferation assay final cell population has (i) a proliferation assay final number of total cells, (ii) a proliferation assay final number of Lgr5+ cells, (iii) a proliferation assay final number of hair cells, (iv) a proliferation assay final Lgr5+ cell fraction that equals the ratio of the proliferation assay final number of Lgr5+ cells to the proliferation assay final number of total cells and (v) a proliferation assay final hair cell fraction that equals the ratio of the proliferation assay final number of hair cells to the proliferation assay final number of total cells; (c) the differentiation assay initial cell population has (i) a differentiation assay initial number of total cells, (ii) a differentiation assay initial number of Lgr5+ cells, (iii) a differentiation assay initial number of hair cells, (iv) a differentiation assay initial Lgr5+ cell fraction that equals the ratio of the differentiation assay initial number of Lgr5+ cells to the differentiation assay initial number of total cells, and (v) a differentiation assay initial hair cell fraction that equals the ratio of the differentiation assay initial number of hair cells to the differentiation assay initial number of total cells; (d) the differentiation assay final cell population has (i) a differentiation assay final number of total cells, (ii) a differentiation assay final number of Lgr5+ cells, (iii) a differentiation assay final number of hair cells, (iv) a differentiation assay final Lgr5+ cell fraction that equals the ratio of the differentiation assay final number of Lgr5+ cells to the differentiation assay final number of total cells, and (v) a differentiation assay final hair cell fraction that equals the ratio of the differentiation assay final number of hair cells to the differentiation assay final number of total cells; (e) the proliferation assay final number of Lgr5+ cells exceeds the proliferation assay initial number of Lgr5+ cells by a factor of at least 10; and/or (f) the differentiation assay final number of hair cells is a non-zero number.

The expanded population is capable of differentiating into hair cells as measured in a stem cell differentiation assay.

In some embodiments, the cochlear cell is in a cochlear tissue. In some embodiments, the cochlear tissue is in a subject.

Some embodiments relate to methods of treating a subject who has, or is at risk for developing, hearing loss or reduced auditory function. The prophylaxis and/or treatment of acute and chronic ear disease and hearing loss, dizziness and balance problems especially of sudden hearing loss, acoustic trauma, hearing loss due to chronic noise exposure, presbycusis, trauma during implantation of the inner ear prosthesis (insertion trauma), dizziness due to diseases of the inner ear area, dizziness related and/or as a symptom of Meniere's disease, vertigo related and/or as a symptom of Meniere's disease, tinnitus, hyperacusis and hearing loss due to antibiotics and cytostatics and other drugs.

In some embodiments the hearing loss is senorineural hearing loss or hidden hearing loss.

Sensorineural hearing loss accounts for approximately 90% of hearing loss and it often arises from damage or loss of hair cells in the cochlea. There are numerous causes of hair cell damage and loss, and the agents and treatments described herein may be used in the context of sensorineural hearing loss arising from any cause of hair cell damage or loss. For example, hair cells may be damage and loss may be induced by noise exposure, leading to noise-induced sensorineural hearing loss. Thus, in some embodiments sensorineural hearing loss is noise-induced sensorineural hearing loss. Noise-induced sensorineural hearing loss can be a result of chronic noise exposure or acute noise exposure. Ototoxic drugs, for example cisplatin and its analogs, aminoglycoside antibiotics, salicylate and its analogs, or loop diuretics, can also cause sensorineural hearing loss. In some embodiments sensorineural hearing loss is drug-induced sensorineural hearing loss. Infection may damage cochlear hair cells, and may be a cause of sudden sensorineural hearing loss. In some embodiments sensorineural hearing loss is sudden sensorineural hearing loss (SSNHL). Sudden sensorineural hearing can also be idiopathic. Hair cells can also be lost or damaged over time as part of the ageing process in humans. In some embodiments, sensorineural hearing loss is age-related sensorineural hearing loss (also known as presbycusis).

A patient with hidden hearing loss has a difficulty hearing in noisy environments but does not have sensorineural hearing loss when assessed at standard audiometric frequencies (and so has a normal audiogram). A patient with hidden hearing loss therefore has normal hearing function in terms of audibility but reduced intelligibility function. The reduced intelligibility function may become apparent when the patient is presented with background noise.

Some embodiments include methods to prevent, reduce, or treat the incidence and/or severity of inner ear disorders and hearing impairments involving inner ear tissue, particularly inner ear hair cells, their progenitors, and optionally, the stria vascularis, and associated auditory nerves. Of particular interest are those conditions that lead to permanent hearing loss where reduced number of hair cells may be responsible and/or decreased hair cell function.

Hearing loss or reduced auditory function is treated or prevented in a subject by contacting a Lgr5+ cochlear cell or administering to the subject a Jag-1 agonist, a Deltex-1 agonist and or a non-canonical Notch signaling agonist form an expanded population of cells in the cochlear tissue. In some embodiments the cell is further contacted with a Jag-1 synergist or a Deltex synergist and/or a Wnt agonist. Optionally, the cell is further contacted with an epigenetic agent such as an HDAC inhibitor such as a class I HDAC inhibitor In some embodiment, the class I HDAC inhibitor is a short chain carboxylic acid such as for example, valproic acid (VPA).

Effective treatment of hearing loss may be determined using different criteria. These criteria can be categorized as either improvements in sound audibility or improvements in sound intelligibility or both. An improvement in audibility function means that the patient has an improved ability to detect when a sound is present or absent. In other words, an improvement in audibility means that the patient is able to detect the presence of a quieter sound. An improvement in sound intelligibility means that the patient has improved ability to correctly identify a sound. In some embodiments, the treatment provides the patient with improved audibility function. In some embodiments, the treatment provides the patient with improved intelligibility function. In some embodiments, the treatment provides the patient with improved audibility function and improved intelligibility function.

An improvement in audibility function may be associated with an improvement in intelligibility function. For example, in these situations, the patient may be able to detect the sound of a word more easily, and correctly identify the word. However, in other situations, an improvement in audibility may not be associated with an improvement in intelligibility. In these situations, a patient may now be able to hear a word, but unable to correctly identify the word. An improvement in audibility is nevertheless advantageous as it may allow a patient to hear sounds that were previously inaudible to the patient.

In other situations, a patient may experience little or no change in audibility function as measured by standard audiometry tests yet nonetheless experience an improvement in intelligibility function following treatment. For example, in these situations a patient may be able to detect the presence of a word stimulus at the same sound level as prior to the treatment, but is now able to correctly identify the word, whereas prior to the treatment the word was incorrectly identified. An improvement in intelligibility is an important therapeutic benefit because as a result a patient may be able to understand more sounds in a real world situation. Thus, in preferred embodiments, the treatment provides the patient with improved intelligibility function. In some situations, a patient may experience little or no change in audibility function as measured by standard audiometry tests but nonetheless an improvement in audibility function is observed at the ultra-high frequencies.

Improvements in audibility may be measured using pure tone audiometry as described herein. However an improvement in audibility does not necessarily need to be measured in order for an improvement to be provided by the treatment. Similarly, an improvement in intelligibility may be measured using word recognition tests as described herein. However an improvement in intelligibility does not necessarily need to be measured in order for an improvement to be provided by the treatment. The treatments described herein may be used to provide an improvement in hearing function without measurement of hearing function before and after the treatment.

The treatments described herein may be particularly effective at improving audibility function at high frequencies. Thus, in some embodiments, the treatment provides an improved hearing threshold at 4 kHz, 6 kHz, and/or 8 kHz. This improvement may be observed as a reduced pure tone threshold at 4 kHz, 6 kHz, and/or 8 kHz, when measured by pure tone audiometry. In some embodiments, the patient has a reduced pure tone threshold at 4 kHz after treatment relative to the patient's pure tone threshold prior to treatment. In some embodiments, the patient has a reduced pure tone threshold at 6 kHz after treatment relative to the patient's pure tone threshold prior to treatment. In some embodiments, the patient has a reduced pure tone threshold at 8 kHz after treatment relative to the patient's pure tone threshold prior to treatment.

In some embodiments the improved hearing threshold at 4 kHz, 6 kHz, and/or 8 kHz is at least 5 dB relative to the patient's hearing threshold at 4 kHz, 6 kHz and/or 8 kHz prior to the treatment. In some embodiments the improved hearing threshold at 4 kHz, 6 kHz, and/or 8 kHz is at least 10 dB relative to the patient's hearing threshold at 4 kHz, 6 kHz and/or 8 kHz prior to the treatment. In some embodiments the improved hearing threshold at 4 kHz, 6 kHz, and/or 8 kHz is at least 20 dB relative to the patient's hearing threshold at 4 kHz, 6 kHz and/or 8 kHz prior to the treatment. In some embodiments the improved hearing threshold at 4 kHz, 6 kHz, and/or 8 kHz is at least 30 dB relative to the patient's hearing threshold at 4 kHz, 6 kHz and/or 8 kHz prior to the treatment.

In a preferred embodiment, the treatment provides an improved hearing threshold of at least 5 dB at 8 kHz relative to a patient's hearing threshold at 8 kHz prior to the treatment, when measured by pure tone audiometry.

In a preferred embodiment, the treatment provides an improved hearing threshold of at least 5 dB at 6 kHz relative to a patient's hearing threshold at 6 kHz prior to the treatment, when measured by pure tone audiometry.

In a particularly preferred embodiment, the treatment provides an improved hearing threshold of at least 5 dB at 6 kHz and 8 kHz relative to a patient's hearing threshold at 6 kHz and 8 kHz prior to the treatment, when measured by pure tone audiometry.

In some embodiments, the improvement in audibility is assessed using the average of the patient's pure tone thresholds when measured across 4 kHz, 6 kHz and 8 kHz. In certain embodiments, the treatment provides an improvement to the average of the patient hearing thresholds across 4 kHz, 6 kHz and 8 kHz when measured by pure tone audiometry, wherein said improvement is at least 1, 2, 3, 4, 5, 6, 7, 8, 9, 10, 12, 15, 20, 25, 30 dB relative to the average of the patient hearing thresholds across 4 kHz, 6 kHz and 8 kHz when measured by pure tone audiometry prior to the treatment.

Improvements in audibility function may be observed in an individual patient, or as an average across a population of patients.

Improvements in intelligibility may be measured using word recognition tests as described herein.

In some embodiments, improvement in intelligibility is measured using a standard word recognition score, as described herein. Alternatively, or in addition to, improvement in intelligibility may be measured using a words-in-noise test, as described herein.

The treatments described herein may be effective at improving intelligibility of words when assessed using a standard word recognition test. Accordingly, in some embodiments, the treatment provides an improved standard word recognition score, wherein said improvement is at least 10%, at least 20%, at least 30%, at least 50%, at least 70%, at least 100%, wherein said percentage improvement is calculated using the following formula:

$$100 \times \left( \frac{\text{patient's word recognition score after treatment}}{\text{patient's word recognition score prior to treatment}} - 1 \right)$$

In a preferred embodiment, the improved word recognition score is at least 10% wherein said percentage improvement is calculated using the following formula:

$$100 \times \left( \frac{\text{patient's word recognition score after treatment}}{\text{patient's word recognition score prior to treatment}} - 1 \right)$$

A standard word recognition test of 50 words may be used to assess hearing function. In some embodiments, the treatment provides an improved standard word recognition for the patient, wherein said improvement, if tested, would be at least 5, at least 10, at least 15 words relative to the number of words recognized by the patient in a standard word recognition test of 50 words prior to the treatment.

In a preferred embodiments, the treatment provides an improved standard word recognition for the patient, wherein said improvement, if tested, would be at least 5 words relative to the number of words recognized by the patient in a standard word recognition test of 50 words prior to the treatment.

The treatments described herein are particularly effective at improving intelligibility of sounds in background noise. Thus, in some embodiments, the treatment provides an improved words-in-noise score for the patient, wherein said improvement is at least 10%, at least 20%, at least 30%, at least 50%, at least 70%, at least 100%, wherein said percentage improvement is calculated using the following formula:

$$100 \times \left( \frac{\text{patient's words in noise score after treatment}}{\text{patient's words in noise score prior to treatment}} - 1 \right)$$

In a preferred embodiment, the improved words-in-noise score is at least 10% wherein said percentage improvement is calculated using the following formula:

$$100 \times \left( \frac{\text{patient's words in noise score after treatment}}{\text{patient's words in noise score prior to treatment}} - 1 \right)$$

A words-in-noise test of 70 words may be used to assess hearing function. Accordingly, in some embodiments, the treatment provides improved words-in-noise recognition for the patient, wherein said improvement, if tested, would be at least 5, at least 7, at least 10 words relative to the number of words recognized by the patient in a words-in-noise test of 70 words prior to the treatment.

In a preferred embodiments, the treatment provides an improved words-in-noise recognition for the patient, wherein said improvement, if tested, would be at least 5 words relative to the number of words recognized by the patient in a words-in-noise test of 70 words prior to the treatment.

A words-in-noise test of 35 words may be used to assess hearing function. Thus, in some embodiments, the treatment provides improved words-in-noise recognition for the patient, wherein said improvement, if tested, would be at least 2, at least 3, at least 5 words relative to the number of words recognized by the patient in a words-in-noise test of 35 words prior to the treatment.

In a preferred embodiment, the treatment provides improved words-in-noise recognition for the patient, wherein said improvement, if tested, would be at least 2 words relative to the number of words recognized by the patient in a words-in-noise test of 35 words prior to the treatment.

An improvement in words-in-noise score may be seen without a corresponding improvement in audibility function. Accordingly, in some embodiments, the treatment provides an improved words-in-noise score without a change in audibility function when measured by pure tone audiometry. In certain such embodiments, the average of the patient's hearing thresholds across 0.5 kHz, 1 kHz, 2 kHz and 4 kHz after the treatment is no more than 5 dB increased or decreased to the average of the patient's hearing thresholds across 0.5 kHz, 1 kHz, 2 kHz and 4 kHz prior to the treatment, wherein said hearing thresholds are measured by pure tone audiometry.

In a preferred embodiment, the treatment provides (i) an improved hearing threshold at 8 kHz, wherein said improvement, if tested, would be at least 5 dB relative to the patient's hearing threshold at 8 kHz prior to the treatment, wherein said hearing threshold is measured by pure tone audiometry and (ii) an improved standard word recognition score for the patient or an improved words-in-noise score for the patient, wherein said improvement in standard word recognition score, if tested, would be at least 10%, wherein said percentage improvement is calculated using the following formula:

$$100 \times \left( \frac{\text{patient's word recognition score after treatment}}{\text{patient's word recognition score prior to treatment}} - 1 \right)$$

wherein said improvement in words-in-noise score, if tested, would be at least 10%, wherein said percentage improvement is calculated using the following formula:

$$100 \times \left( \frac{\text{patient's words in noise score after treatment}}{\text{patient's words in noise score prior to treatment}} - 1 \right)$$

In certain such embodiments, the treatment also provides an improved hearing threshold at 6 kHz, wherein said improvement, if tested, would be at least 5 dB relative to the patient's hearing threshold at 6 kHz prior to the treatment.

Improvement in sound intelligibility may be particularly relevant in the context of treating two patient groups that have normal audibility function but reduced intelligibility function. These two groups are (i) patients with hidden hearing loss, and (ii) patients having hearing thresholds within normal ranges (i.e. up to 25 dB) at standard audiometric frequencies (0.25 kHz-8 kHz) yet have difficulty in perceiving sound correctly. These patients typically show reduced function in a words-in-noise test. Thus, for patients in either of these patient groups, an effective treatment manifests in an improved intelligibility function. An improvement in audibility function may also be observed. Without wishing to be bound by theory, the improvement in words-in-noise score may arise due to the treatment providing an improvement in the ultra-high frequency range.

The inventors have found that an improvement in audibility function and/or intelligibility function may be observed shortly after treatment. In some embodiments, the treatment provides an improvement in audibility function and/or intelligibility function within 15, 30, 60 or 90 days. In a preferred embodiment, an improvement in audibility function and/or intelligibility function is provided within 90 days.

The improvement in audibility function and/or intelligibility function may be maintained following treatment. In some embodiments, the improvement is maintained until at least 90, 120, 180 or 365 days. In certain embodiments, the improvement is maintained until at least 90 days. In certain embodiments, the improvement is maintained until at least 120 days. In certain embodiments, the improvement is maintained until at least 180 days. In certain embodiments, the improvement is maintained until at least 365 days.

In various embodiments, a Jag-1 agonist, a Deltex-1 agonist and or a non-canonical Notch signaling agonist and optionally, the one or more additional agents, as described herein are administered to the subject systemically or locally.

Systemic administration includes, but is not limited, to oral or parenteral administration. Parenteral routes include for example intramuscular (IM), subcutaneous (SC) and intravenous (IV). Local administration is for example, is administration to the inner ear and/or middle ear. More specifically, local administration to the round window membrane or intratympanic or transtympanic administration, for example, to cochlear tissue. More specific methods of local delivery are described herein.

Hearing loss or reduced auditory function is treated or prevented utilizing the various methods described herein to increase Lgr5+ cochlear cell proliferation. The cochlear cell is contacted with the Jag-1 agonist, the Deltex-1 agonist and or the non-canonical Notch signaling agonist at a "cell effective concentration" to form an expanded population of cells in the cochlear tissue. Optionally, the cell is further contacted with one or more additional agents, as described herein.

A "cell effective concentration" is the minimum concentration of the compound that induces at least an 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more in gene expression and/or about a 1.5-fold increase in number of Lgr5+ cells in a Stem Cell Proliferation Assay compared to a vehicle control.

In some embodiments, the Lgr5+ cochlear cell is contacted in vitro with the compound(s) at the "cell effective concentration", such as for example, in a cell culture (and then implanted into the cochlea). In other embodiments, the Lgr5+ cochlear cell is contacted with the compound(s) at the "cell effective concentration", in situ (i.e., within the cochlea). In some embodiments, sufficient compound is delivered the achieve the "cell effective concentration" throughout the speech region of the human cochlea. In order to achieve this target concentration, a higher concentration of drug may be instilled in the cochlea and diffuse throughout the speech region. In other embodiments, the Lgr5+ cochlear cell is contacted with the compound(s) at 2, 3, 4, 5, 10, 20, 50, 100, 200, 300, 400, 500, 600, 700, 800, 900, 1000-fold more than the "cell effective concentration", in situ (i.e., within the cochlea).

Alternatively, hearing loss or reduced auditory function is treated by administering the compound(s) at the "formulation effective concentration". A "formulation effective concentration" is a higher concentration than the "cell effective formulation". For example, the "formulation effective concentration" is at least about 100 to 5000 fold higher than the "cell effective concentration", or about 100, 250, 500, 750, 1000, 1250, 1500, 1750, 2000 fold higher than the "cell effective concentration", or about 100, 200, 300, 400, 500, 600, 700, 800, 900 or 1000 fold higher than the "cell effective concentration". Typically, the "formulation effective concentration" is at least about 1000 fold higher than the "cell effective concentration".

Alternatively, hearing loss or reduced auditory function is treated by administering the compound(s) at a set daily dose.

The compound(s) are formulated at the "cell effective concentration" and the "formulation effective concentration" as described supra.

In some embodiments, the "cell effective concentration" of the compound(s) is about 0.01 pM to 1000 nM, about 1 pM to 100 nM, about 10 pM to 10 nM, 1 nM to 1000 µM, about 10 nM to 100 µM, about 0.1 µM to 10 µM, about 1 µM to 1 mM, about 1 pM to 10 pM, about 10 pM to 100 pM, about 100 pM to 1 nM, about 1 nM to 10 nM, about 10 nM to 100 nM, about 100 nM to 1000 nM, about 1 µM to 10 µM, about 10 µM to 100 µM, about 100 µM to 1 mM, 1 mM to 10 mM, or about 10 mM to 100 mM.

In some embodiment the compound is administered to the subject systemically at a daily dose of about 0.01 mg to 1000 mg/day; about 0.01 mg to 500 mg/day; about 0.01 mg to 250 mg/day; about 0.01 mg to 100 mg/day; about 0.01 mg to 50 mg/day; about 0.01 mg to 25 mg/day; about 0.01 mg to 10 mg/day; about 0.01 mg to 5 mg/day; 0.1 mg to 100 mg/day; about 0.1 mg to 50 mg/day; about 0.1 mg to 25 mg/day; about 0.1 mg to 10 mg/day; about 0.1 mg to 5 mg/day; about 0.1 mg to 2.5 mg/day; about 0.1 mg to 10 mg/day; about 0.1 mg to 5 mg/day about 0.1 mg to 4 mg/day; about 0.1 mg to 3 mg/day; about 0.1 mg to 2 mg/day; about 0.1 mg to 2 mg/day or about 1 mg to 5 mg/day.

In some embodiments, compound is administered to the subject at a concentration ratio of about 0.001 to 100 fold relative to an FDA approved concentration or about 0.1 to 50 fold relative to an FDA approved concentration, or about 0.1 to 5 fold relative to an FDA approved, or about 1 to 5 fold relative to an FDA approved concentration. In some embodiments, compound administered to the subject at about 0.01×. about 0.1×, about 1×, about 2×, about 3×, about 5× or about 10×, relative to an FDA approved concentration.

In some embodiments, the JAG-1 agonist is administered for example to a cochlear cell in amount sufficient to achieve a concentration of about 1 nM to 1000 mM, 10 nM to 1000 mM, about 100 nM to 100 mM, about 1 uM to 10 mM, about 10 uM to 1 mM, about 1 nM to 10 nM, about 10 nM to 100 nM, about 0.1 uM to 1 uM, about 1 uM to 10 uM, about 10 uM to 100 uM, about 100 uM to 1000 uM, about 1 mM to 10 mM, or about 10 mM to 100 mM in the perilymph fluid in the inner ear.

Preferably, the JAG-1 agonist is administered in amount sufficient to achieve a concentration of about 0.01 uM to 1000 mM, about 0.1 uM to 100 mM, about 1 uM to 10 mM, about 10 uM to 1 mM, about 0.001 uM to 0.01 uM, about 0.01 uM to 0.1 uM, about 0.1 uM to 1 uM, about 1 uM to 10 uM, about 10 uM to 100 uM, about 100 uM to 1000 uM, about 1 mM to 10 mM, or about 10 mM to 100 mM, about 1 µM, about 2 µM, about 3 µM, about 4 µM, about 5 µM, about 6 µM, about 7 µM, about 8 µM, about 9 µM, or about 10 µM, in the perilymph fluid in the inner ear.

In some embodiments, the Jag-1 agonist is administered to a subject, for example to the middle ear at a concentration of about 1 uM to 1,000,000 mM, 10 uM to 100,000 mM, about 100 uM to 10,000 mM, about 1,000 uM to 1,000 mM, about 1 uM to 10 uM, about 10 uM to 100 uM, about 100 uM to 1,000 uM, about 1 mM to 10 mM, about 10 mM to 100 mM, about 100 mM to 1,000 mM, about 1,000 mM to 10,000 mM, about 10,000 mM to 100,000 mM or about 100,000 mM to 1,000,000 mM.

Preferably, the Jag-1 agonist is administered to a subject, for example to the middle ear at a concentration of about 100 uM, about 1 mM, about 2 mM, about 3 mM, about 4 mM, about 5 mM, about 6 mM, about 7 mM, about 8 mM, about 9 mM, about 10 mM or about 100 mM.

In some embodiments, Jag-1 agonist is administered to the subject at a concentration ratio of about 0.001 to 100 fold relative to an FDA approved concentration or about 0.1 to 50 fold relative to an FDA approved concentration, or about 0.1 to 5 fold relative to an FDA approved, or about 1 to 5 fold relative to an FDA approved concentration.

In some embodiments, the Jag-1 agonist is administered to the subject at about 0.01×. 0.1×, about 2×, about 3×, about 5× or about 10×, relative to an FDA approved concentration.

In some embodiments, the Jag-1 agonist is a soluble Jag-1 peptide, and is administered for example to a cochlear cell in amount sufficient to achieve a concentration of about 1 nM to 100 mM, about 10 nM to 10 mM, about 100 nM to 1 mM, about 1 nM to 10 nM, about 10 nM to 100 nM, about 100 nM to 1 uM, about 1 uM to 10 uM, about 10 uM to 100 uM, about 100 uM to 1000 uM, about 1 mM to 10 mM, or about 10 mM to 100 mM in the perilymph fluid in the inner ear.

Preferably, the soluble Jag-1 peptide is administered, in amount sufficient to achieve a concentration of about 50 nM, about 100 nM, about 200 nM, about 300 nM, about 400 nM, about 500 nM, or about 1000 nM in the perilymph fluid in the inner ear.

In some embodiments, the Jag-1 agonist is a soluble Jag-1 peptide, and is administered to a subject, for example to the middle ear at a concentration of about 1 uM to 1,000,000 mM, about 10 uM to 100,000 mM, about 100 uM to 10,000 mM, about 1 mM to 1,000 mM, about 1 uM to 10 uM, about 10 uM to 100 uM, about 100 uM to 1,000 uM, about 1 mM to 10 mM, about 10 mM to 100 mM, about 100 mM to 1,000 mM, about 1,000 mM to 10,000 mM, or about 10,000 mM to 100,000 mM.

Preferably, the Jag-1 agonist the is administered to a subject, for example to the middle ear at a concentration of about 50 uM, about 100 uM, about 200 uM, about 300 uM, about 400 uM, about 500 uM, about 1 mM, about 5 mM, about 10 mM, about 20 mM, about 30 mM, about 40 mM, about 50 mM, or about 100 mM.

In some embodiments, Jag-1 agonist is a soluble Jag-1 peptide and is administered to the subject at a concentration ratio of about 0.001 to 100 fold relative to an FDA approved concentration or about 0.1 to 50 fold relative to an FDA approved concentration, or about 0.1 to 5 fold relative to an FDA approved, or about 1 to 5 fold relative to an FDA approved concentration.

In some embodiments, the Jag-1 agonist is a soluble Jag-1 peptide and is administered to the subject at about 0.01×. about 0.1×, about 1×, about 2×, about 3×, about 5× or about 10×, relative to an FDA approved concentration.

In some embodiments, the Jag-1 agonist is a HIF1-α activator, and is administered for example to a cochlear cell in amount sufficient to achieve a concentration of about 1 nM to 100 mM, about 10 nM to 10 mM, about 100 nM to 1 mM, about 1 nM to 10 nM, about 10 nM to 100 nM, about 100 nM to 1 uM, about 1 uM to 10 uM, about 10 uM to 100 uM, about 100 uM to 1000 uM, about 1 mM to 10 mM, or about 10 mM to 100 mM in the perilymph fluid in the inner ear.

Preferably, the HIF1-α activator is administered in an amount sufficient to achieve a concentration of about 100 nM, about 500 nM, about 1 uM, about 5 uM, about 10 uM, about 20 uM, about 30 uM, about 40 uM, about 50 uM, or about 100 uM, in the perilymph fluid in the inner ear.

In some embodiments, the HIF1-α activator is 1,4-DPCA, and is administered for example to a cochlear cell in amount sufficient to achieve a concentration of about 1 nM to 100 mM, about 10 nM to 10 mM, about 100 nM to 1 mM, about 1 nM to 10 nM, about 10 nM to 100 nM, about 100 nM to 1 uM, about 1 uM to 10 uM, about 10 uM to 100 uM, about 100 uM to 1000 uM, about 1 mM to 10 mM, or about 10 mM to 100 mM in the perilymph fluid in the inner ear.

Preferably, the HIF1-α activator is 1,4-DPCA is administered, in amount sufficient to achieve a concentration of about 100 nM, about 500 nM, about 1 uM, about 5 uM, about 10 uM, about 20 uM, about 30 uM, about 40 uM, about 50 uM, or about 100 uM, in the perilymph fluid in the inner ear.

In some embodiments, the HIF1-α activator is 1,4-DPCA, and is administered to a subject, for example to the middle ear at a concentration of about 1 uM to 1,000,000 mM, about 10 uM to 100,000 mM, about 100 uM to 10,000 mM, about 1 mM to 1,000 mM, about 1 uM to 10 uM, about 10 uM to 100 uM, about 100 uM to 1,000 uM, about 1 mM to 10 mM, about 10 mM to 100 mM, about 100 mM to 1,000 mM, about 1,000 mM to 10,000 mM, or about 10,000 mM to 100,000 mM.

Preferably, the 1,4-DPCA agonist the is administered to a subject, for example to the middle ear at a concentration of about 100 uM, about 500 uM, about 1 mM, about 5 mM, about 10 mM, about 20 mM, about 30 mM, about 40 mM, about 50 mM, or about 100 mM in the perilymph fluid in the inner ear.

In some embodiments, HIF1-α activator is 1,4-DPCA and is administered to the subject at a concentration ratio of about 0.001 to 100 fold relative to an FDA approved concentration or about 0.1 to 50 fold relative to an FDA approved concentration, or about 0.1 to 5 fold relative to an FDA approved, or about 1 to 5 fold relative to an FDA approved concentration.

In some embodiments, the HIF1-α activator is 1,4-DPCA and is administered to the subject at about 0.01×. about 0.1×, about 1×, about 2×, about 3×, about 5× or about 10×, relative to an FDA approved concentration.

In some embodiments, the HIF1-α activator is FG2216, and is administered for example to a cochlear cell in amount sufficient to achieve a concentration of about 1 nM to 1000 mM, about 10 nM to 100 mM, about 100 nM to 10 mM, about 1 uM to 1 mM, about 1 uM to 100 uM, about 1 nM to 10 nM, about 10 nM to 100 nM, about 100 nM to 1 uM, about 1 uM to 10 uM, about 10 uM to 100 uM, about 100 uM to 1000 uM, about 1 mM to 10 mM, about 10 mM to 100 mM, or about 100 mM to 1000 mM in the perilymph fluid in the inner ear.

Preferably, the HIF1-α activator is FG2216 and is administered, in an amount sufficient to achieve a concentration of about 1 uM, about 5 uM, about 10 uM, about 15 uM, about 20 uM, about 30 uM, about 40 uM or about 50 uM in the perilymph fluid in the inner ear.

In some embodiments, the HIF1-α activator is FG2216, and is administered to a subject, for example to the middle ear at a concentration of about 1 uM to 1,000,000 mM, about 10 uM to 100,000 mM, about 100 uM to 10,000 mM, about 1 mM to 1,000 mM, about 1 uM to 10 uM, about 10 uM to 100 uM, about 100 uM to 1,000 uM, about 1 mM to 10 mM, about 10 mM to 100 mM, about 100 mM to 1,000 mM, about 1,000 mM to 10,000 mM, or about 10,000 mM to 100,000 mM Preferably, the HIF1-α activator is FG2216 is administered to a subject, for example to the middle ear at a concentration of about 0.5 mM, about 1 mM, about 5 mM, about 10 mM, about 15 mM, about 20 mM, about 30 mM, about 40 mM, or about 50 mM.

In some embodiments, HIF1-α activator is FG2216 and is administered to the subject at a concentration ratio of about 0.001 to 100 fold relative to an FDA approved concentration or about 0.1 to 50 fold relative to an FDA approved concentration, or about 0.1 to 5 fold relative to an FDA approved, or about 1 to 5 fold relative to an FDA approved concentration.

In some embodiments, the HIF1-α activator is FG2216 and is administered to the subject at about 0.01×. about 0.1×, about 1×, about 2×, about 3×, about 5× or about 10×, relative to an FDA approved concentration.

In some embodiments, the HIF1-α activator is Daprodusat, and is administered for example to a cochlear cell in amount sufficient to achieve a concentration of about 1 nM to 1000 mM, about 10 nM to 100 mM, about 100 nM to 10 mM, about 1 uM to 1 mM, about 1 uM to 100 uM, about 1 nM to 10 nM, about 10 nM to 100 nM, about 100 nM to 1 uM, about 1 uM to 10 uM, about 10 uM to 100 uM, about 100 uM to 1000 uM, about 1 mM to 10 mM, about 10 mM to 100 mM, or about 100 mM to 1000 mM in the perilymph fluid in the inner ear.

Preferably, the HIF1-α activator is Daprodusat is administered, in amount sufficient to achieve a concentration of about 0.1 uM, about 0.5 uM, about 1 uM, about 5 uM, about 10 uM, about 15 uM, about 20 uM, about 30 uM, about 40 uM or about 50 uM in the perilymph fluid in the inner ear.

In some embodiments, the HIF1-α activator is Daprodusat, and is administered to a subject, for example to the middle ear at a concentration of about 1 uM to 1,000,000 mM, about 10 uM to 100,000 mM, about 100 uM to 10,000 mM, about 1 mM to 1,000 mM, about 1 uM to 10 uM, about 10 uM to 100 uM, about 100 uM to 1,000 uM, about 1 mM to 10 mM, about 10 mM to 100 mM, about 100 mM to 1,000 mM, about 1,000 mM to 10,000 mM, or about 10,000 mM to 100,000 mM.

Preferably, the HIF1-α activator is Daprodusat administered to a subject, for example to the middle ear at a concentration of about 0.5 mM, about 1 mM, about 5 mM, about 10 mM, about 15 mM, about 20 mM, about 30 mM, about 40 mM, or about 50 mM.

In some embodiments, HIF1-α activator is Daprodusat and is administered to the subject at a concentration ratio of about 0.001 to 100 fold relative to an FDA approved concentration or about 0.1 to 50 fold relative to an FDA approved concentration, or about 0.1 to 5 fold relative to an FDA approved, or about 1 to 5 fold relative to an FDA approved concentration.

In some embodiments, the HIF1-α activator is Daprodusat and is administered to the subject at about 0.01×. about 0.1×, about 1×, about 2×, about 3×, about 5× or about 10×, relative to an FDA approved concentration.

In some embodiments, the Jag-1 agonist is a PI3K agonist, and is administered for example to a cochlear cell in amount sufficient to achieve a concentration of about 1 nM to 100 mM, about 10 nM to 10 mM, about 100 nM to 1 mM, about 1 nM to 10 nM, about 10 nM to 100 nM, about 100 nM to 1 uM, about 1 uM to 10 uM, about 10 uM to 100 uM, about 100 uM to 1000 uM, about 1 mM to 10 mM, or about 10 mM to 100 mM in the perilymph fluid in the inner ear.

Preferably, the PI3K agonist is administered, in amount sufficient to achieve a concentration of about 50 nM, about 100 nM, about 200 nM, about 400 nM, about 600 nM, about 1200 nM, about 2500 nM or about 10 uM in the perilymph fluid in the inner ear.

In some embodiments, the Jag-1 agonist is a PI3K agonist, and is administered to a subject, for example to the middle ear at a concentration of about 10 uM to 1,000,000 mM, about 100 uM to 100,000 mM, about 1 mM to 10,000 mM, about 10 mM to 1,000 mM, about 10 uM to 100 uM, about 100 uM to 1 mM, about 1 mM to 10 mM, about 10 mM to 100 mM, about 100 mM to 1,000 mM, about 1,000 mM to 10,000 mM, about 10,000 mM to 100,000 mM or about 100,000 mM to 1,000,000 mM.

Preferably, the PI3K agonist the is administered to a subject, for example to the middle ear at a concentration of about 100 uM, about 250 uM, about 500 uM, about 750 uM, about 1 mM, about 5 mM, about 10 mM, about 15 mM, about 20 mM, about 30 mM, about 40 mM, or about 50 mM.

In some embodiments, Jag-1 agonist is a PI3K agonist and is administered to the subject at a concentration ratio of about 0.001 to 100 fold relative to an FDA approved concentration or about 0.1 to 50 fold relative to an FDA approved concentration, or about 0.1 to 5 fold relative to an FDA approved, or about 1 to 5 fold relative to an FDA approved concentration.

In some embodiments, the Jag-1 agonist is a PI3K agonist and is administered to the subject at about 0.01×. about 0.1×, about 1×, about 2×, about 3×, about 5× or about 10×, relative to an FDA approved concentration.

In some embodiments, the PI3K agonist is a FOXO inhibitor and is administered for example to a cochlear cell in amount sufficient to achieve a concentration of about 1 nM to 100 mM, about 10 nM to 10 mM, about 100 nM to 1 mM, about 1 nM to 10 nM, about 10 nM to 100 nM, about 100 nM to 1 uM, about 1 uM to 10 uM, about 10 uM to 100 uM, about 100 uM to 1000 uM, about 1 mM to 10 mM, or about 10 mM to 100 mM in the perilymph fluid in the inner ear.

Preferably, the FOXO inhibitor is administered, in amount sufficient to achieve a concentration of about 50 nM, about 100 nM, about 200 nM, about 400 nM, about 600 nM, about 1200 nM, about 2500 nM or about 10 uM in the perilymph fluid in the inner ear.

In some embodiments the PI3K agonist is a FOXO inhibitor, and is administered to a subject, for example to the middle ear at a concentration of about 1 uM to 1,000,000 mM, about 10 uM to 100,000 mM, about 100 uM to 10,000 mM, about 1 mM to 1,000 mM, about 1 uM to 10 uM, about 10 uM to 100 uM, about 100 uM to 1,000 uM, about 1 mM to 10 mM, about 10 mM to 100 mM, about 100 mM to 1,000 mM, about 1,000 mM to 10,000 mM, or about 10,000 mM to 100,000 mM.

Preferably, the FOXO inhibitor the is administered to a subject, for example to the middle ear at a concentration of about 50 uM, about 100 uM, about 200 uM, about 400 uM, about 600 uM, about 1200 uM, about 2500 uM or about 10 mM.

In some embodiments, PI3K agonist is a FOXO inhibitor and is administered to the subject at a concentration ratio of about 0.001 to 100 fold relative to an FDA approved concentration or about 0.1 to 50 fold relative to an FDA approved concentration, or about 0.1 to 5 fold relative to an FDA approved, or about 1 to 5 fold relative to an FDA approved concentration.

In some embodiments, PI3K agonist is a FOXO inhibitor and is administered to the subject at about 0.01×. about 0.1×, about 1×, about 2×, about 3×, about 5× or about 10×, relative to an FDA approved concentration.

In some embodiments, the FOXO inhibitor is AS1842856, and is administered for example to a cochlear cell in amount sufficient to achieve a concentration of about 0.1 nM to 100 uM, about 1 nM to 10 uM, about 10 nM to 1 uM, about 0.1 nM to 1 nM, about 1 nM to 10 nM, about 10 nM to 100 nM, about 100 nM to 1 uM, about 1 uM to 10 uM, and about 10 uM to 100 uM.

Preferably, the AS1842856 is administered, in amount sufficient to achieve a concentration of about 50 nM, about 100 nM, about 200 nM, about 300 nM, about 400 nM, about 500 nM, about 600 nM, about 700 nM, about 800 nM, about 900 nM, and about 1 uM in the perilymph fluid in the inner ear.

In some embodiments, the FOXO inhibitor is AS1842856, and is administered to a subject, for example to the middle ear at a concentration of about 0.1 uM to 100 mM, about 1 uM to 10 mM, about 10 uM to 1 mM, about 0.1 uM to 1 uM, about 1 uM to 10 uM, about 10 uM to 100 uM, about 100 uM to 1 mM, about 1 mM to 10 mM, and about 10 mM to 100 mM.

Preferably, the AS1842856 is administered to a subject, for example to the middle ear at a concentration of about 50 uM, about 100 uM, about 200 uM, about 300 uM, about 400 uM, about 500 uM, about 600 uM, about 700 uM, about 800 uM, about 900 uM, and about 1 mM.

In some embodiments, the FOXO inhibitor is AS1842856 and is administered to the subject at a concentration ratio of about 0.001 to 100 fold relative to an FDA approved concentration or about 0.1 to 50 fold relative to an FDA approved concentration, or about 0.1 to 5 fold relative to an FDA approved, or about 1 to 5 fold relative to an FDA approved concentration.

In some embodiments, the FOXO inhibitor is AS1842856 and is administered to the subject at about 0.01×. about 0.1×, about 1×, about 2×, about 3×, about 5× or about 10×, relative to an FDA approved concentration.

In some embodiments, the Deltex-1 agonist is administered for example to a cochlear cell in amount sufficient to achieve a concentration of about 1 nM to 100 mM, about 10 nM to 10 mM, about 100 nM to 1 mM, about 1 nM to 10 nM, about 10 nM to 100 nM, about 100 nM to 1 uM, about 1 uM to 10 uM, about 10 uM to 100 uM, about 100 uM to 1000 uM, about 1 mM to 10 mM, or about 10 mM to 100 mM in the perilymph fluid in the inner ear.

Preferably, the Deltex-1 agonist is administered, is administered, in amount sufficient to achieve a concentration of about 50 nM, about 100 nM, about 200 nM, about 400 nM, about 600 nM, about 1200 nM, about 2500 nM or about 10 uM the perilymph fluid in the inner ear.

In some embodiments, the Deltex-1 agonist is administered to a subject, for example to the middle ear at a concentration of about 1 uM to 1,000,000 mM, about 10 uM to 100,000 mM, about 100 uM to 10,000 mM, about 1 mM to 1,000 mM, about 1 uM to 10 uM, about 10 uM to 100 uM, about 100 uM to 1,000 uM, about 1 mM to 10 mM, about 10 mM to 100 mM, about 100 mM to 1,000 mM, about 1,000 mM to 10,000 mM, or about 10,000 mM to 100,000 mM.

Preferably, the Deltex-1 agonist is administered to a subject, for example to the middle ear at a concentration of about 10 uM, 100 uM, 1 mM, 5 mM, 10 mM, or 100 mM.

In some embodiments, Deltex-1 agonist is administered to the subject at a concentration ratio of about 0.001 to 100 fold relative to an FDA approved concentration or about 0.1 to 50 fold relative to an FDA approved concentration, or about 0.1 to 5 fold relative to an FDA approved, or about 1 to 5 fold relative to an FDA approved concentration.

In some embodiments, the Deltex-1 agonist is administered to the subject at about 0.01×. about 0.1×, about 1×, about 2×, about 3×, about 5× or about 10×, relative to an FDA approved concentration.

In some embodiments, the Jag-1 synergist is administered for example to a cochlear cell in amount sufficient to achieve a concentration of about 1 nM to 100 mM, about 10 nM to 10 mM, about 100 nM to 1 mM, about 1 nM to 10 nM, about 10 nM to 100 nM, about 100 nM to 1 uM, about 1 uM to 10 uM, about 10 uM to 100 uM, about 100 uM to 1000 uM, about 1 mM to 10 mM, or about 10 mM to 100 mM in the perilymph fluid in the inner ear.

Preferably, the Jag-1 synergist is administered, is administered, in amount sufficient to achieve a concentration of about is about 50 nM, about 100 nM, about 200 nM, about 400 nM, about 600 nM, about 1200 nM, about 2500 nM or about 10 uM in the perilymph fluid in the inner ear.

In some embodiments, the Jag-1 synergist is administered to a subject, for example to the middle ear at a concentration of about 1 uM to 1,000,000 mM, about 10 uM to 100,000 mM, about 100 uM to 10,000 mM, about 1 mM to 1,000 mM, about 1 uM to 10 uM, about 10 uM to 100 uM, about 100 uM to 1,000 uM, about 1 mM to 10 mM, about 10 mM to 100 mM, about 100 mM to 1,000 mM, about 1,000 mM to 10,000 mM, or about 10,000 mM to 100,000 mM.

Preferably, the Jag-1 synergist is administered to a subject, for example to the middle ear at a concentration of about 10 uM, about 100 uM, about 1 mM, about 5 mM, about 10 mM, or about 100 mM.

In some embodiments, Jag-1 synergist is administered to the subject at a concentration ratio of about 0.001 to 100 fold relative to an FDA approved concentration or about 0.1 to 50 fold relative to an FDA approved concentration, or about 0.1 to 5 fold relative to an FDA approved, or about 1 to 5 fold relative to an FDA approved concentration.

In some embodiments, the Jag-1 synergist is administered to the subject at about 0.01×. 0.1×, about 2×, about 3×, about 5× or about 10×, relative to an FDA approved concentration.

PI3k

In some embodiments, the Jag-1 synergist is a PI3K synergist and is administered for example to a cochlear cell in amount sufficient to achieve a concentration of about 1 nM to 100 mM, about 10 nM to 10 mM, about 100 nM to 1 mM, about 1 nM to 10 nM, about 10 nM to 100 nM, about 100 nM to 1 uM, about 1 uM to 10 uM, about 10 uM to 100 uM, about 100 uM to 1000 uM, about 1 mM to 10 mM, or about 10 mM to 100 mM in the perilymph fluid in the inner ear.

Preferably, the PI3K synergist administered, is administered, in amount sufficient to achieve a concentration of about is about 50 nM, about 100 nM, about 200 nM, about 400 nM, about 600 nM, about 1200 nM, about 2500 nM or about 10 uM in the perilymph fluid in the inner ear.

In some embodiments, the PI3K synergist is administered to a subject, for example to the middle ear at a concentration about 1 uM to 1,000,000 mM, about 10 uM to 100,000 mM, about 100 uM to 10,000 mM, about 1 mM to 1,000 mM, about 1 uM to 10 uM, about 10 uM to 100 uM, about 100 uM to 1,000 uM, about 1 mM to 10 mM, about 10 mM to 100 mM, about 100 mM to 1,000 mM, about 1,000 mM to 10,000 mM, or about 10,000 mM to 100,000 mM.

Preferably, the PI3K synergist is administered to a subject, for example to the middle ear at a concentration of about 10 uM, about 100 uM, about 1 mM, about 5 mM, about 10 mM, or about 100 mM.

In some embodiments, the PI3K synergist administered to the subject at a concentration ratio of about 0.001 to 100 fold relative to an FDA approved concentration or about 0.1 to 50 fold relative to an FDA approved concentration, or about 0.1 to 5 fold relative to an FDA approved, or about 1 to 5 fold relative to an FDA approved concentration.

In some embodiments, the PI3K synergist is administered to the subject at about 0.01×. 0.1×, 2×, 3×, 5× or 10×, relative to an FDA approved concentration.

In some embodiments, the PI3K synergist is a PTEN inhibitor is administered for example to a cochlear cell in amount sufficient to achieve a concentration of about 1 nM to 100 mM, about 10 nM to 10 mM, about 100 nM to 1 mM, about 1 nM to 10 nM, about 10 nM to 100 nM, about 100 nM to 1 uM, about 1 uM to 10 uM, about 10 uM to 100 uM, about 100 uM to 1000 uM, about 1 mM to 10 mM, or about 10 mM to 100 mM in the perilymph fluid in the inner ear.

Preferably, the PTEN inhibitor is administered, is administered, in amount sufficient to achieve a concentration of about 50 nM, about 100 nM, about 200 nM, about 400 nM, about 600 nM, about 1200 nM, about 2500 nM or about 10 uM in the perilymph fluid in the inner ear.

In some embodiments, the PTEN inhibitor is administered to a subject, for example to the middle ear at a concentration of about 1 uM to 1,000,000 mM, about 10 uM to 100,000 mM, about 100 uM to 10,000 mM, about 1 mM to 1,000 mM, about 1 uM to 10 uM, about 10 uM to 100 uM, about 100 uM to 1,000 uM, about 1 mM to 10 mM, about 10 mM to 100 mM, about 100 mM to 1,000 mM, about 1,000 mM to 10,000 mM, or about 10,000 mM to 100,000 mM.

Preferably, the PTEN inhibitor is administered to a subject, for example to the middle ear at a concentration of about 10 uM, about 100 uM, about 1 mM, about 5 mM, about 10 mM, or about 100 mM.

In some embodiments, PTEN inhibitor is administered to the subject at a concentration ratio of about 0.001 to 100 fold relative to an FDA approved concentration or about 0.1 to 50 fold relative to an FDA approved concentration, or about 0.1 to 5 fold relative to an FDA approved, or about 1 to 5 fold relative to an FDA approved concentration.

In some embodiments, the PTEN inhibitor is administered to the subject at about 0.01×. about 0.1×, about 1×, about 2×, about 3×, about 5× or about 10×, relative to an FDA approved concentration.

In some embodiments, the PTEN inhibitor is SF1670 and is administered for example to a cochlear cell in amount sufficient to achieve a concentration of about 1 nM to 100 mM, about 10 nM to 10 mM, about 100 nM to 1 mM, about 1 nM to 10 nM, about 10 nM to 100 nM, about 100 nM to 1 uM, about 1 uM to 10 uM, about 10 uM to 100 uM, about 100 uM to 1000 uM, about 1 mM to 10 mM, or about 10 mM to 100 mM in the perilymph fluid in the inner ear.

Preferably, SF1670 is administered, is administered, in amount sufficient to achieve a concentration of about 10 nM, about 25 nM, about 50 nM, about 75 nM, about 100 nM, about 250 nM, about 500 nM, about 750 nM, and about 1 uM in the perilymph fluid in the inner ear.

In some embodiments, the PTEN inhibitor is SF1670 and is administered to a subject, for example to the middle ear at a concentration of about 1 uM to 1,000,000 mM, about 10 uM to 100,000 mM, about 100 uM to 10,000 mM, about 1 uM to 1,000 mM, about 1 uM to 10 uM, about 10 uM to 100 uM, about 100 uM to 1,000 uM, about 1 mM to 10 mM, about 10 mM to 100 mM, about 100 mM to 1,000 mM, about 1,000 mM to 10,000 mM, or about 10,000 mM to 100,000 mM.

Preferably, the SF1670 is administered to a subject, for example to the middle ear at a concentration of about 10 uM, about 25 uM, about 50 uM, about 75 uM, about 100 uM, about 250 uM, about 500 uM, about 750 uM, and about 1 mM in the perilymph fluid in the inner ear.

In some embodiments, the SF1670 is administered to the subject at a concentration ratio of about 0.001 to 100 fold relative to an FDA approved concentration or about 0.1 to 50 fold relative to an FDA approved concentration, or about 0.1 to 5 fold relative to an FDA approved, or about 1 to 5 fold relative to an FDA approved concentration.

In some embodiments, the SF1670 is administered to the subject at about 0.01×. 0.1×, 2×, 3×, 5× or 10×, relative to an FDA approved concentration.

In some embodiments, PTEN inhibitor is VO-Ohpic is administered for example to a cochlear cell in amount sufficient to achieve a concentration of about 1 nM to 100 mM, about 10 nM to 10 mM, about 100 nM to 1 mM, about 1 nM to 10 nM, about 10 nM to 100 nM, about 100 nM to 1 uM, about 1 uM to 10 uM, about 10 uM to 100 uM, about 100 uM to 1000 uM, about 1 mM to 10 mM, or about 10 mM to 100 mM in the perilymph fluid in the inner ear.

Preferably, VO-Ohpic is administered, is administered, in amount sufficient to achieve a concentration of about 0.5 uM, about 1 uM, about 2 uM, about 4 uM, about 6 uM, about 8 uM, about 10 uM, about 25 uM, or about 50 uM in the perilymph fluid in the inner ear.

In some embodiments, VO-Ohpic is administered to a subject, for example to the middle ear at a concentration of about 1 uM to 1,000,000 mM, about 10 uM to 100,000 mM, about 100 uM to 10,000 mM, about 1 mM to 1,000 mM, about 1 uM to 10 uM, about 10 uM to 100 uM, about 100 uM to 1,000 uM, about 1 mM to 10 mM, about 10 mM to 100 mM, about 100 mM to 1,000 mM, about 1,000 mM to 10,000 mM, or about 10,000 mM to 100,000 mM Preferably, VO-Ohpic is administered to a subject, for example to the middle ear at a concentration of about 0.5 mM, about 1 mM, about 2 mM, about 4 mM, about 6 mM, about 8 mM, about 10 mM, about 25 mM, or about 50 mM.

In some embodiments, VO-Ohpic is administered to the subject at a concentration ratio of about 0.001 to 100 fold relative to an FDA approved concentration or about 0.1 to 50 fold relative to an FDA approved concentration, or about 0.1 to 5 fold relative to an FDA approved, or about 1 to 5 fold relative to an FDA approved concentration.

In some embodiments, VO-Ohpic is administered to the subject at about 0.01×, about 0.1×, about 1×, about 2×, about 3×, about 5× or about 10× relative to an FDA approved concentration.

In some embodiments, PTEN inhibitor is bpV(phen) administered for example to a cochlear cell in amount sufficient to achieve a concentration of about 1 nM to 100 mM, about 10 nM to 10 mM, about 100 nM to 1 mM, about 1 nM to 10 nM, about 10 nM to 100 nM, about 100 nM to 1 uM, about 1 uM to 10 uM, about 10 uM to 100 uM, about 100 uM to 1000 uM, about 1 mM to 10 mM, or about 10 mM to 100 mM in the perilymph fluid in the inner ear.

Preferably, PTEN inhibitor is bpV(phen) administered in amount sufficient to achieve a concentration of about 0.5 uM, about 1 uM, about 2 uM, about 4 uM, about 6 uM, about 8 uM, about 10 uM, about 25 uM, or about 50 uM in the perilymph fluid in the inner ear.

In some embodiments, PTEN inhibitor bpV(phen) is administered to a subject, for example to the middle ear at a concentration of about 1 uM to 1,000,000 mM, about 10 uM to 100,000 mM, about 100 uM to 10,000 mM, about 1 mM to 1,000 mM, about 1 uM to 10 uM, about 10 uM to 100 uM, about 100 uM to 1,000 uM, about 1 mM to 10 mM, about 10 mM to 100 mM, about 100 mM to 1,000 mM, about 1,000 mM to 10,000 mM, or about 10,000 mM to 100,000 mM.

Preferably, PTEN inhibitor is bpV(phen) administered to a subject, for example to the middle ear at a concentration of about 0.5 mM, about 1 mM, about 2 mM, about 4 mM, about 6 mM, about 8 mM, about 10 mM, about 25 mM, or about 50 mM.

In some embodiments, PTEN inhibitor is bpV(phen) is administered to the subject at a concentration ratio of about 0.001 to 100 fold relative to an FDA approved concentration or about 0.1 to 50 fold relative to an FDA approved concentration, or about 0.1 to 5 fold relative to an FDA approved, or about 1 to 5 fold relative to an FDA approved concentration.

In some embodiments, PTEN inhibitor is bpV(phen) is administered to the subject at about 0.01× about 0.1×, about 1×, about 2×, about 3×, about 5× or about 10×, relative to an FDA approved concentration.

In some embodiments, PTEN inhibitor is bpV(pic) is administered for example to a cochlear cell in amount sufficient to achieve a concentration of about 1 nM to 100 mM, about 10 nM to 10 mM, about 100 nM to 1 mM, about 1 nM to 10 nM, about 10 nM to 100 nM, about 100 nM to 1 uM, about 1 uM to 10 uM, about 10 uM to 100 uM, about 100 uM to 1000 uM, about 1 mM to 10 mM, or about 10 mM to 100 mM in the perilymph fluid in the inner ear.

Preferably, PTEN inhibitor is bpV(pic) administered in amount sufficient to achieve a concentration of about 0.5 uM, about 1 uM, about 2 uM, about 4 uM, about 6 uM, about 8 uM, about 10 uM, about 25 uM, or about 50 uM in the perilymph fluid in the inner ear.

In some embodiments, PTEN inhibitor is bpV(pic) is administered to a subject, for example to the middle ear at a concentration of about 1 uM to 1,000,000 mM, about 10 uM to 100,000 mM, about 100 uM to 10,000 mM, about 1 mM to 1,000 mM, about 1 uM to 10 uM, about 10 uM to 100 uM, about 100 uM to 1,000 uM, about 1 mM to 10 mM, about 10 mM to 100 mM, about 100 mM to 1,000 mM, about 1,000 mM to 10,000 mM, or about 10,000 mM to 100,000 mM.

Preferably, PTEN inhibitor is bpV(pic) is administered to a subject, for example to the middle ear at a concentration of about 0.5 mM, about 1 mM, about 2 mM, about 4 mM, about 6 mM, about 8 mM, about 10 mM, about 25 mM, or about 50 mM.

In some embodiments, PTEN inhibitor is bpV(pic) is administered to the subject at a concentration ratio of about 0.001 to 100 fold relative to an FDA approved concentration or about 0.1 to 50 fold relative to an FDA approved concentration, or about 0.1 to 5 fold relative to an FDA approved, or about 1 to 5 fold relative to an FDA approved concentration.

In some embodiments, the Jag-1 synergist is administered to the subject at about 0.01×, about 0.1×, about 1×, about 2×, about 3×, about 5× or about 10× relative to an FDA approved concentration.

PI3k

In some embodiments, the Jag-1 synergist is a PI3K synergist and is administered for example to a cochlear cell in amount sufficient to achieve a concentration of about 1 nM to 100 mM, about 10 nM to 10 mM, about 100 nM to 1 mM, about 1 nM to 10 nM, about 10 nM to 100 nM, about 100 nM to 1 uM, about 1 uM to 10 uM, about 10 uM to 100 uM, about 100 uM to 1000 uM, about 1 mM to 10 mM, or about 10 mM to 100 mM in the perilymph fluid in the inner ear.

Preferably, the PI3K synergist is administered, is administered, in amount sufficient to achieve a concentration of about 50 nM, about 100 nM, about 200 nM, about 400 nM, about 600 nM, about 1200 nM, about 2500 nM or about 10 uM in the perilymph fluid in the inner ear.

In some embodiments, the PI3K synergist is administered to a subject, for example to the middle ear at a concentration of about 1 uM to 1,000,000 mM, about 10 uM to 100,000 mM, about 100 uM to 10,000 mM, about 1 mM to 1,000 mM, about 1 uM to 10 uM, about 10 uM to 100 uM, about 100 uM to 1,000 uM, about 1 mM to 10 mM, about 10 mM to 100 mM, about 100 mM to 1,000 mM, about 1,000 mM to 10,000 mM, or about 10,000 mM to 100,000 mM.

Preferably, the PI3K synergist is administered to a subject, for example to the middle ear at a concentration of about 10 uM, about 100 uM, about 1 mM, about 5 mM, about 10 mM, or about 100 mM.

In some embodiments, PI3K synergist is administered to the subject at a concentration ratio of about 0.001 to 100 fold relative to an FDA approved concentration or about 0.1 to 50 fold relative to an FDA approved concentration, or about 0.1 to 5 fold relative to an FDA approved, or about 1 to 5 fold relative to an FDA approved concentration.

In some embodiments, the Deltex-1 synergist is administered for example to a cochlear cell in amount sufficient to achieve a concentration of about 1 nM to 100 mM, about 10 nM to 10 mM, about 100 nM to 1 mM, about 1 nM to 10 nM, about 10 nM to 100 nM, about 100 nM to 1 uM, about 1 uM to 10 uM, about 10 uM to 100 uM, about 100 uM to 1000 uM, about 1 mM to 10 mM, or about 10 mM to 100 mM in the perilymph fluid in the inner ear.

Preferably, the Deltex-1 synergist is administered, is administered, in amount sufficient to achieve a concentration of about 50 nM, about 100 nM, about 200 nM, about 400 nM, about 600 nM, about 1200 nM, about 2500 nM or about 10 uM in the perilymph fluid in the inner ear.

In some embodiments, the Deltex-1 synergist is administered to a subject, for example to the middle ear at a concentration of about 1 uM to 1,000,000 mM, about 10 uM to 100,000 mM, about 100 uM to 10,000 mM, about 1 mM to 1,000 mM, about 1 uM to 10 uM, about 10 uM to 100 uM, about 100 uM to 1,000 uM, about 1 mM to 10 mM, about 10 mM to 100 mM, about 100 mM to 1,000 mM, about 1,000 mM to 10,000 mM, or about 10,000 mM to 100,000 mM.

Preferably, the Deltex-1 synergist is administered to a subject, for example to the middle ear at a concentration of about 10 uM, about 100 uM, about 1 mM, about 5 mM, about 10 mM, or about 100 mM.

In some embodiments, Deltex-1 synergist is administered to the subject at a concentration ratio of about 0.001 to 100 fold relative to an FDA approved concentration or about 0.1 to 50 fold relative to an FDA approved concentration, or about 0.1 to 5 fold relative to an FDA approved, or about 1 to 5 fold relative to an FDA approved concentration.

In some embodiments, the Deltex-1 synergist is administered to the subject at about 0.01×, about 0.1×, about 1×, about 2×, about 3×, about 5× or about 10× relative to an FDA approved concentration.

In some embodiments, the GSK3 Inhibitor is AZD1080, and is administered for example to a cochlear cell in amount sufficient to achieve a concentration of about 0.001 µM to 10 mM, about 0.01 uM to 1 mM, about 0.1 µM to 100 µM, about 0.001 µM to 0.01 µM, about 0.01 µM to 0.1 µM, about 0.1 µM to 1 µM, about 1 µM to 10 µM, about 10 µM to 100 µM, about 100 µM to 1,000 µM, or about 1 mM to 10 mM in the perilymph fluid in the inner ear.

Preferably, the AZD1080 is administered, is administered, in amount sufficient to achieve a concentration of about is about 1 µM, 2 µM, 3 µM, 4 µM, 5 µM, 6 µM, 7 µM, 8 µM, 9 µM, or 10 µM, in the perilymph fluid in the inner ear.

In some embodiments, the GSK3 Inhibitor is AZD1080, and is administered to a subject, for example to the middle ear at a concentration of about 0.001 mM to 10,000 mM, about 0.01 mM to 1,000 mM, about 0.1 mM to 100 mM, about 0.001 mM to 0.01 mM, about 0.01 mM to 0.1 mM, about 0.1 mM to 1 mM, about 1 mM to 10 mM, about 10 mM to 100 mM, about 100 mM to 1,000 mM, or about 1,000 mM to 10,000 mM.

Preferably, the AZD1080 is administered to a subject, for example to the middle ear at a concentration of about 1 mM, 2 mM, 3 mM, 4 mM, 5 mM, 6 mM, 7 mM, 8 mM, 9 mM, or 10 mM.

In some embodiments, the GSK3 Inhibitor is AZD1080 and is administered to the subject at a concentration ratio of about 0.001 to 100 fold relative to an FDA approved concentration or about 0.1 to 50 fold relative to an FDA approved concentration, or about 0.1 to 5 fold relative to an FDA approved, or about 1 to 5 fold relative to an FDA approved concentration.

In some embodiments, the GSK3 Inhibitor is AZD1080 and is administered to the subject at about 0.01×. 0.1×, 2×, 3×, 5× or 10×, relative to an FDA approved concentration In some embodiments, the GSK3 Inhibitor is LY2090314, and is administered for example to a cochlear cell in amount sufficient to achieve a concentration of about 0.001 nM to 10 mM, about 0.01 nM to 1 µM, about 0.1 nM to 100 nM, about 0.001 nM to 0.01 nM, about 0.01 nM to 0.1 nM, about 0.1 nM to 1 nM, about 1 nM to 10 nM, about 10 nM to 100 nM, about 100 nM to 1 µM, or about 1 µM to 10 µM, in the perilymph fluid in the inner ear.

Preferably, the LY2090314 is administered, in amount sufficient to achieve a concentration of about 1 nM, 5 nM, 10 nM, 15 nM, 20 nM, or 40 nM, in the perilymph fluid in the inner ear.

In some embodiments, the GSK3 Inhibitor is LY2090314, and is administered to a subject, for example to the middle ear at a concentration of about 0.001 µM to 10 mM, about 0.01 µM to 1 mM, about 0.1 µM to 100 uM, about 0.001 µM to 0.01 µM, about 0.01 µM to 0.1 µM, about 0.1 µM to 1 µM, about 1 µM to 10 µM, about 10 µM to 100 µM, about 100 µM to 1 mM, or about 1 mM to 10 mM.

Preferably, LY2090314 the is administered to a subject, for example to the middle ear at a concentration of about 1 µM, 5 µM, 10 µM, 15 µM, 20 µM, or 40 µM.

In some embodiments, the GSK3 Inhibitor is LY2090314 and is administered to the subject at a concentration ratio of about 0.001 to 10 fold relative to an FDA approved concentration or about 0.1 to 50 fold relative to an FDA approved concentration, or about 0.1 to 5 fold relative to an FDA approved, or about 1 to 5 fold relative to an FDA approved concentration.

In some embodiments, the GSK3 Inhibitor is LY2090314 and is administered to the subject at about 0.01×. 0.1×, 2×, 3×, 5× or 10×, relative to an FDA approved concentration.

In some embodiments, the GSK3 Inhibitor is a substituted 3-Imidazo[1,2-a]pyridin-3-yl-4-(1,2,3,4-tetrahydro-[1,4]diazepino-[6,7,1-hi]indol-7-yl)pyrrole-2,5-dione, and is 0.001 nM to 10 mM, about 0.01 nM to 1 µM, about 0.1 nM to 100 nM, about 0.001 nM to 0.01 nM, about 0.01 nM to 0.1 nM, about 0.1 nM to 1 nM, about 1 nM to 10 nM, about 10 nM to 100 nM, about 100 nM to 1 µM, or about 1 µM to 10 µM, in the perilymph fluid in the inner ear.

Preferably, the substituted 3-Imidazo[1,2-a]pyridin-3-yl-4-(1,2,3,4-tetrahydro-[1,4]diazepino-[6,7,1-hi]indol-7-yl)pyrrole-2,5-dione, is administered, in amount sufficient to achieve a concentration of about 1 nM, 5 nM, 10 nM, 15 nM, 20 nM, 50 nM, 100 nM, 250 nM, or 500 nM, in the perilymph fluid in the inner ear.

In some embodiments, the GSK3 Inhibitor is a substituted 3-Imidazo[1,2-a]pyridin-3-yl-4-(1,2,3,4-tetrahydro-[1,4]diazepino-[6,7,1-hi]indol-7-yl)pyrrole-2,5-dione, and is administered to a subject, for example to the middle ear at a concentration of about 0.001 µM to 10 mM, about 0.01 µM to 1 mM, about 0.1 µM to 100 uM, about 0.001 µM to 0.01 µM, about 0.01 µM to 0.1 µM, about 0.1 µM to 1 µM, about 1 µM to 10 µM, about 10 µM to 100 µM, about 100 µM to 1 mM, or about 1 mM to 10 mM.

Preferably, the substituted 3-Imidazo[1,2-a]pyridin-3-yl-4-(1,2,3,4-tetrahydro-[1,4]diazepino-[6,7,1-hi]indol-7-yl)pyrrole-2,5-dione, the is administered to a subject, for example to the middle ear at a concentration of about 1 µM, 5 µM, 10 µM, 15 µM, 20 µM, 50 µM, 100 µM, 250 µM, or 500 µM.

In some embodiments, the GSK3 Inhibitor is a substituted 3-Imidazo[1,2-a]pyridin-3-yl-4-(1,2,3,4-tetrahydro-[1,4]diazepino-[6,7,1-hi]indol-7-yl)pyrrole-2,5-dione, and is administered to the subject at a concentration ratio of about 0.001 to 10 fold relative to an FDA approved concentration or about 0.1 to 50 fold relative to an FDA approved concentration, or about 0.1 to 5 fold relative to an FDA approved, or about 1 to 5 fold relative to an FDA approved concentration.

In some embodiments, the GSK3 Inhibitor is a substituted 3-Imidazo[1,2-a]pyridin-3-yl-4-(1,2,3,4-tetrahydro-[1,4]diazepino-[6,7,1-hi]indol-7-yl)pyrrole-2,5-dione and is administered to the subject at about 0.01×. 0.1×, 2×, 3×, 5× or 10×, relative to an FDA approved concentration In some embodiments, the GSK3 Inhibitor is GSK3-inhibitor XXII, and is administered for example to a cochlear cell in amount sufficient to achieve a concentration of about 0.1 nM to 1 mM, about 1 nM to 100 µM, about 10 nM to 10 µM, about 0.1 nM to 1 nM, about 1 nM to 10 nM, about 10 nM to 100 nM, about 100 nM to 1 µM, about 1 µM to 10 µM, about 10 µM to 100 µM, or about 100 µM to 1000 µM, in the perilymph fluid in the inner ear.

Preferably, the GSK3-inhibitor XXII is administered, in amount sufficient to achieve a concentration of about 0.1 µM, 0.2 µM, 0.3 µM, 0.4 µM, 0.5 µM, 0.6 µM, 0.7 µM, 0.8 µM, 0.9 µM, or 1.0 µM, in the perilymph fluid in the inner ear.

In some embodiments, the GSK3 Inhibitor is GSK3-inhibitor XXII, is administered to a subject, for example to the middle ear at a concentration of about of about 0.1 µM to 1,000 mM, about 1 µM to 100 mM, about 10 µM to 10 mM, about 0.1 µM to 1 µM, about 1 µM to 10 µM, about 10 µM to 100 µM, about 100 µM to 1 mM, about 1 mM to 10 mM, about 10 mM to 100 mM, or about 100 mM to 1000 mM. Preferably, the GSK3-inhibitor XXII is administered, to a subject, for example to the middle ear at a concentration of about 0.1 mM, 0.2 mM, 0.3 mM, 0.4 mM, 0.5 mM, 0.6 mM, 0.7 mM, 0.8 mM, 0.9 mM, or 1.0 mM In some embodiments, the GSK3 Inhibitor is GSK3-inhibitor XXII and is administered to the subject at a concentration ratio of about 0.001 to 10 fold relative to an FDA approved concentration or about 0.1 to 50 fold relative to an FDA approved concentration, or about 0.1 to 5 fold relative to an FDA approved, or about 1 to 5 fold relative to an FDA approved concentration.

In some embodiments, the GSK3 Inhibitor is GSK3-inhibitor XXII and is administered to the subject at about 0.01×. 0.1×, 2×, 3×, 5× or 10×, relative to an FDA approved concentration.

In some embodiments, the GSK3 Inhibitor is CHIR99021, and is administered for example to a cochlear cell in amount sufficient to achieve a concentration of about 0.001 mM to 10 mM, about 0.01 mM to 1 mM, about 0.1 µM to 100 µM, about 0.001 µM to 0.01 µM, about 0.01 µM to 0.1 µM, about 0.1 µM to 1 µM, about 1 µM to 10 µM, about 10 µM to 100 µM, about 100 µM to 1,000 µM, or about 1 mM to 10 mM, in the perilymph fluid in the inner ear.

Preferably, the CHIR99021 is administered, in amount sufficient to achieve a concentration of about 1 µM, 2 µM, 3 µM, 4 µM, 5 µM, 6 µM, 7 µM, 8 µM, 9 µM, or 10 µM, in the perilymph fluid in the inner ear.

In some embodiments, the GSK3 Inhibitor is CHIR99021, is administered to a subject, for example to the middle ear at a concentration of about 0.001 mM to 10,000 mM, about 0.01 mM to 1,000 mM, about 0.1 mM to 100 mM, about 0.001 mM to 0.01 mM, about 0.01 mM to 0.1 mM, about 0.1 mM to 1 mM, about 1 mM to 10 mM, about 10 mM to 100 mM, about 100 mM to 1,000 mM, or about 1,000 mM to 10,000 mM.

Preferably, the CHIR99021 is administered to a subject, for example to the middle ear at a concentration of about 1 mM, 2 mM, 3 mM, 4 mM, 5 mM, 6 mM, 7 mM, 8 mM, 9 mM, or 10 mM.

In some embodiments, the GSK3 Inhibitor is CHIR9902 1and is administered to the subject at a concentration ratio of about 0.001 to 100 fold relative to an FDA approved concentration or about 0.1 to 50 fold relative to an FDA approved concentration, or about 0.1 to 5 fold relative to an FDA approved, or about 1 to 5 fold relative to an FDA approved concentration.

In some embodiments, the GSK3 Inhibitor is CHIR99021 and is administered to the subject at about 0.01×. 0.1×, 2×, 3×, 5× or 10×, relative to an FDA approved concentration.

In some embodiments the HDAC inhibitor is administered for example to a cochlear cell in amount sufficient to achieve a concentration of about is about 0.01 uM to 1000 mM, about 1 uM to 100 mM, about 10 uM to 10 mM, about 1 uM to 10 uM, about 10 uM to 100 uM, about 100 uM to 1000 uM, about 1 mM to 10 mM, or about 10 mM to 100 mM in the perilymph fluid in the inner ear.

In some embodiments the HDAC inhibitor is administered, to a subject, for example to the middle ear at a concentration about 10 uM to 1,000,000 mM, about 1000 uM to 100,000 mM, about 10,000 uM to 10,000 mM, about 1000 uM to 10,000 uM, about 10,000 uM to 100,000 uM, about 100,000 uM to 1,000,000 uM, about 1,000 mM to 10,000 mM, or about 10,000 mM to 100,000 mM.

In some embodiments, the HDAC inhibitor is VPA and is administered for example to a cochlear cell in amount sufficient to achieve a concentration of about is about 10 $\mu$M to 4 mM in the perilymph fluid in the inner ear.

In some embodiments VPA is administered, to a subject, for example to the middle ear at a concentration about 100 mM to 4,000 mM.

In some embodiments, the HDAC inhibitor is VPA and is administered to a subject systemically at a daily dose of about 50 mg, about 100 mg, about 125 mg, about 250 mg, about 500 mg, 1000 mg, 2000 mg, 3000 mg, 4000 mg, or about 5000 mg Preferably, the VPA is administered as an oral dosage form of about 50 mg, about 100 mg, about 125 mg, about 250 mg, about 500 mg, 1000 mg, 2000 mg, 3000 mg, 4000 mg, or about 5000 mg In some embodiments, the HDAC inhibitor is 2-hexyl-4-pentynoic acid and is administered for example to a cochlear cell in amount sufficient to achieve a concentration of about is about 10 $\mu$M to 4 mM in the perilymph fluid in the inner ear.

In some embodiments 2-hexyl-4-pentynoic acid is administered, to a subject, for example to the middle ear at a concentration about 100 mM to 4,000 mM.

In some embodiments, the HDAC inhibitor is 2-hexyl-4-pentynoic acid and is administered to a subject systemically at a daily dose of about 50 mg, about 100 mg, about 125 mg, about 250 mg, about 500 mg, 1000 mg, 2000 mg, 3000 mg, 4000 mg, or about 5000 mg Preferably, the VPA is administered as an oral dosage form of about 50 mg, about 100 mg, about 125 mg, about 250 mg, about 500 mg, 1000 mg, 2000 mg, 3000 mg, 4000 mg, or about 5000 mg In some embodiments, the HDAC inhibitor is Na phenylbutyrate and is administered for example to a cochlear cell in amount sufficient to achieve a concentration of about is about 10 $\mu$M to 4 mM in the perilymph fluid in the inner ear.

In some embodiments Na phenylbutyrate is administered, to a subject, for example to the middle ear at a concentration about 100 mM to 4,000 mM.

In some embodiments, the HDAC inhibitor is Na phenylbutyrate and is administered to a subject systemically at a daily dose of about 50 mg, about 100 mg, about 125 mg, about 250 mg, about 500 mg, 1000 mg, 2000 mg, 3000 mg, 4000 mg, or about 5000 mg Preferably, the VPA is administered as an oral dosage form of about 50 mg, about 100 mg, about 125 mg, about 250 mg, about 500 mg, 1000 mg, 2000 mg, 3000 mg, 4000 mg, or about 5000 mg.

Some embodiments include combination therapies, which comprise contacting the cell or administering (i) the Jag-1 agonist in combination with a (ii) Jag-1 synergist, wherein the combination increases Lgr5+ cochlear cell proliferation relative to each of (i) and (ii) alone. In some instances, the combination is administered transtympanically to the subject. Some embodiments comprise administering the (i) Jag-1 agonist and (ii) a Jag-1 synergist together in the same pharmaceutical composition, as described herein. Some embodiments comprise administering the (i) Jag-1 agonist and the (ii) Jag-1 synergist separately in separate pharmaceutical compositions. In some embodiments, administering the combination of (i) and (ii) results in improved hearing in the subject relative to each of (i) and (ii) alone.

Exemplary combinations therapies include administering two or more of the following compounds: CHIR99021, Vo-Ohpic, AZD1080, LY2090314, GSK3 inhibitor XXII AS1842856 and VPA.

Preferred combinations therapies include: 1) CHIR99021 and Vo-Ohpic; 2) AZD1080 and Vo-Ohpic; 3) LY2090314 and Vo-Ohpic; 4) GSK3 inhibitor XXII and Vo-Ohpic; 5) AS1842856 and VPA or 6) AS842856 and Vo-Ohpic.

In some embodiments the Jag-1 synergist is Vo-Ohpic and the Jag-1 agonist is CHIR99021. Preferably, Vo-Ohpic is administered, in amount sufficient to achieve a concentration of about 1 $\mu$M, 2 $\mu$M, 3 $\mu$M, 4 $\mu$M, 5 $\mu$M, 6 $\mu$M, 7 $\mu$M, 8 $\mu$M, 9 $\mu$M, or 10 $\mu$Min the perilymph fluid in the inner ear and CHIR99021 is administered, in amount sufficient to achieve a concentration of about 1 $\mu$M, 2 $\mu$M, 3 $\mu$M, 4 $\mu$M, 5 $\mu$M, 6 $\mu$M, 7 $\mu$M, 8 $\mu$M, 9 $\mu$M, or 10 $\mu$M, in the perilymph fluid in the inner ear.

Alternatively, Vo-Ohpic is administered to a subject, for example to the middle ear at a concentration of 1 mM, 2 mM, 3 mM, 4 mM, 5 mM, 6 mM, 7 mM, 8 mM, 9 mM, or 10 mM and CHIR99021 is administered to a subject, for example to the middle ear at a concentration of about 1 mM, 2 mM, 3 mM, 4 mM, 5 mM, 6 mM, 7 mM, 8 mM, 9 mM, or 10 mM.

In some embodiments the Jag-1 synergist is Vo-Ohpic and the Jag-1 agonist is AZD1080. Preferably, the Vo-Ohpic is administered, in amount sufficient to achieve a concentration of 1 $\mu$M, 2 $\mu$M, 3 $\mu$M, 4 $\mu$M, 5 $\mu$M, 6 $\mu$M, 7 $\mu$M, 8 $\mu$M, 9 $\mu$M, or 10 $\mu$M in the perilymph fluid in the inner ear and AZD1080 is administered, in amount sufficient to achieve a concentration of about is about 1 $\mu$M, 2 $\mu$M, 3 $\mu$M, 4 $\mu$M, 5 $\mu$M, 6 $\mu$M, 7 $\mu$M, 8 $\mu$M, 9 $\mu$M, or 10 $\mu$M, in the perilymph fluid in the inner ear.

Alternatively, the Vo-Ohpic to a subject, for example to the middle ear at a concentration of about 1 mM, 2 mM, 3 mM, 4 mM, 5 mM, 6 mM, 7 mM, 8 mM, 9 mM, or 10 mM and AZD1080, and is administered to a subject, for example to the middle ear at a concentration of about 1 mM, 2 mM, 3 mM, 4 mM, 5 mM, 6 mM, 7 mM, 8 mM, 9 mM, or 10 mM.

In some embodiments the Jag-1 synergist is Vo-Ohpic and the Jag-1 agonist is LY209031. Preferably, the Vo-Ohpic is administered, in amount sufficient to achieve a concentration of about 1 μM, 2 μM, 3 μM, 4 μM, 5 μM, 6 μM, 7 μM, 8 μM, 9 μM, or 10 μM in the perilymph fluid in the inner ear and LY2090314 is administered, in amount sufficient to achieve a concentration of about 1 nM, 5 nM, 10 nM, 15 nM, 20 nM or 40 nM, in the perilymph fluid in the inner ear.

Alternatively, the Vo-Ohpic to a subject, for example to the middle ear at a concentration of about 1 mM, 2 mM, 3 mM, 4 mM, 5 mM, 6 mM, 7 mM, 8 mM, 9 mM, or 10 mM and LY2090314, and is administered to a subject, for example to the middle ear at a concentration of about 1 μM, 5 μM, 10 μM, 15 μM, 20 μM, or 40 nM.

In some embodiments the Jag-1 synergist is Vo-Ohpic and the Jag-1 agonist is GSK3 inhibitor XXII. Preferably, Vo-Ohpic is administered, in amount sufficient to achieve a concentration of about 1 μM, 2 μM, 3 μM, 4 μM, 5 μM, 6 μM, 7 μM, 8 μM, 9 μM, or 10 μM in the perilymph fluid in the inner ear and GSK3-inhibitor XXII is administered, in amount sufficient to achieve a concentration of about 0.1 μM, 0.2 μM, 0.3 μM, 0.4 μM, 0.5 μM, 0.6 μM, 0.7 μM, 0.8 μM, 0.9 μM, or 1.0 μM, in the perilymph fluid in the inner ear.

Alternatively, the Vo-Ohpic is administered to a subject, for example to the middle ear at a concentration of about 1 mM, 2 mM, 3 mM, 4 mM, 5 mM, 6 mM, 7 mM, 8 mM, 9 mM, or 10 mM or about 30 mM and the GSK3-inhibitor XXII is administered, is administered to a subject, for example to the middle ear at a concentration of about 0.1 mM, 0.2 mM, 0.3 mM, 0.4 mM, 0.5 mM, 0.6 mM, 0.7 mM, 0.8 mM, 0.9 mM, or 1.0 mM.

In some embodiments the Jag-1 agonist is AS1843856 and the additional agent is VPA. Preferably, AS1843856 is administered, in amount sufficient to achieve a concentration of about 0.1 μM, 0.2 μM, 0.3 μM, 0.4 μM, 0.5 μM, 0.6 μM, 0.7 μM, 0.8 μM, 0.9 uM, or 1 μM. in the perilymph fluid in the inner ear and VPA is administered in amount sufficient to achieve a concentration of about is about 100 μM to 4 mM in the perilymph fluid in the inner ear.

Alternatively, the AS1843856 is administered to a subject, for example to the middle ear at a concentration of about 0.1 mM, 0.2 mM, 0.3 mM, 0.4 mM, 0.5 mM, 0.6 mM, 0.7 mM, 0.8 mM, 0.9 mM, or 1 mM and VPA to a subject, for example to the middle ear at a concentration about 100 mM to 4,000 mM.

In some embodiments the Jag-1 agonist is AS1843856 and the additional agent is Vo-Ohpic. Preferably, AS1843856 is administered, in amount sufficient to achieve a concentration of about 0.1 μM, 0.2 μM, 0.3 μM, 0.4 μM, 0.5 μM, 0.6 μM, 0.7 μM, 0.8 μM, 0.9 uM, or 1 μM. in the perilymph fluid in the inner ear and Vo-Ohpic is administered in amount sufficient to achieve a concentration of about is about 1 μM, 2 μM, 3 μM, 4 μM, 5 μM, 6 μM, 7 μM, 8 μM, 9 μM, or 10 μM in the perilymph fluid in the inner ear.

Alternatively, the AS1843856 is administered to a subject, for example to the middle ear at a concentration of about 0.1 mM, 0.2 mM, 0.3 mM, 0.4 mM, 0.5 mM, 0.6 mM, 0.7 mM, 0.8 mM, 0.9 mM, or 1 mM and Vo-Ohpic to a subject, for example to the middle ear at a concentration about 1 mM, 2 mM, 3 mM, 4 mM, 5 mM, 6 mM, 7 mM, 8 mM, 9 mM, or 10 mM.

Pharmaceutical Compositions and Administration

Certain embodiments relate to pharmaceutical, prophylactic, and/or therapeutic compositions, comprising a pharmaceutically-acceptable carrier and a to Jag-1 agonist, a Deltex-1 agonist or a non-canonical Notch signaling agonist (and optionally an additional agent,) a pharmaceutically-acceptable salt thereof or combinations thereof as described herein (collectively referred to herein as the "hair cell regeneration agent(s)" or compound(s)").

In some embodiments, the concentration of the compound (s) in the pharmaceutical compositions of the invention are at the "formulation effective concentration" as described supra.

In some embodiments, the pharmaceutical composition comprises a Jag-1 agonist at a concentration of about 10 uM to 1,000,000 mM, about 100 uM to 1,000,000 mM, about 1000 uM to 100,000 mM, about 10,000 uM to 10,000 mM, about 1,000 uM to 10,000 uM, about 10,000 uM to 100,000 uM, about 100,000 uM to 1,000,000 uM, about 1000 mM to 10,000 mM, or about 10,000 mM to 100,000 mM.

In some embodiments, the pharmaceutical composition comprises a Jag-1 agonist that is a soluble Jag-1 peptide at a concentration of about 10 uM to 1,000,000 mM, about 100 uM to 1,000,000 mM, about 1000 uM to 100,000 mM, about 10,000 uM to 10,000 mM, about 1,000 uM to 10,000 uM, about 10,000 uM to 100,000 uM, about 100,000 uM to 1,000,000 uM, about 1000 mM to 10,000 mM, or about 10,000 mM to 100,000 mM.

In some embodiments, the pharmaceutical composition comprises a Jag-1 agonist that is HIF1-α activator at a concentration of about 10 uM to 1,000,000 mM, about 100 uM to 1,000,000 mM, about 1000 uM to 100,000 mM, about 10,000 uM to 10,000 mM, about 1,000 uM to 10,000 uM, about 10,000 uM to 100,000 uM, about 100,000 uM to 1,000,000 uM, about 1000 mM to 10,000 mM, or about 10,000 mM to 100,000 mM.

In some embodiments, the pharmaceutical composition comprises a HIF1-α activator that is 1, 4-DPCA at a concentration of about 10 uM to 1,000,000 mM, about 100 uM to 1,000,000 mM, about 1000 uM to 100,000 mM, about 10,000 uM to 10,000 mM, about 1,000 uM to 10,000 uM, about 10,000 uM to 100,000 uM, about 100,000 uM to 1,000,000 uM, about 1000 mM to 10,000 mM, or about 10,000 mM to 100,000 mM.

In some embodiments, the pharmaceutical composition comprises a HIF1-α activator that is FG-2216 at a concentration of about 10 uM to 1,000,000 mM, about 100 uM to 1,000,000 mM, about 1000 uM to 100,000 mM, about 10,000 uM to 10,000 mM, about 1,000 uM to 10,000 uM, about 10,000 uM to 100,000 uM, about 100,000 uM to 1,000,000 uM, about 1000 mM to 10,000 mM, or about 10,000 mM to 100,000 mM.

In some embodiments, the pharmaceutical composition comprises a HIF1-α activator that is Daprodusat at a concentration of about 10 uM to 1,000,000 mM, about 100 uM to 1,000,000 mM, about 1000 uM to 100,000 mM, about 10,000 uM to 10,000 mM, about 1,000 uM to 10,000 uM, about 10,000 uM to 100,000 uM, about 100,000 uM to 1,000,000 uM, about 1000 mM to 10,000 mM, or about 10,000 mM to 100,000 mM.

In some embodiments, the pharmaceutical composition comprises a PI3K agonist at a concentration of about 10 uM to 1,000,000 mM, about 100 uM to 1,000,000 mM, about 1000 uM to 100,000 mM, about 10,000 uM to 10,000 mM, about 1,000 uM to 10,000 uM, about 10,000 uM to 100,000 uM, about 100,000 uM to 1,000,000 uM, about 1000 mM to 10,000 mM, or about 10,000 mM to 100,000 mM In some embodiments, the pharmaceutical composition comprises a PI3K agonist that is a FOXO inhibitor at a concentration of about 10 uM to 1,000,000 mM, about 100 uM to 1,000,000 mM, about 1000 uM to 100,000 mM, about 10,000 uM to 10,000 mM, about 1,000 uM to 10,000 uM, about 10,000 uM to 100,000 uM, about 100,000 uM to 1,000,000 uM, about 1000 mM to 10,000 mM, or about 10,000 mM to 100,000 mM In some embodiments, the pharmaceutical composition comprises a FOXO inhibitor that is AS1842856 at a concentration of about 10 uM to 1,000,000 mM, about 100 uM to 1,000,000 mM, about 1000 uM to 100,000 mM, about 10,000 uM to 10,000 mM, about 1,000 uM to 10,000 uM, about 10,000 uM to 100,000 uM, about 100,000 uM to 1,000,000 uM, about 1000 mM to 10,000 mM, or about 10,000 mM to 100,000 mM. Preferably, the AS1842856 "formulation effective concentration" is about 0.1 mM, 0.2 mM, 0.3 mM, 0.4 mM, 0.5 mM, 0.6 mM, 0.7 mM, 0.8 mM, 0.9 mM, or 1 mM.

In other embodiments the pharmaceutical composition comprises a Deltex-1 agonist at a concentration of about 10 uM to 1,000,000 mM, about 1000 uM to 100,000 mM, about 10,000 uM to 10,000 mM, about 1000 uM to 10,000 uM, about 10,000 uM to 100,000 uM, about 100,000 uM to 1,000,000 uM, about 1,000 mM to 10,000 mM, or about 10,000 mM to 100,000 mM.

In other embodiments the pharmaceutical composition comprises a Jag-1synergist at a concentration of about 10 uM to 1,000,000 mM, about 1000 uM to 100,000 mM, about 10,000 uM to 10,000 mM, about 1000 uM to 10,000 uM, about 10,000 uM to 100,000 uM, about 100,000 uM to 1,000,000 uM, about 1,000 mM to 10,000 mM, or about 10,000 mM to 100,000 mM.

In other embodiments the pharmaceutical composition comprises a Jag-1synergist that is a PI3K synergist at a concentration of about 10 uM to 1,000,000 mM, about 1000 uM to 100,000 mM, about 10,000 uM to 10,000 mM, about 1000 uM to 10,000 uM, about 10,000 uM to 100,000 uM, about 100,000 uM to 1,000,000 uM, about 1,000 mM to 10,000 mM, or about 10,000 mM to 100,000 mM.

In some embodiments, the pharmaceutical composition comprises a PI3K synergist that is a PTEN inhibitor at a concentration of about 10 uM to 1,000,000 mM, about 1000 uM to 100,000 mM, about 10,000 uM to 10,000 mM, about 1000 uM to 10,000 uM, about 10,000 uM to 100,000 uM, about 100,000 uM to 1,000,000 uM, about 1,000 mM to 10,000 mM, or about 10,000 mM to 100,000 mM In some embodiments, the pharmaceutical composition comprises a PTEN inhibitor that is SF1670 at a concentration of about 10 uM to 1,000,000 mM, about 1000 uM to 100,000 mM, about 10,000 uM to 10,000 mM, about 1000 uM to 10,000 uM, about 10,000 uM to 100,000 uM, about 100,000 uM to 1,000,000 uM, about 1,000 mM to 10,000 mM, or about 10,000 mM to 100,000 mM.

In some embodiments, the pharmaceutical composition comprises a PTEN inhibitor that is VO-Ohpic at a concentration of about 10 uM to 1,000,000 mM, about 1000 uM to 100,000 mM, about 10,000 uM to 10,000 mM, about 1000 uM to 10,000 uM, about 10,000 uM to 100,000 uM, about 100,000 uM to 1,000,000 uM, about 1,000 mM to 10,000 mM, or about 10,000 mM to 100,000 mM. Preferably, the VO-Ohpic concentration in the pharmaceutical composition is about 1 mM, 2 mM, 3 mM, 4 mM, 5 mM, 6 mM, 7 mM, 8 mM, 9 mM, or 10 mM.

In some embodiments, the pharmaceutical composition comprises a PTEN inhibitor that is bpV(phen) at a concentration of about 10 uM to 1,000,000 mM, about 1000 uM to 100,000 mM, about 10,000 uM to 10,000 mM, about 1000 uM to 10,000 uM, about 10,000 uM to 100,000 uM, about 100,000 uM to 1,000,000 uM, about 1,000 mM to 10,000 mM, or about 10,000 mM to 100,000 mM. Preferably, the bpV(phen) concentration in the pharmaceutical composition is about 1 mM, 2 mM, 3 mM, 4 mM, 5 mM, 6 mM, 7 mM, 8 mM, 9 mM, or 10 mM.

In some embodiments, the pharmaceutical composition comprises a PTEN inhibitor that is bpV(pic) at a concentration of about 10 uM to 1,000,000 mM, about 1000 uM to 100,000 mM, about 10,000 uM to 10,000 mM, about 1000 uM to 10,000 uM, about 10,000 uM to 100,000 uM, about 100,000 uM to 1,000,000 uM, about 1,000 mM to 10,000 mM, or about 10,000 mM to 100,000 mM. Preferably, the bpV(pic) concentration in the pharmaceutical composition is about 1 mM, 2 mM, 3 mM, 4 mM, 5 mM, 6 mM, 7 mM, 8 mM, 9 mM, or 10 mM.

In some embodiments, the pharmaceutical composition comprises a GSK3 Inhibitor that is AZD1080, at a concentration of about 0.001 mM to 10,000 mM, about 0.01 mM to 1,000 mM, about 0.1 mM to 100 mM, about 0.001 mM to 0.01 mM, about 0.01 mM to 0.1 mM, about 0.1 mM to 1 mM, about 1 mM to 10 mM, about 10 mM to 100 mM, about 100 mM to 1,000 mM, or about 1,000 mM to 10,000 mM. Preferably, the AZD1080 is at a concentration of about 1 mM, 2 mM, 3 mM, 4 mM, 5 mM, 6 mM, 7 mM, 8 mM, 9 mM, or 10 mM.

In some embodiments, the pharmaceutical composition comprises a GSK3 Inhibitor that is LY2090314 at a concentration of about 0.001 µM to 10 mM, about 0.01 µM to 1 mM, about 0.1 µM to 100 uM, about 0.001 µM to 0.01 µM, about 0.01 µM to 0.1 µM, about 0.1 µM to 1 µM, about 1 µM to 10 µM, about 10 µM to 100 µM, about 100 µM to 1 mM, or about 1 mM to 10 mM. Preferably, LY2090314 the is at a concentration of about 1 µM, 5 µM, 10 µM, 15 µM, 20 µM, or 40 µM.

In some embodiments, the pharmaceutical composition comprises a GSK3 Inhibitor that is a substituted 3-Imidazo[1,2-a]pyridin-3-yl-4-(1,2,3,4-tetrahydro-[1,4]diazepino-[6,7,1-hi]indol-7-yl)pyrrole-2,5-dione at a concentration of about 0.001 µM to 10 mM, about 0.01 µM to 1 mM, about 0.1 µM to 100 uM, about 0.001 µM to 0.01 µM, about 0.01 µM to 0.1 µM, about 0.1 µM to 1 µM, about 1 µM to 10 µM, about 10 µM to 100 µM, about 100 µM to 1 mM, or about 1 mM to 10 mM. Preferably, the substituted 3-Imidazo[1,2-a]pyridin-3-yl-4-(1,2,3,4-tetrahydro-[1,4]diazepino-[6,7,1-hi]indol-7-yl)pyrrole-2,5-dione, is at a concentration of about 1 µM, 5 µM, 10 µM, 15 µM, 20 µM, 50 µM, 100 µM, 250 µM, or 500 µM.

In some embodiments, the pharmaceutical composition comprises a GSK3 Inhibitor that is GSK3-inhibitor XXII, at a concentration of about of about 0.1 µM to 1,000 mM, about 1 µM to 100 mM, about 10 µM to 10 mM, about 0.1 µM to 1 µM, about 1 µM to 10 µM, about 10 µM to 100 µM, about 100 µM to 1 mM, about 1 mM to 10 mM, about 10 mM to 100 mM, or about 100 mM to 1000 mM. Preferably, the GSK3-inhibitor XXII is at a concentration of about 0.1 mM, 0.2 mM, 0.3 mM, 0.4 mM, 0.5 mM, 0.6 mM, 0.7 mM, 0.8 mM, 0.9 mM, or 1.0 mM.

In some embodiments, the pharmaceutical composition comprises a GSK3 Inhibitor that is CHIR99021 at a concentration of about 0.001 mM to 10,000 mM, about 0.01 mM to 1,000 mM, about 0.1 mM to 100 mM, about 0.001 mM to 0.01 mM, about 0.01 mM to 0.1 mM, about 0.1 mM to 1 mM, about 1 mM to 10 mM, about 10 mM to 100 mM, about 100 mM to 1,000 mM, or about 1,000 mM to 10,000 mM. Preferably, the CHIR99021 is at a concentration of about 1 mM, 2 mM, 3 mM, 4 mM, 5 mM, 6 mM, 7 mM, 8 mM, 9 mM, or 10 mM.

In some embodiments, the pharmaceutical composition comprises an epigenetic agent that is an HDAC inhibitor at a concentration about 10 uM to 1,000,000 mM, about 1000 uM to 100,000 mM, about 10,000 uM to 10,000 mM, about 1000 uM to 10,000 uM, about 10,000 uM to 100,000 uM, about 100,000 uM to 1,000,000 uM, about 1,000 mM to 10,000 mM, or about 10,000 mM to 100,000 mM.

In some embodiments, the pharmaceutical composition comprises a HDAC inhibitor that is VPA at a concentration about 100 mM to 4,000 mM.

In some embodiments, the pharmaceutical composition comprises VPA at a unit dose of about 50 mg, about 100 mg, about 125 mg, about 250 mg, about 500 mg, 1000 mg, 2000 mg, 3000 mg, 4000 mg, or about 5000 mg In some embodiments, the pharmaceutical composition comprises an oral dosage form of VPA at a unit dose of about 50 mg, about 100 mg, about 125 mg, about 250 mg, about 500 mg, 1000 mg, 2000 mg, 3000 mg, 4000 mg, or about 5000 mg In some embodiments, the pharmaceutical composition comprises a HDAC inhibitor that is 2-hexyl-4-pentynoic acid at concentration about 100 mM to 4,000 mM.

In some embodiments, the pharmaceutical composition comprises 2-hexyl-4-pentynoic acid at a unit dose of 50 mg, about 100 mg, about 125 mg, about 250 mg, about 500 mg, 1000 mg, 2000 mg, 3000 mg, 4000 mg, or about 5000 mg In some embodiments, the pharmaceutical composition comprises an oral dosage form of 2-hexyl-4-pentynoic acid at a unit dose of about 50 mg, about 100 mg, about 125 mg, about 250 mg, about 500 mg, 1000 mg, 2000 mg, 3000 mg, 4000 mg, or about 5000 mg In some embodiments, the pharmaceutical composition comprises, Na phenylbutyrate that is at a concentration about 100 mM to 4,000 mM.

In some embodiments, the pharmaceutical composition comprises Na phenylbutyrate at a unit dose of about 50 mg, about 100 mg, about 125 mg, about 250 mg, about 500 mg, 1000 mg, 2000 mg, 3000 mg, 4000 mg, or about 5000 mg In some embodiments, the pharmaceutical composition comprises an oral dosage form of the Na phenylbutyrate at a unit dose of about 50 mg, about 100 mg, about 125 mg, about 250 mg, about 500 mg, 1000 mg, 2000 mg, 3000 mg, 4000 mg, or about 5000 mg In some embodiments, the pharmaceutical composition comprises a Jag-1 synergist that is Vo-Ohpic and a Jag-1 agonist that is CHIR99021. The Vo- at a concentration of 1 mM, 2 mM, 3 mM, 4 mM, 5 mM, 6 mM, 7 mM, 8 mM, 9 mM, or 10 mM and the CHIR99021 is at a concentration of about 1 mM, 2 mM, 3 mM, 4 mM, 5 mM, 6 mM, 7 mM, 8 mM, 9 mM, or 10 mM.

In some embodiments, the pharmaceutical composition comprises a the Jag-1 synergist that is Vo-Ohpic and a Jag-1 agonist that is AZD1080. The Vo-Ohpic is at a concentration of about 1 mM, 2 mM, 3 mM, 4 mM, 5 mM, 6 mM, 7 mM, 8 mM, 9 mM, or 10 mM and AZD1080, is at a concentration of about 1 mM, 2 mM, 3 mM, 4 mM, 5 mM, 6 mM, 7 mM, 8 mM, 9 mM, or 10 mM.

In some embodiments, the pharmaceutical composition comprises a Jag-1 synergist that is Vo-Ohpic and a Jag-1 agonist that is LY209031. The Vo-Ohpic is at a concentration of about 1 mM, 2 mM, 3 mM, 4 mM, 5 mM, 6 mM, 7 mM, 8 mM, 9 mM, or 10 mM and LY2090314, is at a concentration of about 1 $\mu$M, 5 $\mu$M, 10 $\mu$M, 15 $\mu$M, 20 $\mu$M, or 40 nM.

In some embodiments, the pharmaceutical composition comprises a Jag-1 synergist that is Vo-Ohpic and a Jag-1 agonist that is GSK3 inhibitor XXII. The Vo-Ohpic is at a concentration of about 1 mM, 2 mM, 3 mM, 4 mM, 5 mM, 6 mM, 7 mM, 8 mM, 9 mM, or 10 mM or about 30 mM and the GSK3-inhibitor XXII is at a concentration of about 0.1 mM, 0.2 mM, 0.3 mM, 0.4 mM, 0.5 mM, 0.6 mM, 0.7 mM, 0.8 mM, 0.9 mM, or 1.0 mM.

Alternatively, the Vo-Ohpic is administered to a subject, for example to the middle ear at a concentration of about 1 mM, 2 mM, 3 mM, 4 mM, 5 mM, 6 mM, 7 mM, 8 mM, 9 mM, or 10 mM or about 30 mM and the GSK3-inhibitor XXII is administered, in amount sufficient to achieve a concentration of about 0.1 mM, 0.2 mM, 0.3 mM, 0.4 mM, 0.5 mM, 0.6 mM, 0.7 mM, 0.8 mM, 0.9 mM, or 1.0 mM, in the perilymph fluid in the inner ear.

In some embodiments, the pharmaceutical composition comprises a Jag-1 agonist that is AS1843856 and an additional agent that is VPA. The AS1843856 is at a concentration of about 0.1 mM, 0.2 mM, 0.3 mM, 0.4 mM, 0.5 mM, 0.6 mM, 0.7 mM, 0.8 mM, 0.9 mM, or 1 mM and VPA is at a concentration about 100 mM to 4,000 mM.

In some embodiments, the pharmaceutical composition comprises a Jag-1 agonist that is AS1843856 and a Jag-1 synergist that is Vo-Ohpic. The AS1843856 is at a concentration of about 0.1 mM, 0.2 mM, 0.3 mM, 0.4 mM, 0.5 mM, 0.6 mM, 0.7 mM, 0.8 mM, 0.9 mM, or 1 mM and Vo-is at a concentration about 1 mM, 2 mM, 3 mM, 4 mM, 5 mM, 6 mM, 7 mM, 8 mM, 9 mM, or 10 mM.

In some embodiments, as noted above, a composition is adapted for administration to the inner ear and/or middle ear, for example, local administration to the round window membrane or intratympanic or transtympanic administration, for example, to cochlear tissue. Alternatively, as noted above, a composition is adapted for administration systemically for example, orally or parentally.

When administered locally, for example to the inner and/or middle ear, the compounds (s) are administered at a unit dose of about 25 $\mu$l to 500 $\mu$l, or about 50 $\mu$l to 200 $\mu$l.

The phrase "pharmaceutically-acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically-acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Exemplary pharmaceutically-acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations.

Certain compositions comprise at least one biocompatible matrix. The term "biocompatible matrix" as used herein is a polymeric carrier that is acceptable for administration to humans for the release of therapeutic agents. In some instances, a biocompatible matrix may be a biocompatible gel, foam, fiber, film, or mats. In some embodiments the biocompatible matrix is derived from silk.

In some embodiments the biocompatible matrix comprises hyaluronic acid, hyaluronates, lecithin gels, pluronics, poly(ethyleneglycol), polymers, poloxamers, chitosans, xyloglucans, collagens, fibrins, polyesters, poly(lactides), poly(glycolide), poly(lactic-co-glycolic acid (PLGA), sucrose acetate isobutyrate, glycerol monooleate, poly anhydrides, poly caprolactone sucrose, glycerol monooleate or a combination thereof.

Exemplary polymers suitable for formulating the biologically active compositions of the present disclosure include, but are not limited to polyamides, polycarbonates, polyalkylenes (polyethylene glycol (PEG)), polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly (lactide-co-caprolactone), polysaccharides, proteins, polyhyaluronic acids, polycyanoacrylates, and blends, mixtures, or copolymers thereof.

In some embodiments, the polymer is in a concentration between about 5 wt % and about 25 wt % relative to the composition, or about 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, or 25 wt % relative to the composition. In certain embodiments, the polymer is in a concentration between about 10 wt % and about 23 wt % relative to the composition. In some embodiments the polymer is in a concentration between about 15 wt % and about 20 wt % relative to the composition. In particular embodiments, the polymer is in a concentration is approximately 17 wt % relative to the composition.

In one embodiment, a biologically active composition of the present disclosure is formulated in a ABA-type or BAB-type triblock copolymer or a mixture thereof, wherein the A-blocks are relatively hydrophobic and comprise biodegradable polyesters or poly(orthoester), and the B-blocks are relatively hydrophilic and comprise polyethylene glycol (PEG). The biodegradable, hydrophobic A polymer block comprises a polyester or poly(ortho ester), in which the polyester is synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxyhexanoic acid, γ-butyrolactone, γ-hydroxybutyric acid, δ-valerolactone, δ-hydroxyvaleric acid, hydroxybutyric acids, malic acid, and copolymers thereof.

In some embodiments, the copolymer is in a concentration between about 5 wt % and about 25 wt % relative to the composition, or about 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, or 25 wt % relative to the composition. In certain embodiments, the copolymer is in a concentration between about 10 wt % and about 23 wt % relative to the composition. In some embodiments the copolymer is in a concentration between about 15 wt % and about 20 wt % relative to the composition. In particular embodiments, the copolymer is in a concentration is approximately 17 wt % relative to the composition.

Certain compositions comprise at least one poloxamer. Poloxamers are triblock copolymers formed of (i.e., hydrophilic poly(oxyethylene) blocks and hydrophobic poly(oxypropylene) blocks) configured as a triblock of poly(oxyethylene)-poly(oxypropylene)-poly(oxyethylene). Poloxamers are one class of block copolymer surfactants having a propylene oxide block hydrophobe and an ethylene oxide hydrophile. Poloxamers are commercially available (e.g., Pluronic® polyols are available from BASF Corporation). Alternatively, poloxamers can be synthesized by known techniques.

Exemplary poloxamers include Poloxamer 124, Poloxamer 188, Poloxamer 237, Poloxamer 338, and Poloxamer 407. In some embodiments, the poloxamer comprises mixtures of two or more of Poloxamer 124, Poloxamer 188, Poloxamer 237, Poloxamer 338 or Poloxamer 407. In some embodiments, the mixture of two or more poloxamers comprise Poloxamer 407 and Poloxamer 124. In certain embodiments the poloxamer comprises at least one of Poloxamer 188 and Poloxamer 407 or mixtures thereof. In some embodiments, the poloxamer is Poloxamer 407.

In some embodiments, the poloxamer is in a concentration between about 5 wt % and about 25 wt % relative to the composition, or about 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, or 25 wt % relative to the composition. In certain embodiments, the poloxamer is in a concentration between about 10 wt % and about 23 wt % relative to the composition. In some embodiments the poloxamer is in a concentration between about 15 wt % and about 20 wt % relative to the composition. In particular embodiments, the poloxamer is in a concentration is approximately 17 wt % relative to the composition.

In some embodiments, wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Certain compositions comprise at least one antioxidant. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In specific embodiments, the viscosity of the composition at about body temperature is substantially different (e.g., lesser, greater) than the viscosity of the composition at room temperature.

In some embodiments, the composition comprises a buffer. For example, in certain instances, the buffer is physiological saline or phosphate-buffered saline (PBS).

In some embodiments, the composition is at or near physiological pH. For instance, in some embodiments, the composition has a pH of between about 6 and about 8, including all integers, decimals, and ranges in between, for example, about 6 to about 6.5 to about 7 to about 7.5 to about 8. In specific embodiments, the composition has a pH of about 7.4 (±0.2).

In some aspects, the present disclosure the pharmaceutical compositions are lyophilized. comprising one or more agents described herein and a gelling agent.

In some embodiments, the lyophilized pharmaceutical composition is in the form of a lyophilized cake.

In some embodiments, the lyophilized pharmaceutical composition has a higher stability to oxygen and/or light as compared to a comparable pharmaceutical composition comprising one or more solvents.

In some embodiments, the present disclosure provides a reconstituted solution of the lyophilized pharmaceutical compositions.

As used herein, the term "gelling agent" refers to an agent capable of imparting a gel-like or thickening quality to the pharmaceutical composition or reconstituted solution of the present disclosure upon being subjected to a gelling condition (e.g., a particular temperature or temperature range, the presence of an ion, a pH value or range, or a concentration of gelling agent that causes the gelling agent to undergoing a change or transition from low viscosity to high viscosity, or the reverse). In some embodiments, the gelling condition is a particular temperature (e.g., about 26° C., about 27° C., about 28° C., about 29° C., about 30° C., about 31° C., about 32° C., about 33° C., about 34° C., about 35° C., about 36° C., about 37° C., about 38° C., about 39° C., or about 40° C.). In some embodiments, the gelling condition is a particular temperature range (e.g., about 26° C. or higher, about 27° C. or higher, about 28° C. or higher, about 29° C. or higher, about 30° C. or higher, about 31° C. or higher, about 32° C. or higher, about 33° C. or higher, about 34° C. or higher, about 35° C. or higher, about 36° C. or higher, about 37° C. or higher, about 38° C. or higher, about 39° C. or higher, or about 40° C. or higher). In some embodiments, the gelling agent provides a viscosity of between about 1,000 and 10,000,000 centipoise, between about 5,000 and 5,000,000 centipoise, or between about 100,000 and 4,000,000 centipoise, to the pharmaceutical composition or reconstituted solution of the present disclosure. In some embodiments, the gelling agent provides a viscosity of between about 50,000 and 2,000,000 centipoise to the pharmaceutical composition or reconstituted solution of the present disclosure.

In some embodiments, prior to gelling (e.g., at ambient temperature (e.g., between about 20° C. and about 26° C.)), the gelling agent provides a viscosity of less than about 100,000 centipoise, less than about 50,000 centipoise, 20,000 centipoise, less than about 10,000 centipoise, less than about 8,000 centipoise, less than about 7,000 centipoise, less than about 6,000 centipoise, less than about 5,000 centipoise, less than about 4,000 centipoise, less than about 3,000 centipoise, less than about 2,000 centipoise, or less than about 1,000 centipoise to the pharmaceutical composition or reconstituted solution of the present disclosure.

In some embodiments, upon gelling (e.g., at the temperature of a human body (e.g., between about 35° C. to about 39° C., between about 36° C. to about 38° C., or at about 37° C.)), the gelling agent provides a viscosity of greater than about 1,000 centipoise, greater than about 5,000 centipoise, greater than about 10,000 centipoise, greater than about 20,000 centipoise, greater than about 50,000 centipoise, greater than about 60,000 centipoise, greater than about 70,000 centipoise, greater than about 80,000 centipoise, greater than about 90,000 centipoise, or greater than about 100,000 centipoise.

In some embodiments, upon gelling (e.g., at the temperature of a human body (e.g., between about 36° C. to about 39° C., or at about 37° C.)), the viscosity of the pharmaceutical composition or reconstituted solution of the present disclosure, as measured in units of centipoise, being about 2 fold or greater, about 5 fold or greater, about 10 fold or greater, about 20 fold or greater, about 50 fold or greater, about 60 fold or greater, about 7 fold or greater, about 80 fold or greater, about 90 fold or greater, about 100 fold or greater as compared to the viscosity of the pharmaceutical composition or reconstituted solution prior to gelling (e.g., at ambient temperature (e.g., at about 25° C.)).

It is understood that the gelling condition (e.g., gelling temperature) of the pharmaceutical composition or reconstituted solution of the present disclosure may be measured with a variety of techniques in the art. In some embodiment, the gelling temperature is determined using a commercially available rheomoeter having a parallel plate geometry (e.g., with plate distance ranging from 0.5 mm to 1.0 mm). In some embodiments, the analysis is performed over a continuous temperature range (e.g., 15° C. to 40° C.) at a constant rate (e.g., 2 to 3° C./min) and a deformation frequency of 0.74 Hz to 1 Hz. The gelation temperature is determined at the temperature whereby the shear storage modulus (G') and the shear loss modulus (G") are equal.

In some embodiments, the gelling agent comprises acacia, alginic acid, bentonite, poly(acrylic acid) (Carbomer), carboxymethyl cellulose, ethylcellulose, gelatin, hydroxyethyl cellulose, hydroxypropyl cellulose, magnesium aluminum silicate (Veegum), methylcellulose, poloxamer, hyaluronic acid sodium, polylacticglycolic acid sodium, chitosan, polyvinyl alcohol, sodium alginate, tragacanth, xanthan gum, or any combination thereof. In some embodiment, the gelling agent comprises poloxamer.

In some embodiments, the gelling agent is a thermoreversible gelling agent.

As used herein, the term "thermoreversible" refers to a capability of being reversible by the application of heat. The "thermoreversible gelling agent" refers to an agent capable of reversibly imparting a gel-like or thickening quality to the pharmaceutical composition or reconstituted solution of the present disclosure upon application of heat.

In some embodiments, the thermoreversible gelling agent comprises a poloxamer.

It is understood that the gelling agent (e.g., the thermoreversible gelling agent) may also be a bulking agent of the pharmaceutical composition or reconstituted solution of the present disclosure. In some embodiments, a poloxamer (e.g., poloxamer 407) is the gelling agent and/or the bulking agent of the pharmaceutical composition or reconstituted solution of the present disclosure. Poloxomers are a general class of commercially available and pharmaceutically acceptable triblock copolymers of polyethylene oxide-polypropylene oxide-polyethylene oxide which exhibit relatively low viscosity at low temperatures (e.g., room temperature or below) but much high viscosities at elevated temperatures (e.g., body temperatures of approximately 37° C.) whereby compositions containing such thermoreversible gelling agents effectively solidify in place. Other thermoreversible gelling agents such as polyethylene oxide-polylactic acid-polyethylene oxide polymers are also suitable in various embodiments of the present invention.

In some embodiments, the poloxamer (e.g., poloxamer 407) is the gelling agent and the bulking agent of the pharmaceutical composition or reconstituted solution of the present disclosure. In some embodiments, the presence of the poloxamer (e.g., poloxamer 407) in the pharmaceutical composition (e.g., the lyophilized pharmaceutical composition) alleviates the need for any other excipient (e.g., additional bulking agent). Such alleviation may provide one or more advantages to the pharmaceutical composition (e.g., enhanced stability and/or reduced reconstitution time).

In some embodiments, the poloxamer is selected from the group consisting of Poloxamer 101, Poloxamer 105, Poloxamer 108, Poloxamer 122, Poloxamer 123, Poloxamer 124, Poloxamer 181, Poloxamer 182, Poloxamer 183, Poloxamer 184, Poloxamer 185, Poloxamer 188, Poloxamer 212, Poloxamer 215, Poloxamer 217, Poloxamer 231, Poloxamer 234, Poloxamer 235, Poloxamer 237, Poloxamer 238, Poloxamer 282, Poloxamer 284, Poloxamer 288, Poloxamer 331, Poloxamer 333, Poloxamer 334, Poloxamer 335, Poloxamer 338, Poloxamer 401, Poloxamer 402, Poloxamer 403, and Poloxamer 407.

In some embodiments, the poloxamer is Poloxamer 188 or Poloxamer 407.

In some embodiments, the poloxamer is Poloxamer 407.

In some embodiments, the poloxamer is a purified poloxamer (e.g., purified Poloxamer 407).

In some embodiments, the purified poloxamer (e.g., purified Poloxamer 407) has an average molecular weight of about 9 kDa or greater, about 9.2 kDa or greater, about 9.4 kDa or greater, about 9.6 kDa or greater, about 9.8 kDa or greater, about 10 kDa or greater, about 10.2 kDa or greater, about 10.4 kDa or greater, about 10.6 kDa or greater, about 10.8 kDa or greater, about 11 kDa or greater, about 11.2 kDa or greater, about 11.4 kDa or greater, about 11.6 kDa or greater, about 11.8 kDa or greater, about 12 kDa or greater, or about 12.1 kDa or greater.

In some embodiments, the purified poloxamer (e.g., purified Poloxamer 407) has a reduced level of polymer chains with molecular weight below 9 kDa as compared to the unpurified poloxamer (e.g., unpurified Poloxamer 407).

In some embodiments, the purified poloxamer (e.g., purified Poloxamer 407) has about 99% or less, about 98% or less, about 95% or less, about 90% or less, about 80% or less, about 70% or less, about 60% or less, about 50% or less, about 40% or less, about 30% or less, about 20% or less, or about 10% or less of polymer chains with molecular weight below 9 kDa as compared to the unpurified poloxamer (e.g., unpurified Poloxamer 407).

In some embodiments, the purified poloxamer (e.g., purified Poloxamer 407) is prepared by liquid-liquid extraction or size exclusion chromatography.

In some embodiments, about 10% or more, about 20% or more, about 30% or more, about 40% or more, about 50% or more, about 60% or more, about 70% or more, about 80% or more, about 90% or more, about 95% or more, about 98% or more, or about 99% or more of the one or more impurities having molecular weights below 9 kDa are removed from the poloxamer (e.g., Poloxamer 407) during the purification.

In some embodiments, about 10% or more, about 20% or more, about 30% or more, about 40% or more, about 50% or more, about 60% or more, about 70% or more, about 80% or more, about 90% or more, about 95% or more, about 98% or more, or about 99% or more of the one or more diblock copolymers (e.g., PEO-PPO), single block polymers (e.g., PEO), and/or aldehydes are removed from the poloxamer (e.g., Poloxamer 407) during the purification.

In some embodiments, the pharmaceutical composition, pharmaceutical composition, the lyophilized pharmaceutical composition or reconstituted solution of the present disclosure comprises a buffering agent. The buffer controls the pH of the reconstituted solution to a range of from about 4 to about 13, from about 5 to about 12, from about 6 to about 11, from about 6.5 to about 10.5, or from about 7 to about 10.

Examples of the buffering agent include, but are not limited to, citrate buffering agents, acetate buffering agents, phosphate buffering agents, ammonium chloride, calcium carbonate, calcium chloride, calcium citrate, calcium glubionate, calcium gluceptate, calcium gluconate, d-gluconic acid, calcium glycerophosphate, calcium lactate, calcium lactobionate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, amino-sulfonate buffers (e.g., HEPES), magnesium hydroxide, aluminum hydroxide, alginic acid, pyrogen-free water, isotonic saline, Ringer's solution, ethyl alcohol, and/or combinations thereof. Lubricating agents may be selected from the non-limiting group consisting of magnesium stearate, calcium stearate, stearic acid, silica, talc, malt, glyceryl behenate, hydrogenated vegetable oils, polyethylene glycol, sodium benzoate, sodium acetate, sodium chloride, leucine, magnesium lauryl sulfate, sodium lauryl sulfate, and combinations thereof.

In some embodiments, the buffering agent comprises phosphate buffered saline, TRIS, tris acetate, tris HCl-65, sodium citrate, histidine, arginine, sodium phosphate, tris base-65, hydroxyethyl starch, or any combination thereof.

In some embodiments, the pharmaceutical composition, pharmaceutical composition, the lyophilized pharmaceutical composition or reconstituted solution of the present disclosure comprises a bulking agent.

In some embodiments, the bulking agent comprises poloxamer (e.g., poloxamer 407), mannitol, sucrose, maltose, trehalose, dextrose, sorbitol, glucose, raffinose, glycine, histidine, polyvinylpyrrolidone (e.g., polyvinylpyrrolidone K12 or polyvinylpyrrolidone K17), lactose, or any combination thereof.

In some embodiments, the pharmaceutical composition, pharmaceutical composition, the lyophilized pharmaceutical composition or reconstituted solution of the present disclosure comprises a stabilizing agent.

In some embodiments, the stabilizing agent comprises a cryoprotectant. In some embodiments, the cryoprotectant is a polyol (e.g., a diol or a triol such as propylene glycol (i.e., 1,2-propanediol), 1,3-propanediol, glycerol, (+/−)-2-methyl-2,4-pentanediol, 1,6-hexanediol, 1,2-butanediol, 2,3-butanediol, ethylene glycol, or diethylene glycol), a nondetergent sulfobetaine (e.g., NDSB-201 (3-(1-pyridino)-1-propane sulfonate), an osmolyte (e.g., L-proline or trimethylamine N-oxide dihydrate), a polymer (e.g., polyethylene glycol 200 (PEG 200), PEG 400, PEG 600, PEG 1000, PEG 3350, PEG 4000, PEG 8000, PEG 10000, PEG 20000, polyethylene glycol monomethyl ether 550 (mPEG 550), mPEG 600, mPEG 2000, mPEG 3350, mPEG 4000, mPEG 5000, polyvinylpyrrolidone (e.g., polyvinylpyrrolidone K 15), pentaerythritol propoxylate, or polypropylene glycol P 400), an organic solvent (e.g., dimethyl sulfoxide (DMSO) or ethanol), a sugar (e.g., D-(+)-sucrose, D-sorbitol, trehalose, D-(+)-maltose monohydrate, meso-erythritol, xylitol, myo-inositol, D-(+)-raffinose pentahydrate, D-(+)-trehalose dihydrate, or D-(+)-glucose monohydrate), or a salt (e.g., lithium acetate, lithium chloride, lithium formate, lithium nitrate, lithium sulfate, magnesium acetate, sodium chloride, sodium formate, sodium malonate, sodium nitrate, sodium sulfate, or any hydrate thereof) or any combination thereof.

In some embodiments, the stabilizing agent comprises a salt. In some embodiment, the salt is selected from the group consisting of lithium salts (e.g., lithium acetate, lithium chloride, lithium formate, lithium nitrate, lithium sulfate, or any hydrate thereof), magnesium salts (e.g., magnesium acetate or a hydrate thereof), and sodium salts (e.g., sodium chloride, sodium formate, sodium malonate, sodium nitrate, sodium sulfate, or any hydrate thereof). For another example, the formulation comprises one or more sodium salts. For yet another example, the formulation comprises sodium chloride.

In some embodiment, the stabilizing agent comprises a surfactant. In some embodiments, the surfactant comprises one or more anionic surfactants (e.g., 2-acrylamido-2-methylpropane sulfonic acid, ammonium lauryl sulfate, ammonium perfluorononanoate, docusate, disodium cocoamphodiacetate, magnesium laureth sulfate, perfluorobutanesulfonic acid, perfluorononanoic acid, perfluorooctanesulfonic acid, perfluorooctanoic acid, potassium lauryl sulfate, sodium alkyl sulfate, sodium dodecyl sulfate, sodium dodecylbenzenesulfonate, sodium laurate, sodium laureth sulfate, sodium lauroyl sarcosinate, sodium myreth sulfate, sodium nonanoyloxybenzenesulfonate, sodium pareth sulfate, sodium stearate, or sulfolipid), one or more cationic surfactants (e.g., behentrimonium chloride, benzalkonium chloride, benzethonium chloride, benzododecinium bromide, bronidox, carbethopendecinium bromide, cetalkonium chloride, cetrimonium bromide, cetrimonium chloride, cetylpyridinium chloride, didecyldimethylammonium chloride, dimethyldioctadecylammonium bromide, dimethyldioctadecylammonium chloride, domiphen bromide, lauryl methyl gluceth-10 hydroxypropyl dimonium chloride, octenidine dihydrochloride, olaflur, n-oleyl-1,3-propanediamine, pahutoxin, stearalkonium chloride, tetramethylammonium hydroxide, or thonzonium bromide), one or more zwitterionic surfactants (e.g., cocamidopropyl betaine, cocamidopropyl hydroxysultaine, dipalmitoylphosphatidylcholine, egg lecithin, hydroxysultaine, lecithin, myristamine oxide, peptitergents, or sodium lauroamphoacetate), and/or one or more non-ionic surfactants (e.g., alkyl polyglycoside, cetomacrogol 1000, cetostearyl alcohol, cetyl alcohol, cocamide dea, cocamide mea, decyl glucoside, decyl polyglucose, glycerol monostearate, igepal ca-630, isoceteth-20, lauryl glucoside, maltosides, monolaurin, mycosubtilin, narrow-range ethoxylate, nonidet p-40, nonoxynol-9, nonoxynols, np-40, octaethylene glycol monododecyl ether, n-octyl beta-d-thioglucopyranoside, octyl glucoside, oleyl alcohol, peg-10 sunflower glycerides, pentaethylene glycol monododecyl ether, polidocanol, α-tocopheryl polyethylene glycol succinate (TPGS), poloxamer (e.g., poloxamer 407), polyethoxylated tallow amine, polyglycerol polyricinoleate, polysorbate (e.g., polysorbate 20, polysorbate 40, polysorbate 60, or polysorbate 80), sorbitan, sorbitan monolaurate, sorbitan monostearate, sorbitan tristearate, stearyl alcohol, surfactin, triton x-100).

In some embodiments, the pharmaceutical composition, pharmaceutical composition, the lyophilized pharmaceutical composition or reconstituted solution of the present disclosure comprises a tonicity-adjusting agent.

In some embodiments, the tonicity-adjusting agent comprises NaCl, dextrose, dextran, ficoll, gelatin, mannitol, sucrose, glycine, glycerol, or any combination thereof.

In some embodiments, the pharmaceutical composition or reconstituted solution of the present disclosure comprises a soothing agent. In some embodiments, the soothing agent comprises lidocaine In addition to these components, the pharmaceutical composition, pharmaceutical composition, the lyophilized pharmaceutical composition or reconstituted solution of the present disclosure includes any substance useful in pharmaceutical compositions.

In some embodiments, the pharmaceutical composition, pharmaceutical composition, the lyophilized pharmaceutical composition or reconstituted solution of the present disclosure includes one or more pharmaceutically acceptable excipients or accessory ingredients such as, but not limited to, one or more solvents, dispersion media, diluents, dispersion aids, suspension aids, granulating aids, disintegrants, fillers, glidants, liquid vehicles, binders, surface active agents, isotonic agents, thickening or emulsifying agents, buffering agents, lubricating agents, oils, preservatives, and other species. Excipients such as waxes, butters, coloring agents, coating agents, flavorings, and perfuming agents may also be included. Pharmaceutically acceptable excipients are well known in the art (see for example Remington's *The Science and Practice of Pharmacy*, $21^{st}$ Edition, A. R. Gennaro; Lippincott, Williams & Wilkins, Baltimore, Md., 2006).

Examples of diluents may include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and/or combinations thereof. Granulating and dispersing agents may be selected from the non-limiting list consisting of potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, and/or combinations thereof.

Surface active agents and/or emulsifiers may include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite [aluminum silicate] and VEEGUM® [magnesium aluminum silicate]), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate [TWEEN®20], polyoxyethylene sorbitan [TWEEN® 60], polyoxyethylene sorbitan monooleate [TWEEN®80], sorbitan monopalmitate [SPAN®40], sorbitan monostearate [SPAN®60], sorbitan tristearate [SPAN®65], glyceryl monooleate, sorbitan monooleate [SPAN®80]), polyoxyethylene esters (e.g., polyoxyethylene monostearate [MYRJ® 45], polyoxyethylene hydrogenated castor oil, polyethoxylated castor oil, polyoxymethylene stearate, and SOLUTOL®), sucrose fatty acid esters, polyethylene glycol fatty acid esters (e.g., CREMOPHOR®), polyoxyethylene ethers, (e.g., polyoxyethylene lauryl ether [BRIJ® 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, PLURONIC®F 68, POLOXAMER® 188, cetrimonium bromide, cetylpyridinium chloride, benzalkonium chloride, docusate sodium, and/or combinations thereof.

A binding agent may be starch (e.g., cornstarch and starch paste); gelatin; sugars (e.g., sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM®), and larch arabogalactan); alginates; polyethylene oxide; polyethylene glycol; inorganic calcium salts; silicic acid; polymethacrylates; waxes; water; alcohol; and combinations thereof, or any other suitable binding agent.

Examples of preservatives may include, but are not limited to, antioxidants, chelating agents, antimicrobial preservatives, antifungal preservatives, alcohol preservatives, acidic preservatives, and/or other preservatives. Examples of antioxidants include, but are not limited to, alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Examples of chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Examples of antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Examples of antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Examples of alcohol preservatives include, but are not limited to, ethanol, polyethylene glycol, benzyl alcohol, phenol, phenolic compounds, bisphenol, chlorobutanol, hydroxybenzoate, and/or phenylethyl alcohol. Examples of acidic preservatives include, but are not limited to, vitamin A, vitamin C, vitamin E, beta-carotene, citric acid, acetic acid, dehydroascorbic acid, ascorbic acid, sorbic acid, and/or phytic acid. Other preservatives include, but are not limited to, tocopherol, tocopherol acetate, deteroxime mesylate, cetrimide, butylated hydroxyanisole (BHA), butylated hydroxytoluene (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL® 115, GERMABEN®II, NEOLONE™, KATHON™, and/or EUXYL®.

Examples of oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils as well as butyl stearate, caprylic triglyceride, capric triglyceride, cyclomethicone, diethyl sebacate, dimethicone 360, simethicone, isopropyl myristate, mineral oil, octyldodecanol, oleyl alcohol, an/or silicone oil.

Compounds or compositions described herein can be formulated in any manner suitable for a desired delivery route, e.g., transtympanic injection, transtympanic wicks and catheters, cochlear implants, and injectable depots. In some instances, compositions or formulations include one or more physiologically-acceptable components, including derivatives or prodrugs, solvates, stereoisomers, racemates, or tautomers thereof with any physiologically acceptable carriers, diluents, and/or excipients.

As noted above, certain compositions are adapted for, and certain methods employ, administration to the middle ear or inner ear, for example, by local administration to the round window membrane. The membrane of the round window is the biological barrier to the inner ear space and represents the major obstacle for the local treatment of hearing impairment. The administered drug must overcome this membrane to reach the inner ear space. The drug can operatively (e.g., injection through the tympanic membrane) be placed locally to the round window membrane and can then penetrate through the round window membrane. Substances that penetrate the round window typically distribute in the perilymph and thus reach the hair cells and supporting cells.

The pharmaceutical compositions or formulations may also contain a membrane penetration enhancer, which supports the passage of the agents mentioned herein through the round window membrane. Accordingly, liquid, gel or foam formulations may be used. It is also possible to apply the active ingredient orally or to employ a combination of delivery approaches.

Certain compositions are adapted for, and certain methods employ, administration to the middle ear or inner ear, for example, by intratympanic or transtympanic administration. Intratympanic (IT) delivery of drugs to the ear is increasingly used for both clinical and research purposes. Some groups have applied drugs in a sustained manner using microcatheters and microwicks, while the majority have applied them as single or as repeated IT injections (up to 8 injections over periods of up to 2 weeks).

Intratympanically applied drugs are thought to enter the fluids of the inner ear primarily by crossing the round window (RW) membrane. Calculations show that a major factor controlling both the amount of drug entering the ear and the distribution of drug along the length of the ear is the duration the drug remains in the middle ear space. Single, 'one-shot' applications or applications of aqueous solutions for few hours' duration result in steep drug gradients for the applied substance along the length of the cochlea and rapidly declining concentration in the basal turn of the cochlea as the drug subsequently becomes distributed throughout the ear.

Other injection approaches include by osmotic pump, or, by combination with implanted biomaterial, and more preferably, by injection or infusion. Biomaterials that can aid in controlling release kinetics and distribution of drug include hydrogel materials, degradable materials. One class of materials that is most preferably used includes in situ gelling materials. All potential materials and methodologies mentioned in references (Almeida H, Amaral M H, Lobao P, Lobo J M, Drug Discov Today 2014; 19:400-12; Wise A K, Gillespie L N, J Neural Eng 2012; 9:065002; Surovtseva E V, Johnston A H, Zhang W, et al, Int J Pharmaceut 2012; 424:121-7; Roy S, Glueckert R, Johnston A H, et al., Nanomedicine 2012; 7:55-63; Rivera T, Sanz L, Camarero G, Varela-Nieto I, Curr Drug Deliv 2012; 9:231-42; Pararas E E, Borkholder D A, Borenstein J T, Adv Drug Deliv Rev 2012; 64:1650-60; Li M L, Lee L C, Cheng Y R, et al., IEEE T Bio-Med Eng 2013; 60:2450-60; Lajud S A, Han Z, Chi F L, et al., J Control Release 2013; 166:268-76; Kim D K, Park S N, Park K H, et al., Drug Deliv 2014; Engleder E, Honeder C, Klobasa J, Wirth M, Arnoldner C, Gabor F, Int J Pharmaceut 2014; 471:297-302; Bohl A, Rohm H W, Ceschi P, et al., J Mater Sci Mater Med 2012; 23:2151-62; Hoskison E, Daniel M, Al-Zahid S, Shakesheff K M, Bayston R, Birchall J P, Ther Deliv 2013; 4:115-24; Staecker H, Rodgers B, Expert Opin Drug Deliv 2013; 10:639-50; Pritz C O, Dudas J, Rask-Andersen H, Schrott-Fischer A, Glueckert R, Nanomedicine 2013; 8:1155-72), which are included herein by reference in their entirety. Other materials include collagen or other natural materials including fibrin, gelatin, and decellularized tissues. Gelfoam may also be suitable.

Delivery may also be enhanced via alternate means including but not limited to agents added to the delivered composition such as penetration enhancers, or could be through devices via ultrasound, electroporation, or high-speed jet.

Methods described herein can also be used for inner ear cell types that may be produced using a variety of methods know to those skilled in the art including those cell types described in PCT Application No. WO2012103012 A1.

With regard to human and veterinary treatment, the amount of a particular agent(s) that is administered may be dependent on a variety of factors, including the disorder being treated and the severity of the disorder; activity of the specific agent(s) employed; the age, body weight, general health, sex and diet of the patient; the time of administration, route of administration, and rate of excretion of the specific agent(s) employed; the duration of the treatment; drugs used in combination or coincidental with the specific agent(s) employed; the judgment of the prescribing physician or veterinarian; and like factors known in the medical and veterinary arts.

The agents described herein may be administered in a therapeutically effective amount to a subject in need of treatment. Administration of compositions described herein can be via any of suitable route of administration, for example, by intratympanic administration. Other routes include ingestion, or alternatively parenterally, for example intravenously, intra-arterially, intraperitoneally, intrathecally, intraventricularly, intraurethrally, intrasternally, intracranially, intramuscularly, intranasally, subcutaneously, sublingually, transdermally, or by inhalation or insufflations, or topical by ear instillation for absorption through the skin of the ear canal and membranes of the eardrum. Such administration may be as a single or multiple oral dose, defined number of ear drops, or a bolus injection, multiple injections, or as a short- or long-duration infusion. Implantable devices (e.g., implantable infusion pumps) may also be employed for the periodic parenteral delivery over time of equivalent or varying dosages of the particular formulation. For such parenteral administration, the compounds are preferably formulated as a sterile solution in water or another suitable solvent or mixture of solvents. The solution may contain other substances such as salts, sugars (particularly glucose or mannitol), to make the solution isotonic with blood, buffering agents such as acetic, citric, and/or phosphoric acids and their sodium salts, and preservatives.

Compositions described herein can be administered by several methods sufficient to deliver the composition to the inner ear. Delivering a composition to the inner ear includes administering the composition to the middle ear, such that the composition may diffuse across the round window to the inner ear. It also includes administering a composition to the inner ear by direct injection through the round window membrane. Such methods include, but are not limited to auricular administration, by transtympanic wicks or catheters, or parenteral administration, for example, by intraauricular, transtympanic, or intracochlear injection.

In particular embodiments, the compounds, compositions and formulations of the disclosure are locally administered, meaning that they are not administered systemically.

In one embodiment, a syringe and needle apparatus is used to administer compounds or compositions to a subject using auricular administration. A suitably sized needle is used to pierce the tympanic membrane and a wick or catheter comprising the composition is inserted through the pierced tympanic membrane and into the middle ear of the subject. The device may be inserted such that it is in contact with the round window or immediately adjacent to the round window. Exemplary devices used for auricular administration include, but are not limited to, transtympanic wicks, transtympanic catheters, round window microcatheters (small catheters that deliver medicine to the round window), and Silverstein Microwicks™ (small tube with a "wick" through the tube to the round window, allowing regulation by subject or medical professional).

In some embodiments, a syringe and needle apparatus is used to administer compounds or compositions to a subject using transtympanic injection, injection behind the tympanic membrane into the middle and/or inner ear. The formulation may be administered directly onto the round window membrane via transtympanic injection or may be administered directly to the cochlea via intracochlear injection or directly to the vestibular organs via intravestibular injection.

In some embodiments, the delivery device is an apparatus designed for administration of compounds or compositions to the middle and/or inner ear. By way of example only: GYRUS Medical GmbH offers micro-otoscopes for visualization of and drug delivery to the round window niche; Arenberg has described a medical treatment device to deliver fluids to inner ear structures in U.S. Pat. Nos. 5,421,818; 5,474,529; and 5,476,446, each of which is incorporated by reference herein for such disclosure. U.S. patent application Ser. No. 08/874,208, which is incorporated herein by reference for such disclosure, describes a surgical method for implanting a fluid transfer conduit to deliver compositions to the inner ear. U.S. Patent Application Publication 2007/0167918, which is incorporated herein by reference for such disclosure, further describes a combined otic aspirator and medication dispenser for transtympanic fluid sampling and medicament application.

In some embodiments, a compound or composition disclosed herein is administered to a subject in need thereof once. In some embodiments, a compound or composition disclosed herein is administered to a subject in need thereof more than once. In some embodiments, a first administration of a compound or composition disclosed herein is followed by a second, third, fourth, or fifth administration of a compound or composition disclosed herein.

The number of times a compound or composition is administered to an subject in need thereof depends on the discretion of a medical professional, the disorder, the severity of the disorder, and the subject's response to the formulation. In some embodiments, the compound or composition disclosed herein is administered once to a subject in need thereof with a mild acute condition. In some embodiments, a compound or composition disclosed herein is administered more than once to a subject in need thereof with a moderate or severe acute condition. In the case wherein the subject's condition does not improve, upon the doctor's discretion the compound or composition may be administered chronically, that is, for an extended period of time, including throughout the duration of the subject's life in order to ameliorate or otherwise control or limit the symptoms of the subject's disease or condition.

In the case wherein the subject's status does improve, upon the doctor's discretion the compound or composition may administered continuously; alternatively, the dose of drug being administered may be temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday may be from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once the subject's hearing and/or balance has improved, a maintenance dose can be administered, if necessary. Subsequently, the dosage or the frequency of administration, or both, is optionally reduced, as a function of the symptoms, to a level at which the improved disease, disorder or condition is retained. In certain embodiments, subjects require intermittent treatment on a long-term basis upon any recurrence of symptoms.

Certain embodiments include is a pharmaceutical product comprising a sealed packaging and the compound(s) according to the invention in the container. The container size can be optimized to reduce head space in the container after packaging and any head space may be filled with an inert gas such as nitrogen. Furthermore, container material of construction can be chosen to minimize the moisture and oxygen ingress inside the container after packaging.

Measurement of Sensorineural Hearing Loss

Hearing loss can be assessed by several different tests. Such tests may determine the audibility of a sound to a patient and/or the intelligibility of the sound to a patient prior to or after treatment. The audibility of a sound is a measure of a patient's ability to detect the sound (i.e. whether the patient can determine the presence or absence of a sound). The intelligibility of a sound is a measure of a patient's ability to correctly identify the sound. For instance, hearing may be assessed according to whether a patient can correctly identify a word or not. A patient with hearing loss may therefore neither be able to detect a sound nor correctly identify it (i.e. the sound is inaudible and unintelligible). However, audibility is not necessarily associated with intelligibility, and a patient may, for example, be able detect a sound, but not correctly identify it (i.e. the sound is audible but unintelligible).

Pure Tone Audiometry

Assessment of a patient's audibility function is typically carried out by an audiologist using an audiometer in a hearing test known as pure tone audiometry. Pure tone audiometry is a standard test used to assess the audibility of a sounds and is described in detail elsewhere (see, for example, Katz, J., Medwetsky, L., Burkard, R., & Hood, L. (2009) Handbook of Clinical Audiology. Philadelphia, Pa.: Lippincott Williams and Wilkins). Pure tone audiometry is typically carried out in a sound-treated booth, which reduces ambient noise levels that may interfere with the detection of low-level sound stimuli.

In pure tone audiometry, a patient is exposed to pure tone stimuli at specific frequencies to determine the patient's hearing threshold at each frequency. Standard audiometry measures a patient's pure tone hearing threshold at each of the following frequencies 0.25 kHz, 0.5 kHz, 1 kHz, 2 kHz, 3 kHz, 4 kHz, 6 kHz and 8 kHz. However, a patient's hearing threshold does not need to be determined at all of these frequencies to ascertain whether or not the patient has sensorineural hearing loss. For instance, a subset frequencies, or a single frequency may be tested to identify a patient with sensorineural hearing loss.

To determine the hearing threshold, the volume of the pure tone is altered to determine the lowest level of stimuli that the patient is able to detect. The lowest level of stimuli (corresponding to the quietest sound) is the pure tone hearing threshold at a given frequency. The pure tone threshold is typically measured in a patient using according decibels in hearing level (dB HL) on an audiometer. However, hearing thresholds may also be determined using other methods known to the person skilled in the art. For example, hearing function may be measured by Auditory Brainstem Response (ABR) testing or Auditory Steady State Response (ASSR) testing. Other tests can also be used to determine hearing function in a patient. For instance, Distortion product otoacoustic emissions (DPOAEs) can be used to measure outer hair cell function and loss and may be used in differential diagnosis of hearing loss arising from hair cell loss from hearing loss associated with higher level processing (e.g. auditory neuropathy).

Pure tone thresholds may be plotted on a graph to produce an audiogram for the patient.

Pure tone thresholds measured across different frequencies may also be averaged to provide a pure tone average. For instance, a patient that has pure tone hearing thresholds of 50 dB HL at 0.5 Hz, 60 dB HL at 1 kHz, 65 dB HL at 2 kHz and 70 dB at 4 kHz would have a pure tone average of 61.25 dB HL, when measured across 0.5 kHz, 1 kHz, 2 kHz and 4 kHz.

Pure tone averages may be calculated across different frequencies. Pure tone thresholds at any subset of frequencies may be used to calculate pure tone averages. In some embodiments, the average of the patient hearing threshold is measured across 0.5 kHz, 1 kHz, 2 kHz and 4 kHz. In some embodiments, pure tone average is measured across 4 kHz, 6 kHz and 8 kHz. Measurement of pure tone average across 4 kHz, 6 kHz and 8 kHz is useful when seeking to assess the patient's hearing function at the higher frequencies within the standard audiometric frequencies.

Sensorineural hearing loss can be categorized according to its severity. The severity of hearing loss is determined by the hearing levels at which a threshold level is obtained in a patient by pure tone audiometry. Severity of hearing loss is classified according to hearing thresholds using the following definitions:

Normal: 25 dB HL or less
Mild: at least 25 dB HL and no more than 40 dB HL
Moderate: at least 40 dB HL and no more than 55 dB HL
Moderately Severe: at least 55 dB HL and no more than 70 dB HL
Severe: at least 70 dB HL and no more than 90 dB HL
Profound: at least 90 dB HL or more These measures of severity are standard measures in the field (see Goodman, A. (1965). Reference zero levels for pure tone audiometer. ASHA, 7, 262-263). In some embodiments, the severity of hearing loss is classified according to a patient's hearing threshold at a single frequency (for example, 0.25 kHz, 0.5 kHz, 1 kHz, 2 kHz, 3 kHz, 4 kHz, 6 kHz or 8 kHz). For instance, a patient may have mild hearing loss at 8 kHz, and normal hearing at the other standard audiometric frequencies. In some embodiments, the severity of hearing loss is classified according to pure tone average, when measured across a subset of frequencies. In certain such embodiments, the severity of hearing loss is classified according to the pure tone average across 0.5 kHz, 1 kHz, 2 kHz and 4 kHz. For example, a patient may have moderate hearing loss according to their pure tone average across 0.5 kHz, 1 kHz, 2 kHz and 4 kHz, but have moderately severe hearing loss at a single frequency (e.g. 8 kHz). In other embodiments, the severity of hearing loss is classified according to the pure tone average across 4 kHz, 6 kHz and 8 kHz.

A patient that has hearing threshold of 25 dB HL or less at standard audiometric frequencies (i.e. 0.25 kHz, 0.5 kHz, 1 kHz, 2 kHz, 3 kHz, 4 kHz, 6 kHz and 8 kHz) has normal hearing. The patient's audiogram is also a normal audiogram.

The inventors have found that patients with moderate or moderately severe hearing loss are particularly amenable to the treatments disclosed herein. Thus, in certain preferred embodiments the sensorineural hearing loss is moderate sensorineural hearing loss. In other preferred embodiments, the sensorineural hearing loss is moderately severe sensorineural hearing loss. In other embodiments, a therapeutic benefit may be provided in patient having less severe hearing loss than moderate sensorineural hearing loss. Thus, in some embodiments, sensorineural hearing loss is mild sensorineural hearing loss. In other embodiments, a therapeutic benefit may be provided in a patient having more severe sensorineural hearing loss than moderately severe hearing loss. In other embodiments, sensorineural hearing loss is severe sensorineural hearing loss. In other embodiments, sensorineural hearing loss is profound sensorineural hearing loss.

In some embodiments, the moderate or moderately severe sensorineural hearing loss is determined according to the average of the patient's hearing thresholds across 0.5 kHz, 1 kHz, 2 kHz and 4 kHz when assessed by pure tone audiometry. In these embodiments, the average of the patient's hearing thresholds across 0.5 kHz, 1 kHz, 2 kHz and 4 kHz when assessed by pure tone audiometry is at least 40 dB HL and no more than 70 dB HL. In certain such embodiments, the average of the patient's hearing thresholds across 0.5 kHz, 1 kHz, 2 kHz and 4 kHz when assessed by pure tone audiometry is at least 40 dB HL and no more than 55 dB HL. In other embodiments, the average of the patient's hearing thresholds across 0.5 kHz, 1 kHz, 2 kHz and 4 kHz when assessed by pure tone audiometry is at least 55 dB HL and no more than 70 dB HL.

The inventors have found that the patients with hearing loss at higher frequencies are particularly amenable to the treatments disclosed herein. Thus, in certain embodiments, the patient has more severe hearing less at 4 kHz, and/or 6 kHz, and/or 8 kHz that at the other standard audiometric frequencies (i.e. 0.25 kHz, 0.5 kHz, 1 kHz, 2 kHz and 3 kHz), when measured by pure tone audiometry. For example, in embodiment the patient has moderate or moderately severe hearing loss at 4 kHz, 6 kHz, and 8 kHz and mild hearing loss at the other standard audiometric frequencies. In another embodiment, the patient has moderate hearing loss at 4 kHz, 6 kHz and 8 kHz and mild hearing loss at the other standard audiometric frequencies. In another embodiment, the patient has mild hearing loss at 4 kHz, 6 kHz and 8 kHz and normal hearing at the other standard audiometric frequencies.

In some embodiments, the patient has a hearing threshold of at least 40 dB HL at 4 kHz, when measured by pure tone audiometry. In some embodiments, the patient has a hearing threshold of at least 40 dB HL at 6 kHz, when measured by pure tone audiometry. In some embodiments, the patient has a hearing threshold of at least 40 dB HL at 8 kHz, when measured by pure tone audiometry.

In some embodiments, the patient has an audiogram with hearing thresholds in the following ranges when measured by pure tone audiometry:
  8 kHz-40 dB HL to 95 dB HL; and/or
  6 kHz-40 dB HL to 85 dB HL; and/or
  4 kHz-40 dB HL to 80 dB HL; and/or
  3 kHz-40 dB HL to 70 dB HL; and/or
  2 kHz-40 dB HL to 70 dB HL; and/or
  1 kHz-40 dB HL to 70 dB HL; and/or
  0.5 kHz-40 dB HL to 70 dB HL; and/or
  0.25 Hz-40 dB HL to 70 dB HL.

In some embodiments, the patient has an audiogram with a hearing threshold has in the range of 40 dB HL to 95 dB HL at 8 kHz, when measured by pure tone audiometry. In certain such embodiments, the patient has an audiogram with a hearing threshold has in the range of 40 dB HL to 70 dB HL at 8 kHz, when measured by pure tone audiometry.

In some embodiments, the patient has an audiogram with a hearing threshold has in the range of 40 dB HL to 85 dB HL at 6 kHz, when measured by pure tone audiometry. In certain such embodiments, the patient has an audiogram with a hearing threshold has in the range of 40 dB HL to 70 dB HL at 6 kHz, when measured by pure tone audiometry.

In some embodiments, the patient has an audiogram with a hearing threshold has in the range of 40 dB HL to 80 dB HL at 4 kHz, when measured by pure tone audiometry. In certain such embodiments, the patient has an audiogram with a hearing threshold has in the range of 40 dB HL to 70 dB HL at 4 kHz, when measured by pure tone audiometry.

In some embodiments, the patient has an audiogram with a hearing threshold has in the range of 40 dB HL to 70 dB HL at 3 kHz, when measured by pure tone audiometry.

In some embodiments, the patient has an audiogram with a hearing threshold has in the range of 40 dB HL to 70 dB HL at 2 kHz, when measured by pure tone audiometry.

In some embodiments, the patient has an audiogram with a hearing threshold has in the range of 40 dB HL to 70 dB HL at 1 kHz, when measured by pure tone audiometry.

In some embodiments, the patient has an audiogram with a hearing threshold has in the range of 40 dB HL to 70 dB HL at 0.5 kHz, when measured by pure tone audiometry.

In some embodiments, the patient has an audiogram with a hearing threshold has in the range of 40 dB HL to 70 dB HL at 0.25 kHz, when measured by pure tone audiometry.

In some embodiments, the patient has an audiogram with hearing thresholds in the following ranges when measured by pure tone audiometry:

8 kHz-40 dB HL to 95 dB HL; and
6 kHz-40 dB HL to 85 dB HL; and
4 kHz-40 dB HL to 80 dB HL; and
3 kHz-40 dB HL to 70 dB HL; and
2 kHz-40 dB HL to 70 dB HL; and
1 kHz-40 dB HL to 70 dB HL; and
0.5 kHz-40 dB HL to 70 dB HL; and
0.25 Hz-40 dB HL to 70 dB HL.

In some embodiments, the patient has an audiogram with hearing thresholds in the following ranges when measured by pure tone audiometry:
8 kHz-40 dB HL to 70 dB HL; and
6 kHz-40 dB HL to 70 dB HL; and
4 kHz-40 dB HL to 70 dB HL; and
3 kHz-40 dB HL to 70 dB HL; and
2 kHz-40 dB HL to 70 dB HL; and
1 kHz-40 dB HL to 70 dB HL; and
0.5 kHz-40 dB HL to 70 dB HL; and
0.25 Hz-40 dB HL to 70 dB HL.

In some embodiments, mild sensorineural hearing loss is determined according to the average of the patient's hearing thresholds across 0.5 kHz, 1 kHz, 2 kHz and 4 kHz when assessed by pure tone audiometry. In these embodiments, the average of the patient's hearing thresholds is at least 25 dB HL and no more than 40 dB HL.

In some embodiments, the patient has a hearing threshold of at least at least 25 dB HL and no more than 40 dB HL at 4 kHz, when measured by pure tone audiometry. In some embodiments, the patient has a hearing threshold of at least 25 dB HL and no more than 40 dB HL at 6 kHz, when measured by pure tone audiometry. In some embodiments, the patient has a hearing threshold of at least 25 dB HL and no more than 40 dB HL at 8 kHz, when measured by pure tone audiometry.

In some embodiments, the patient has an audiogram with hearing thresholds in the following ranges when measured by pure tone audiometry:
8 kHz-25 dB HL to 40 dB HL; and/or
6 kHz-25 dB HL to 40 dB HL; and/or
4 kHz-25 dB HL to 40 dB HL; and/or
3 kHz-25 dB HL to 40 dB HL; and/or
2 kHz-25 dB HL to 40 dB HL; and/or
1 kHz-25 dB HL to 40 dB HL; and/or
0.5 kHz-25 dB HL to 40 dB HL; and/or
0.25 Hz-25 dB HL to 40 dB HL.

In some embodiments, the patient has an audiogram with a hearing threshold has in the range of 25 dB HL to 40 dB HL at 8 kHz, when measured by pure tone audiometry.

In some embodiments, the patient has an audiogram with a hearing threshold has in the range of 25 dB HL to 40 dB HL at 6 kHz, when measured by pure tone audiometry.

In some embodiments, the patient has an audiogram with a hearing threshold has in the range of 25 dB HL to 40 dB HL at 4 kHz, when measured by pure tone audiometry.

In some embodiments, the patient has an audiogram with a hearing threshold has in the range of 25 dB HL to 40 dB HL at 3 kHz, when measured by pure tone audiometry.

In some embodiments, the patient has an audiogram with a hearing threshold has in the range of 25 dB HL to 40 dB HL at 2 kHz, when measured by pure tone audiometry.

In some embodiments, the patient has an audiogram with a hearing threshold has in the range of 25 dB HL to 40 dB HL at 1 kHz, when measured by pure tone audiometry.

In some embodiments, the patient has an audiogram with a hearing threshold has in the range of 25 dB HL to 40 dB HL at 0.5 kHz, when measured by pure tone audiometry.

In some embodiments, the patient has an audiogram with a hearing threshold has in the range of 25 dB HL to 40 dB HL at 0.25 kHz, when measured by pure tone audiometry.

In some embodiments, the patient has an audiogram with hearing thresholds in the following ranges when measured by pure tone audiometry:
8 kHz-25 dB HL to 40 dB HL; and
6 kHz-25 dB HL to 40 dB HL; and
4 kHz-25 dB HL to 40 dB HL; and
3 kHz-25 dB HL to 40 dB HL; and
2 kHz-25 dB HL to 40 dB HL; and
1 kHz-25 dB HL to 40 dB HL; and
0.5 kHz-25 dB HL to 40 dB HL; and
0.25 Hz-25 dB HL to 40 dB HL.

The treatments disclosed herein are also suitable for use in patients having an audiogram with hearing thresholds at different severity levels for each of the standard audiometric frequencies. For example, a patient may have moderate hearing loss at a first frequency, mild hearing loss at a second frequency etc. These patients may therefore have an audiogram in which some hearing thresholds in the mild hearing loss range (i.e. at least 25 dB HL and no more than 40 dB HL) and other hearing thresholds fall in the moderate hearing loss range (i.e. at least 40 dB HL and no more than 55 dB HL). In certain embodiments, the patient has an audiogram with hearing thresholds in the moderate hearing loss range at 4 kHz, 6 kHz and 8 kHz and hearing thresholds in the mild hearing loss range at 0.25 kHz, 05. kHz, 1 kHz, 2 kHz and 3 kHz.

Hearing function in a patient can also be assessed at frequencies falling outside the standard audiometric range. For example, hearing function may be assessed in the ultra-high frequencies. Ultra-high frequencies in the context of pure tone audiometry are frequencies above 8 kHz. Hearing function in the ultra-high frequency range can be assessed by pure tone audiometry which may be performed at 10 kHz, 12 kHz, 14 kHz and 16 kHz. The severity of hearing loss in the ultra-high frequency range may be classified according to the hearing thresholds used to classify severity of hearing loss in the standard audiometric frequency range. The severity of hearing loss in the ultra-high frequency range is classified using the following ranges:

Normal: 25 dB HL or less
Mild: at least 25 dB HL and no more than 40 dB HL
Moderate: at least 40 dB HL and no more than 55 dB HL
Moderately Severe: at least 55 dB HL and no more than 70 dB HL
Severe: at least 70 dB HL and no more than 90 dB HL
Profound: at least 90 dB HL or more In some embodiments, the severity of hearing loss in the ultra-high frequency range is classified according to a patient's hearing threshold at a single ultra-high frequency (for example, 10 kHz, 12 kHz, 14 kHz or 16 kHz). The severity of hearing loss at a single ultra-high frequency may be mild, moderate, moderately severe, severe or profound, as summarized above. For instance, in some embodiments, a patient may have mild hearing loss at 16 kHz, and normal hearing at the other ultra-high frequencies. In other embodiments, a patient may have moderate hearing loss at 16 kHz and mild hearing loss at the other ultra-high frequencies. In some embodiments, the severity of hearing loss is classified according to pure tone average, when measured across a subset of ultra-high frequencies. Any subset of ultra-high frequencies may be used to calculate pure tone average. In certain such embodiments, the severity of hearing loss is classified according to the pure tone average across 10 kHz, 12 kHz, 14 kHz and 16 kHz.

A patient having sensorineural hearing loss when assessed at standard audiometric frequencies may also have hearing loss in the ultra-high frequencies. Thus, in some embodiments the patient having sensorineural hearing loss also has a hearing threshold of between 40 dB HL to 70 dB HL at 16 kHz when measured by pure tone audiometry. In some embodiments, the patient has an audiogram with hearing thresholds in the following ranges when measured by pure tone audiometry:

16 kHz-40 dB HL to 70 dB HL; and/or 14 kHz-40 dB HL to 85 dB HL; and/or 12 kHz-40 dB HL to 95 dB HL; and/or 10 kHz-40 dB HL to 95 dB HL.

In some embodiments, the patient has an audiogram with a hearing threshold has in the range of 40 dB HL to 85 dB HL at 14 kHz, when measured by pure tone audiometry.

In some embodiments, the patient has an audiogram with a hearing threshold has in the range of 40 dB HL to 95 dB HL at 12 kHz, when measured by pure tone audiometry.

In some embodiments, the patient has an audiogram with a hearing threshold has in the range of 40 dB HL to 95 dB HL at 10 kHz, when measured by pure tone audiometry.

Word Recognition Tests

Alternatively, or in addition to pure tone audiometry, hearing loss may be assessed using a word recognition test. A word recognition test measures the patient's ability to correctly identify a word, thereby providing a measure of sound intelligibility (in particular, speech intelligibility) that may not be provided by pure tone audiometry. In some embodiments, a word recognition score is used to determine the patient's ability to correctly identify words prior to treatment.

The inventors have found that the treatments disclosed herein may be particularly effective at improving sound intelligibility and so patients having poor word recognition scores may be particularly suitable for the disclosed treatments.

A standard word recognition in quiet test, also referred to herein as a standard word recognition test, is a test administered by an audiologist that measures a patient's speech intelligibility in recognizing words in a quiet environment. A quiet environment is an environment with little to no background noise.

A standard word recognition test may be used to determine a person's ability to recognize words selected from a word list and presented to the patient at a given decibel (dB) level. In some embodiments, the standard word recognition test is used to determine a patient's ability to recognize words at more than one decibel level.

In some embodiments, the standard word recognition test assesses the patient's ability to identify 50 words. However, the number of words presented to the patient may be more or less than 50. For example, in some embodiments, the standard word recognition test is for 25 words. In other embodiments, the standard word recognition test is for 10 words.

A standard word recognition test may be used to generate a standard word recognition (%) score which is calculated using the formula:

$$\text{standard word recogntion score (\%)} = 100 \times \left( \frac{\text{words recognised in standard word recognition test}}{\text{total words}} \right)$$

In some embodiments, the patient has a standard word recognition score of 90% or less, 85% or less, or 80% or less, 70% or less, 60% or less, or 50% or less prior to treatment. In a preferred embodiment, the patient has a standard word recognition score of 60% or less prior to treatment.

In some embodiments, the standard word recognition score is expressed as the number of words that are correctly recognized in the test. For example, in some embodiments the patient identifies 45 or fewer words, 42 or fewer words, or 40 or fewer words, 35 or fewer words, 30 or fewer words or 25 or fewer words correctly in a standard word recognition test for 50 words. In a preferred embodiment, the patient identified 30 or fewer words correctly in a standard word recognition test for 50 words.

In some embodiments, a list of words is administered to each ear, and a standard word recognition score is calculated for each ear. Herein the results of the standard word recognition score refer to the ear that has been/will be treated.

A standard word recognition test may be carried out using any list of words. However, standard word lists are typically used in a standard word recognition test. In some embodiments, each test word is embedded in a carrier phrase. Example of carrier phrases are: "Say the word _ again", "You will say _", or "Say the word _".

In some embodiments, the standard word recognition test is the Maryland consonant-vowel nucleus-consonant (CNC) word test. The Maryland CNC word test has been described, for example, in Mendel, L. L., Mustain, W. D., & Magro, J. (2014). Normative data for the Maryland CNC Test. Journal of the American Academy of Audiology, 25, 775-781.

The Maryland CNC word test is a standard word recognition test that uses phonemically balanced word lists comprising words that are consonant-nucleus-consonant (CNC) monosyllables. These CNC lists are balanced so that each initial consonant, each vowel, and each final consonant appears with the same frequency within each list. The Maryland CNC test has 10 lists of 50 words.

In some embodiments, the Maryland CNC Test uses words from Lehiste and Peterson's phonemically balanced word lists, all of which were CNC monosyllables, for example as described in Lehiste I, Peterson G E. (1959) Linguistic considerations in the study of speech intelligibility. Journal of the Acoustical Society of America 31(3): 280-286.

In some embodiments, the Maryland CNC Test uses words from revised CNC lists that eliminate rare literary words and proper names, for example as described in Peterson G E, Lehiste I. (1962) Revised CNC lists for auditory tests. Journal of Speech and Hearing Disorders 27:62-70.

In some embodiments, the Maryland CNC Test uses words from modified CNC word lists that take into consideration the effects of coarticulation, where the acoustic properties of phonemes are influenced by those phonemes that immediately precede and follow them, for example as described in Causey G D, Hood L J, Hermanson C L, Bowling L S. (1984) The Maryland CNC Test: normative studies. Audiology 23(6): 552-568. The words of the Maryland CNC test are spoken within the carrier phrase: 'Say the _ again,'

In some embodiments, the standard word recognition test is the C.I.D Auditory Test W-22 (CID W-22) test. The CID W-22 test has been described, for example, in Hirsh, I. J., Davis, H. Silverman, S. R., Reynolds, E. G., Eldert, E., & Benson, R. W. (1952). Development of Materials for Speech Audiometry. Journal of Speech, Language, and Hearing Research, 17(3), 321-337.

The CID W-22 test uses 200 monosyllabic words which are divided into four lists of 50 words each. Each list is phonetically balanced. The speech sounds within the list occur with the same relative frequency as they do in a representative sample of English speech. There are three criteria for the vocabulary in the phonetically balanced word lists. First, all the words must be one-syllable words with no repetition of words in the different lists. Second, any word chosen should be a familiar word. This second criterion is to minimize the effect of differences in the educational background of subjects. Third, the phonetic composition of each word list should correspond to that of English as a whole as closely as possible. The words of the CID W-22 test are spoken with the carrier phrase: "You will say _".

In some embodiments the standard word recognition test is the NU No. 6 test. The NU No. 6 has been described, for example, in Tillman, T. W., & Carhart, R. (1966). An expanded test for speech discrimination utilizing CNC monosyllabic words: Northwestern University Auditory Test No. 6. Northwestern Univ Evanston Ill. Auditory Research Lab.

In some embodiments, the NU No. 6 test uses 4 lists of 50 words, for example, as described in Table 28-2 of Tillman, T. W., & Carhart, R. (1966). The words of the NU No. 6 test are spoken with the carrier phrase: "Say the word _".

In a preferred embodiment, the standard word recognition test is the Maryland CNC test, using the words list and carrier phrases as defined in Causey G D, Hood L J, Hermanson C L, Bowling L S. (1984) The Maryland CNC Test: normative studies. Audiology 23(6): 552-568. In certain such preferred embodiments, the word signal is provided to the patient at 40 dB above speech perception level.

Words-in-Noise (WIN) Test

A "Words-in-Noise (WIN) Test" is a test administered by an audiologist to measure a patient's speech intelligibility in recognizing words in the presence of background noise.

The WIN test consists of administering words to an ear at a varying signal-to-noise ratio (SNR) level. The signal-to-noise ratio is the ratio of the strength of the signal carrying information (e.g. the test word signal), relative to the signal of interference (e.g. noise), and is typically expressed in decibels. In some embodiments, the background noise is multi-talker babble at a fixed decibel level.

In some embodiments, the multi-talker babble is comprised of six talkers (three female, three male) at a fixed level, for example, as described in Wilson, R. H., Abrams, H. B., & Pillion, A. L. (2003). A word-recognition task in multi-talker babble using a descending presentation mode from 24 dB to 0 dB signal to babble. Journal of Rehabilitation Research and Development, 40(4), 321-328.

In some embodiments, the background noise is maintained at a fixed decibel level, and the variation in the SNR decibel level is achieved by varying the decibel level of the test word signal. The SNR decibel level is therefore the SNR above the background noise. For example if the level of multi-talker babble is fixed at 70 dB SPL, and the level of the test word signal varied from 70 dB SPL to 94 dB SPL, this would give a SNR decibel level variation of 0 dB to 24 dB.

In some embodiments, the test words that are used may be from any list described herein for the word recognition tests. In some embodiments, the word-in-noise test is for 70 words. In other embodiments, the words-in-noise test is for 35 words.

In some embodiments, the test consists of administering 35 or 70 monosyllabic words from the NU No. 6 word lists. The test words may be spoken with the carrier phrase: "Say the word _".

In some embodiments, the WIN test is administered in a descending-level SNR paradigm. In these embodiments, the test words at the high SNR decibel level are presented first, followed by test words at gradually lower SNR decibel levels, with words at the lowest SNR decibel level administered last. The high SNR decibel level is the easiest setting for the patient to identify the signal words. The low SNR decibel levels is the most difficult setting for the patient to identify the signal words. In other embodiments, the WIN test is administered in a randomized-level SNR paradigm. In these embodiments, the test words are presented at different SNR decibel levels in a randomized order.

In some embodiments the SNR decibel level of the test words varies from 24 dB SNR (easiest condition) to 0 dB SNR (most difficult condition) in 4 dB decrements, for a total of seven SNR levels (i.e. 24 dB SNR, 20 dB SNR, 16 dB SNR, 12 dB SNR, 8 dB SNR, 4 dB SNR and 0 dB SNR).

In a preferred embodiment the WIN test consists of administering 70 monosyllabic words from the NU No. 6 word lists, where the SNR decibel level of the test words varies from 24 dB SNR (easiest condition) to 0 dB SNR (most difficult condition) in 4 dB decrements, for a total of seven SNR levels (i.e. 24 dB SNR, 20 dB SNR, 16 dB SNR, 12 dB SNR, 8 dB SNR, 4 dB SNR and 0 dB SNR). In this preferred embodiment, the level of multi-talker babble is fixed at 70 dB SPL, and the level of the test word signal varies from 70 dB SPL to 94 dB SPL.

The 'words-in-noise' test may be used to generate a words-in-noise score.

In some embodiments the words-in-noise score is given as a percentage of the total correct words recognized by the patient in the test and calculated using the formula:

$$\text{words in noise score } (\%) = 100 \times \left( \frac{\text{words recognised in standard words in noise test}}{\text{total words}} \right)$$

In some embodiments, the patient has a words-in-noise score of 90% or less, 80% or less, 70% or less, 60% or less, 50% or less, 40% or less, or 30% or less prior to treatment. In a preferred embodiment, the patient has a words-in-noise score of 50% or less prior to treatment.

In some embodiments the words-in-noise score is expressed as the number of words that are correctly recognized in the test. For example, in some embodiments the patient correctly identifies 63 or fewer, 56 or fewer, 49 or fewer, 42 or fewer, 35 or fewer, 28 or fewer, or 21 or fewer words in a word-in-noise test for 70 words. In a preferred embodiment, the patient correctly identifies 35 or fewer words in a words-in-noise test for 70 words. In other embodiments, the patient correctly identifies 32 or fewer, 28 or fewer, 24 or fewer, 21 or fewer, 17 or fewer, 14 or fewer or 11 or fewer words in a words-in-noise test for 35 words.

In some embodiments the patient's signal-to-noise ratio (SNR) for the predicted mean of 50% correct words in a words-in-noise test is calculated using the words-in-noise score at each SNR level and the Spearman-Karber equation. The predicted mean of 50% correct words is used to provide the mean dB SNR level at which the person is expected to identify 50% of the words correctly in a words-in-noise test. In some embodiments, the patient's SNR for a predicted mean of 50% correct words in a words-in-noise test is about 25 dB, about 24 dB, about 23 dB, about 22 dB, about 21 dB, about 20 dB, about 19 dB, 18 dB, about 17 dB, about 16 dB, about 15 dB, about 14 dB, about 13 dB, about 12 dB, about 11 dB, about 10 dB, about 9 dB, about 8 dB, about 7 dB, about 6 dB. In a preferred embodiment, the patient's signal-to-noise ratio (SNR) for the predicted mean of 50% correct words in a words-in-noise test is about 21 dB, for example 20.8 dB, about 20 dB, about 19 dB, for example 18.8 dB, about 18 dB, for example 17.6 dB, about 17 dB, for example 16.8 dB, or about 16 dB, for example 16.4 dB.

Definitions

In this application, the use of "or" includes "and/or" unless stated otherwise. As used in this application, the term "comprise" and variations of the term, such as "comprising" and "comprises," are not intended to exclude other additives, components, integers or steps. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether they materially affect the activity or action of the listed elements.

The terms "about" and "approximately" are used as equivalents. Any numerals used in this disclosure with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Any reference to a compound is also a reference to a pharmaceutically acceptable salt of that compound (regardless of whether or not pharmaceutically acceptable salts are explicitly mentioned). Any compound can be provided for use in the invention in any pharmaceutically acceptable solid form, e.g. salt, solvate, hydrate, polymorph, amorphous material form etc. Any references to a compound also include references to artificially deuterated forms of that compound.

"Activity" refers to biological function mediated by proteins of a cell measured by methods known in the art such as immunostaining and western blotting in conjunction with cellular effects such as proliferation, cellular growth, or cellular gene expression.

"Administration" refers to introducing a substance into a subject. In some embodiments, administration is auricular, intraauricular, intracochlear, intravestibular, or transtympanically, e.g., by injection. In some embodiments, administration is directly to the inner ear, e.g. injection through the round window, otic capsule, or vestibular canals. In some embodiments, administration is directly into the inner ear via a cochlear implant delivery system. In some embodiments, the substance is injected transtympanically to the middle ear. In certain embodiments the substance is administered systemically (e.g. orally or parenterally). In certain embodiments "causing to be administered" refers to administration of a second component after a first component has already been administered (e.g., at a different time and/or by a different actor).

"Agonist" refers to an agent that causes an increase in the expression, levels, and/or activity of a target gene, protein, and/or pathway. In some instances, an agonist directly binds to and activates a target protein. In some instances, an agonist increases the activity of a pathway by binding to and modulating the activity of one or more pathway components, for example, by inhibiting the activity of negative regulator(s) of the pathway, or by activating upstream or downstream regulator(s) of the pathway.

"Auricular administration" refers to a method of using a catheter or wick device to administer a composition across the tympanic membrane to the inner ear of the subject. To facilitate insertion of the wick or catheter, the tympanic membrane may be pierced using a suitably sized syringe or pipette. The devices could also be inserted using any other methods known to those of skill in the art, e.g., surgical implantation of the device. In particular embodiments, the wick or catheter device may be a stand-alone device, meaning that it is inserted into the ear of the subject and then the composition is controllably released to the inner ear. In other particular embodiments, the wick or catheter device may be attached or coupled to a pump or other device that allows for the administration of additional compositions. The pump may be automatically programmed to deliver dosage units or may be controlled by the subject or medical professional.

"Canonical Notch Signaling" refers to Notch mediated transcription through the complex of Mastermind-like protein (MAML), CSL/RBPJ(CBF-1, Suppressor of hairless, Lag-1/Recombining binding protein suppressor of hairless), and NICD (Notch Intracellular Domain) that causes upregulation of Hes and Hey target genes. For example, canonical notch signaling is measured in a cochlear Lgr5+ cell by measuring Hes and Hey gene expression in a Stem Cell Proliferation Assay. Gene expression is measured using methods known in the art such as by PCR, Nanostring or Western blot analysis.

"Cell Aggregate" as used herein refers to a body cells in the organ of Corti that have proliferated to form a cluster of a given cell type that is greater than 40 microns in diameter and/or produced a morphology in which greater than 3 cell layers reside perpendicular to the basilar membrane.

"Cell Aggregate" can also refer a process in which cell division creates a body of cells that cause one or more cell types to breach the reticular lamina, or the boundary between endolymph and perilymph.

"Cell Density" as used herein in connection with a specific cell type is the mean number of that cell type per area in a Representative Microscopy Sample. The cell types may include but are not limited to Lgr5+ cells, hair cells, or supporting cells. The Cell Density may be assessed with a given cell type in a given organ or tissue, including but not limited to the cochlea or organ of Corti. For instance, the Lgr5+ Cell Density in the organ of Corti is the Cell Density of Lgr5+ cells as measured across the organ of Corti. Typically, supporting cells and Lgr5+ cells will be enumerated by taking cross sections of the organ of Corti. Typically, hair cells will be enumerated by looking down at the surface of the organ of Corti, though cross sections may be used in some instances, as described in a Representative Microscopy Sample. Typically, Cell Density of Lgr5+ cells will be measured by analyzing whole mount preparations of the Organ of Corti and counting the number of Lgr5 cells across a given distance along the surface of the epithelia, as described in a Representative Microscopy Sample. Hair cells may be identified by their morphological features such as bundles or hair cell specific stains (e.g., Myosin VIIa, Prestin, vGlut3, Pou4f3, Espin, conjugated-Phalloidin, PMCA2, Ribeye, Atoh1, etc.). Lgr5+ cells may be identified by specific stains or antibodies (e.g., Lgr5-GFP transgenic reporter, anti-Lgr5 antibody, etc.)

"Cochlear Concentration" as used herein will be the concentration of a given agent as measured through sampling cochlear fluid or tissue. Unless otherwise noted, the sample should contain a substantial enough portion of the cochlear fluid or tissue so that it is approximately representative of the average concentration of the agent in the cochlea. For example, samples may be drawn from a vestibular canal, and a series of fluid samples drawn in series such that individual samples are comprised of cochlear fluid in specified portions of the cochlea "Complementary nucleic acid sequence" refers to a nucleic acid sequence capable of hybridizing with another nucleic acid sequence comprised of complementary nucleotide base pairs.

"Cross-Sectional Cell Density" as used herein in connection with a specific cell type is the mean number of that cell type per area of cross section through a tissue in a Representative Microscopy Sample. Cross sections of the organ of Corti can also be used to determine the number of cells in a given plane. Typically, hair cells Cross-sectional Cell Density will be measured by analyzing whole mount preparations of the organ of Corti and counting the number of hair cells across a given distance in cross sections taken along a portion of the epithelia, as described in a Representative Microscopy Sample. Typically, Cross-sectional Cell Density of Lgr5+ cells will be measured by analyzing whole mount preparations of the organ of Corti and counting the number of Lgr5+ cells across a given distance in cross sections taken along a portion of the epithelia, as described in a Representative Microscopy Sample. Hair cells may be identified by their morphological features such as bundles or hair cell specific stains (suitable stains include e.g., Myosin VIIa, Prestin, vGlut3, Pou4f3, conjugated-Phalloidin, PMCA2, Atoh1, etc.). Lgr5+ cells may be identified by specific stains or antibodies (suitable stains and antibodies include fluorescence in situ hybridization of Lgr5 mRNA, Lgr5-GFP transgenic reporter system, anti-Lgr5 antibodies, etc.).

"Decreasing" or "decreases" refers to decreasing by at least 5%, for example, 5, 6, 7, 8, 9, 10, 15, 20, 25, 30, 35, 40, 45, 50, 55, 60, 65, 70, 75, 80, 85, 90, 95, 99 or 100%, for example, as compared to the level of reference or control.

"Decreasing" or "decreases" also includes decreasing by at least about 1.1-fold, for example, at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more, for example, as compared to the level of a reference or control.

"Deltex-1 Agonist" refers to an agent that causes an increase in the expression, levels, and/or activity of Deltex-1 1gene, protein, and/or pathway. In some instances, an agonist directly binds to and activates Deltex-1. In some instances, an agonist increases the activity of Deltex-1 by binding to and modulating the activity of one or more Deltex-1 pathway components, for example, by inhibiting the activity of negative regulator(s) of the pathway, or by activating upstream or downstream regulator(s) of the pathway.

"Deltex-1 Synergist" refers to an agent that causes an increase in the expression, levels, and/or activity of the Deltex-1 gene, protein, and/or pathway when used in combination with a Jag-1 agonist, Deltex-1 agonist, PI3K agonist, or non-canonical Notch agonist.

"Effective Concentration" is the minimum concentration of a compound that induces at least an 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more in gene expression and/or about a 1.5-fold increase in number of Lgr5+ cells in a Stem Cell Proliferation Assay compared to the number of Lgr5+ cells in a Stem Cell Proliferation Assay performed without the compound.

"Effective Release Rate" (mass/time) as used herein is the Effective Concentration (mass/volume)*30 uL/1 hour.

"Eliminate" means to decrease to a level that is undetectable.

"Engraft" or "engraftment" refers to the process of stem or progenitor cell incorporation into a tissue of interest in vivo through contact with existing cells of the tissue. "Epithelial progenitor cell" refers to a multipotent cell which has the potential to become restricted to cell lineages resulting in epithelial cells.

"Epithelial stem cell" refers to a multipotent cell which has the potential to become committed to multiple cell lineages, including cell lineages resulting in epithelial cells.

"Expression" refers to gene levels as measured by the amount of RNA

"HDAC inhibitor" refers to any compound that inhibits the cellular activity of Histone Deacetylase classes I-IV "Hybridize" refers to pairing to form a double-stranded molecule between complementary nucleotide bases (e.g., adenine (A) forms a base pair with thymine (T), as does guanine (G) with cytosine (C) in DNA) under suitable conditions of stringency. (See, e.g., Wahl, G. M. and S. L. Berger (1987) Methods Enzymol. 152:399; Kimmel, A. R. (1987) Methods Enzymol. 152:507).

An "inhibitor" refers to an agent that causes a decrease in the expression, levels, and/or activity of a target gene, protein, and/or pathway. An "antagonist" is one example of an "inhibitor".

As used herein, an "inhibitory nucleic acid" is a double-stranded RNA, RNA interference, miRNA, siRNA, shRNA, or antisense molecule, or a portion thereof, or a mimetic thereof, that when administered to a mammalian cell results in a decrease in the expression of a target gene. Typically, a nucleic acid inhibitor comprises at least a portion of a target nucleic acid molecule, or an ortholog thereof, or comprises at least a portion of the complementary strand of a target nucleic acid molecule. In some instances, expression of a target gene is reduced by 10%, 25%, 50%, 75%, or even 90-100%.

"In Vitro Lgr5 activity" refers to the level of expression or activity of Lgr5 in an in vitro population of cells. It may be measured, for example, in cells derived from a Lgr5-GFP expressing mouse such as a B6.129P2-Lgr5tm1(cre/ERT2) Cle/J mouse (also known as Lgr5-EGFP-IRES-creERT2 or Lgr5-GFP mouse, Jackson Lab Stock No: 008875) by dissociating cells to single cells, staining with propidium iodide (PI), and analyzing the cells using a flow cytometer for Lgr5-GFP expression. Inner ear epithelial cells from wild-type (non-Lgr5-GFP) mice that passing the same culturing and analyzing procedures can be used as a negative control. Typically, two population of cells are shown in the bivariate plot with GFP/FITC as one variable, which include both GFP positive and GFP negative populations. Lgr5+ cells can be identified by gating GFP positive cell population. The percentage of Lgr5+ cells can be measured by gating GFP positive cell population against both GFP negative population and the negative control. The number of Lgr5+ cells can be calculated by multiplying the total number of cells by the percentage of Lgr5-positive cells. For cells derived from non-Lgr5-GFP mice, Lgr5 activity can be measured using an anti-Lgr5 antibody or quantitative-PCR on the Lgr5 gene.

"In Vivo Lgr5 activity" as used herein is the level of expression or activity of Lgr5 in a subject. It may be measured, for example, by removing an animal's inner ear and measuring Lgr5 protein or Lgr5 mRNA. Lgr5 protein production can be measured using an anti-Lgr5 antibody to measure fluorescence intensity as determined by imaging cochlear samples, where fluorescence intensity is used as a measure of Lgr5 presence. Western blots can be used with an anti-Lgr5 antibody, where cells can be harvested from the treated organ to determine increases in Lgr5 protein. Quantitative-PCR or RNA in situ hybridization can be used to measure relative changes in Lgr5 mRNA production, where cells can be harvested from the inner ear to determine changes in Lgr5 mRNA. Alternatively, Lgr5 expression can be measured using an Lgr5 promoter driven GFP reporter transgenic system, where the presence or intensity GFP fluoresce can be directly detected using flow cytometry, imaging, or indirectly using an anti-GFP antibody.

"Increasing" or "increases" refers to increasing by at least 5%, for example, 5, 6, 7, 8, 9, 10, 15, 20, 25, 30, 35, 40, 45, 50, 55, 60, 65, 70, 75, 80, 85, 90, 95, 99, 100, 150, 200, 250, 300, 350, 400, 450, or 500% or more, for example, as compared to the level of a reference.

"Increasing" or "increases" also means increases by at least about 1.1-fold, for example, at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more, for example, as compared to the level of a reference standard.

"Intraauricular administration" refers to administration of a composition to the middle or inner ear of a subject by directly injecting the composition.

"Intracochlear" administration refers to direct injection of a composition across the tympanic membrane and across the round window membrane into the cochlea.

"Intravestibular" administration refers to direct injection of a composition across the tympanic membrane and across the round window or oval window membrane into the vestibular organs.

"Isolated" refers to a material that is free to varying degrees from components which normally accompany it as found in its native state. "Isolate" denotes a degree of separation from original source or surroundings.

"Jagged-1 Agonist" or "Jag-1 Agonist" as used herein is a compound that causes an increase in the expression, levels, and/or activity of a Jag-1 gene, protein, and/or pathway. In some instances, an agonist directly binds to and activates Jag-1 protein. In some instances, an agonist increases the activity of a pathway by binding to and modulating the activity of one or more Jag-1 pathway components, for example, by inhibiting the activity of negative regulator(s) of the pathway, or by activating upstream or downstream regulator(s) of the pathway.

"Jagged-1 Synergist" or "Jag-1 Synergist" as used herein is a compound that causes an increase in the expression, levels, and/or activity of a Jag-1 gene, protein, and/or pathway when used in combination with a Jag-1 agonist, Deltex-1 agonist, PI3K agonist, or Non-canonical Notch agonist.

"Lgr5" is an acronym for the Leucine-rich repeat-containing G-protein coupled receptor 5, also known as G-protein coupled receptor 49 (GPR49) or G-protein coupled receptor 67 (GPR67). It is a protein that in humans is encoded by the Lgr5 gene.

"Lgr5 Activity" is defined as the level of activity of Lgr5 in a population of cells. In an in vitro cell population, Lgr5 activity may be measured in an in vitro Lgr5 Activity assay. In an in vivo cell population, Lgr5 activity may be measured in an in vivo Lgr5 Activity assay.

"Lgr5+ cell" or "Lgr5-positive cell" as used herein is a cell that expresses Lgr5. "Lgr5-cell" or "Lgr5-negative" as used herein is a cell that is not Lgr5+.

"Lineage Tracing" as used herein is using a mouse line that enables fate tracing of any cell that expresses a target gene at the time of reporter induction. This can include hair cell or supporting cells genes (Sox2, Lgr5, MyosinVlla, Pou4f3, etc.). For example, lineage tracing may use an Lgr5-EGFP-IRES-creERT2 mouse crossed with a reporter mouse, which upon induction, allows one to trace the fate of cells that expressed Lgr5 at the time of induction. By further example, Lgr5 cells can be isolated into single cells and cultured in a Stem Cell Proliferation Assay to generate colonies, then subsequently differentiated in a Differentiation Assay and analyzed for cell fate by staining for hair cell and/or supporting cell proteins and determining the reporter co-localization with either hair cell or supporting cell staining to determine the Lgr5 cells' fate. In addition, lineage tracing can be performed in cochlear explants to track supporting cell or hair cell fate within the intact organ after treatment. For example, Lgr5 cell fate can be determined by isolating the cochlea from a Lgr5-EGFP-IRES-creERT2 mouse crossed with a reporter mouse and inducing the reporter in Lgr5 cells before or during treatment. The organ can then be analyzed for cell fate by staining for hair cell and/or supporting cell proteins and determining the reporter co-localization with either hair cell or supporting cell staining to determine the Lgr5 cells' fate. In addition, lineage tracing can be performed in vivo track supporting cell or hair cell fate within the intact organ after treatment. For example, Lgr5 cell fate can be determined inducing a reporter in an Lgr5-EGFP-IRES-creERT2 mouse crossed with a reporter mouse, treating the animal, then isolating the cochlea. The organ can then be analyzed for cell fate by staining for hair cell and/or supporting cell proteins and determining the reporter co-localization with either hair cell or supporting cell staining to determine the Lgr5 cells' fate. Lineage tracing may be performed using alternative reporters of interest as is standard in the art.

"Mammal" refers to any mammal including but not limited to human, mouse, rat, sheep, monkey, goat, rabbit, hamster, horse, cow or pig.

"Mean Release Time" as used herein is the time in which one-half of an agent is released into phosphate buffered saline from a carrier in a Release Assay.

"Native Morphology" as used herein is means that tissue organization largely reflects the organization in a healthy tissue.

"Non-canonical Notch signaling" refers to Notch-mediated effects or transcription that is primarily independent of Mastermind-like protein (MAML), CSL/RBPJ(CBF-1, Suppressor of hairless, Lag-1/Recombining binding protein suppressor of hairless), and NICD (Notch Intracellular Domain) complex-driven transcription that causes upregulation of Hes and Hey target genes. Non-canonical Notch signalling may include Jag-1 mediated transcription, increases in γ-secretase activity, Deltex-1 mediated effects, Hif-1 mediated effects, PI3K mediated effects, mTOR mediated effects, AKT mediated effects, NFκB mediated effects, YY1 mediated effects.

"Non-canonical Notch agonist" refers to compounds, proteins, or molecules that upregulate non-canonical Notch targets through mechanisms such as Jag-1 upregulation, increases in γ-secretase activity, Deltex-1 mediated effects, Hif-1 mediated effects, PI3K mediated effects, mTOR mediated effects, AKT mediated effects, NFκB mediated effects, YY1 mediated effects.

"Non-canonical Notch synergist" refers to compounds, proteins, or molecules that when used in combination with a Jag-1 agonist, Deltex-1 agonist, PI3K agonist, or Non-canonical Notch agonist upregulate non-canonical Notch targets through mechanisms such as Jag-1 upregulation, increases in γ-secretase activity, Deltex-1 mediated effects, Hif-1 mediated effects, PI3K mediated effects, mTOR mediated effects, AKT mediated effects, NFκB mediated effects, YY1 mediated effects.

"Non-human mammal", as used herein, refers to any mammal that is not a human.

As used in relevant context herein, the term "number" of cells can be 0, 1, or more cells.

"Organ of Corti" as used herein refers to the sensory epithelia of the cochlea where the sensory cells (inner and outer hair cells) and supporting cells reside.

"Organoid" or "epithelial organoid" refers to a cell cluster or aggregate that resembles an organ, or part of an organ, and possesses cell types relevant to that particular organ.

"Pharmaceutically-acceptable salt" includes both acid and base addition salts.

"Pharmaceutically-acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. For example, inorganic salts include, but are not limited to, ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Example organic bases used in certain embodiments include isopropylamine, diethylamine, ethanolamine, trimethylamine, dicyclohexylamine, choline, and caffeine.

"PI3K Agonist" as used herein is a compound that causes an increase in the expression, levels, and/or activity of a PI3K, protein, and/or pathway, such as FGF upregulation and/or AKT phosphorylation. In some instances, an agonist directly binds to and activates PI3K protein. In some instances, an agonist increases the activity of a pathway by binding to and modulating the activity of one or more PI3K pathway components, for example, by inhibiting the activity of negative regulator(s) of the pathway, or by activating upstream or downstream regulator(s) of the pathway.

"PI3K Synergist" as used herein is a compound that when used in combination with a Jag-1 agonist, Deltex-1 agonist, Non-canonical Notch Agonist, or PI3K agonist causes an increase in the expression, levels, and/or activity of a PI3K, protein, and/or pathway, such as FGF upregulation and/or AKT phosphorylation. In some instances, an agonist directly binds to and activates PI3K protein. In some instances, an agonist increases the activity of a pathway by binding to and modulating the activity of one or more PI3K pathway components, for example, by inhibiting the activity of negative regulator(s) of the pathway, or by activating upstream or downstream regulator(s) of the pathway.

"Population" of cells refers to any number of cells greater than 1, but is preferably at least $1 \times 10^3$ cells, at least $1 \times 10^4$ cells, at least at least $1 \times 10^5$ cells, at least $1 \times 10^6$ cells, at least $1 \times 10^7$ cells, at least $1 \times 10^8$ cells, at least $1 \times 10^9$ cells, or at least $1 \times 10^{10}$ cells.

"Progenitor cell" as used herein refers to a cell that, like a stem cell, has the tendency to differentiate into a specific type of cell, but is already more specific than a stem cell and is pushed to differentiate into its "target" cell.

"Proliferation Period" as used herein is the duration of time in which tissue or cells are exposed to a LSD1 inhibitor alone or in combination with a Wnt agonist.

In certain embodiments, the "purity" of any given agent or compound in a composition may be specifically defined. For instance, certain compositions may comprise an agent that is at least 80, 85, 90, 91, 92, 93, 94, 95, 96, 97, 98, 99, or 100% pure, including all decimals in between, as measured, for example and by no means limiting, by high performance liquid chromatography (HPLC), a well-known form of column chromatography used frequently in biochemistry and analytical chemistry to separate, identify, and quantify compounds.

"Reference" means a standard or control condition (e.g., untreated with a test agent or combination of test agents).

"Release Assay" as used herein is a test in which the rate of release of an agent from a Biocompatible Matrix through dialysis membrane to a saline environment. An exemplary Release Assay may be performed by placing 30 microliters of a composition in 1 ml Phosphate Buffered Saline inside saline dialysis bag with a suitable cutoff, and placing the dialysis bag within 10 mL of Phosphate Buffered Saline at 37° C. The dialysis membrane size may be chosen based on agent size in order to allow the agent being assessed to exit the membrane. For small molecule release, a 3.5-5 kDa cutoff may be used. The Release Rate for a composition may change over time and may be measured in 1 hour increments.

"Representative Microscopy Sample" as used herein describes a sufficient number of fields of view within a cell culture system, a portion of extracted tissue, or an entire extracted organ that the average feature size or number being measured can reasonably be said to represent the average feature size or number if all relevant fields were measured. For example, in order to assess the hair cell counts at a frequency range on the Organ of Corti, ImageJ software (NIH) can used to measure the total length of cochlear whole mounts and the length of individual counted segments. The total number of inner hair cells, outer hair cells, and supporting cells can be counted in the entire or fraction of any of the four cochlear segments of 1200-1400 μm (apical, mid-apical, mid-basal, and basal) at least 3 fields of view at 100 μm field size would be reasonably considered a Representative Microscopy Sample. A Representative Microscopy sample can include measurements within a field of view, which can be measured as cells per a given distance. A Representative Microscopy sample can be used to assess morphology, such as cell-cell contacts, cochlear architecture, and cellular components (e.g., bundles, synapses).

"Rosette Patterning" is a characteristic cell arrangement in the cochlea in which <5% hair cells are adjacent to other hair cells.

The term "sample" refers to a volume or mass obtained, provided, and/or subjected to analysis. In some embodiments, a sample is or comprises a tissue sample, cell sample, a fluid sample, and the like. In some embodiments, a sample is taken from (or is) a subject (e.g., a human or animal subject). In some embodiments, a tissue sample is or comprises brain, hair (including roots), buccal swabs, blood, saliva, semen, muscle, or from any internal organs, or cancer, precancerous, or tumor cells associated with any one of these. A fluid may be, but is not limited to, urine, blood, ascites, pleural fluid, spinal fluid, and the like. A body tissue can include, but is not limited to, brain, skin, muscle, endometrial, uterine, and cervical tissue or cancer, precancerous, or tumor cells associated with any one of these. In an embodiment, a body tissue is brain tissue or a brain tumor or cancer. Those of ordinary skill in the art will appreciate that, in some embodiments, a "sample" is a "primary sample" in that it is obtained from a source (e.g., a subject); in some embodiments, a "sample" is the result of processing of a primary sample, for example to remove certain potentially contaminating components and/or to isolate or purify certain components of interest.

"Self-renewal" refers to the process by which a stem cell divides to generate one (asymmetric division) or two (symmetric division) daughter cells with development potentials that are indistinguishable from those of the mother cell. Self-renewal involves both proliferation and the maintenance of an undifferentiated state.

"siRNA" refers to a double stranded RNA. Optimally, an siRNA is 18, 19, 20, 21, 22, 23 or 24 nucleotides in length and has a 2 base overhang at its 3' end. These dsRNAs can be introduced to an individual cell or culture system. Such siRNAs are used to downregulate mRNA levels or promoter activity.

"Stem cell" refers to a multipotent cell having the capacity to self-renew and to differentiate into multiple cell lineages.

"Stem Cell Differentiation Assay" as used herein is an assay to determine the differentiation capacity of stem cells. In an exemplary Stem Cell Differentiation Assay, the number of cells for an initial cell population is harvested from a Atoh1-GFP mouse between the age of 3 to 7 days, by isolating the Organ of Corti sensory epithelium, dissociating the epithelium into single cells, and passing the cells through a 40 um cell strainer. Approximately 5000 cells are entrapped in 40 µl of culture substrate (for example: Matrigel (Corning, Growth Factor Reduced)) and placed at the center of wells in a 24-well plate with 500 µl of an appropriate culture media, growth factors and agent being tested. Appropriate culture media and growth factors include Advanced DMEM/F12 with media Supplements (1×N2, 1× B27, 2 mM Glutamax, 10 mM HEPES, 1 mM N-acetylcysteine, and 100 U/ml Penicillin/100 µg/ml Streptomycin) and growth factors (50 ng/ml EGF, 50 ng/ml bFGF, and 50 ng/ml IGF-1) as well as the agent(s) being assessed are added into each well. Cells are cultured for 10 days in a standard cell culture incubator at 37° C. and 5% CO2, with media change every 2 days. These cells are then cultured by removing the Stem Cell Proliferation Assay agents and replacing with Basal culture media and molecules to drive differentiation. An appropriate Basal culture media is Advanced DMEM/F12 supplemented with 1×N2, 1× B27, 2 mM Glutamax, 10 mM HEPES, 1 mM N-acetylcysteine, and 100 U/ml Penicillin/100 µg/ml Streptomycin and appropriate molecules to drive differentiation are 3 µM CHIR99021 and 5 µM DAPT for 10 days, with media change every 2 days. The number of hair cells in a population may be measured by using flow cytometry for GFP. Hair cell differentiation level can further be assessed using qPCR to measure hair cell marker (e.g., Myo7a) expression level normalized using suitable and unregulated references or housekeeping genes (e.g., Hprt). Hair cell differentiation level can also be assessed by immunostaining for hair cell markers (e.g. Myosin7a, vGlut3, Espin, PMCAs, Ribeye, conjugated-phalloidin, Atoh1, Pou4f3, etc.). Hair cell differentiation level can also be assessed by Western Blot for Myosin7a, vGlut3, Espin, PMCAs, Prestin, Ribeye, Atoh1, Pou4f3.

"Stem Cell Assay" as used herein is an assay in which a cell or a cell population are tested for a series of criteria to determine whether the cell or cell population are stem cells or enriched in stem cells or stem cell markers. In a stem cell assay, the cell/cell population are tested for stem cell characteristics such as expression of Stem Cell Markers, and further optionally are tested for stem cell function, including the capacity of self-renewal and differentiation. Gene expression is measured using methods known in the art such as by PCR, Nanostring, immunostaining, RNAseq, RNA hybridization, or Western blot analysis.

"Stem Cell Proliferation Assay" as used herein is an assay to determine the capacity for agent(s) to induce the creation of stem cells from a starting cell population. In an exemplary Stem Cell Proliferation Assay, the number of cells for an initial cell population is harvested from a Lgr5-GFP mouse such as a B6.129P2-Lgr5tm1(cre/ERT2)Cle/J mouse (also known as Lgr5-EGFP-IRES-creERT2 or Lgr5-GFP mouse, Jackson Lab Stock No: 008875) between the age of 0 to 5 days, by isolating the organ of Corti sensory epithelium and dissociating the epithelium into single cells. Approximately 5000 cells are entrapped in 40 µl of culture substrate (for example: Matrigel (Corning, Growth Factor Reduced)) and placed at the center of wells in a 24-well plate with 500 µl of an appropriate culture media, growth factors and agent being tested. Appropriate culture media and growth factors include Advanced DMEM/F12 with media Supplements (1×N2, 1× B27, 2 mM Glutamax, 10 mM HEPES, 1 mM N-acetylcysteine, and 100 U/ml Penicillin/100 µg/ml Streptomycin) and growth factors (50 ng/ml EGF, 50 ng/ml bFGF, and 50 ng/ml IGF-1) as well as the agent(s) being assessed are added into each well. Cells are cultured for 10 days in a standard cell culture incubator at 37° C. and 5% CO2, with media change every 2 days. The number of Lgr5+ cells is quantified by counting the number of cells identified as Lgr5+ in an In Vitro Lgr5 activity assay. The fraction of cells that are Lgr5+ is quantified by dividing the number of cells identified as Lgr5+ in a cell population by the total number of cells present in the cell population. The number of hair cells in a population may be measured by staining with hair cell marker (e.g., Myosin VIIa), or using an endogenous reporter of hair cell genes (e.g., Pou4f3-GFP, Atoh1-nGFP) and analyzing using flow cytometry. The fraction of cells that are hair cells is quantified by dividing the number of cells identified as hair cells in a cell population by the total number of cells present in the cell population. Gene and/or protein expression and/or activity is measured in this assay using methods known in the art such as by PCR, Nanostring, immunostaining, RNAseq, RNA hybridization, or Western blot analysis.

"Stem Cell Markers" as used herein can be defined as gene products (e.g. protein, RNA, etc.) that specifically expressed in stem cells. One type of stem cell marker is gene products that are directly and specifically support the maintenance of stem cell identity. Examples include Lgr5 and Sox2. Additional stem cell markers can be identified using assays that were described in the literatures. To determine whether a gene is required for maintenance of stem cell identity, gain-of-function and loss-of-function studies can be used. In gain-of-function studies, over expression of specific gene product (the stem cell marker) would help maintain the stem cell identity. While in loss-of-function studies, removal of the stem cell marker would cause loss of the stem cell identity or induced the differentiation of stem cells. Another type of stem cell marker is gene that only expressed in stem cells but does not necessary to have specific function to maintain the identity of stem cells. This type of markers can be identified by comparing the gene expression signature of sorted stem cells and non-stem cells by assays such as micro-array and qPCR. This type of stem cell marker can be found in the literature. (e.g. Liu Q. et al., Int J Biochem Cell Biol. 2015 March; 60: 99-111. http://www.ncbi.nlm.nih.gov/pubmed/25582750). Potential stem cell markers include Ccdc121, Gdf10, Opcm1, Phex, etc. The expression of stem cell markers such as Lgr5 or Sox2 in a given cell or cell population can be measure using assays such as qPCR, immunohistochemistry, western blot, and RNA hybridization. The expression of stem cell markers can also be measured using transgenic cells express reporters which can indicate the expression of the given stem cell markers, e.g. Lgr5-GFP or Sox2-GFP. Flow cytometry analysis can then be used to measure the activity of reporter expression. Fluorescence microscopy can also be used to directly visualize the expression of reporters. The expression of stem cell markers may further be determined using microarray analysis for global gene expression profile analysis. The gene expression profile of a given cell population or purified cell population can be compared with the gene expression profile of the stem cell to determine similarity between the 2 cell populations. Stem cell function can be measured by colony forming assay or sphere forming assay, self-renewal assay and differentiation assay. In colony (or sphere) forming assay, when cultured in appropriate culture media, the stem cell should be able to form colonies, on cell culture surface (e.g. cell culture dish) or embedded in cell culture substrate (e.g. Matrigel) or be able to form spheres when cultured in suspension. In colony/sphere forming assay, single stem cells are seeded at low cell density in appropriate culture media and allowed to proliferate for a given period of time (7-10 days). Colony formed are then counted and scored for stem cell marker expression as an indicator of stemness of the original cell. Optionally, the colonies that formed are then picked and passaged to test its self-renewal and differentiation potential. In self-renewal assay, when cultured in appropriate culture media, the cells should maintain stem cell marker (e.g. Lgr5) expression over at least one (e.g., 1, 2, 3, 4, 5, 10, 20, etc.) cell divisions. In a Stem Cell Differentiation Assay, when cultured in appropriate differentiation media, the cells should be able to generate hair cell which can be identified by hair cell marker expression measured by qPCR, immunostaining, western blot, RNA hybridization or flow cytometry.

"Subject" includes humans and mammals (e.g., mice, rats, pigs, cats, dogs, and horses). In some embodiments, subjects are be mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

"Supporting Cell" as used herein in connection with a cochlear epithelium comprises epithelial cells within the organ of Corti that are not hair cells. This includes inner pillar cells, outer pillar cells, inner phalangeal cells, Deiter cells, Hensen cells, Boettcher cells, and/or Claudius cells.

By "statistically significant", it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

"Substantially" or "essentially" means nearly totally or completely, for instance, 95% or greater of some given quantity.

"Synergist" refers to a compound that causes a more than additive increase in target gene expression or protein levels by 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold more than the additive value of each compound used individually.

"Tissue" is an ensemble of similar cells from the same origin that together carry out a specific function including, for example, tissue of cochlear, such as the organ of Corti.

"Transtympanic" administration refers to direct injection of a composition across the tympanic membrane into the middle ear.

"Treating" as used herein in connection with a cell population means delivering a substance to the population to affect an outcome. In the case of in vitro populations, the substance may be directly (or even indirectly) delivered to the population. In the case of in vivo populations, the substance may be delivered by administration to the host subject.

"Vehicle Control" or "Control" refers to treatment with the carrier that is absent of drug, such as DMSO for in vitro assays, poloxamer for middle ear delivery, and/or carrier or solution used to deliver drug compounds to cochlear cells describe here.

It is to be appreciated that references to "treating" or "treatment" include the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Wnt agonist" refers to an agent that increases the expression, protein levels, and/or activity of a Wnt gene or protein when used in combination with another compound. Gene expression is measured using methods known in the art such as by PCR, Nanostring, immunostaining, RNAseq, RNA hybridization, or Western blot analysis.

"Wnt activation" as used herein is an activation of the Wnt signaling pathway.

"Wnt alone" as used herein means when the activity as described herein of another agent or combination of agents is compared the activity of "Wnt alone" it is meant comparison is made using the same the Wnt agent at the same concentration.

The term "alkyl" as used herein refers to a straight or branched saturated hydrocarbon. For example, an alkyl group can have 1 to 8 carbon atoms (i.e., ($C_1$-$C_8$)alkyl) or 1 to 6 carbon atoms (i.e., ($C_1$-$C_6$ alkyl) or 1 to 4 carbon atoms.

The term "alkenyl" as used herein refers to a linear or branched hydrocarbon radical which includes one or more double bonds and can include divalent radicals, having from 2 to about 15 carbon atoms. Examples of alkenyl groups include but are not limited to, ethenyl, propenyl, butenyl, and higher homologs and isomers.

The term "alkynyl" as used herein refers to a linear or branched hydrocarbon radical which includes one or more triple bonds and can include divalent radicals, having from 2 to about 15 carbon atoms. Examples of alkynyl groups include but are not limited to, ethynyl, propynyl, butynyl, and higher homologs and isomers.

The term "halo" or "halogen" as used herein refers to fluoro, chloro, bromo and iodo.

The term "aryl" as used herein refers to a single all carbon aromatic ring or a multiple condensed all carbon ring system wherein at least one of the rings is aromatic. For example, an aryl group can have 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems may be optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring.

The term "heteroaryl" as used herein refers to a single aromatic ring that has at least one atom other than carbon in the ring, wherein the atom is selected from the group consisting of oxygen, nitrogen and sulfur; the term also includes multiple condensed ring systems that have at least one such aromatic ring, which multiple condensed ring systems are further described below. Thus, the term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. The term also includes multiple condensed ring systems (e.g., ring systems comprising 2, 3 or 4 rings) wherein a heteroaryl group, as defined above, can be condensed with one or more rings selected from heteroaryls (to form for example a naphthyridinyl such as 1,8-naphthyridinyl), heterocycles, (to form for example a 1, 2, 3, 4-tetrahydronaphthyridinyl such as 1, 2, 3, 4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system and at any suitable atom of the multiple condensed ring system including a carbon atom and heteroatom (e.g., a nitrogen).

The term "cycloalkyl" as used herein refers to a saturated or partially saturated ring structure having about 3 to about 8 ring members that has only carbon atoms as ring atoms and can include divalent radicals. Examples of cycloalkyl groups include but are not limited to, cyclopropyl, cyclobutyl, cyclopentyl, cyclohexyl, cyclohexene, cyclopentenyl, cyclohexenyl.

The terms "heterocyclyl" or "heterocyclic" refer to monocyclic or polycyclic 3 to 24-membered rings containing carbon and heteroatoms selected from oxygen, phosphorous, nitrogen, or sulfur and wherein there are no delocalized π electrons (aromaticity) shared among the ring carbon or heteroatoms. Examples of heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl. A heterocyclyl or heterocycloalkyl ring can also be fused or bridged, e.g., can be a bicyclic ring. Examples of heterocyclyl also include, but are not limited to, fused rings, bridged rings (e.g., 2,5-diazabicyclo[2,2,1]heptane), and spirocyclic rings, (e.g., 2,8-diazaspiro[4,5]decane).

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intends to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, i-pentyl or n-hexyl. In some embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl, or an aromatic or heteroaromatic moiety.

As used herein, the term "alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

As used herein, the term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, heterocyclyl, alkylaryl, or an aromatic or heteroaromatic moiety.

As used herein, the term "alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms. As used herein, "$C_2$-$C_6$ alkenylene linker" or "$C_2$-$C_6$ alkynylene linker" is intended to include $C_2$, $C_3$, $C_4$, $C_5$ or $C_6$ chain (linear or branched) divalent unsaturated aliphatic hydrocarbon groups. For example, $C_2$-$C_6$ alkenylene linker is intended to include $C_2$, $C_3$, $C_4$, $C_5$ and $C_6$ alkenylene linker groups.

As used herein, the term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

As used herein, the term "cycloalkyl" refers to a saturated or partially unsaturated hydrocarbon monocyclic or polycyclic (e.g., fused, bridged, or spiro rings) system having 3 to 30 carbon atoms (e.g., $C_3$-$C_{12}$, $C_3$-$C_{10}$, or $C_3$-$C_8$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, and adamantyl. In the case of polycyclic cycloalkyl, only one of the rings in the cycloalkyl needs to be non-aromatic. In some embodiments, the cycloalkyl is hexahydroindacenyl. In some embodiments, the cycloalkyl is

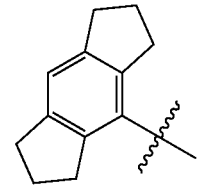

As used herein, the term "heterocycloalkyl" refers to a saturated or partially unsaturated 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, P, or Se), e.g., 1 or 1-2 or 1-3 or 1-4 or 1-5 or 1-6 heteroatoms, or e.g. 1, 2, 3, 4, 5, or 6 heteroatoms, independently selected from the group consisting of nitrogen, oxygen and sulphur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[0.5]decanyl, 1,4-dioxaspiro[4.5]decanyl, 1-oxaspiro[4.5]decanyl, 1-azaspiro[0.5]decanyl, 3 'H-spiro[cyclohexane-1,1'-isobenzofuran]-yl, 7'H-spiro[cyclohexane-1,5'-furo[3,4-b]pyridin]-yl, 3 'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, and the like. In the case of multicyclic heterocycloalkyl, only one of the rings in the heterocycloalkyl needs to be non-aromatic (e.g., 4,5,6,7-tetrahydrobenzo[c]isoxazolyl).

As used herein, the term "aryl" includes groups with aromaticity, including "conjugated," or multicyclic systems with one or more aromatic rings and do not contain any heteroatom in the ring structure. The term aryl includes both monovalent species and divalent species. Examples of aryl groups include, but are not limited to, phenyl, biphenyl, naphthyl and the like. Conveniently, an aryl is phenyl.

As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulphur. The nitrogen atom may be substituted or unsubstituted (i.e., N or NR wherein R is H or other substituents, as defined). The nitrogen and sulphur heteroatoms may optionally be oxidised (i.e., N→O and $S(O)_p$, where p=1 or 2). It is to be noted that total number of S and O atoms in the aromatic heterocycle is not more than 1. Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like. Heteroaryl groups can also be fused or bridged with alicyclic or heterocyclic rings, which are not aromatic so as to form a multicyclic system (e.g., 4,5,6,7-tetrahydrobenzo[c]isoxazolyl).

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthrydine, indole, benzofuran, purine, benzofuran, deazapurine, indolizine.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein, the term "substituted," means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

As used herein, the term "hydroxy" or "hydroxyl" includes groups with an —OH or —O.

As used herein, the term "halo" or "halogen" refers to fluoro, chloro, bromo and iodo.

The term "haloalkyl" or "haloalkoxyl" refers to an alkyl or alkoxyl substituted with one or more halogen atoms.

As used herein, the term "optionally substituted haloalkyl" refers to unsubstituted haloalkyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl, or an aromatic or heteroaromatic moiety.

As used herein, the term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

EXAMPLES

Example 1: Materials and Methods

Mice for Cell Screening

Neonatal Lgr5-EGFP-IRES-Cre-ER mice (The Jackson Laboratory, strain 8875) were used to analyze the effects of small molecules on cochlear stem cell expansion (see Barker et al., Nature 449, 1003-7 (2007). This strain allowed for visualization and quantification of EGFP cells.

Cell Assays

All animal studies were conducted under an approved institutional protocol per National Institutes of Health guidelines. Using neonatal animals, *cochleae* were dissected and the organ of Corti (sensory epithelium) was separated from the stria vascularis (ion transport epithelium) and the modiolus (nerve tissue). Epithelia were then collected and treated with TrypLE for 15-20 minutes to obtain single cells. The cells were then filtered (40 mm) and suspended in a Matrigel (Corning) dome for 3D culture seeded at 0.5 cochlea per well.

Expansion of Lgr5 Cells: Cells were cultured in a 3D system and bathed in a serum free 1:1 mixture of DMEM and F12, supplemented with Glutamax (GIBCO), N2, B27 (Invitrogen), EGF (50 ng/mL; Chemicon), bFGF (50 ng/mL; Chemicon), IGF-1 (50 ng/mL; Chemicon), and small molecules for seven days. Media was changed every other day. Treatments were run in triplicate or quadruplicate.

Quantification of Cell Proliferation:

Lgr5 cells were quantified after 7-10 days. Cell colonies were dissociated into single cells using TrypLE. The cells were then stained with propidium iodide (PI) and analyzed using a flow cytometer to count Lgr5-EGFP cells. The percentage of viable Lgr5 cells was plotted against the concentration in GraphPad Prism.

Quantification of Cell Proliferation, Expansion and Enrichment

Organ of Corti are dissected from Lgr5 GFP+ mice and dissociated as single cells as described above. Background media contains the same supplements and growth factors at the same concentrations as described above. Assays for image quantification are run in 96 well black plates with clear bottom with cells embedded in 50% Matrigel at cell density of 500 k cells/mL with 50 uL applied to each well. Cells are cultured for 7 days, with media change every 3-4 days. After 7 days of exposure to experimental conditions (e.g. small molecules), media is then removed from culture and replaced with media containing Hoescht at a 1:2000 dilution for a final concentration of 5 ug/mL (200 uL/well). The plate is then placed in a cell culture incubator at 37 C for 1 hr. The media containing Hoescht is then removed and 200 uL/well of Cell Recovery Solution is added. The plate is then incubated on a plastic-wrapped (e.g. Saran wrap) CoolRack™ on ice for 80 minutes. Next, the plate is centrifuged for 5 minutes at 2300 RPMs (Beckman Coulter Allegra 6R centrifuge; GH 3.8 A plate rotor; ambient temperature). Cells are then imaged on Celigo using 3 channels for brightfield, blue (Hoescht), and green (Lgr5 GFP). Proliferated cell colonies are captured as summed objects in the blue channel and the green channel. The green Lgr5 GFP+ cell colonies are quantified for total GFP(+) cell area, while the blue hoescht stained colonies are quantified as total cell area. The % GFP(+) Cell Area is calculated using the total GFP(+) cell area divided by the total cell area multiplied by 100. All results are compiled and utilized to determine the effects of experimental conditions (e.g. small molecules) on the expansion and enrichment of the Lgr5 cell population.

Lateral Canal Sampling

Animals were initially anesthetized with 100 mg/kg sodium thiobutabarbital (Inactin, Sigma, St Louis, Mo.) and maintained on 0.8 to 1.2% isofluorane in oxygen. Animals were mechanically ventilated through a tracheal cannula. Tidal volume was set to maintain a 5% end-tidal $CO_2$ level. Heart rate and blood oxygen saturation were monitored with a pulse-oximeter (Surgivet. Waukesha, Wis.). Body temperature was maintained near 38° C. with a thermistor-controlled heating pad.

Access to the LSCC was obtained with a post-auricular incision and a lateral opening in the auditory bulla. To prepare the LSCC for injection and sampling, the bone over the canal was thinned with a dental burr, where necessary removing a branch of the facial nerve that in some animals runs parallel to the LSCC for a short distance. When the canal was visible through the thinned bone, a layer of thin cyanoacrylate glue was applied to the dry bone followed by layers of two-part silicone adhesive (Kwik-Cast, World Precision Instruments, Sarasota, Fla.). The silicone was applied thinly over the canal but multiple layers were built up at the periphery to form a hydrophobic cup structure. A 30-40 μm fenestration into the canal wall was made through the adhesives and bone using a 30° House stapes pick (N1705 80, Bausch and Lomb Inc.). The pick was sharp at the tip, but rapidly widened so that entry into the canal, and potential damage to the endolymphatic system, was minimized.

Figure 1B:
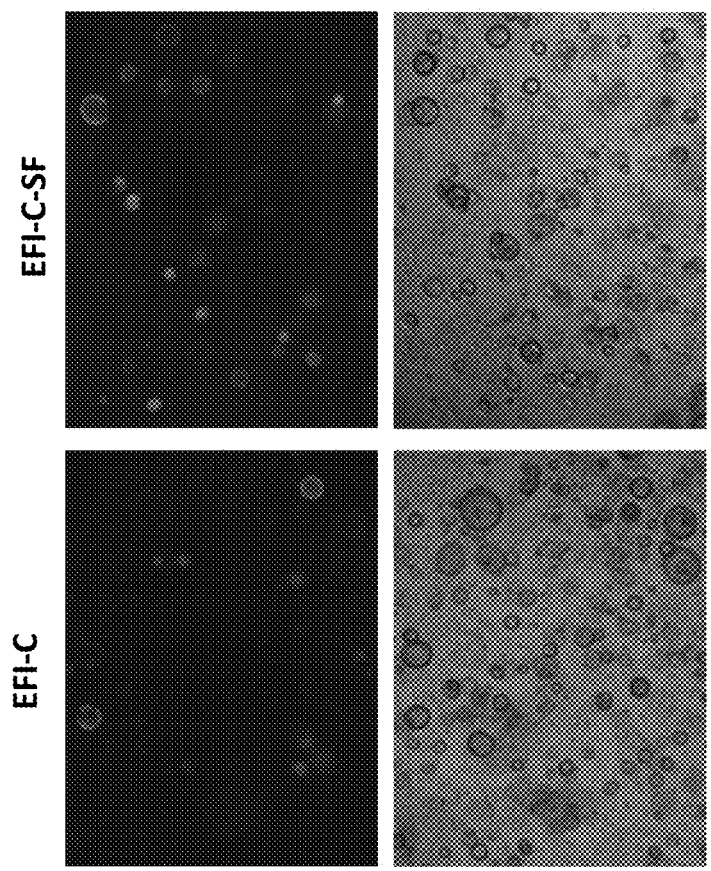
FIG. 1B shows Images of Lgr5 cell culture depicting Lgr5-GFP cell colonies. EFI-C-SF enhances Lgr5-GFP colony formation in a background of growth factors including: 50 ng/mL EGF (E), 50 ng/mL bFGF (F), and 50 ng/mL IGF1 (I).
Figure 2A:
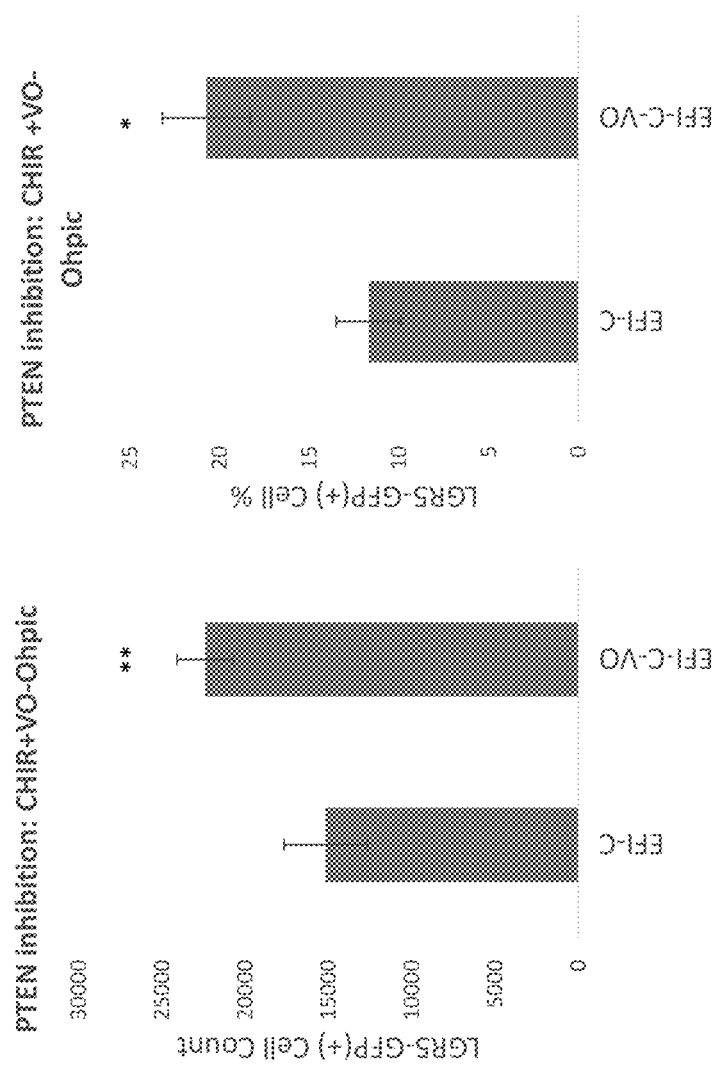
FIG. 2A is a graph that demonstrates that CHIR elicits the expansion (LGR5-GFP(+) cell count) and enrichment (percent LGR5-GFP(+) cell) of cochlear Lgr5 progenitor cells in culture, which is enhanced by addition of the PTEN inhibitor/PI3K synergist VO-Ohpic (VO) at 3 µM in a background of growth factors including: 50 ng/mL EGF (E), 50 ng/mL bFGF (F), and 50 ng/mL IGF1 (I).
Figure 2B:
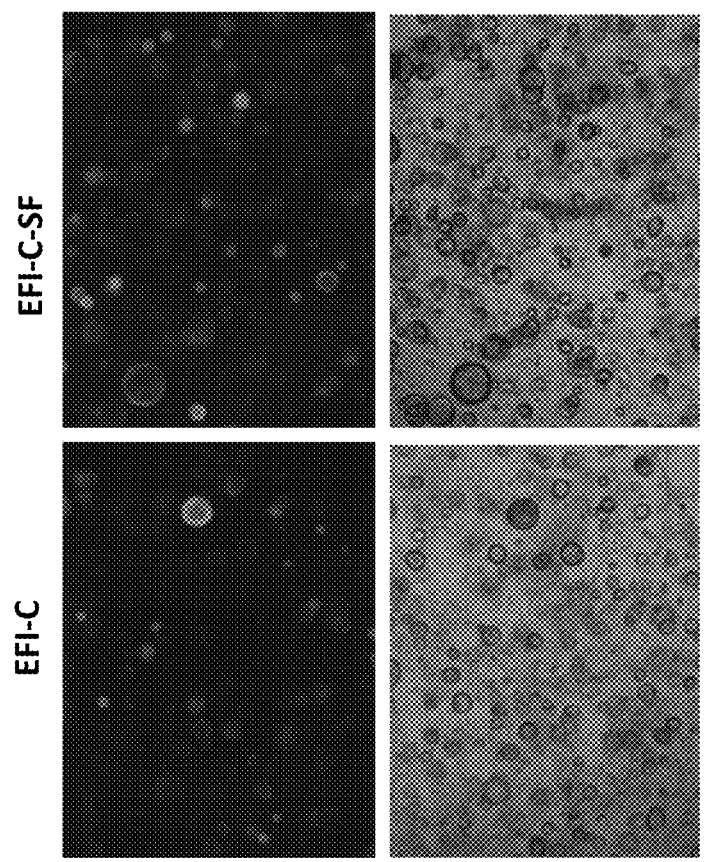
FIG. 2B shows images of Lgr5 cell culture depicting Lgr5-GFP cell colonies. EFI-C-VO-Ohpic enhances Lgr5-GFP colony formation in a background of growth factors including: 50 ng/mL EGF (E), 50 ng/mL bFGF (F), and 50 ng/mL IGF1 (I).

At times varied from 15 min to 4 h after the end of injection, multiple perilymph samples were taken from the LSCC. The injection pipette was first removed and the drop of cyanoacrylate glue that sealed it in place was broken up with the pick, taking care to leave the silicone cup intact. The fenestration was widened to 50-70 μm to allow perilymph leakage and the emerging perilymph was collected in blunt-tipped capillaries (#53432-706, 5 μL, VWR International, Radnor, Pa.). Each capillary was marked at a nominal volume of 1 μL. Sixteen to twenty individual 1 μL perilymph samples were collected sequentially, over a 20-30 min time period. The length of each sample was immediately measured with a calibrated dissecting microscope. Samples were expelled into dilutent (25 uL of 50:50 acetonitrile), with pairs of samples pooled, resulting in 8-10 measurements each. All data are presented as the 8-10 measured samples from each experiment. Analysis of compound concentration was determined by LCMS Apical Sampling Gradients of drug along the perilymphatic spaces were measured directly from multiple samples obtained by a technique called "sequential sampling". When the apex is perforated, perilymph is driven out by cerebrospinal fluid (CSF) entering the basal turn of ST through the cochlear aqueduct, pushing perilymph in an apical direction along the scala. The first sample collected originates from perilymph near the apex and each following sample from perilymph that originated from a scala location progressively closer to the base. After all ST perilymph has been pushed out, subsequent samples contain CSF that has passed through the scala. Samples collected in this manner allow drug gradients along the length of ST to be quantified. Perilymph was collected from the cochlear apex as a series of individual 1 µL samples collected over a 10-20 min period. To prepare the cochlea for sample collection the middle ear mucosa overlying the cochlear apex was first removed and the bone was allowed to dry. A thin layer of cyanoacrylate glue (Permabond 101; Permabond, Pottstown, Pa.) was applied to the dry bone, followed by layers of two-part silicone adhesive (Kwik-Cast, World Precision Instruments, Sarasota, Fla.), built up at the edges to form a hydrophobic cup. At the time of sampling a 30-40 µm fenestration was made at the apex through the adhesives using a 30° House stapes pick (N1705 80, Bausch and Lomb Inc.). Clear, uncontaminated fluid flows from the fenestration, accumulating on the hydrophobic surface. Fluid was collected with hand-held, blunt tipped capillary tubes (VWR 53432-706; VWR Radnor, Pa.), each marked for a nominal volume of 1 µL and taking 1-2 min to collect. The length of each sample in its capillary tube was measured with a calibrated dissecting microscope, from which the exact sample volume was established. Ten individual samples were collected in this manner, with the first sample representing the apex and each subsequent sample representing further towards the base and eventually the CSF. Samples were expelled into diluent (25 uL of 50:50 acetonitrile) and analysis of compound concentration was determined by LCMS Example 2: PTEN Inhibition Enhances Expansion of Cochlear Progenitor Cells GSK3 inhibition with CHIR, elicits the expansion and enrichment of cochlear Lgr5 progenitor cells in culture. As shown in FIGS. 1 A &B the expansion and enrichment of cochlear Lgr5 progenitor cells in culture is further enhanced by addition of the PTEN inhibitor/PI3K agonist SF1670 at 0.1 uM. Similarly, as shown in FIGS. 3 A & B CHIR induced cochlear Lgr5 progenitor cells expansion also enhanced is enhanced by addition of the PTEN inhibitor/PI3K synergist VO-Ohpic (VO) at 3 uM.

Example 3: PTEN Effects on Progenitor Cell Expansion Correlate with Synergistic Upregulation of Jag1

Figure 5:
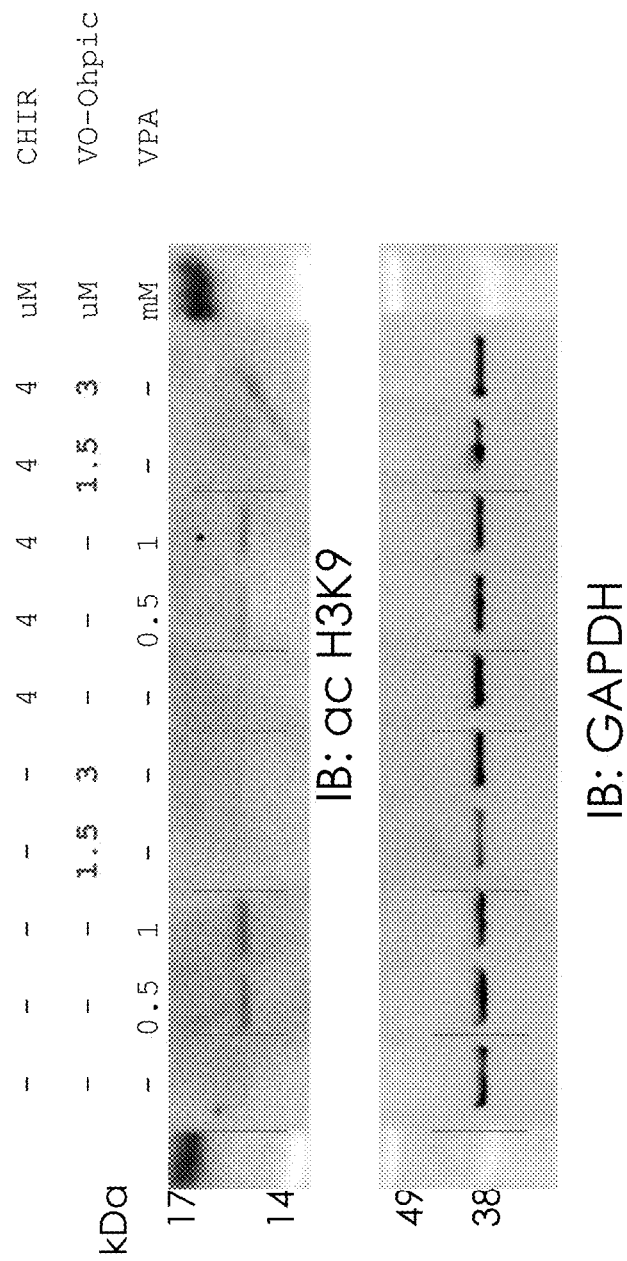
FIG. 5 is an image that demonstrates that VO-Ohpic does not elicit a detectable increase in HDAC inhibition whereas VPA elicits a concentration dependent increase in HDAC inhibition with and without CHIR in a background of growth factors including: 50 ng/mL EGF (E), 50 ng/mL bFGF (F), and 50 ng/mL IGF1 (I).

As shown in FIG. 3, GSK3 inhibition by CHIR upregulated Jag-1 while PTEN inhibition with VO does not upregulate Jag-1. However, as demonstrated in FIG. 3, PTEN inhibition with VO-Ohpic at 3 uM in combination of GSK3 inhibition with CHIR synergistically enhances Jag-1 upregulation. Thus the PTEN inhibitor effect of enhanced cochlear progenitor cell expansion correlates with the synergistic upregulation of Jag1. FIG. 4 shows these effects as analyzed by Western blot analysis Example 4: The Enhancement of Cochlear Progenitor Cell Expansion and Jag1 Upregulation by PTEN Inhibition is Independent of HDAC Inhibition As shown in FIG. 5, PTEN inhibition with VO-Ohpic does not elicit a detectable increase in HDAC inhibition. In contrast, HDAC inhibitor, VPA elicits a concentration dependent increase in HDAC inhibition with and without GSK3 inhibition. Together, these data suggest that enhancement of cochlear cell proliferation and upregulation of Jag1 can be achieved without HDAC inhibition.

Example 5: Jag-1 Antagonism Enhances Expansion of Cochlear Progenitor Cells

Figure 6B:
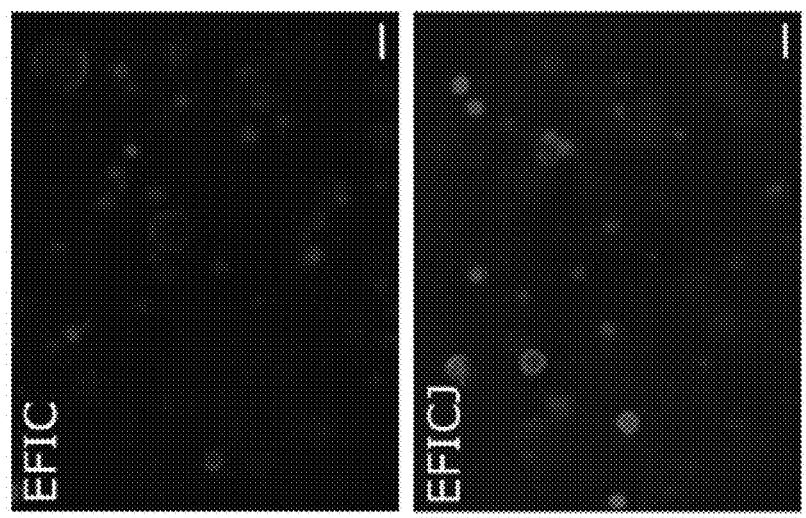
FIG. 6B is a series of images that shows that adding 0.25 µM Jag-1 peptide (J) to 4 µM CHIR is able to recapitulate enhancement of Lgr5+ cell proliferation when combined with CHIR (EFICJ) in a background of growth factors including: 50 ng/mL EGF (E), 50 ng/mL bFGF (F), and 50 ng/mL IGF1 (I). Scale bar 400 µm. *=$p<0.05$, =$p<0.01$, *=$p<0.001$.

As shown in FIG. 6 Jag-1 antagonism with a Jag-1 peptide enhances CHIR induced Lgr5+ cell proliferation), further suggesting that Jag-1 upregulation mediates cochlear progenitor cell expansion.

Example 6: FOXO1 Inhibition Enhances Expansion of Cochlear Progenitor Cells and Upregulates Jag-1

Figure 7:
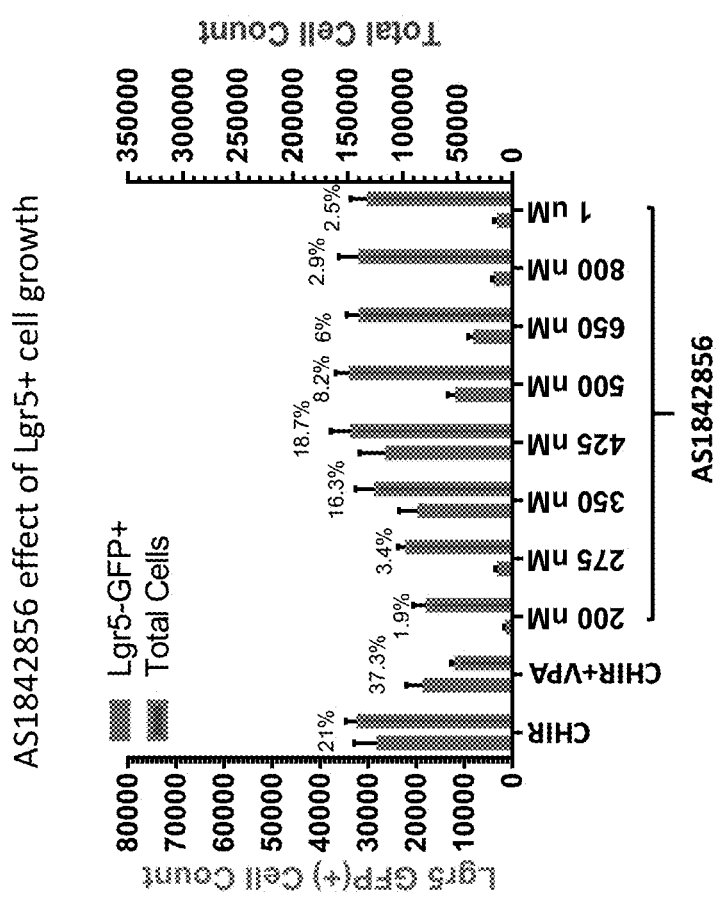
FIG. 7 is a graph that displays the concentration-dependent effects of FOXO1 inhibitor AS1842856 on LGR5+ cell growth (Lgr5 GFP(+) Cell Count) and enrichment (Lgr5 GFP (%)) in a background of growth factors including: 50 ng/mL EGF (E), 50 ng/mL bFGF (F), and 50 ng/mL IGF1 (I).
Figure 8A:
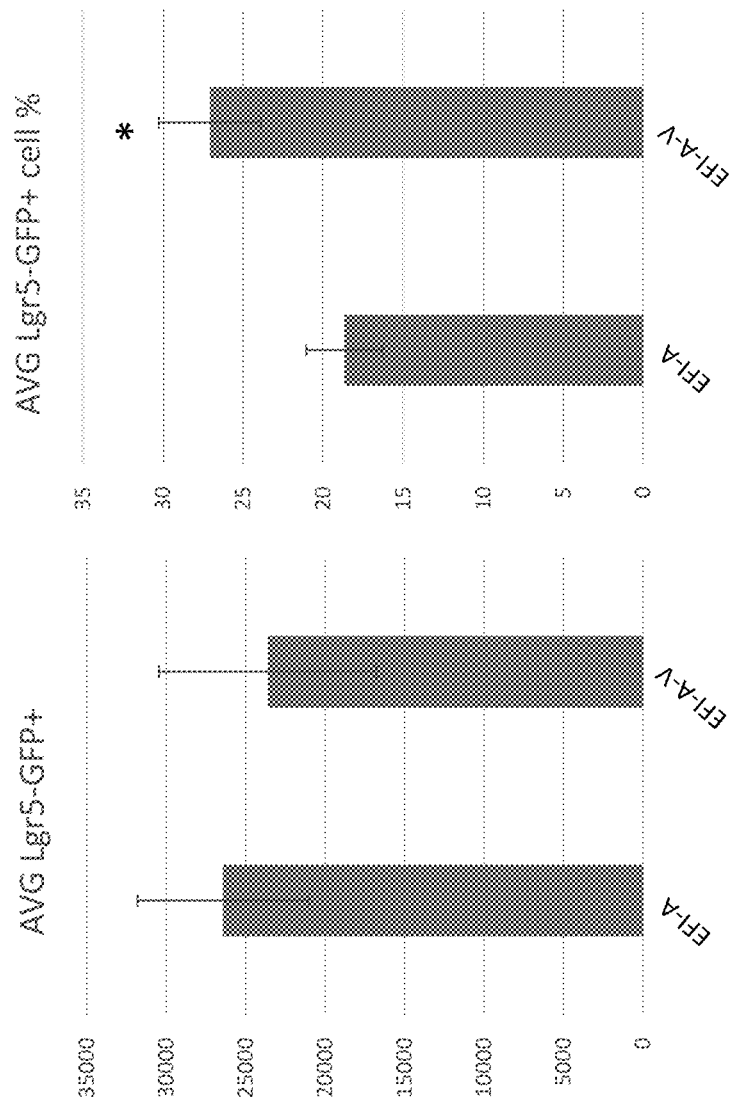
FIG. 8A is a series of graphs that display that FOXO1 inhibitor, AS1842856 (425 nM), elicits the expansion cochlear Lgr5+ progenitor cells in culture. Lgr5 cells are enriched according to percentage when AS1842856 is combined with VPA (1 mM) in a background of growth factors including: 50 ng/mL EGF (E), 50 ng/mL bFGF (F), and 50 ng/mL IGF1 (I).
Figure 8B:
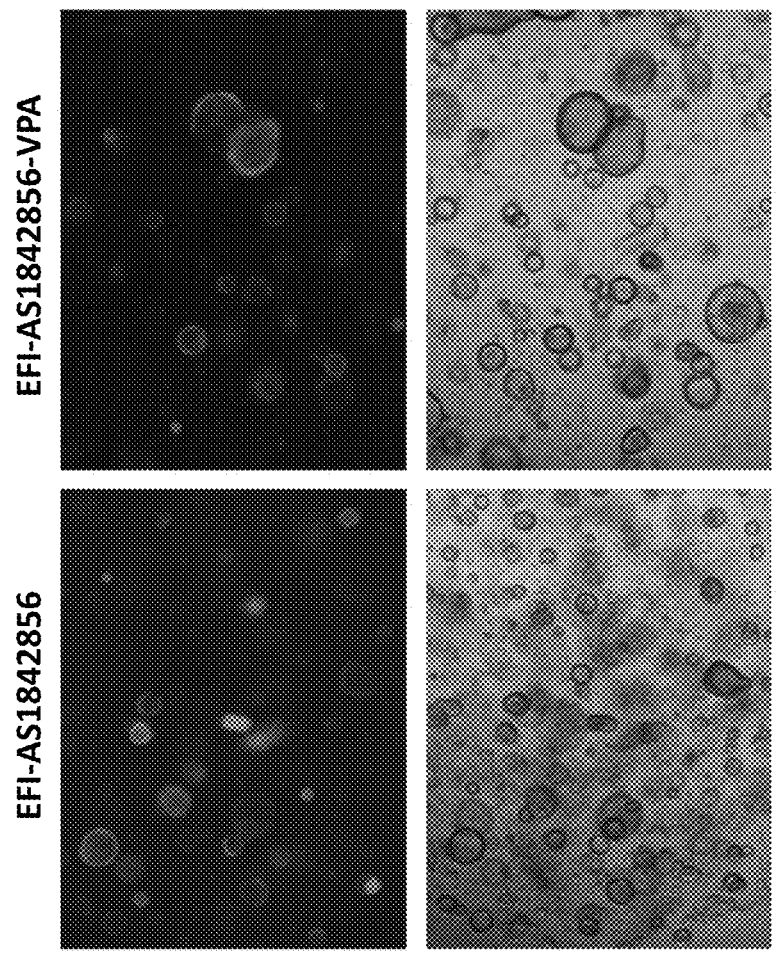
FIG. 8B is a series of images of Lgr5+ cell culture depicting Lgr5-GFP cell colonies. EFI-AS1842856 (425 nM) promotes Lgr5-GFP colony formation, which is enriched when VPA is added, as shown by less Lgr5-negative cells in culture in a background of growth factors including: 50 ng/mL EGF (E), 50 ng/mL bFGF (F), and 50 ng/mL IGF1 (I).
Figure 10B:
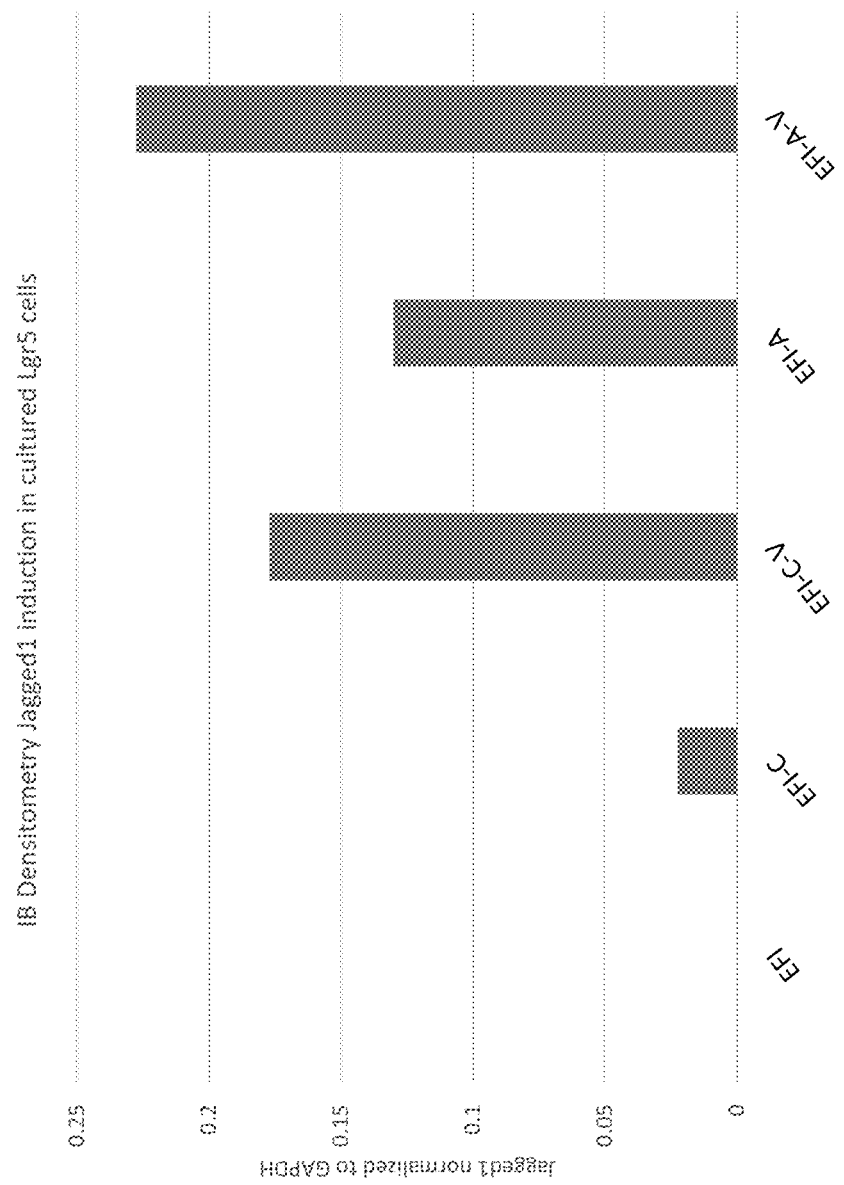
FIG. 10B is a graph demonstrating that 1 mM VPA enhanced the effects of 425 nM AS1842856 on Jag-1 upregulation. Calculated Jag-1 normalized to GAPDH using GelQuant software and bands quantified. Net volumes of Jag-1 bands were divided by net volume values of matched GAPDH bands. These values were normalized to vehicle.

As shown in FIG. 7, FOXO 1 inhibition with AS1842856 (EFI-A) enhances expansion of cochlear progenitor cells concentration-dependent manner. Moreover, as shown in FIGS. 8 A & B, Lgr5 cells are enriched when AS1842856 (425 nM) is combined with VPA (1 mM). FIGS. 9 and 10 show that FOXO 1 inhibition with AS21842856 (EFI-A) upregulates Jag-1 expression which is enhanced by the addition of VPA (EFI-A-V), as determined by qPCR and Western blot.

These values were normalized to vehicle, then vehicle was set to 0 (i.e. subtract 1 from all).

Example 7: HIF1-α Activation Enhances Expansion of Cochlear Progenitor Cells

Figure 11A:
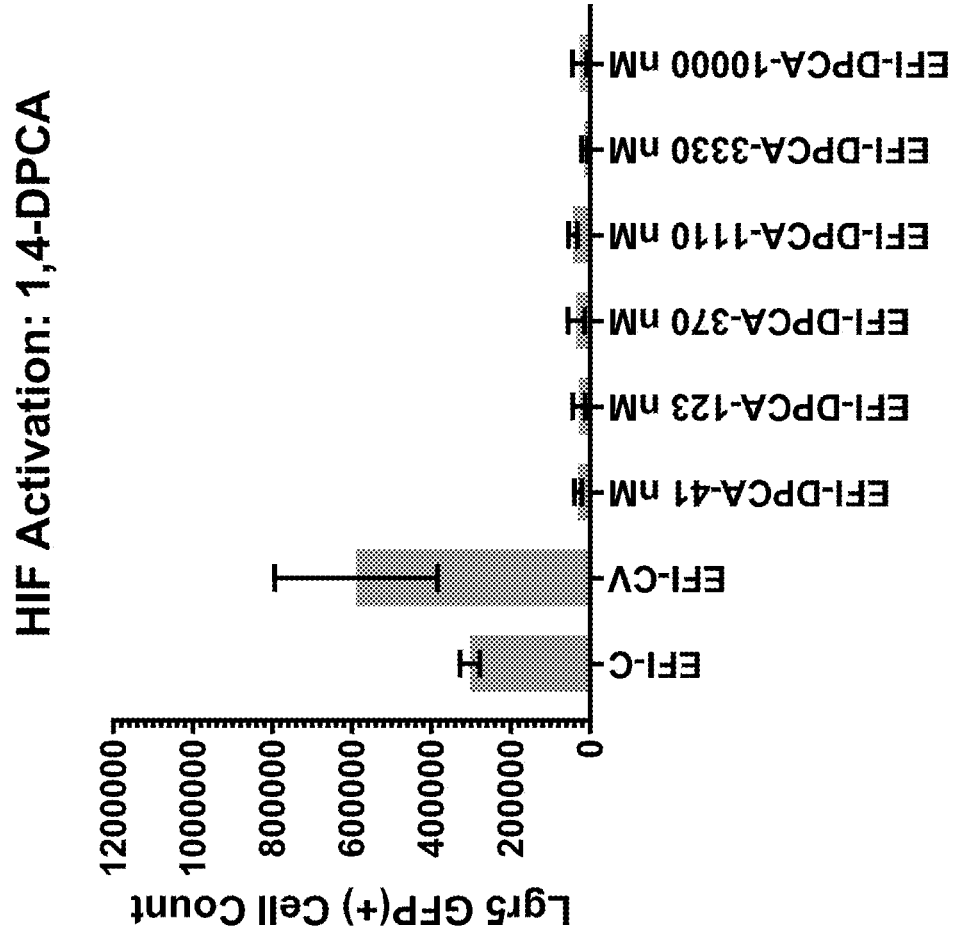
FIG. 11A is a graph demonstrating that the HIF1-α activator/prolyl 4-hydroxylation inhibitor, 1,4-DPCA (DPCA), does not proliferate Lgr5 GFP+ cochlear progenitor cells in a background of growth factors including: 50 ng/mL EGF (E), 50 ng/mL bFGF (F), and 50 ng/mL IGF1 (I). Control compounds CHIR99021 (4 µM; C) and Valproic Acid (1 mM; V) enrich for Lgr5 GFP+ cochlear progenitor cells.
Figure 11B:
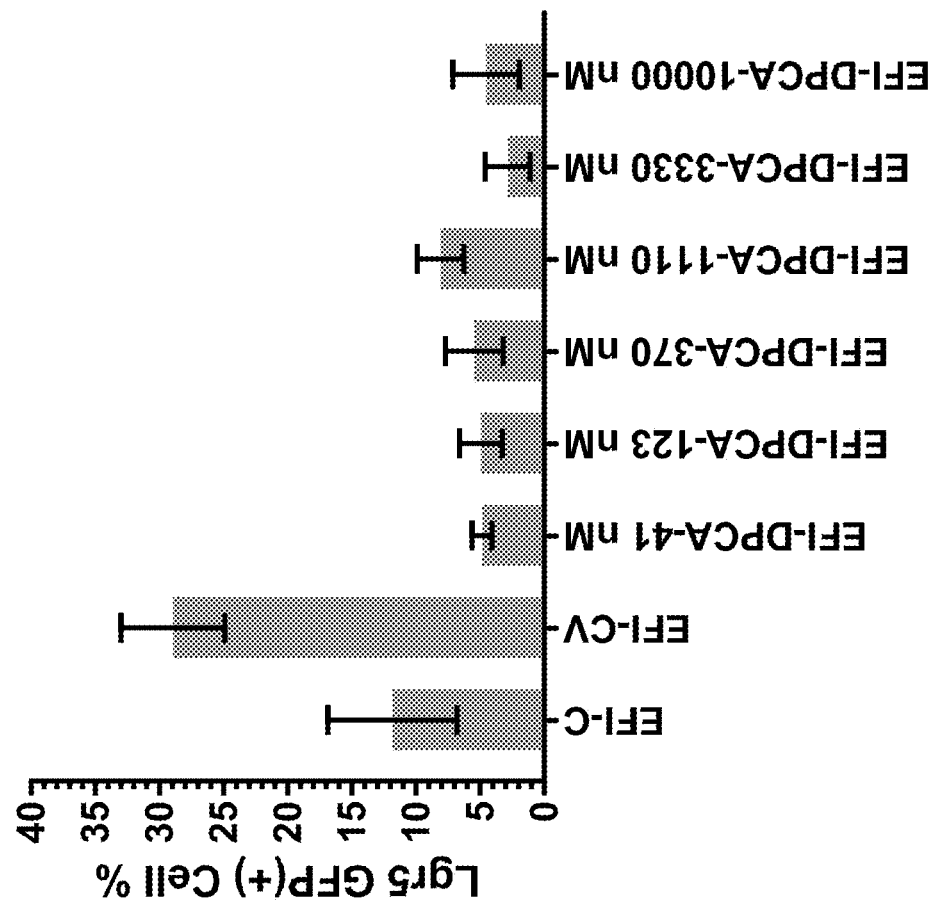
FIG. 11B is a graph demonstrating that the HIF1-α activator/HIF-PH inhibitor, 1,4-DPCA (DPCA), does not enrich for Lgr5 GFP+ cochlear progenitor cells in a background of growth factors including: 50 ng/mL EGF (E), 50 ng/mL bFGF (F), and 50 ng/mL IGF1 (I). Control compounds CHIR99021 (4 µM; C) and Valproic Acid (1 mM; V) enrich for Lgr5 GFP+ cochlear progenitor cells.
Figure 12A:
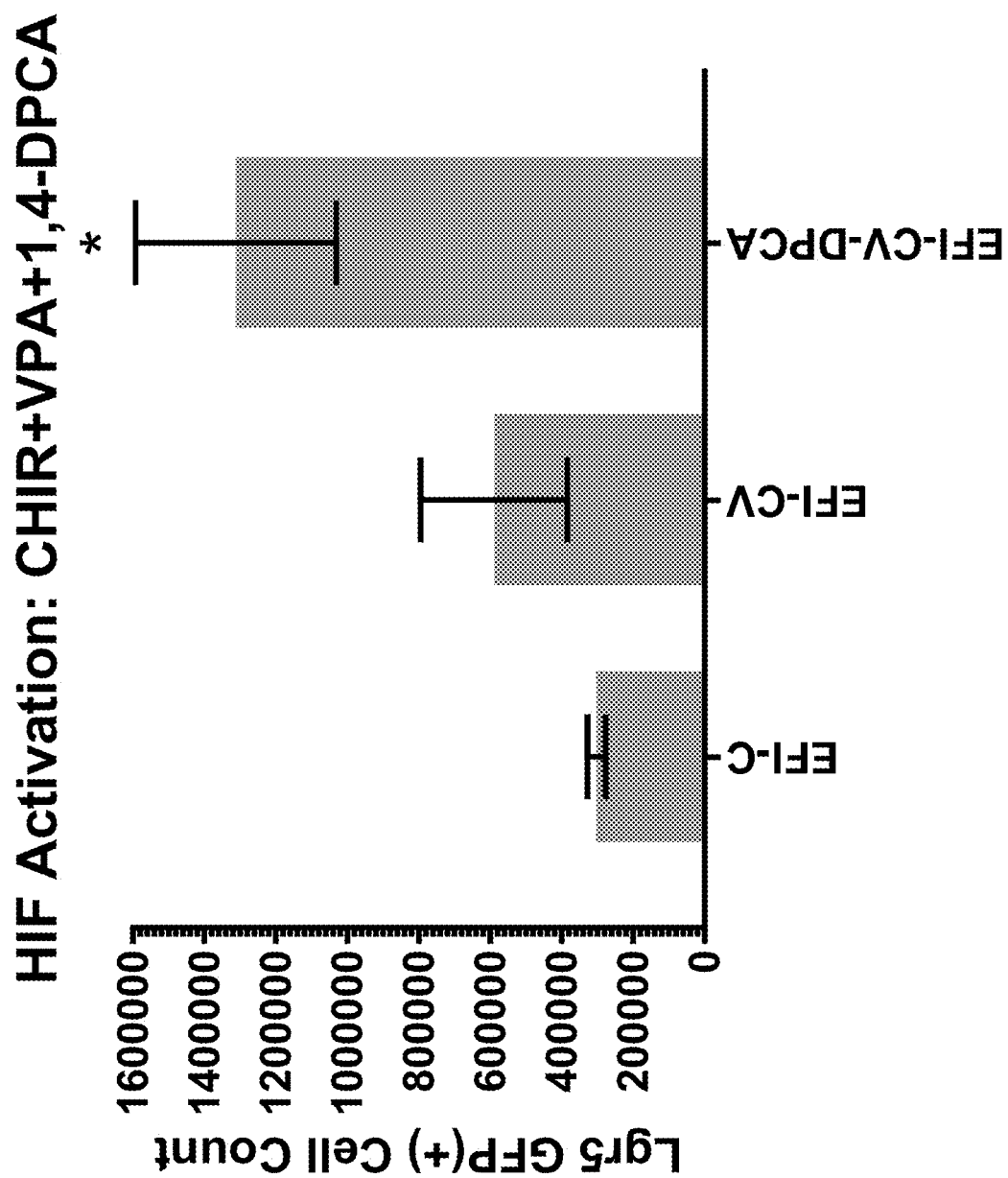
FIG. 12A is a graph demonstrating that the HIF1-α activator/prolyl 4-hydroxylation inhibitor, 1,4-DPCA (370 nM DPCA), enhances Lgr5 GFP+ progenitor cell proliferation over CHIR (4 µM)+VPA (1 mM) when combined with CHIR (4+VPA (1 mM) in a background of growth factors including: 50 ng/mL EGF (E), 50 ng/mL bFGF (F), and 50 ng/mL IGF1 (I).
Figure 12C:
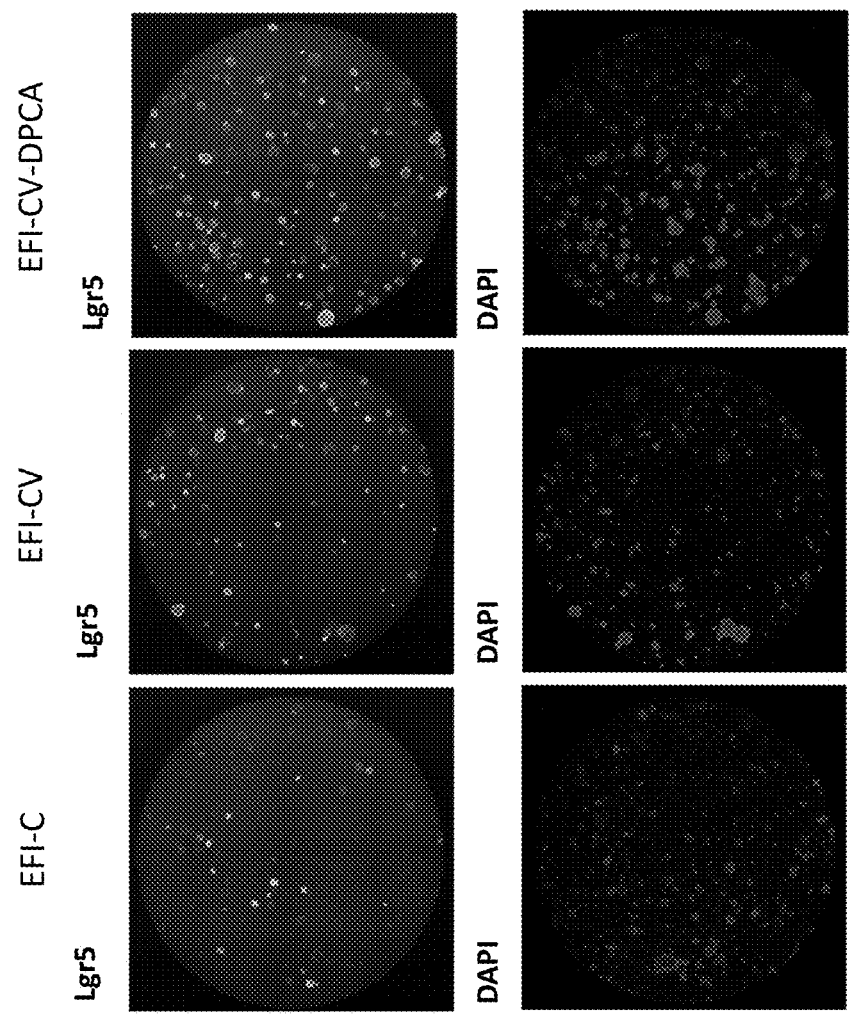
FIG. 12C is a series of images depicting the culture of Lgr5 GFP+ cells treated with CHIR (4 μM), CHIR (4 μM)+VPA (1 mM), or CHIR (4 μM)+VPA (1 mM)+1,4-DPCA (370 nM) in a background of growth factors including: 50 ng/mL EGF (E), 50 ng/mL bFGF (F), and 50 ng/mL IGF1 (I).

As shown in FIG. 11, HIF1-α activation with 1,4-DPCA does not proliferate or enrich Lgr5+ cochlear progenitor cells. However, as shown in FIG. 12, 1,4-DPCA (370 nM) in combination with CHIR (4 µM) and VPA (1 mM) enhances Lgr5 GFP+ progenitor cell proliferation and enrichment over CHIR and VPA.

Example 8: HIF-PH Inhibition Enhances Expansion of Cochlear Progenitor Cells

Figure 13A:
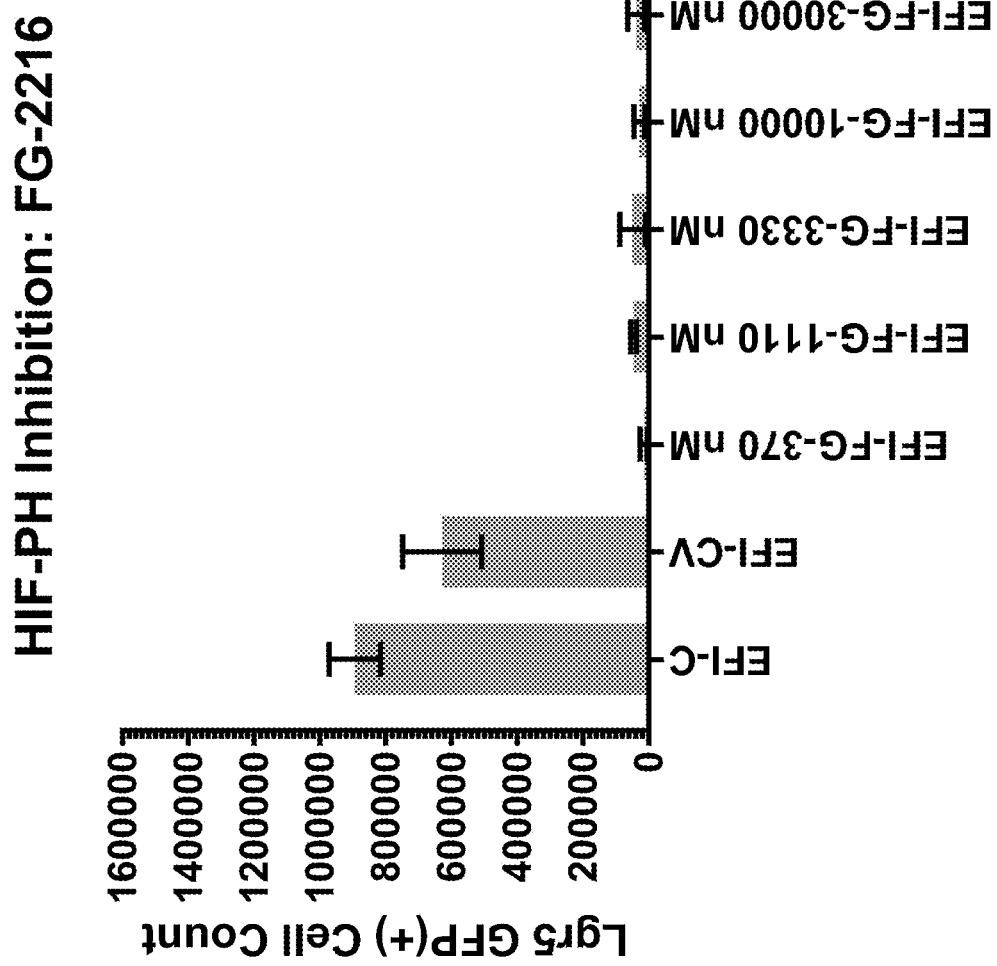
FIG. 13A is a graph demonstrating that the HIF1-α activator/HIF-PH inhibitor, FG-2216 (FG), does not proliferate Lgr5 GFP+ cochlear progenitor cells in a background of growth factors including: 50 ng/mL EGF (E), 50 ng/mL bFGF (F), and 50 ng/mL IGF1 (I). Control compounds CHIR99021 (4 μM; C) and Valproic Acid Sodium Salt (1 mM; V) enrich for Lgr5 GFP+ cochlear progenitor cells.
Figure 13B:
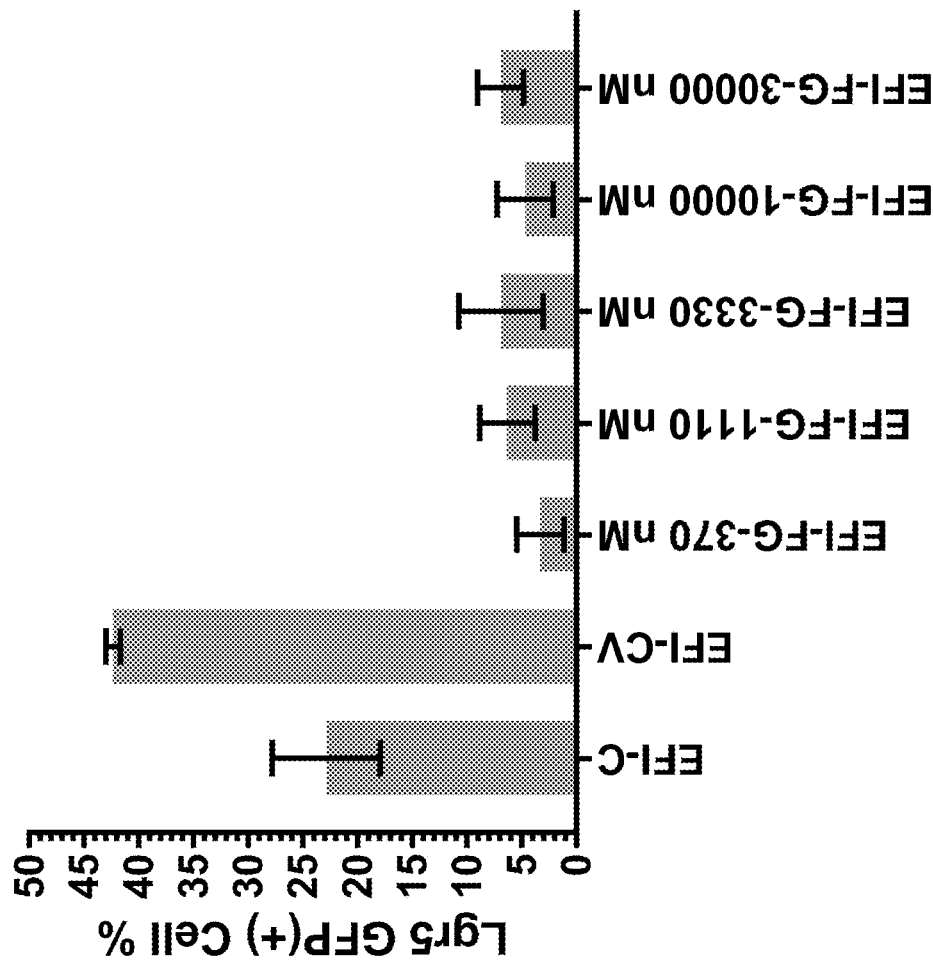
FIG. 13B is a graph demonstrating that the HIF1-α activator/HIF-PH inhibitor, FG-2216 (FG), does not enrich for Lgr5 GFP+ cochlear progenitor cells in a background of growth factors including: 50 ng/mL EGF (E), 50 ng/mL bFGF (F), and 50 ng/mL IGF1 (I). Control compounds CHIR99021 (4 μM; C) and Valproic Acid Sodium Salt (1 mM; V) enrich for Lgr5 GFP+ cochlear progenitor cells.
Figure 14A:
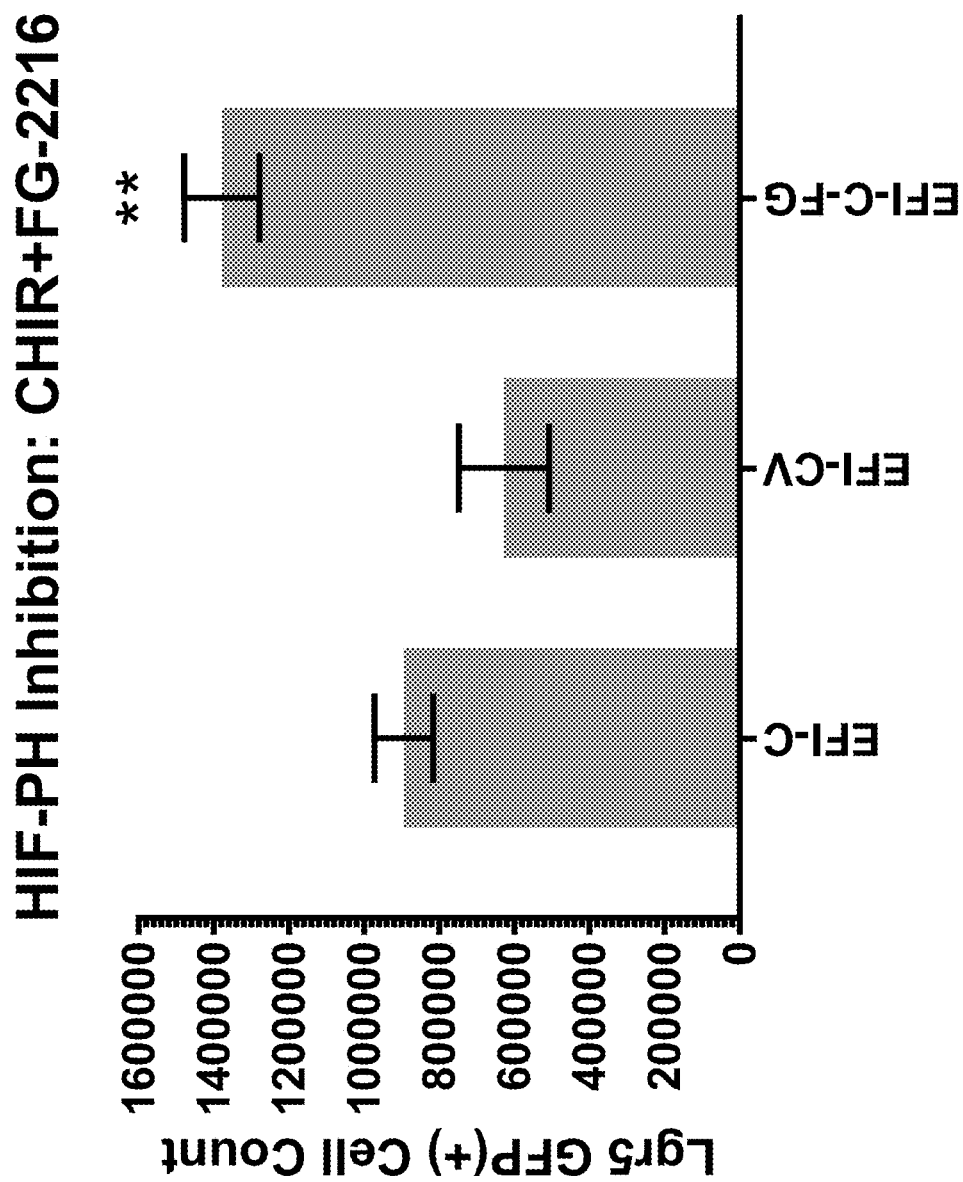
FIG. 14A is a graph demonstrating that the HIF1-α activator/HIF-PH inhibitor, FG-2216 (30 μM; FG), enhances Lgr5 GFP+ progenitor cell proliferation over CHIR (4 μM) and CHIR (4 μM)+VPA (1 mM) when combined with CHIR (4 μM) in a background of growth factors including: 50 ng/mL EGF (E), 50 ng/mL bFGF (F), and 50 ng/mL IGF1 (I).
Figure 14B:
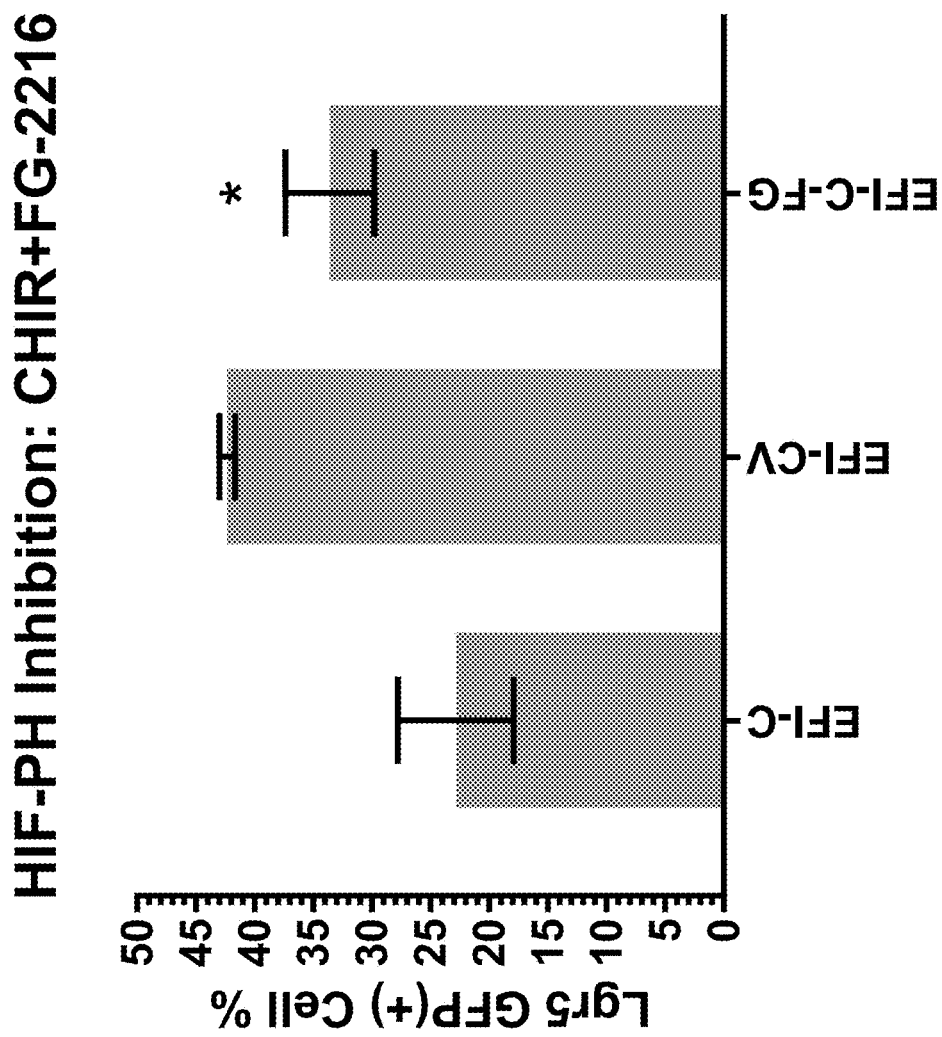
FIG. 14B is a graph depicting that the demonstrating that the HIF1-α activator/HIF-PH inhibitor, FG-2216 (30 μM; FG), enhances enrichment of Lgr5 GFP+ progenitor cell proliferation over CHIR (4 μM)+VPA (1 mM) when combined with CHIR (4 μM) in a background of growth factors including: 50 ng/mL EGF (E), 50 ng/mL bFGF (F), and 50 ng/mL IGF1 (I).
Figure 15A:
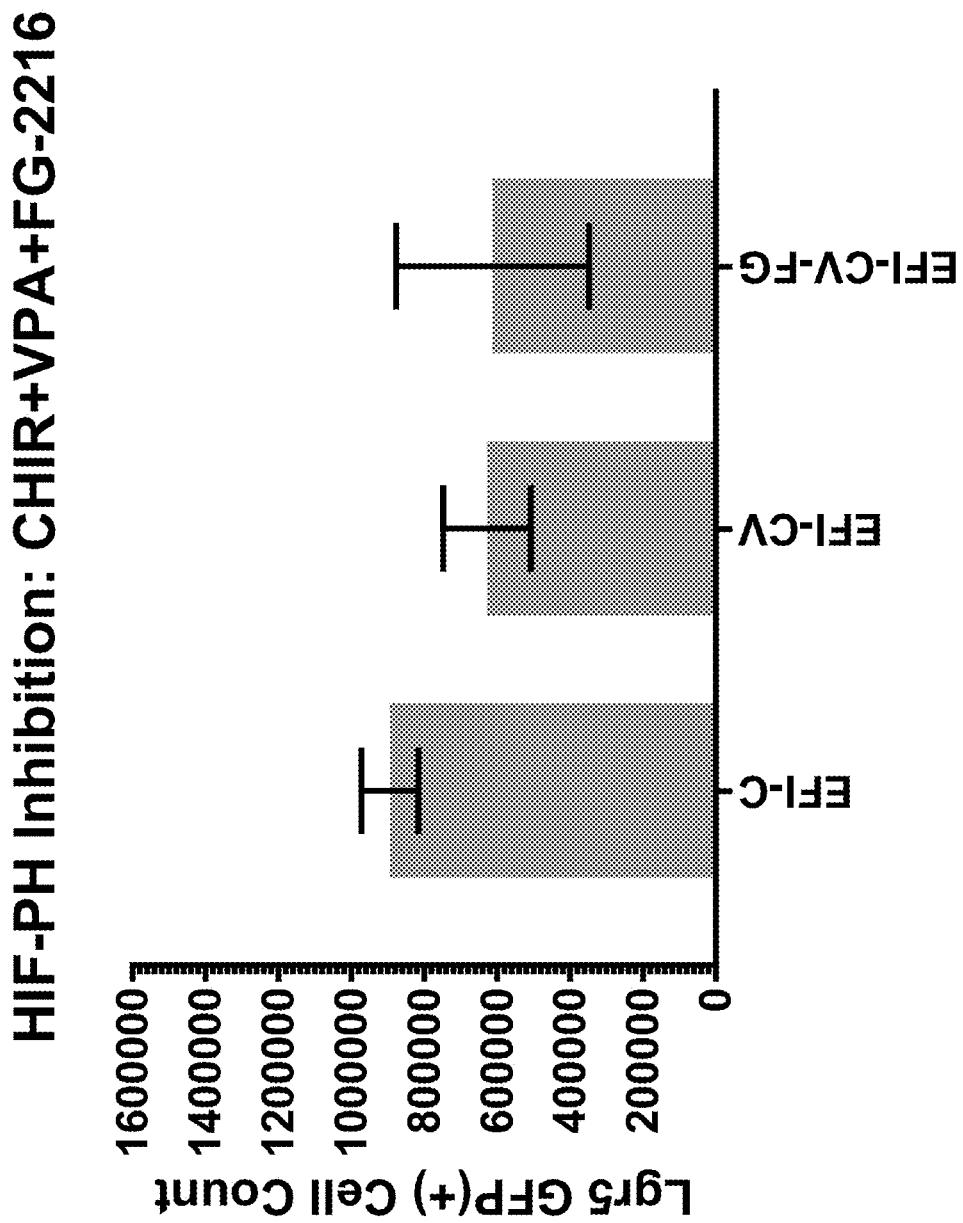
FIG. 15A is a graph demonstrating that the HIF1-α activator/HIF-PH inhibitor, FG-2216 (30 μM; FG), proliferates Lgr5 GFP+ progenitor cell similarly to CHIR (4 μM) and CHIR (4 μM)+VPA (1 mM) when combined with CHIR (4+VPA (1 mM) in a background of growth factors including: 50 ng/mL EGF (E), 50 ng/mL bFGF (F), and 50 ng/mL IGF1 (I).
Figure 15B:
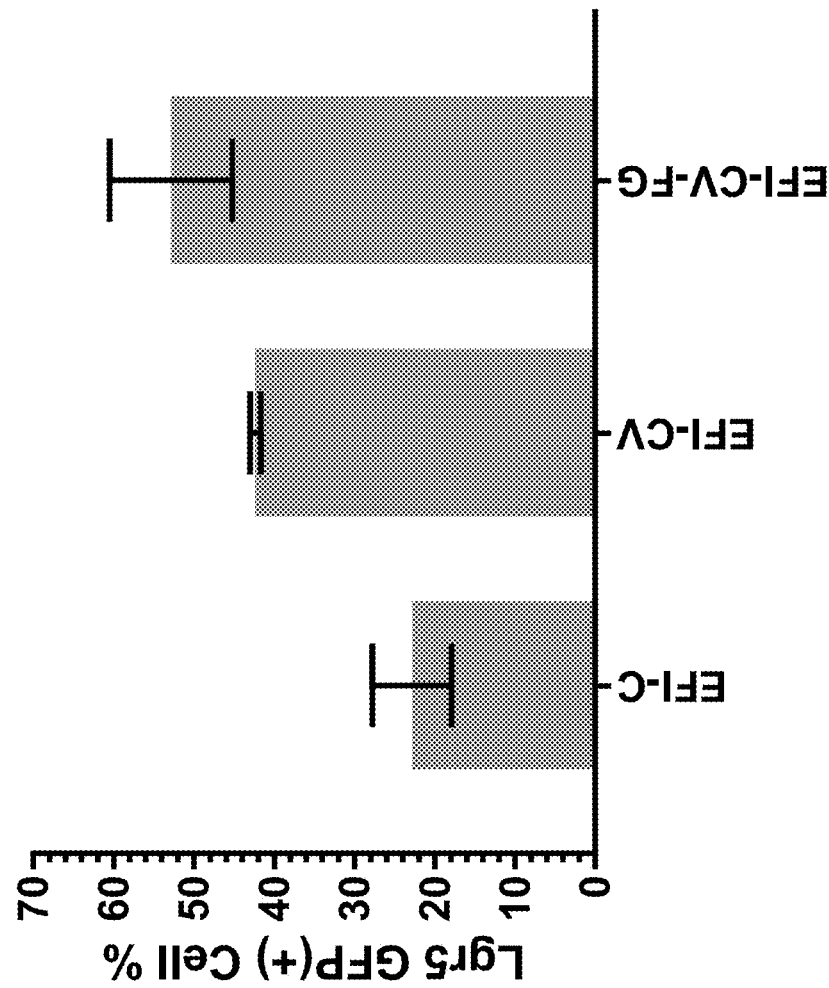
FIG. 15B is a graph depicting that the demonstrating that the HIF1-α activator/HIF-PH inhibitor, FG-2216 (30 μM; FG), shows a trend for enhanced enrichment of Lgr5 GFP+ progenitor cell proliferation over CHIR (4 μM)+VPA (1 mM) when combined with CHIR (4 μM)+VPA (1 mM) in a background of growth factors including: 50 ng/mL EGF (E), 50 ng/mL bFGF (F), and 50 ng/mL IGF1 (I).
Figure 15C:
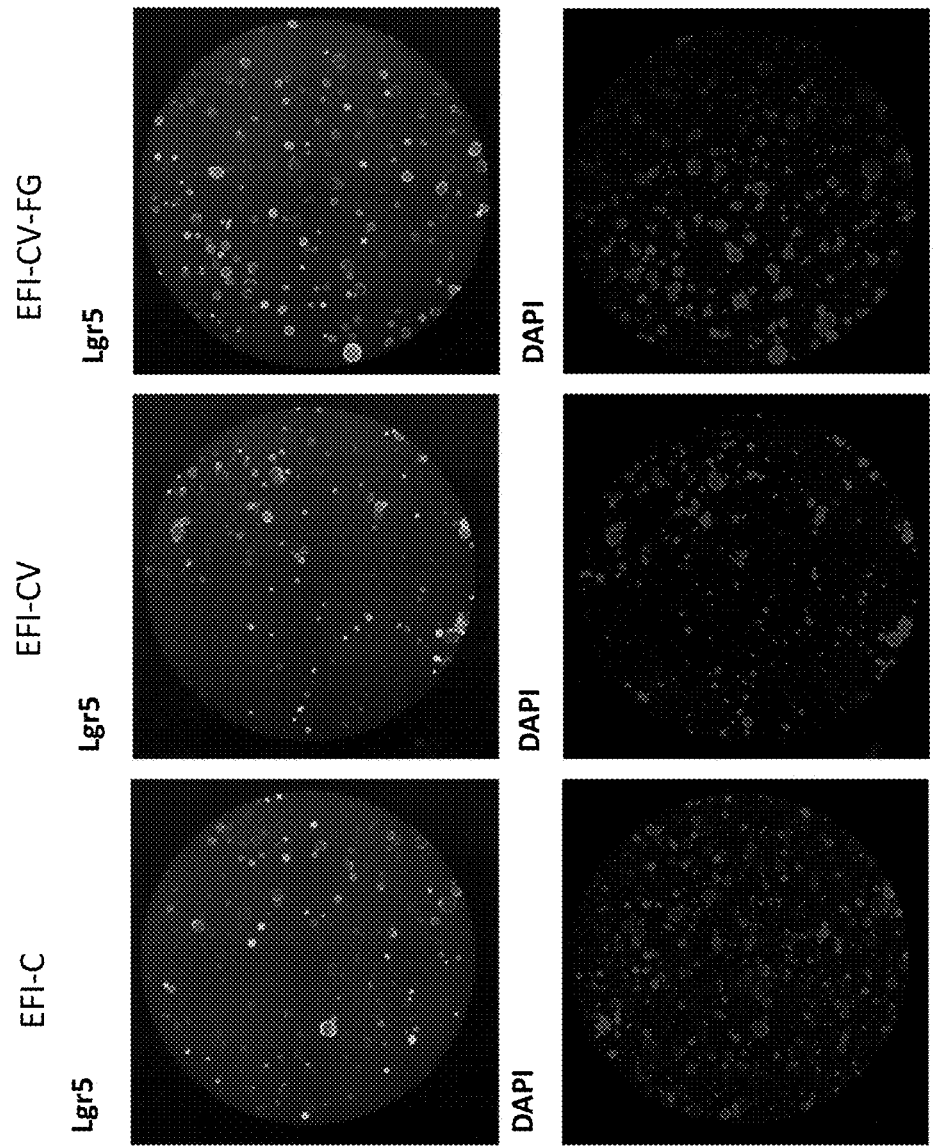
FIG. 15C is a series of images depicting the culture of Lgr5 GFP+ cells treated with CHIR (4 μM), CHIR (4 μM)+VPA (1 mM), or CHIR (4 μM)+VPA (1 mM)+FG-2216 (30 μM; FG) in a background of growth factors including: 50 ng/mL EGF (E), 50 ng/mL bFGF (F), and 50 ng/mL IGF1 (I).

As shown in FIG. 13, HIF-PH inhibition with FG-2216 does not proliferate or enrich Lgr5+ cochlear progenitor cells. However, as shown in FIG. 14A, FG-2216 (30 µM) in combination with CHIR (4 µM) enhances Lgr5 GFP+ progenitor cell proliferation over CHIR (4 µM) or CHIR (4 µM) and VPA (1 mM). Additionally, FG-2216 (30 µM) in combination with CHIR (4 µM) enriches Lgr5 GFP+ progenitor cell enrichment (FIG. 14B). Further, FIG. 15 demonstrates that the HIF1-PH inhibitor, FG-2216 (30 µM; FG), proliferates Lgr5 GFP+ progenitor cell similarly to CHIR (4 µM) and CHIR (4 µM) plus VPA (1 mM) when combined with CHIR (4 µM) plus VPA (1 mM) and shows a trend for enhanced enrichment of Lgr5 GFP+ progenitor cell proliferation over CHIR (4 µM) plus VPA (1 mM) when combined with CHIR (4 µM) plus VPA (1 mM).

Figure 16A:
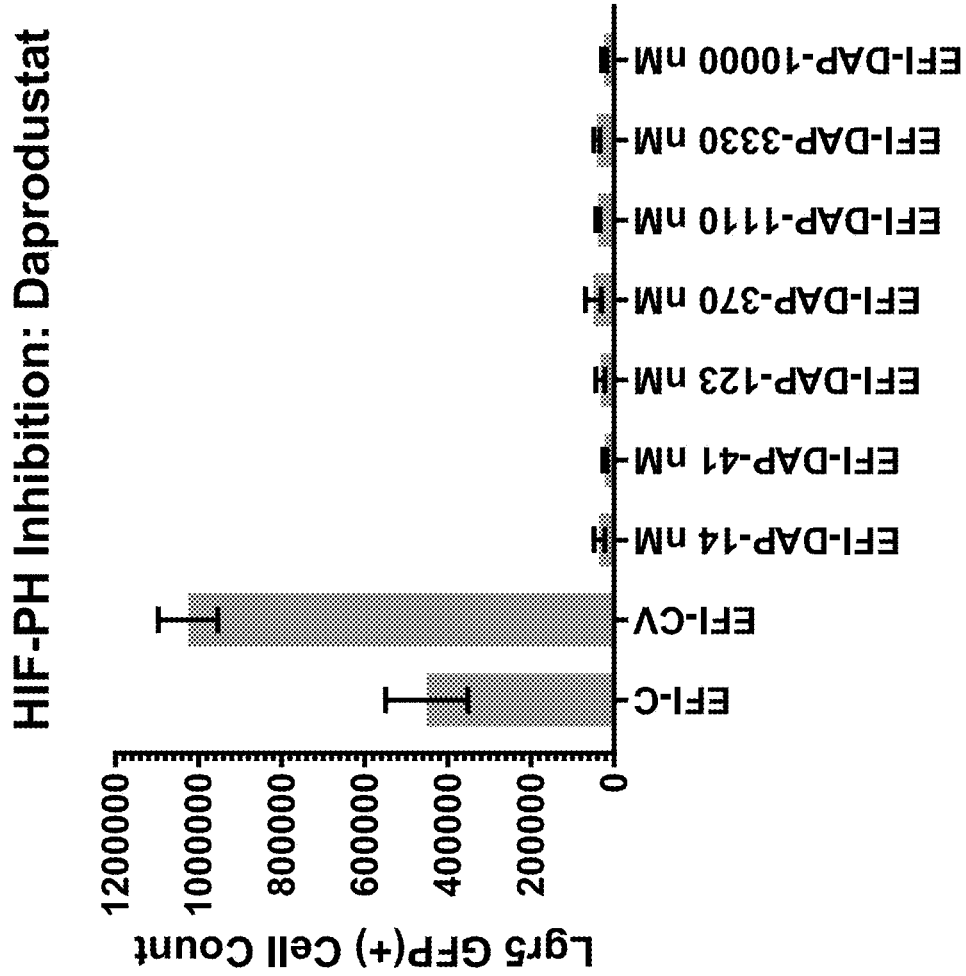
FIG. 16A is a graph demonstrating that the HIF1-α activator/HIF-PH inhibitor, daprodustat (DAP), does not proliferate Lgr5 GFP+ cochlear progenitor cells in a background of growth factors including: 50 ng/mL EGF (E), 50 ng/mL bFGF (F), and 50 ng/mL IGF1 (I). Control compounds CHIR99021 (4 μM; C) and Valproic Acid Sodium Salt (1 mM; V) enrich for Lgr5 GFP+ cochlear progenitor cells.
Figure 16B:
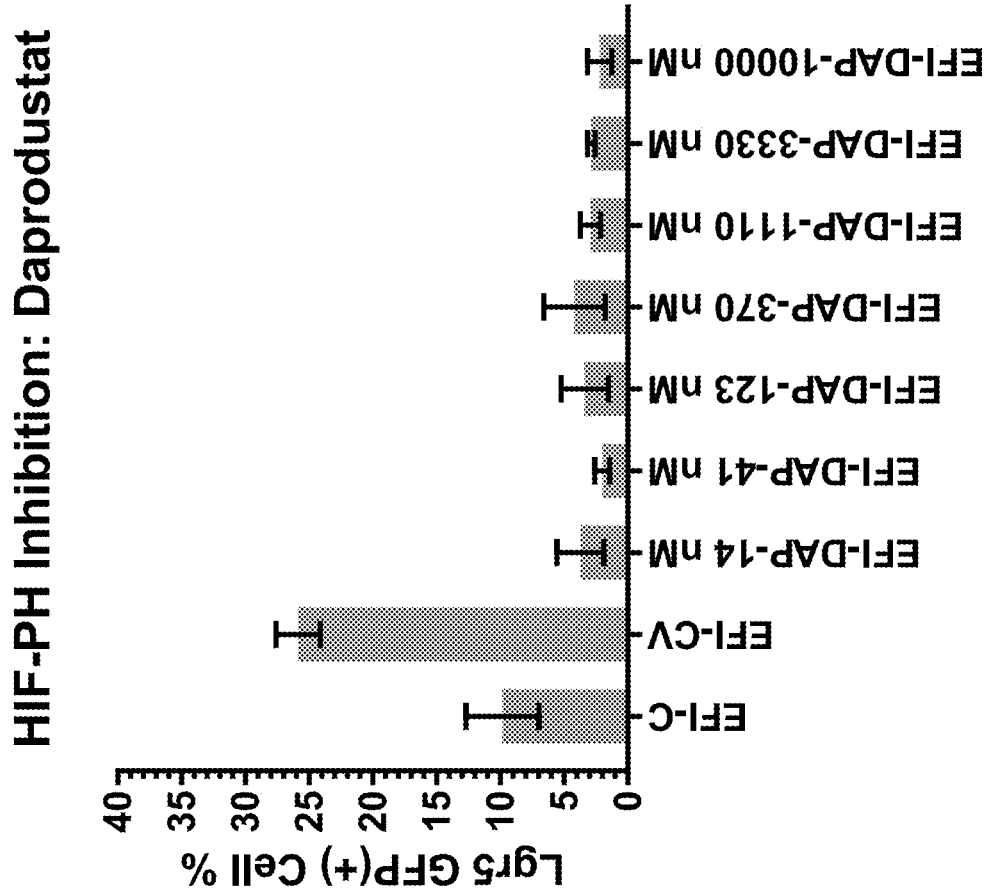
FIG. 16B is a graph demonstrating that the HIF1-α activator/HIF-PH inhibitor, daprodustat (DAP), does not enrich for Lgr5 GFP+ cochlear progenitor cells in a background of growth factors including: 50 ng/mL EGF (E), 50 ng/mL bFGF (F), and 50 ng/mL IGF1 (I). Control compounds CHIR99021 (4 μM; C) and Valproic Acid Sodium Salt (1 mM; V) enrich for Lgr5 GFP+ cochlear progenitor cells.
Figure 17A:
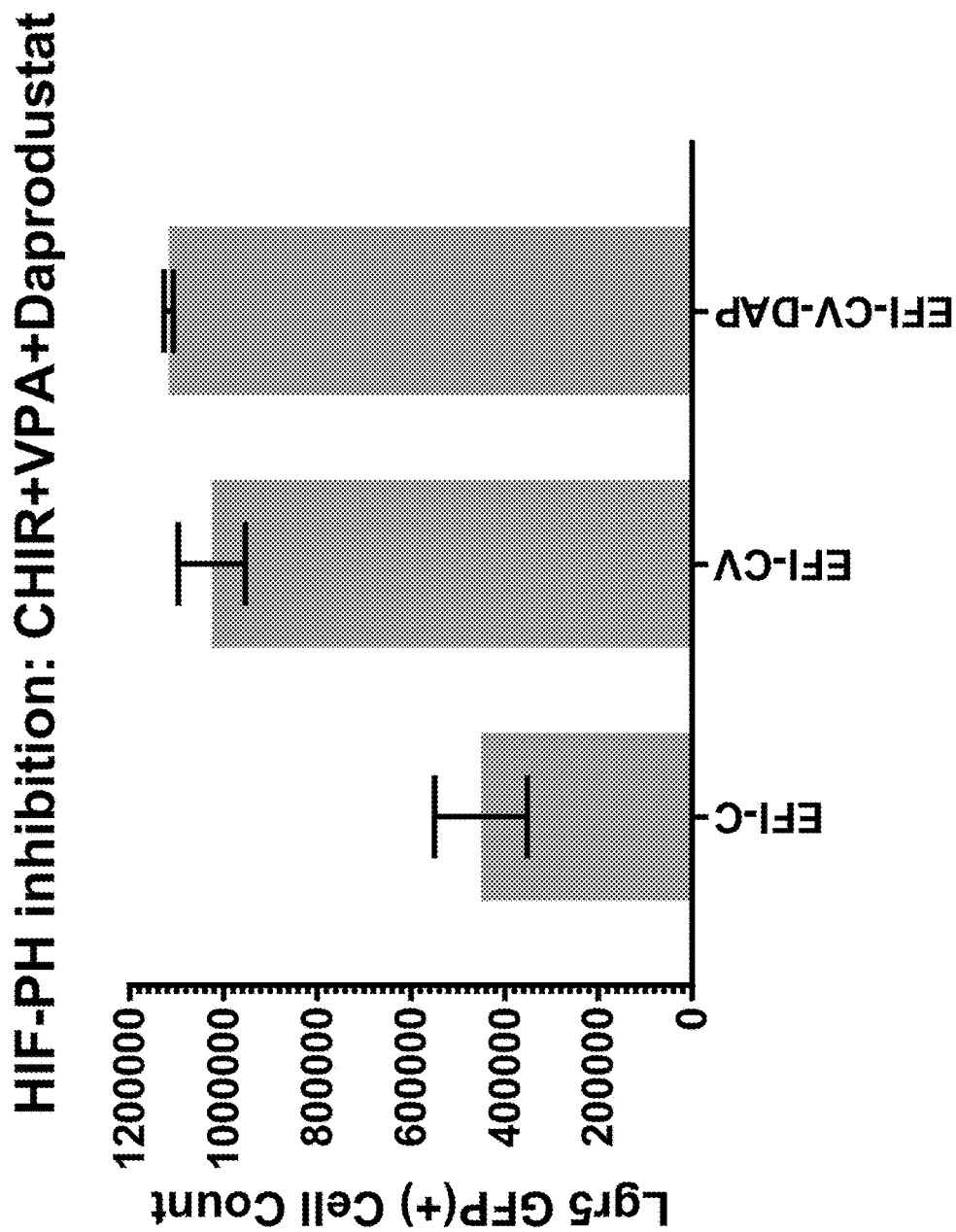
FIG. 17A is a graph demonstrating that the HIF1-α activator/HIF-PH inhibitor, daprodustat (1.11 μM; DAP), does not enhance Lgr5 GFP+ progenitor cell proliferation compared to CHIR (4 μM) and CHIR (4 μM)+VPA (1 mM) when combined with CHIR (4 μM)+VPA (1 mM) in a background of growth factors including: 50 ng/mL EGF (E), 50 ng/mL bFGF (F), and 50 ng/mL IGF1 (I).
Figure 17B:
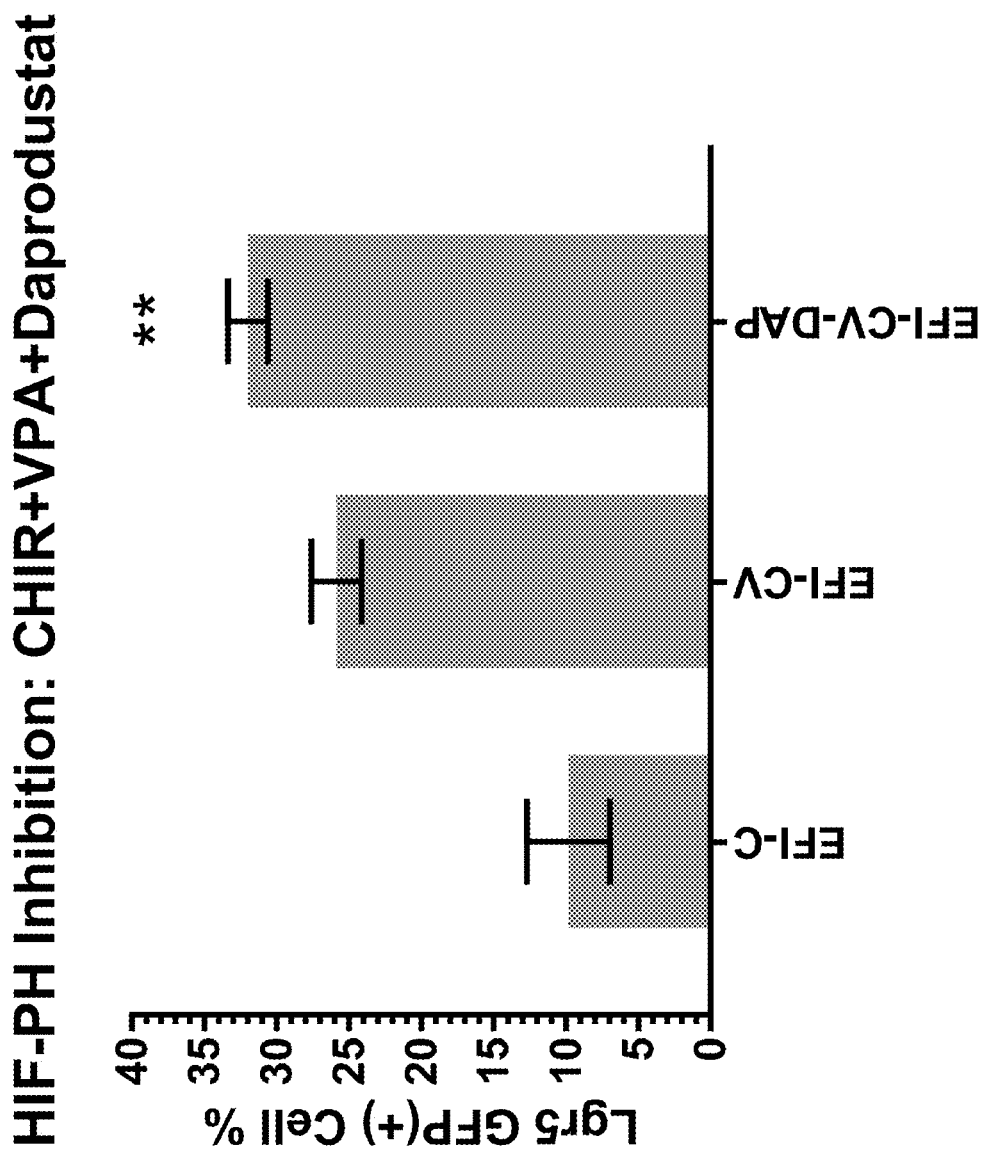
FIG. 17B is a graph depicting that the demonstrating that the HIF1-α activator/HIF-PH inhibitor, daprodustat (1.11 μM; DAP), enhances enrichment of Lgr5 GFP+ progenitor cell proliferation over CHIR (4 μM) and CHIR (4 μM)+VPA (1 mM) when combined with CHIR (4 μM)+VPA (1 mM) in a background of growth factors including: 50 ng/mL EGF (E), 50 ng/mL bFGF (F), and 50 ng/mL IGF1 (I).
Figure 17C:
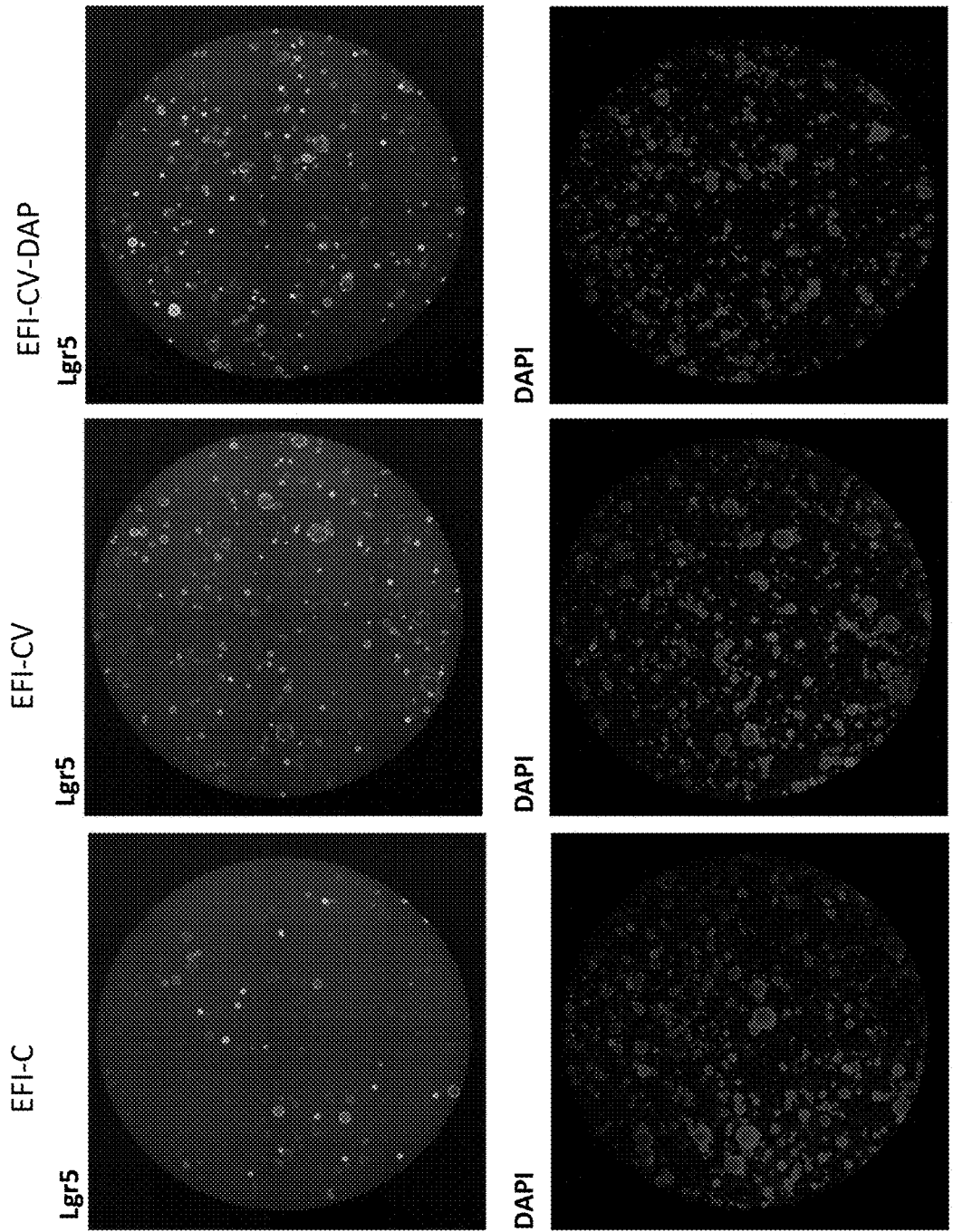
FIG. 17C is a series of images depicting the culture of Lgr5 GFP+ cells treated with CHIR (4 CHIR (4 μM)+VPA (1 mM), or CHIR (4 μM)+VPA (1 mM)+ daprudostat (1.11 μM; DAP) in a background of growth factors including: 50 ng/mL EGF (E), 50 ng/mL bFGF (F), and 50 ng/mL IGF1 (I).

As shown in FIG. 16, HIF-PH inhibition with daprodustat does not proliferate or enrich Lgr5+ cochlear progenitor cells. As shown in FIG. 17A, daprodustat (1.11 µM) in combination with CHIR (4 µM) and VPA (1 mM) does not enhance Lgr5 GFP+ progenitor cell proliferation over CHIR (4 µM) or CHIR (4 µM) and VPA (1 mM). However, as shown in FIG. 17B, daprodustat enhances enrichment of Lgr5 GFP+ progenitor cell proliferation over CHIR (4 µM) and CHIR (4 µM) plus VPA (1 mM) when combined with CHIR (4 µM) plus VPA (1 mM).

We claim:

1. A method for increasing proliferation of a cochlear supporting cell or a vestibular supporting cell, comprising contacting the supporting cell with CHIR99021, and
  a Jagged-1 (Jag-1) agonist, wherein the Jag-1 agonist is a HIF1-α activator, wherein the HIF1-α activator is 4,4α-dihydro-4-oxo-1,10-phenanthroline-3-carboxylic acid (1,4-DPCA), N-[(1-chloro-4-hydroxy-3-isoquinolinyl)carbonyl]-glycine (FG-2216) or N-[(1,3-dicyclohexylhexahydro-2,4,6-trioxo-5-pyrimidinyl)carbonyl]-glycine (daprodusat).

2. A method for producing an expanded population of cochlear or vestibular cells, comprising contacting a population of cochlear supporting cells or vestibular supporting cells with CHIR99021, and
  a Jagged-1 (Jag-1) agonist, wherein the Jag-1 agonist is a HIF1-α activator, wherein the HIF1-α activator is 4,4α-dihydro-4-oxo-1,10-phenanthroline-3-carboxylic acid (1,4-DPCA), N-[(1-chloro-4-hydroxy-3-isoquinolinyl)carbonyl]-glycine (FG-2216) or N-[(1,3-dicyclohexylhexahydro-2,4,6-trioxo-5-pyrimidinyl)carbonyl]-glycine (daprodusat).

3. The method of anyone of claim 1, wherein the cochlear supporting cell or vestibular supporting cell expresses leucine-rich repeat-containing G-protein coupled receptor 5 (Lgr5).

4. The method of claim 1, wherein the cochlear supporting cell or vestibular supporting cell is a mature cell.

5. The method of claim 1, wherein the cochlear supporting cell or vestibular supporting cell is a cochlear supporting cell.

6. The method of claim 1, wherein the CHIR99021 and HIF1-α activator are administered locally and/or systemically.

7. The method of claim 6, wherein the local administration is to the tympanic membrane, the middle ear or the inner ear.

8. The method of claim 6, wherein the systemic administration is oral or parenteral.

9. The method of claim 1, wherein:
  1,4-DPCA is administered at a concentration of between 1 nM to 100 mM;
  FG-2216 is administered at a concentration of between 1 nM to 1000 mM; or
  daprodusat is administered at a concentration of between 1 nM to 1000 mM.

10. The method of claim 1, wherein CHIR99021 is at a concentration of about between 1 μM to 10 μM.

11. The method of claim 1, wherein the CHIR99021 and HIF1-α activator are in a biocompatible matrix.

12. The method of claim 1, wherein the biocompatible matrix comprises hyaluronic acid, hyaluronates, lecithin gels, pluronics, poly(ethyleneglycol), poloxamers, chitosans, xyloglucans, collagens, fibrins, polyesters, poly(lactides), poly(glycolide), poly(lactic-co-glycolic acid (PLGA), sucrose acetate isobutyrate, glycerol monooleate, poly anhydrides, poly caprolactone sucrose, glycerol monooleate, silk materials, or a combination thereof.

13. The method of claim 1, further comprises contacting the supporting cell with valproic acid.

14. The method of claim 2, further comprises contacting a population of cochlear supporting cells or vestibular supporting cells with valproic acid.

* * * * *

UNITED STATES PATENT AND TRADEMARK OFFICE
CERTIFICATE OF CORRECTION

| | |
|---|---|
| PATENT NO. | : 11,162,071 B2 |
| APPLICATION NO. | : 16/544792 |
| DATED | : November 2, 2021 |
| INVENTOR(S) | : Christopher Loose et al. |

It is certified that error appears in the above-identified patent and that said Letters Patent is hereby corrected as shown below:

In the Specification

At Column 1, after Line number 10, please insert:
--This invention was made with government support under Grant No. W81XWH-18-1-0043 awarded by the Army. The government has certain rights in the invention."--

Signed and Sealed this
Ninth Day of May, 2023

Katherine Kelly Vidal
*Director of the United States Patent and Trademark Office*